United States Patent
Müller et al.

(10) Patent No.: US 9,226,505 B2
(45) Date of Patent: Jan. 5, 2016

(54) 4-SUBSTITUTED 1-PHENYLPYRAZOLE-3-CARBOXYLIC ACID DERIVATIVES AS AGENTS AGAINST ABIOTIC PLANT STRESS

(71) Applicant: BAYER INTELLECTUAL PROPERTY GMBH, Monheim (DE)

(72) Inventors: Thomas Müller, Frankfurt (DE); Lothar Willms, Hofheim (DE); Stefan Lehr, Lyons (FR); Monika H. Schmitt, Frankfurt (DE); Ines Heinemann, Hofheim (DE); Jan Dittgen, Frankfurt (DE); Christopher Hugh Rosinger, Hofheim (DE); Martin Jeffrey Hills, Idstein (DE); Pascal Von Kosküll-Döring, Leverkusen (DE); Isolde Häuser-Hahn, Leverkusen (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/345,741

(22) PCT Filed: Sep. 20, 2012

(86) PCT No.: PCT/EP2012/068501
§ 371 (c)(1),
(2) Date: Mar. 19, 2014

(87) PCT Pub. No.: WO2013/041602
PCT Pub. Date: Mar. 28, 2013

(65) Prior Publication Data
US 2014/0329684 A1    Nov. 6, 2014

(30) Foreign Application Priority Data

Sep. 23, 2011   (EP) .................................... 11182501

(51) Int. Cl.
| | | |
|---|---|---|
| *A01N 43/56* | (2006.01) | |
| *C07D 231/14* | (2006.01) | |
| *C07D 413/04* | (2006.01) | |
| *C07D 403/04* | (2006.01) | |
| *C07D 405/04* | (2006.01) | |

(52) U.S. Cl.
CPC .............. *A01N 43/56* (2013.01); *C07D 231/14* (2013.01); *C07D 403/04* (2013.01); *C07D 405/04* (2013.01); *C07D 413/04* (2013.01)

(58) Field of Classification Search
CPC .... A01N 43/56; C07D 231/14; C07D 403/04; C07D 413/04; C07D 405/04
See application file for complete search history.

(56) References Cited

U.S. PATENT DOCUMENTS

2007/0149406 A1   6/2007  Bastiaans et al.

FOREIGN PATENT DOCUMENTS

| | | | | |
|---|---|---|---|---|
| DE | 25 36 003 A1 | 2/1977 | | |
| DE | 2536003 A1 * | 2/1977 | ............. | A61K 31/40 |
| DE | 2633992 A1 | 2/1978 | | |
| DE | 2633992 A1 * | 2/1978 | ............. | A61K 31/40 |
| DE | 41 03 253 A1 | 8/1992 | | |
| DE | 4103253 A1 * | 8/1992 | ............. | A01N 31/12 |
| EP | 0 933 363 A1 | 8/1999 | | |
| WO | 2005/063020 A1 | 7/2005 | | |
| WO | WO2005/063020 A1 * | 7/2005 | ............. | A01N 43/56 |
| WO | 2006068933 A2 | 6/2006 | | |

OTHER PUBLICATIONS

Ramirez et al. "Efficient Synthesis of Novel 3-Aryl-5-(4-Chloro-2-Morpholinothiazol-5-Yl)-4,5-Dihydro-1 H-Pyrazoles and Their Antifungal Activity Alone and in Combination With Commercial Antifungal Agents", Arch. Pharm. Chem. Life Sci. (2014) vol. 347, pp. 1-10.
Gazetta Chmiica Italiana (1943) vol. 73, pp. 13-23. Also Cited on p. 1 of Specification.

(Continued)

*Primary Examiner* — Jane C Oswecki
(74) *Attorney, Agent, or Firm* — Miles & Stockbridge PC

(57) ABSTRACT

The invention relates to the use of 4-substituted 1-phenylpyrazole-3-carboxylic acid derivatives of the general formula (I), or salts thereof,

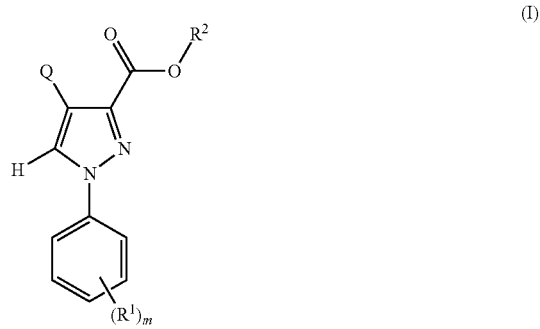

where the radicals in the general formula (I) correspond to the definitions given in the description,
for enhancing stress tolerance in plants to abiotic stress, for strengthening plant growth and/or for increasing plant yield, and to selected processes for preparing the compounds mentioned above.

16 Claims, No Drawings

(56) References Cited

OTHER PUBLICATIONS

Donohue et al. "Cycloaddition of Nitrile Imines to Resin-Bound Enamines: A Solid Phase Synthesis of 1,4-Diarylpyrazoles", J. Chem. Soc. Perkin Trans. vol. 1. (2001) p. 2817-2822. Also Cited on p. 1 of the Specification.

Al-Matar Studies With Enamines: Reactivity of N,N-Dimethyl-N-[(E)-2-(4-Nitro-Phenyl)-1-Ethenyl]amine Towards Nitrilimine and Aromatic Diazonium Salts, J. Heterocyclis Chem, (2007) vol. 44, p. 603-607. Also Cited on p. 1 of the Specification.

Bonini et al. "1,3-Dipolar Cycloaddition of Nitrile Imines With Functionalized Acetylenes: Regiocontrolled SC(OTF)3-Catalyzed Synthesis of 4- and 5-Substituted Pyrazoles", (2009) vol. 14, p. 2328-2332. Also Cited on p. 1 of the Specification.

Ruccia et al. "Cycloadditions in the Pyrrole Series", Tetrahedron Letters, No. 46 (1972) pp. 4703-4706. Also Cited on p. 1 of the Specification.

Archiv der Pharmazie 1983, 316 (7), 588-597. Not Enclosed But Cited on p. 1 of the Specification.

European Journal of Medicinal Chemistry 1982, 17 (1), 27-34). Not Enclosed But Cited on p. 1 of the Specification.

International Search Report of PCT/EP2012/068501 Dated Feb. 14, 2013.

International Preliminary Report and Written Opinion of PCT/EP2012/068501 Dated Mar. 25, 2014.

* cited by examiner

4-SUBSTITUTED 1-PHENYLPYRAZOLE-3-CARBOXYLIC ACID DERIVATIVES AS AGENTS AGAINST ABIOTIC PLANT STRESS

CROSS REFERENCE TO RELATED APPLICATIONS

This application is a §371 National Stage Application of PCT/EP2012/068501, filed Sep. 20, 2012, which claims priority to EP 11182501.4, filed Sep. 23, 2011.

BACKGROUND

1. Field of the Invention

The invention relates to the use of 4-substituted 1-phenylpyrazole-3-carboxylic acid derivatives or salts thereof for enhancing stress tolerance in plants to abiotic stress, for strengthening plant growth and/or for increasing plant yield, and to selected processes for preparing the compounds mentioned above.

2. Description of Related Art

It is known that certain 1,4-diphenylpyrazole-3-carboxylic acid derivatives can be employed as non-steroidal antiinflammatory active compounds (cf. DE2536003, DE2633992, Archiv der Pharmazie 1983, 316 (7), 588-597, European Journal of Medicinal Chemistry 1982, 17 (1), 27-34). Furthermore, it is known that 1,4-diphenylpyrazole-3-carboxylic acid derivatives can be used as mitotic kinesin inhibitors (cf. WO2006068933). The inhibitory action of 1,4-diphenylpyrazole-3-carboxylic acid derivatives on carboanhydrase has also been described (cf. WO2004014430).

Moreover, it is known that 1-phenyl-4-alkylpyrazole-3-carboxylic acid derivatives can be used as pharmaceutically active compounds for treating ischemia (cf. WO9943663) and for treating parasites, and/or as agrochemically active compounds (cf. EP933363). Furthermore, WO2005/063020 describes 5-substituted 1-arylpyrazole-3-carboxylic acid derivatives as plant growth regulators. However, these differ fundamentally in the substitution of position 4 in the pyrazole ring. The preparation of substituted 1,4-diphenylpyrazole-3-carboxylic acid derivatives is described in the literature references (cf. Synthesis 2009 (14), 2328-2332; Journal of Heterocyclic Chemistry 2007 44(3), 603-607; Zeitschrift für Naturforschung B: Chemical Sciences 2004 59(10), 1132-1136; Journal of Chemical Society, Perkin Transactions) 2001 21, 2817-2822; Tetrahedron Letters 1972 46, 4703-4706; Gazetta Chimica Italiana 1943 73, 13-23).

It is known that plants react to natural stress conditions, for example cold, heat, drought, injury, pathogenic attack (viruses, bacteria, fungi, insects), etc., but also to herbicides, with specific or unspecific defense mechanisms [Pflanzenbiochemie, pp. 393-462, Spektrum Akademischer Verlag, Heidelberg, Berlin, Oxford, Hans W. Heldt, 1996; Biochemistry and Molecular Biology of Plants, pp. 1102-1203, American Society of Plant Physiologists, Rockville, Md., eds. Buchanan, Gruissem, Jones, 2000].

In plants, there is knowledge of numerous proteins, and the genes which code for them, which are involved in defense reactions to abiotic stress (for example cold, heat, drought, salt, flooding). Some of these form part of signal transduction chains (for example transcription factors, kinases, phosphatases) or cause a physiological response of the plant cell (for example ion transport, deactivation of reactive oxygen species). The signaling chain genes of the abiotic stress reaction include inter alia transcription factors of the DREB and CBF classes (Jaglo-Ottosen et al., 1998, Science 280: 104-106). The reaction to salinity stress involves phosphatases of the ATPK and MP2C types. In addition, in the event of salinity stress, the biosynthesis of osmolytes such as proline or sucrose is often activated. This involves, for example, sucrose synthase and proline transporters (Hasegawa et al., 2000, Annu Rev Plant Physiol Plant Mol Biol 51: 463-499). The stress defense of the plants to cold and drought uses some of the same molecular mechanisms. There is a known accumulation of what are called late embryogenesis abundant proteins (LEA proteins), which include the dehydrins as an important class (Ingram and Bartels, 1996, Annu Rev Plant Physiol Plant Mol Biol 47: 277-403, Close, 1997, Physiol Plant 100: 291-296). These are chaperones which stabilize vesicles, proteins and membrane structures in stressed plants (Bray, 1993, Plant Physiol 103: 1035-1040). In addition, there is frequently induction of aldehyde dehydrogenases, which deactivate the reactive oxygen species (ROS) which form in the event of oxidative stress (Kirch et al., 2005, Plant Mol Biol 57: 315-332).

Heat shock factors (HSF) and heat shock proteins (HSP) are activated in the event of heat stress and play a similar role here as chaperones to that of dehydrins in the event of cold and drought stress (Yu et al., 2005, Mol Cells 19: 328-333).

A number of signaling substances which are endogenous to plants and are involved in stress tolerance or pathogenic defense are already known. Examples include salicylic acid, benzoic acid, jasmonic acid or ethylene [Biochemistry and Molecular Biology of Plants, pp. 850-929, American Society of Plant Physiologists, Rockville, Md., eds. Buchanan, Gruissem, Jones, 2000]. Some of these substances or the stable synthetic derivatives and derived structures thereof are also effective on external application to plants or in seed dressing, and activate defense reactions which cause elevated stress tolerance or pathogen tolerance of the plant [Sembdner, and Parthier, 1993, Ann. Rev. Plant Physiol. Plant Mol. Biol. 44: 569-589].

It is additionally known that chemical substances can increase the tolerance of plants to abiotic stress. Such substances are applied either by seed dressing, by leaf spraying or by soil treatment. For instance, an increase in the abiotic stress tolerance of crop plants by treatment with elicitors of systemic acquired resistance (SAR) or abscisic acid derivatives is described (Schading and Wei, WO200028055; Abrams and Gusta, U.S. Pat. No. 5,201,931; Abrams et al, WO9723441, Churchill et al., 1998, Plant Growth Regul 25: 35-45). In addition, effects of growth regulators on the stress tolerance of crop plants have been described (Morrison and Andrews, 1992, J Plant Growth Regul 11: 113-117, RD-259027). In this context, it is likewise known that a growth-regulating naphthylsulfonamide (4-bromo-N-(pyridin-2-ylmethyl)naphthalene-1-sulfonamide) influences the germination of plant seeds in the same way as abscisic acid (Park et al. Science 2009, 324, 1068-1071). It is also known that a further naphthylsulfonamide, N-(6-aminohexyl)-5-chloronaphthalene-1-sulfonamide, influences the calcium level in plants which have been exposed to cold shock (Cholewa et al. Can. J. Botany 1997, 75, 375-382).

Similar effects are also observed on application of fungicides, especially from the group of the strobilurins or of the succinate dehydrogenase inhibitors, and are frequently also accompanied by an increase in yield (Draber et al., DE-3534948, Bartlett et al., 2002, Pest Manag Sci 60: 309). It is likewise known that the herbicide glyphosate in low dosage stimulates the growth of some plant species (Cedergreen, Env. Pollution 2008, 156, 1099).

In the event of osmotic stress, a protective effect has been observed as a result of application of osmolytes, for example glycine betaine or the biochemical precursors thereof, e.g. choline derivatives (Chen et al., 2000, Plant Cell Environ 23: 609-618, Bergmann et al., DE-4103253). The effect of antioxidants, for example naphthols and xanthines, for increasing abiotic stress tolerance in plants has likewise already been described (Bergmann et al., DD-277832, Bergmann et al., DD-277835). However, the molecular causes of the antistress action of these substances are substantially unknown.

It is additionally known that the tolerance of plants to abiotic stress can be increased by a modification of the activity of endogenous poly-ADP-ribose polymerases (PARP) or poly-(ADP-ribose) glycohydrolases (PARG) (de Block et al., The Plant Journal, 2004, 41, 95; Levine et al., FEBS Lett. 1998, 440, 1; WO0004173; WO04090140).

SUMMARY

It is thus known that plants possess several endogenous reaction mechanisms which can bring about effective defense against a wide variety of different harmful organisms and/or natural abiotic stress.

Since the ecological and economic demands on modern crop treatment compositions are increasing constantly, for example with respect to toxicity, selectivity, application rate, formation of residues and favorable manufacture, there is a constant need to develop novel crop treatment compositions which have advantages over those known, at least in some areas.

It was therefore an object of the present invention to provide further compounds which increase tolerance to abiotic stress in plants.

The present invention accordingly provides for the use of 4-substituted 1-phenylpyrazole-3-carboxylic acid derivatives of the general formula (I), or salts thereof,

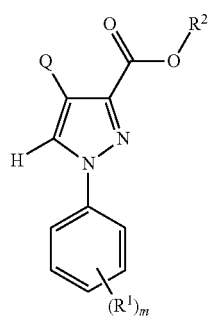

(I)

for increasing tolerance to abiotic stress in plants, where Q represents

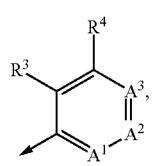

Q-I

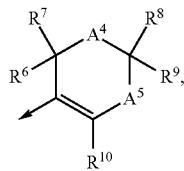

Q-II

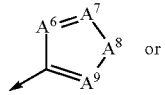

Q-III

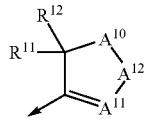

Q-IV where the $R^3$ to $R^{12}$ and $A^1$ to $A^{12}$ moieties each have the meaning according to the definitions below, and where the arrow represents a bond to the pyrazole, $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1$-$C_{10})$-alkyl, $(C_1$-$C_{10})$-alkoxy or $(C_1$-$C_{10})$-alkylthio, where each of the three last-mentioned radicals independently of the others is unsubstituted or substituted by one or more radicals from the group consisting of halogen, CN, $(C_1$-$C_{10})$-alkoxy and $(C_1$-$C_{10})$-alkylthio, $R^2$ represents hydrogen or a radical which can be hydrolyzed to afford the carboxylic acid,
preferably an optionally substituted hydrocarbon radical or an optionally substituted heterocyclyl radical, where each of the two last-mentioned carbon-containing radicals including substituents has 1 to 30 carbon atoms, preferably 1 to 24 carbon atoms, in particular 1 to 20 carbon atoms, or
a radical of the formula —N=$CR^aR^b$, —$NR^cR^d$ or $SiR^eR^f$, $R^g$,
where in the 3 last-mentioned formulae each of the radicals $R^a$, $R^b$, $R^c$, $R^d$, $R^e$, $R^f$ and $R^g$ independently of the others represents hydrogen or an optionally substituted hydrocarbon radical,
or $R^a$ and $R^b$ together with the carbon atom to which they are attached represent a 3- to 9-membered carbocyclic radical or a heterocyclic radical which may contain 1 to 3 ring heteroatoms from the group consisting of N, O and S, where the carbocyclic or heterocyclic radical is unsubstituted or substituted, or $R^c$ and $R^d$ together with the nitrogen atom represent a 3- to 8-membered heterocycle which, in addition to the nitrogen atom, may contain one or two further ring heteroatoms from the group consisting of N, O and S and which is unsubstituted or substituted by one or more radicals from the group consisting of $(C_1$-$C_4)$-alkyl and $(C_1$-$C_4)$-haloalkyl,
where each of the radicals $R^a$, $R^b$, $R^c$, $R^d$, $R^e$, $R^f$ and $R^g$ including substituents has 1 to 30 carbon atoms, preferably 1 to 24 carbon atoms, in particular 1 to 20 carbon atoms, m represents 1, 2, 3, 4 or 5, preferably 1, 2, 3 or 4, in particular 1 or 2.

$A^1, A^2, A^3$ are identical or different and each independently of one another represent N (nitrogen) or the C—$R^5$ moiety, but there are never more than two adjacent nitrogen atoms, and where each $R^5$ in the C—$R^5$ moiety has identical or different meanings according to the definition below, and $A^1$ and $A^2$, when each is a C—$R^5$ group, with the atoms to which they are attached form a fully saturated, partly saturated or fully unsaturated 5- to 6-membered ring optionally interrupted by heteroatoms and optionally with further substitution, $A^2$ and $A^3$, when each is a C—$R^5$ group, with the atoms to which they are attached form a fully saturated, partly saturated or fully unsaturated 5- to 6-membered ring optionally interrupted by heteroatoms and optionally with further substitution, $R^3$, $R^4$ and $R^5$ independently of one another represent hydrogen, nitro, amino, cyano, thiocyanato, isothiocyanato, halogen, $(C_1-C_{10})$-alkyl, $(C_1-C_{10})$-cycloalkyl, $(C_1-C_{10})$-alkenyl, $(C_1-C_{10})$-alkynyl, aryl, aryl-$(C_1-C_{10})$-alkyl, $(C_1-C_{10})$-alkenylalkyl, $(C_1-C_{10})$-alkynylalkyl, aryl-$(C_1-C_{10})$-alkoxy, heteroaryl, $(C_1-C_{10})$-alkoxyalkyl, $(C_1-C_{10})$-hydroxyalkyl, $(C_1-C_{10})$-haloalkyl, $(C_1-C_{10})$-halocycloalkyl, $(C_1-C_{10})$-alkoxy, $(C_1-C_{10})$-haloalkoxy, aryloxy, heteroaryloxy, $(C_1-C_{10})$-cycloalkyloxy, hydroxy, $(C_1-C_{10})$-cycloalkylalkoxy, $(C_1-C_{10})$-alkoxycarbonyl, hydroxycarbonyl, aminocarbonyl, $(C_1-C_{10})$-alkylaminocarbonyl, $(C_1-C_{10})$-cycloalkylaminocarbonyl, $(C_1-C_{10})$-cyanoalkylaminocarbonyl, $(C_1-C_{10})$-alkenylaminocarbonyl, $(C_1-C_{10})$-alkynylaminocarbonyl, $(C_1-C_{10})$-alkylamino, $(C_1-C_{10})$-alkylthio, $(C_1-C_{10})$-haloalkylthio, hydrothio, $(C_1-C_{10})$-bisalkylamino, $(C_1-C_{10})$-cycloalkylamino, $(C_1-C_{10})$-alkylcarbonylamino, $(C_1-C_{10})$-cycloalkylcarbonylamino, formylamino, $(C_1-C_{10})$-haloalkylcarbonylamino, $(C_1-C_{10})$-alkoxycarbonylamino, $(C_1-C_{10})$-alkylaminocarbonylamino, $((C_1-C_{10})$-alkyl)aminocarbonylamino, $(C_1-C_{10})$-alkylsulfonylamino, $(C_1-C_{10})$-cycloalkylsulfonylamino, arylsulfonylamino, hetarylsulfonylamino, $(C_1-C_{10})$-sulfonylhaloalkylamino, aminosulfonyl, $(C_1-C_{10})$-aminoalkylsulfonyl, $(C_1-C_{10})$-aminohaloalkylsulfonyl, $(C_1-C_{10})$-alkylaminosulfonyl, $(C_1-C_{10})$-bisalkylaminosulfonyl, $(C_1-C_{10})$-cycloalkylaminosulfonyl, $(C_1-C_{10})$-haloalkylaminosulfonyl, arylaminosulfonyl, $(C_1-C_{10})$-arylalkylaminosulfonyl, $(C_1-C_{10})$-alkylsulfonyl, $(C_1-C_{10})$-cycloalkylsulfonyl, arylsulfonyl, $(C_1-C_{10})$-alkylsulfinyl, $(C_1-C_{10})$-cycloalkylsulfinyl, arylsulfinyl, $(C_1-C_{10})$—N,S-dialkylsulfonimidoyl, $(C_1-C_{10})$—S-alkylsulfonimidoyl, $(C_1-C_{10})$-alkylsulfonylaminocarbonyl, $(C_1-C_{10})$-cycloalkylsulfonylaminocarbonyl, $(C_1-C_{10})$-cycloalkylaminosulfonyl, $(C_1-C_{10})$-arylalkylcarbonylamino, $(C_1-C_{10})$-cycloalkylalkylcarbonylamino, heteroarylcarbonylamino, $(C_1-C_{10})$-alkoxyalkylcarbonylamino, $(C_1-C_{10})$-hydroxyalkylcarbonylamino, $(C_1-C_{10})$-trialkylsilyl, $R^6$ and $R^7$ independently of one another each represent hydrogen, nitro, amino, hydroxy, hydrothio, thiocyanato, isothiocyanato, halogen, $(C_1-C_{10})$-alkyl, $(C_1-C_{10})$-cycloalkyl, $(C_1-C_{10})$-alkenyl, $(C_1-C_{10})$-alkynyl, aryl, $(C_1-C_{10})$-arylalkyl, $(C_1-C_{10})$-arylalkoxy, heteroaryl, $(C_1-C_{10})$-haloalkyl, $(C_1-C_{10})$-halocycloalkyl, $(C_1-C_{10})$-alkoxy, $(C_1-C_{10})$-haloalkoxy, aryloxy, heteroaryloxy, $(C_1-C_{10})$-cycloalkyloxy, $(C_1-C_{10})$-cycloalkylalkoxy, $(C_1-C_{10})$-hydroxyalkyl, $(C_1-C_{10})$-alkoxyalkyl, $(C_1-C_{10})$-aryloxyalkyl, $(C_1-C_{10})$-heteroaryloxyalkyl, $(C_1-C_{10})$-alkenylaminocarbonyl, $(C_1-C_{10})$-alkylamino, $(C_1-C_{10})$-alkylthio, $(C_1-C_{10})$-haloalkylthio, $(C_1-C_{10})$-bisalkylamino, $(C_1-C_{10})$-cycloalkylamino, $(C_1-C_{10})$-alkylcarbonylamino, $(C_1-C_{10})$-cycloalkylcarbonylamino, formylamino, $(C_1-C_{10})$-haloalkylcarbonylamino, $(C_1-C_{10})$-alkoxycarbonylamino, $(C_1-C_{10})$-alkylaminocarbonylamino, $(C_1-C_{10})$-(alkyl)aminocarbonylamino, $(C_1-C_{10})$-alkylsulfonylamino, $(C_1-C_{10})$-cycloalkylsulfonylamino, arylsulfonylamino, hetarylsulfonylamino, $(C_1-C_{10})$-sulfonylhaloalkylamino, $(C_1-C_{10})$-aminoalkylsulfonyl, $(C_1-C_{10})$-aminohaloalkylsulfonyl, $(C_1-C_{10})$-alkylaminosulfonyl, $(C_1-C_{10})$-bisalkylaminosulfonyl, $(C_1-C_{10})$-cycloalkylaminosulfonyl, $(C_1-C_{10})$-haloalkylaminosulfonyl, arylaminosulfonyl, $(C_1-C_{10})$-arylalkylaminosulfonyl, $(C_1-C_{10})$-alkylsulfonyl, $(C_1-C_{10})$-cycloalkylsulfonyl, arylsulfonyl, $(C_1-C_{10})$-alkylsulfinyl, $(C_1-C_{10})$-cycloalkylsulfinyl, arylsulfinyl, $(C_1-C_{10})$—N,S-dialkylsulfonimidoyl, $(C_1-C_{10})$—S-alkylsulfonimidoyl, $(C_1-C_{10})$-alkylsulfonylaminocarbonyl, $(C_1-C_{10})$-cycloalkylsulfonylaminocarbonyl, $(C_1-C_{10})$-cycloalkylaminosulfonyl, $(C_1-C_{10})$-arylalkylcarbonylamino, $(C_1-C_{10})$-cycloalkylalkylcarbonylamino, heteroarylcarbonylamino, $(C_1-C_{10})$-alkoxyalkylcarbonylamino, $(C_1-C_{10})$-hydroxyalkylcarbonylamino, cyano, $(C_1-C_{10})$-cyanoalkyl, hydroxycarbonyl, $(C_1-C_{10})$-alkoxycarbonyl, $(C_1-C_{10})$-cycloalkoxycarbonyl, $(C_1-C_{10})$-cycloalkylalkoxycarbonyl, aryloxycarbonyl, $(C_1-C_{10})$-arylalkoxycarbonyl, aminocarbonyl, $(C_1-C_{10})$-alkylaminocarbonyl, $(C_1-C_{10})$-bisalkylaminocarbonyl, $(C_1-C_{10})$-alkyl-$((C_1-C_{10})$-alkoxy)aminocarbonyl, $(C_1-C_{10})$-cycloalkylaminocarbonyl, $(C_1-C_{10})$-arylalkylaminocarbonyl, $(C_1-C_{10})$-heteroarylalkylaminocarbonyl, $(C_1-C_{10})$-cyanoalkylaminocarbonyl, $(C_1-C_{10})$-haloalkylaminocarbonyl, $(C_1-C_{10})$-alkynylalkylaminocarbonyl, $(C_1-C_{10})$-alkoxycarbonylaminocarbonyl, $(C_1-C_{10})$-arylalkoxycarbonylaminocarbonyl, $(C_1-C_{10})$-hydroxycarbonylalkyl, $(C_1-C_{10})$-alkoxycarbonylalkyl, $(C_1-C_{10})$-cycloalkoxycarbonylalkyl, $(C_1-C_{10})$-cycloalkylalkoxycarbonylalkyl, $(C_1-C_{10})$-alkylaminocarbonylalkyl, $(C_1-C_{10})$-aminocarbonylalkyl, $(C_1-C_{10})$-bisalkylaminocarbonylalkyl, $(C_1-C_{10})$-cycloalkylaminocarbonylalkyl, $(C_1-C_{10})$-arylalkylaminocarbonylalkyl, $(C_1-C_{10})$-heteroarylalkylaminocarbonylalkyl, $(C_1-C_{10})$-cyanoalkylaminocarbonylalkyl, $(C_1-C_{10})$-haloalkylaminocarbonylalkyl, $(C_1-C_{10})$-alkynylalkylaminocarbonylalkyl, $(C_1-C_{10})$-cycloalkylalkylaminocarbonylalkyl, $(C_1-C_{10})$-alkoxycarbonylaminocarbonylalkyl, $(C_1-C_{10})$-arylalkoxycarbonylaminocarbonylalkyl, $(C_1-C_{10})$-alkoxycarbonylalkylaminocarbonyl, $(C_1-C_{10})$-hydroxycarbonylalkylaminocarbonyl, $(C_1-C_{10})$-aminocarbonylalkylaminocarbonyl, $(C_1-C_{10})$-alkylaminocarbonylalkylaminocarbonyl, $(C_1-C_{10})$-cycloalkylaminocarbonylalkylaminocarbonyl, $(C_1-C_{10})$-cycloalkylalkylaminocarbonyl, $(C_1-C_{10})$-cycloalkylalkylaminocarbonylalkyl, $(C_1-C_{10})$-alkenyloxycarbonyl, $(C_1-C_{10})$-alkenyloxycarbonylalkyl, $(C_1-C_{10})$-alkenylaminocarbonyl, $(C_1-C_{10})$-alkenylalkylaminocarbonyl, $(C_1-C_{10})$-alkenylaminocarbonylalkyl, $(C_1-C_{10})$-alkenylalkylaminocarbonylalkyl, $(C_1-C_{10})$-alkylcarbonyl, $(C_1-C_{10})$-cycloalkylcarbonyl, formyl, hydroxyiminomethyl, aminoiminomethyl, alkoxyiminomethyl, alkylaminoiminomethyl, $(C_1-C_{10})$-dialkylaminoiminomethyl, $(C_1-C_{10})$-cycloalkoxyiminomethyl, $(C_1-C_{10})$-cycloalkylalkoximinomethyl, $(C_1-C_{10})$-aryloximinomethyl, $(C_1-C_{10})$-arylalkoxyiminomethyl, $(C_1-C_{10})$-arylalkylaminoiminomethyl, $(C_1-C_{10})$-alkenyloxyiminomethyl, arylaminoiminomethyl, arylsulfonylaminoiminomethyl, $(C_1-C_{10})$-heteroarylalkyl, $(C_1-C_{10})$-heterocyclylalkyl, $R^8$, $R^9$ and $R^{10}$ independently of one another represent hydrogen, $(C_1-C_{10})$-alkyl, $(C_1-C_{10})$-alkenylalkyl, $(C_1-C_{10})$-alkoxyalkyl, $(C_1-C_{10})$-alkylcarbonyl, arylcarbonyl, heteroarylcarbonyl, ($C_1$-$C_{10}$)-cycloalkylcarbonyl, ($C_1$-$C_{10}$)-alkoxycarbonyl, ($C_1$-$C_{10}$)-allyloxycarbonyl, ($C_1$-$C_{10}$)-aryloxyalkyl, ($C_1$-$C_{10}$)-arylalkyl, ($C_1$-$C_{10}$)-haloalkyl, $R^{11}$ and $R^{12}$ independently of one another represent hydrogen, halogen, ($C_1$-$C_{10}$)-alkyl, ($C_1$-$C_{10}$)-alkoxy, ($C_1$-$C_{10}$)-haloalkyl, ($C_1$-$C_{10}$)-haloalkoxy, aryl, heteroaryl, ($C_1$-$C_{10}$)-arylalkyl or together with the atom to which they are attached form a carbonyl group, $A^4$, $A^5$ are identical or different and independently of one another represent N—$R^{13}$, oxygen, sulfur or the C—$R^{13}$ moiety, but there is never more than one oxygen atom present in the heterocycle, and where each $R^g$ in the N—$R^{13}$ and C—$R^{13}$ moieties has identical or different meanings according to the definition below, $R^{13}$ represents hydrogen, halogen, ($C_1$-$C_{10}$)-alkyl, ($C_1$-$C_{10}$)-alkoxy, ($C_1$-$C_{10}$)-haloalkyl, ($C_1$-$C_{10}$)-haloalkoxy, aryl, heteroaryl, ($C_1$-$C_{10}$)-arylalkyl or together with the atom to which it is attached forms a carbonyl group, $A^6$, $A^7$, $A^8$, $A^9$ are identical or different and independently of one another represent O, S, N, NH, N-alkyl, alkoxycarbonyl-N,N-aryl, N-heteroaryl or the C—$R^{14}$ moiety, where at most two oxygen or sulfur atoms are present in the heterocycle, and where no oxygen or sulfur atoms are adjacent to one another, and where each $R^{14}$ in the C—$R^{14}$ moiety has identical or different meanings according to the definition below, and $R^{14}$ represents hydrogen, nitro, amino, hydroxy, hydrothio, thiocyanato, isothiocyanato, halogen, ($C_1$-$C_{10}$)-alkyl, ($C_1$-$C_{10}$)-cycloalkyl, ($C_1$-$C_{10}$)-alkenyl, ($C_1$-$C_{10}$)-alkynyl, aryl, ($C_1$-$C_{10}$)-arylalkyl, ($C_1$-$C_{10}$)-arylalkoxy, heteroaryl, ($C_1$-$C_{10}$)-haloalkyl, ($C_1$-$C_{10}$)-halocycloalkyl, ($C_1$-$C_{10}$)-alkoxy, ($C_1$-$C_{10}$)-haloalkoxy, aryloxy, heteroaryloxy, ($C_1$-$C_{10}$)-cycloalkyloxy, ($C_1$-$C_{10}$)-cycloalkylalkoxy, ($C_1$-$C_{10}$)-hydroxyalkyl, ($C_1$-$C_{10}$)-alkoxyalkyl, ($C_1$-$C_{10}$)-aryloxyalkyl, ($C_1$-$C_{10}$)-heteroaryloxyalkyl, ($C_1$-$C_{10}$)-alkenylaminocarbonyl, ($C_1$-$C_{10}$)-alkylamino, ($C_1$-$C_{10}$)-alkylthio, ($C_1$-$C_{10}$)-haloalkylthio, ($C_1$-$C_{10}$)-bisalkylamino, ($C_1$-$C_{10}$)-cycloalkylamino, ($C_1$-$C_{10}$)-alkylcarbonylamino, ($C_1$-$C_{10}$)-cycloalkylcarbonylamino, formylamino, ($C_1$-$C_{10}$)-haloalkylcarbonylamino, ($C_1$-$C_{10}$)-alkoxycarbonylamino, ($C_1$-$C_{10}$)-alkylaminocarbonylamino, ($C_1$-$C_{10}$)-(alkyl)aminocarbonylamino, ($C_1$-$C_{10}$)-alkylsulfonylamino, ($C_1$-$C_{10}$)-cycloalkylsulfonylamino, arylsulfonylamino, hetarylsulfonylamino, ($C_1$-$C_{10}$)-sulfonylhaloalkylamino, ($C_1$-$C_{10}$)-aminoalkylsulfonyl, ($C_1$-$C_{10}$)-aminohaloalkylsulfonyl, ($C_1$-$C_{10}$)-alkylaminosulfonyl, ($C_1$-$C_{10}$)-bisalkylaminosulfonyl, ($C_1$-$C_{10}$)-cycloalkylaminosulfonyl, ($C_1$-$C_{10}$)-haloalkylaminosulfonyl, arylaminosulfonyl, ($C_1$-$C_{10}$)-arylalkylaminosulfonyl, ($C_1$-$C_{10}$)-alkylsulfonyl, ($C_1$-$C_{10}$)-cycloalkylsulfonyl, arylsulfonyl, ($C_1$-$C_{10}$)-alkylsulfinyl, ($C_1$-$C_{10}$)-cycloalkylsulfinyl, arylsulfinyl, ($C_1$-$C_{10}$)—N,S-dialkylsulfonimidoyl, ($C_1$-$C_{10}$)—S-alkylsulfonimidoyl, ($C_1$-$C_{10}$)-alkylsulfonylaminocarbonyl, ($C_1$-$C_{10}$)-cycloalkylsulfonylaminocarbonyl, ($C_1$-$C_{10}$)-cycloalkylaminosulfonyl, ($C_1$-$C_{10}$)-arylalkylcarbonylamino, ($C_1$-$C_{10}$)-cycloalkylalkylcarbonylamino, heteroarylcarbonylamino, ($C_1$-$C_{10}$)-alkoxyalkylcarbonylamino, ($C_1$-$C_{10}$)-hydroxyalkylcarbonylamino, cyano, ($C_1$-$C_{10}$)-cyanoalkyl, hydroxycarbonyl, ($C_1$-$C_{10}$)-alkoxycarbonyl, ($C_1$-$C_{10}$)-cycloalkoxycarbonyl, ($C_1$-$C_{10}$)-cycloalkylalkoxycarbonyl, aryloxycarbonyl, ($C_1$-$C_{10}$)-arylalkoxycarbonyl, aminocarbonyl, ($C_1$-$C_{10}$)-alkylaminocarbonyl, ($C_1$-$C_{10}$)-bisalkylaminocarbonyl, ($C_1$-$C_{10}$)-alkyl-(($C_1$-$C_{10}$)-alkoxy)aminocarbonyl, ($C_1$-$C_{10}$)-cycloalkylaminocarbonyl, ($C_1$-$C_{10}$)-arylalkylaminocarbonyl, ($C_1$-$C_{10}$)-heteroarylalkylaminocarbonyl, ($C_1$-$C_{10}$)-cyanoalkylaminocarbonyl, ($C_1$-$C_{10}$)-haloalkylaminocarbonyl, ($C_1$-$C_{10}$)-alkynylalkylaminocarbonyl, ($C_1$-$C_{10}$)-alkoxycarbonylaminocarbonyl, ($C_1$-$C_{10}$)-arylalkoxycarbonylaminocarbonyl, ($C_1$-$C_{10}$)-hydroxycarbonylalkyl, ($C_1$-$C_{10}$)-alkoxycarbonylalkyl, ($C_1$-$C_{10}$)-cycloalkoxycarbonylalkyl, ($C_1$-$C_{10}$)-cycloalkylalkoxycarbonylalkyl, ($C_1$-$C_{10}$)-alkylaminocarbonylalkyl, ($C_1$-$C_{10}$)-aminocarbonylalkyl, ($C_1$-$C_{10}$)-bisalkylaminocarbonylalkyl, ($C_1$-$C_{10}$)-cycloalkylaminocarbonylalkyl, ($C_1$-$C_{10}$)-arylalkylaminocarbonylalkyl, ($C_1$-$C_{10}$)-heteroarylalkylaminocarbonylalkyl, ($C_1$-$C_{10}$)-cyanoalkylaminocarbonylalkyl, ($C_1$-$C_{10}$)-haloalkylaminocarbonylalkyl, ($C_1$-$C_{10}$)-alkynylalkylaminocarbonylalkyl, ($C_1$-$C_{10}$)-cycloalkylalkylaminocarbonylalkyl, ($C_1$-$C_{10}$)-alkoxycarbonylaminocarbonylalkyl, ($C_1$-$C_{10}$)-arylalkoxycarbonylaminocarbonylalkyl, ($C_1$-$C_{10}$)-alkoxycarbonylalkylaminocarbonyl, ($C_1$-$C_{10}$)-hydroxycarbonylalkylaminocarbonyl, ($C_1$-$C_{10}$)-aminocarbonylalkylaminocarbonyl, ($C_1$-$C_{10}$)-alkylaminocarbonylalkylaminocarbonyl, ($C_1$-$C_{10}$)-cycloalkylaminocarbonylalkylaminocarbonyl, ($C_1$-$C_{10}$)-cycloalkylalkylaminocarbonyl, ($C_1$-$C_{10}$)-cycloalkylalkylaminocarbonylalkyl, ($C_1$-$C_{10}$)-alkenyloxycarbonyl, ($C_1$-$C_{10}$)-alkenyloxycarbonylalkyl, ($C_1$-$C_{10}$)-alkenylaminocarbonyl, ($C_1$-$C_{10}$)-alkenylalkylaminocarbonyl, ($C_1$-$C_{10}$)-alkenylaminocarbonylalkyl, ($C_1$-$C_{10}$)-alkenylalkylaminocarbonylalkyl, ($C_1$-$C_{10}$)-alkylcarbonyl, ($C_1$-$C_{10}$)-cycloalkylcarbonyl, formyl, hydroxyiminomethyl, aminoiminomethyl, alkoxyiminomethyl, alkylaminoiminomethyl, ($C_1$-$C_{10}$)-dialkylaminoiminomethyl, ($C_1$-$C_{10}$)-cycloalkoxyiminomethyl, ($C_1$-$C_{10}$)-cycloalkylalkoximinomethyl, ($C_1$-$C_{10}$)-aryloximinomethyl, ($C_1$-$C_{10}$)-arylalkoxyiminomethyl, ($C_1$-$C_{10}$)-arylalkylaminoiminomethyl, ($C_1$-$C_{10}$)-alkenyloxyiminomethyl, arylaminoiminomethyl, arylsulfonylaminoiminomethyl, ($C_1$-$C_{10}$)-heteroarylalkyl, ($C_1$-$C_{10}$)-heterocyclylalkyl, $A^{10}$ represents N—$R^{15}$, oxygen or the C—$R^{15}$ moiety, and where each $R^{15}$ in the N—$R^{15}$ and C—$R^{15}$ moieties has identical or different meanings according to the definition below, $A^{11}$ represents N or the C—$R^{18}$ moiety, and where $R^{18}$ in the C—$R^{18}$ moiety has the meaning according to the definition below, $A^{12}$ represents N—$R^{15}$ or the $C(R^{16})R^{17}$ moiety, and where $R^{16}$ and $R^{17}$ in the $C(R^{16})R^{17}$ moiety are each as defined below, $R^{15}$ represents hydrogen, ($C_1$-$C_{10}$)-alkyl, ($C_1$-$C_{10}$)-alkenylalkyl, ($C_1$-$C_{10}$)-alkoxyalkyl, ($C_1$-$C_{10}$)-alkylcarbonyl, arylcarbonyl, heteroarylcarbonyl, ($C_1$-$C_{10}$)-cycloalkylcarbonyl, ($C_1$-$C_{10}$)-alkoxycarbonyl, ($C_1$-$C_{10}$)-allyloxycarbonyl, ($C_1$-$C_{10}$)-aryloxyalkyl, ($C_1$-$C_{10}$)-arylalkyl, ($C_1$-$C_{10}$)-haloalkyl, aryl, $R^{16}$ and $R^{17}$ each independently of one another represent hydrogen, halogen, alkyl, alkoxy, haloalkyl, haloalkoxy, aryl, heteroaryl, arylalkyl, or together with the atom to which they are attached form a carbonyl group, $R^{18}$ represents hydrogen, nitro, amino, hydroxy, hydrothio, thiocyanato, isothiocyanato, halogen, ($C_1$-$C_{10}$)-alkyl, ($C_1$-$C_{10}$)-cycloalkyl, ($C_1$-$C_{10}$)-alkenyl, ($C_1$-$C_{10}$)-alkynyl, aryl, ($C_1$-$C_{10}$)-arylalkyl, ($C_1$-$C_{10}$)-arylalkoxy, heteroaryl, ($C_1$-$C_{10}$)-haloalkyl, ($C_1$-$C_{10}$)-halocycloalkyl, ($C_1$-$C_{10}$)-alkoxy, ($C_1$-$C_{10}$)-haloalkoxy, aryloxy, heteroaryloxy, ($C_1$-$C_{10}$)-cycloalkyloxy, ($C_1$-$C_{10}$)-cycloalkylalkoxy, ($C_1$-$C_{10}$)-hydroxyalkyl, ($C_1$-$C_{10}$)-alkoxyalkyl, ($C_1$-$C_{10}$)- aryloxyalkyl, (C₁-C₁₀)-heteroaryloxyalkyl, (C₁-C₁₀)-alkenylaminocarbonyl, (C₁-C₁₀)-alkylamino, (C₁-C₁₀)-alkylthio, (C₁-C₁₀)-haloalkylthio, (C₁-C₁₀)-bisalkylamino, (C₁-C₁₀)-cycloalkylamino, (C₁-C₁₀)-alkylcarbonylamino, (C₁-C₁₀)-cycloalkylcarbonylamino, formylamino, (C₁-C₁₀)-haloalkylcarbonylamino, (C₁-C₁₀)-alkoxycarbonylamino, (C₁-C₁₀)-alkylaminocarbonylamino, (C₁-C₁₀)-(alkyl)aminocarbonylamino, (C₁-C₁₀)-alkylsulfonylamino, (C₁-C₁₀)-cycloalkylsulfonylamino, arylsulfonylamino, hetarylsulfonylamino, (C₁-C₁₀)-sulfonylhaloalkylamino, (C₁-C₁₀)-aminoalkylsulfonyl, (C₁-C₁₀)-aminohaloalkylsulfonyl, (C₁-C₁₀)-alkylaminosulfonyl, (C₁-C₁₀)-bisalkylaminosulfonyl, (C₁-C₁₀)-cycloalkylaminosulfonyl, (C₁-C₁₀)-haloalkylaminosulfonyl, arylaminosulfonyl, (C₁-C₁₀)-arylalkylaminosulfonyl, (C₁-C₁₀)-alkylsulfonyl, (C₁-C₁₀)-cycloalkylsulfonyl, arylsulfonyl, (C₁-C₁₀)-alkylsulfinyl, (C₁-C₁₀)-cycloalkylsulfinyl, arylsulfinyl, (C₁-C₁₀)—N,S-dialkylsulfonimidoyl, (C₁-C₁₀)—S-alkylsulfonimidoyl, (C₁-C₁₀)-alkylsulfonylaminocarbonyl, (C₁-C₁₀)-cycloalkylsulfonylaminocarbonyl, (C₁-C₁₀)-cycloalkylaminosulfonyl, (C₁-C₁₀)-arylalkylcarbonylamino, (C₁-C₁₀)-cycloalkylalkylcarbonylamino, heteroarylcarbonylamino, (C₁-C₁₀)-alkoxyalkylcarbonylamino, (C₁-C₁₀)-hydroxyalkylcarbonylamino, cyano, (C₁-C₁₀)-cyanoalkyl, hydroxycarbonyl, (C₁-C₁₀)-alkoxycarbonyl, (C₁-C₁₀)-cycloalkoxycarbonyl, (C₁-C₁₀)-cycloalkylalkoxycarbonyl, aryloxycarbonyl, (C₁-C₁₀)-arylalkoxycarbonyl, aminocarbonyl, (C₁-C₁₀)-alkylaminocarbonyl, (C₁-C₁₀)-bisalkylaminocarbonyl, (C₁-C₁₀)-alkyl-((C₁-C₁₀)-alkoxy)aminocarbonyl, (C₁-C₁₀)-cycloalkylaminocarbonyl, (C₁-C₁₀)-arylalkylaminocarbonyl, (C₁-C₁₀)-heteroarylalkylaminocarbonyl, (C₁-C₁₀)-cyanoalkylaminocarbonyl, (C₁-C₁₀)-haloalkylaminocarbonyl, (C₁-C₁₀)-alkynylalkylaminocarbonyl, (C₁-C₁₀)-alkoxycarbonylaminocarbonyl, (C₁-C₁₀)-arylalkoxycarbonylaminocarbonyl, (C₁-C₁₀)-hydroxycarbonylalkyl, (C₁-C₁₀)-alkoxycarbonylalkyl, (C₁-C₁₀)-cycloalkoxycarbonylalkyl, (C₁-C₁₀)-cycloalkylalkoxycarbonylalkyl, (C₁-C₁₀)-alkylaminocarbonylalkyl, (C₁-C₁₀)-aminocarbonylalkyl, (C₁-C₁₀)-bisalkylaminocarbonylalkyl, (C₁-C₁₀)-cycloalkylaminocarbonylalkyl, (C₁-C₁₀)-arylalkylaminocarbonylalkyl, (C₁-C₁₀)-heteroarylalkylaminocarbonylalkyl, (C₁-C₁₀)-cyanoalkylaminocarbonylalkyl, (C₁-C₁₀)-haloalkylaminocarbonylalkyl, (C₁-C₁₀)-alkynylalkylaminocarbonylalkyl, (C₁-C₁₀)-cycloalkylalkylaminocarbonylalkyl, (C₁-C₁₀)-alkoxycarbonylaminocarbonylalkyl, (C₁-C₁₀)-arylalkoxycarbonylaminocarbonylalkyl, (C₁-C₁₀)-alkoxycarbonylalkylaminocarbonyl, (C₁-C₁₀)-hydroxycarbonylalkylaminocarbonyl, (C₁-C₁₀)-aminocarbonylalkylaminocarbonyl, (C₁-C₁₀)-alkylaminocarbonylalkylaminocarbonyl, (C₁-C₁₀)-cycloalkylaminocarbonylalkylaminocarbonyl, (C₁-C₁₀)-cycloalkylalkylaminocarbonyl, (C₁-C₁₀)-cycloalkylalkylaminocarbonylalkyl, (C₁-C₁₀)-alkenyloxycarbonyl, (C₁-C₁₀)-alkenyloxycarbonylalkyl, (C₁-C₁₀)-alkenylaminocarbonyl, (C₁-C₁₀)-alkenylalkylaminocarbonyl, (C₁-C₁₀)-alkenylaminocarbonylalkyl, (C₁-C₁₀)-alkenylalkylaminocarbonylalkyl, (C₁-C₁₀)-alkylcarbonyl, (C₁-C₁₀)-cycloalkylcarbonyl, formyl, hydroxyiminomethyl, aminoiminomethyl, alkoxyiminomethyl, alkylaminoiminomethyl, (C₁-C₁₀)-dialkylaminoiminomethyl, (C₁-C₁₀)-cycloalkoxyiminomethyl, (C₁-C₁₀)-cycloalkylalkoxyiminomethyl, (C₁-C₁₀)-aryloxyiminomethyl, (C₁-C₁₀)-arylalkoxyiminomethyl, (C₁-C₁₀)-arylalkylaminoiminomethyl, (C₁-C₁₀)-alkenyloxyiminomethyl, arylaminoiminomethyl, arylsulfonylaminoiminomethyl, (C₁-C₁₀)-heteroarylalkyl, (C₁-C₁₀)-heterocyclylalkyl.

DETAILED DESCRIPTION OF A PREFERRED EMBODIMENT

Preference is given to the use according to the invention of compounds of the general formula (I) or salts thereof in which Q represents

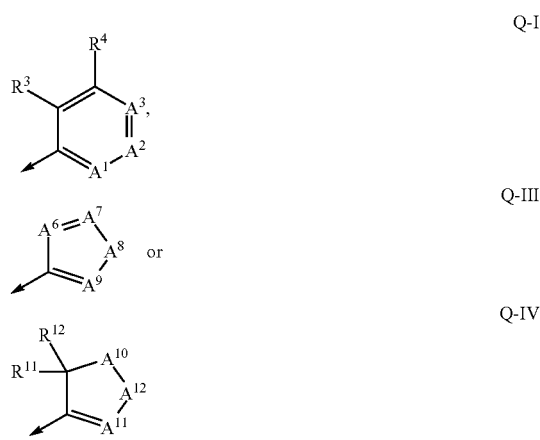

where the R³ to R¹² and A¹ to A¹² moieties each have the meaning according to the definitions below, and where the arrow represents a bond to the pyrazole, (R¹)$_m$ represents m substituents R¹, where in the case that m is the number 1 the radical R¹ or, in the case that m is greater than 1, each of the radicals R¹ in each case independently of the others represents halogen, CN, (C₁-C₈)-alkyl, (C₁-C₈)-alkoxy or (C₁-C₈)-alkylthio, where each of the three last-mentioned radicals independently of the others is unsubstituted or substituted by one or more radicals from the group consisting of halogen, CN, (C₁-C₈)-alkoxy and (C₁-C₈)-alkylthio, R² represents hydrogen or a radical which can be hydrolyzed to afford the carboxylic acid,
  preferably an optionally substituted hydrocarbon radical or an optionally substituted heterocyclyl radical, where each of the two last-mentioned carbon-containing radicals including substituents has 1 to 30 carbon atoms, preferably 1 to 24 carbon atoms, in particular 1 to 20 carbon atoms, or a radical of the formula —N═CR$^a$R$^b$, —NR$^c$R$^d$ or SiR$^e$R$^f$, R$^g$,
  where in the 3 last-mentioned formulae each of the radicals R$^a$, R$^b$, R$^c$, R$^d$, R$^e$, R$^f$ and R$^g$ independently of the others represents hydrogen or an optionally substituted hydrocarbon radical,
  or R$^a$ and R$^b$ together with the carbon atom to which they are attached represent a 3- to 9-membered carbocyclic radical or a heterocyclic radical which may contain 1 to 3 ring heteroatoms from the group consisting of N, O and S, where the carbocyclic or heterocyclic radical is unsubstituted or substituted, or R$^c$ and R$^d$ together with the nitrogen atom represent a 3- to 8-membered heterocycle which, in addition to the nitrogen atom, may contain one or two further ring heteroatoms from the group consisting of N, O and S and which is unsubstituted or substituted by one or more radicals from the group consisting of $(C_1-C_{10})$-alkyl and $(C_1-C_{10})$-haloalkyl, where each of the radicals $R^a$, $R^b$, $R^c$, $R^d$, $R^e$, $R^f$ and $R^g$ including substituents has 1 to 30 carbon atoms, preferably 1 to 24 carbon atoms, in particular 1 to 20 carbon atoms, m represents 1, 2, 3, 4 or 5, preferably 1, 2, 3 or 4, in particular 1 or 2.

$A^1$, $A^2$, $A^3$ are identical or different and each independently of one another represent N (nitrogen) or the C—$R^5$ moiety, but there are never more than two adjacent nitrogen atoms, and where each $R^5$ in the C—$R^5$ moiety has identical or different meanings according to the definition below, and $A^1$ and $A^2$, when each is a C—$R^5$ group, with the atoms to which they are attached form a fully saturated, partly saturated or fully unsaturated 5- to 6-membered ring optionally interrupted by heteroatoms and optionally with further substitution, $A^2$ and $A^3$, when each is a C—$R^5$ group, with the atoms to which they are attached form a fully saturated, partly saturated or fully unsaturated 5- to 6-membered ring optionally interrupted by heteroatoms and optionally with further substitution, $R^3$, $R^4$ and $R^5$ independently of one another represent hydrogen, nitro, amino, cyano, thiocyanato, isothiocyanato, halogen, $(C_1-C_8)$-alkyl, $(C_1-C_8)$-cycloalkyl, $(C_1-C_8)$-alkenyl, $(C_1-C_8)$-alkynyl, aryl, aryl-$(C_1-C_8)$-alkyl, $(C_1-C_8)$-alkenylalkyl, $(C_1-C_8)$-alkynylalkyl, aryl-$(C_1-C_8)$-alkoxy, heteroaryl, $(C_1-C_8)$-alkoxyalkyl, $(C_1-C_8)$-hydroxyalkyl, $(C_1-C_8)$-haloalkyl, $(C_1-C_8)$-halocycloalkyl, $(C_1-C_8)$-alkoxy, $(C_1-C_8)$-haloalkoxy, aryloxy, heteroaryloxy, $(C_1-C_8)$-cycloalkyloxy, hydroxy, $(C_1-C_8)$-cycloalkylalkoxy, $(C_1-C_8)$-alkoxycarbonyl, hydroxycarbonyl, aminocarbonyl, $(C_1-C_8)$-alkylaminocarbonyl, $(C_1-C_8)$-cycloalkylaminocarbonyl, $(C_1-C_8)$-cyanoalkylaminocarbonyl, $(C_1-C_8)$-alkenylaminocarbonyl, $(C_1-C_8)$-alkynylaminocarbonyl, $(C_1-C_8)$-alkylamino, $(C_1-C_8)$-alkylthio, $(C_1-C_8)$-haloalkylthio, hydrothio, $(C_1-C_8)$-bisalkylamino, $(C_1-C_8)$-cycloalkylamino, $(C_1-C_8)$-alkylcarbonylamino, $(C_1-C_8)$-cycloalkylcarbonylamino, formylamino, $(C_1-C_8)$-haloalkylcarbonylamino, $(C_1-C_8)$-alkoxycarbonylamino, $(C_1-C_8)$-alkylaminocarbonylamino, $((C_1-C_8)$-alkyl)aminocarbonylamino, $(C_1-C_8)$-alkylsulfonylamino, $(C_1-C_8)$-cycloalkylsulfonylamino, arylsulfonylamino, hetarylsulfonylamino, $(C_1-C_8)$-sulfonylhaloalkylamino, aminosulfonyl, $(C_1-C_8)$-aminoalkylsulfonyl, $(C_1-C_8)$-aminohaloalkylsulfonyl, $(C_1-C_8)$-alkylaminosulfonyl, $(C_1-C_8)$-bisalkylaminosulfonyl, $(C_1-C_8)$-cycloalkylaminosulfonyl, $(C_1-C_8)$-haloalkylaminosulfonyl, arylaminosulfonyl, $(C_1-C_8)$-arylalkylaminosulfonyl, $(C_1-C_8)$-alkylsulfonyl, $(C_1-C_8)$-cycloalkylsulfonyl, arylsulfonyl, $(C_1-C_8)$-alkylsulfinyl, $(C_1-C_8)$-cycloalkylsulfinyl, arylsulfinyl, $(C_1-C_8)$—N,S-dialkylsulfonimidoyl, $(C_1-C_8)$—S-alkylsulfonimidoyl, $(C_1-C_8)$-alkylsulfonylaminocarbonyl, $(C_1-C_8)$-cycloalkylsulfonylaminocarbonyl, $(C_1-C_8)$-cycloalkylaminosulfonyl, $(C_1-C_8)$-arylalkylcarbonylamino, $(C_1-C_8)$-cycloalkylalkylcarbonylamino, heteroarylcarbonylamino, $(C_1-C_8)$-alkoxyalkylcarbonylamino, $(C_1-C_8)$-hydroxyalkylcarbonylamino, $(C_1-C_8)$-trialkylsilyl.

$A^6$, $A^7$, $A^8$, $A^9$ are identical or different and independently of one another represent O, S, N, NH, N-alkyl, alkoxycarbonyl-N,N-aryl, N-heteroaryl or the C—$R^{14}$ moiety, where at most two oxygen or sulfur atoms are present in the heterocycle, and where no oxygen or sulfur atoms are adjacent to one another, and where each $R^{14}$ in the C—$R^{14}$ moiety has identical or different meanings according to the definition below, and $R^{14}$ represents hydrogen, nitro, amino, cyano, thiocyanato, isothiocyanato, halogen, $(C_1-C_8)$-alkyl, $(C_1-C_8)$-cycloalkyl, $(C_1-C_8)$-alkenyl, $(C_1-C_8)$-alkynyl, aryl, aryl-$(C_1-C_8)$-alkyl, $(C_1-C_8)$-alkenylalkyl, $(C_1-C_8)$-alkynylalkyl, aryl-$(C_1-C_8)$-alkoxy, heteroaryl, $(C_1-C_8)$-alkoxyalkyl, $(C_1-C_8)$-hydroxyalkyl, $(C_1-C_8)$-haloalkyl, $(C_1-C_8)$-halocycloalkyl, $(C_1-C_8)$-alkoxy, $(C_1-C_8)$-haloalkoxy, aryloxy, heteroaryloxy, $(C_1-C_8)$-cycloalkyloxy, hydroxy, $(C_1-C_8)$-cycloalkylalkoxy, $(C_1-C_8)$-alkoxycarbonyl, hydroxycarbonyl, aminocarbonyl, $(C_1-C_8)$-alkylaminocarbonyl, $(C_1-C_8)$-cycloalkylaminocarbonyl, $(C_1-C_8)$-cyanoalkylaminocarbonyl, $(C_1-C_8)$-alkenylaminocarbonyl, $(C_1-C_8)$-alkynylaminocarbonyl, $(C_1-C_8)$-alkylamino, $(C_1-C_8)$-alkylthio, $(C_1-C_8)$-haloalkylthio, hydrothio, $(C_1-C_8)$-bisalkylamino, $(C_1-C_8)$-cycloalkylamino, $(C_1-C_8)$-alkylcarbonylamino, $(C_1-C_8)$-cycloalkylcarbonylamino, formylamino, $(C_1-C_8)$-haloalkylcarbonylamino, $(C_1-C_8)$-alkoxycarbonylamino, $(C_1-C_8)$-alkylaminocarbonylamino, $((C_1-C_8)$-alkyl)aminocarbonylamino, $(C_1-C_8)$-alkylsulfonylamino, $(C_1-C_8)$-cycloalkylsulfonylamino, arylsulfonylamino, hetarylsulfonylamino, $(C_1-C_8)$-sulfonylhaloalkylamino, aminosulfonyl, $(C_1-C_8)$-aminoalkylsulfonyl, $(C_1-C_8)$-aminohaloalkylsulfonyl, $(C_1-C_8)$-alkylaminosulfonyl, $(C_1-C_8)$-bisalkylaminosulfonyl, $(C_1-C_8)$-cycloalkylaminosulfonyl, $(C_1-C_8)$-haloalkylaminosulfonyl, arylaminosulfonyl, $(C_1-C_8)$-arylalkylaminosulfonyl, $(C_1-C_8)$-alkylsulfonyl, $(C_1-C_8)$-cycloalkylsulfonyl, arylsulfonyl, $(C_1-C_8)$-alkylsulfinyl, $(C_1-C_8)$-cycloalkylsulfinyl, arylsulfinyl, $(C_1-C_8)$—N,S-dialkylsulfonimidoyl, $(C_1-C_8)$—S-alkylsulfonimidoyl, $(C_1-C_8)$-alkylsulfonylaminocarbonyl, $(C_1-C_8)$-cycloalkylsulfonylaminocarbonyl, $(C_1-C_8)$-cycloalkylaminosulfonyl, $(C_1-C_8)$-arylalkylcarbonylamino, $(C_1-C_8)$-cycloalkylalkylcarbonylamino, heteroarylcarbonylamino, $(C_1-C_8)$-alkoxyalkylcarbonylamino, $(C_1-C_8)$-hydroxyalkylcarbonylamino, $(C_1-C_8)$-trialkylsilyl, $A^{10}$ represents N—$R^{15}$, oxygen or the C—$R^{15}$ moiety, and where each $R^{15}$ in the N—$R^{15}$ and C—$R^{15}$ moieties has identical or different meanings according to the definition below, $A^{11}$ represents N or the C—$R^{18}$ moiety, and where $R^{18}$ in the C—$R^{18}$ moiety has the meaning according to the definition below, $A^{12}$ represents N—$R^{15}$ or the $C(R^{16})R^{17}$ moiety, and where $R^{16}$ and $R^{17}$ in the $C(R^{18})R^{17}$ moiety are each as defined below, $R^{15}$ represents hydrogen, $(C_1-C_{10})$-alkyl, $(C_1-C_{10})$-alkenylalkyl, $(C_1-C_{10})$-alkoxyalkyl, $(C_1-C_{10})$-alkylcarbonyl, arylcarbonyl, heteroarylcarbonyl, $(C_1-C_{10})$-cycloalkylcarbonyl, $(C_1-C_{10})$-alkoxycarbonyl, $(C_1-C_{10})$-allyloxycarbonyl, $(C_1-C_{10})$-aryloxyalkyl, $(C_1-C_{10})$-arylalkyl, $(C_1-C_{10})$-haloalkyl, aryl, $R^{16}$ and $R^{17}$ independently of one another represent hydrogen, halogen, $(C_1-C_8)$-alkyl, $(C_1-C_8)$-alkoxy, $(C_1-C_8)$-haloalkyl, $(C_1-C_8)$-haloalkoxy, aryl, heteroaryl, $(C_1-C_8)$-arylalkyl or together with the atom to which they are attached form a carbonyl group, $R^{18}$ represents hydrogen, nitro, amino, cyano, thiocyanato, isothiocyanato, halogen, $(C_1-C_8)$-alkyl, $(C_1-C_8)$-cycloalkyl, $(C_1-C_8)$-alkenyl, $(C_1-C_8)$-alkynyl, aryl, aryl-$(C_1-C_8)$-alkyl, $(C_1-C_8)$-alkenylalkyl, $(C_1-C_8)$-alkynylalkyl, aryl-$(C_1-C_8)$-alkoxy, heteroaryl, $(C_1-C_8)$-alkoxyalkyl, $(C_1-C_8)$-hydroxyalkyl, $(C_1-C_8)$-haloalkyl, $(C_1-C_8)$-halocycloalkyl, $(C_1-C_8)$-alkoxy, $(C_1-C_8)$-haloalkoxy, aryloxy, heteroaryloxy, $(C_1-C_8)$-cycloalkyloxy, hydroxy, $(C_1-C_8)$-cycloalkylalkoxy, $(C_1-C_8)$-alkoxycarbonyl, hydroxycarbonyl, aminocarbonyl, $(C_1-C_8)$-alkylaminocarbonyl, $(C_1-$ C₈)-cycloalkylaminocarbonyl, (C₁-C₈)-cyanoalkylaminocarbonyl, (C₁-C₈)-alkenylaminocarbonyl, (C₁-C₈)-alkynylaminocarbonyl, (C₁-C₈)-alkylamino, (C₁-C₈)-alkylthio, (C₁-C₈)-haloalkylthio, hydrothio, (C₁-C₈)-bisalkylamino, (C₁-C₈)-cycloalkylamino, (C₁-C₈)-alkylcarbonylamino, (C₁-C₈)-cycloalkylcarbonylamino, formylamino, (C₁-C₈)-haloalkylcarbonylamino, (C₁-C₈)-alkoxycarbonylamino, (C₁-C₈)-alkylaminocarbonylamino, ((C₁-C₈)-alkyl)aminocarbonylamino, (C₁-C₈)-alkylsulfonylamino, (C₁-C₈)-cycloalkylsulfonylamino, arylsulfonylamino, hetarylsulfonylamino, (C₁-C₈)-sulfonylhaloalkylamino, aminosulfonyl, (C₁-C₈)-aminoalkylsulfonyl, (C₁-C₈)-aminohaloalkylsulfonyl, (C₁-C₈)-alkylaminosulfonyl, (C₁-C₈)-bisalkylaminosulfonyl, (C₁-C₈)-cycloalkylaminosulfonyl, (C₁-C₈)-haloalkylaminosulfonyl, arylaminosulfonyl, (C₁-C₈)-arylalkylaminosulfonyl, (C₁-C₈)-alkylsulfonyl, (C₁-C₈)-cycloalkylsulfonyl, arylsulfonyl, (C₁-C₈)-alkylsulfinyl, (C₁-C₈)-cycloalkylsulfinyl, arylsulfinyl, (C₁-C₈)—N,S-dialkylsulfonimidoyl, (C₁-C₈)—S-alkylsulfonimidoyl, (C₁-C₈)-alkylsulfonylaminocarbonyl, (C₁-C₈)-cycloalkylsulfonylaminocarbonyl, (C₁-C₈)-cycloalkylaminosulfonyl, (C₁-C₈)-arylalkylcarbonylamino, (C₁-C₈)-cycloalkylalkylcarbonylamino, heteroarylcarbonylamino, (C₁-C₈)-alkoxyalkylcarbonylamino, (C₁-C₈)-hydroxyalkylcarbonylamino, (C₁-C₈)-trialkylsilyl.

Particular preference is given to the use according to the invention of compounds of the general formula (I) or salts thereof in which
Q represents

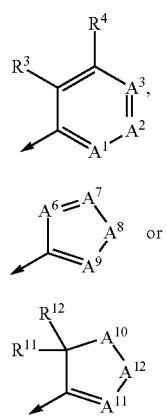

where the R³ to R¹² and A¹ to A¹² moieties each have the meaning according to the definitions below, and where the arrow represents a bond to the pyrazole, (R¹)$_m$ represents m substituents R¹, where in the case that m is the number 1 the radical R¹ or, in the case that m is greater than 1, each of the radicals R¹ in each case independently of the others represents halogen, CN, (C₁-C₆)-alkyl, (C₁-C₆)-alkoxy or (C₁-C₆)-alkylthio, where each of the three last-mentioned radicals independently of the others is unsubstituted or substituted by one or more radicals from the group consisting of halogen, CN, (C₁-C₆)-alkoxy and (C₁-C₆)-alkylthio, R² represents hydrogen or a radical which can be hydrolyzed to afford the carboxylic acid,
preferably an optionally substituted hydrocarbon radical or an optionally substituted heterocyclyl radical, where each of the two last-mentioned carbon-containing radicals including substituents has 1 to 30 carbon atoms, preferably 1 to 24 carbon atoms, in particular 1 to 20 carbon atoms, or a radical of the formula —N=CR$^a$R$^b$, —NR$^c$R$^d$ or SiR$^e$R$^f$, R$^g$, where in the 3 last-mentioned formulae each of the radicals R$^a$, R$^b$, R$^c$, R$^d$, R$^e$, R$^f$ and R$^g$ independently of the others represents hydrogen or an optionally substituted hydrocarbon radical, or R$^a$ and R$^b$ together with the carbon atom to which they are attached represent a 3- to 9-membered carbocyclic radical or a heterocyclic radical which may contain 1 to 3 ring heteroatoms from the group consisting of N, O and S, where the carbocyclic or heterocyclic radical is unsubstituted or substituted, or R$^c$ and R$^d$ together with the nitrogen atom represent a 3- to 8-membered heterocycle which, in addition to the nitrogen atom, may contain one or two further ring heteroatoms from the group consisting of N, O and S and which is unsubstituted or substituted by one or more radicals from the group consisting of (C₁-C₆)-alkyl and (C₁-C₆)-haloalkyl, where each of the radicals R$^a$, R$^b$, R$^c$, R$^d$, R$^e$, R$^f$ and R$^e$ including substituents has 1 to 30 carbon atoms, preferably 1 to 24 carbon atoms, in particular 1 to 20 carbon atoms, m represents 1, 2, 3, 4 or 5, preferably 1, 2, 3 or 4, in particular 1 or 2.

A¹, A², A³ are identical or different and each independently of one another represent N (nitrogen) or the C—R⁵ moiety, but there are never more than two adjacent nitrogen atoms, and where each R⁵ in the C—R⁵ moiety has identical or different meanings according to the definition below, and A¹ and A², when each is a C—R⁵ group, with the atoms to which they are attached form a fully saturated, partly saturated or fully unsaturated 5- to 6-membered ring optionally interrupted by heteroatoms and optionally with further substitution, A² and A³, when each is a C—R⁵ group, with the atoms to which they are attached form a fully saturated, partly saturated or fully unsaturated 5- to 6-membered ring optionally interrupted by heteroatoms and optionally with further substitution, R³, R⁴ and R⁵ independently of one another represent hydrogen, nitro, amino, cyano, thiocyanato, isothiocyanato, halogen, (C₁-C₆)-alkyl, (C₁-C₆)-cycloalkyl, (C₁-C₆)-alkenyl, (C₁-C₆)-alkynyl, aryl, aryl-(C₁-C₆)-alkyl, (C₁-C₆)-alkenylalkyl, (C₁-C₆)-alkynylalkyl, aryl-(C₁-C₆)-alkoxy, heteroaryl, (C₁-C₆)-alkoxyalkyl, (C₁-C₆)-hydroxyalkyl, (C₁-C₆)-haloalkyl, (C₁-C₆)-halocycloalkyl, (C₁-C₆)-alkoxy, (C₁-C₆)-haloalkoxy, aryloxy, heteroaryloxy, (C₁-C₆)-cycloalkyloxy, hydroxy, (C₁-C₆)-cycloalkylalkoxy, (C₁-C₆)-alkoxycarbonyl, hydroxycarbonyl, aminocarbonyl, (C₁-C₆)-alkylaminocarbonyl, (C₁-C₆)-cycloalkylaminocarbonyl, (C₁-C₆)-cyanoalkylaminocarbonyl, (C₁-C₆)-alkenylaminocarbonyl, (C₁-C₆)-alkynylaminocarbonyl, (C₁-C₆)-alkylamino, (C₁-C₆)-alkylthio, (C₁-C₆)-haloalkylthio, hydrothio, (C₁-C₆)-bisalkylamino, (C₁-C₆)-cycloalkylamino, (C₁-C₆)-alkylcarbonylamino, (C₁-C₆)-cycloalkylcarbonylamino, formylamino, (C₁-C₆)-haloalkylcarbonylamino, (C₁-C₆)-alkoxycarbonylamino, (C₁-C₆)-alkylaminocarbonylamino, ((C₁-C₆)-alkyl)aminocarbonylamino, (C₁-C₆)-alkylsulfonylamino, (C₁-C₆)-cycloalkylsulfonylamino, arylsulfonylamino, hetarylsulfonylamino, (C₁-C₆)-sulfonylhaloalkylamino, aminosulfonyl, (C₁-C₆)-aminoalkylsulfonyl, (C₁-C₆)-aminohaloalkylsulfonyl, (C₁-C₆)-alkylaminosulfonyl, (C₁-C₆)-bisalkylaminosulfonyl, (C₁-C₆)-cycloalkylaminosulfonyl, $(C_1-C_6)$-haloalkylaminosulfonyl, arylaminosulfonyl, $(C_1-C_6)$-arylalkylaminosulfonyl, $(C_1-C_6)$-alkylsulfonyl, $(C_1-C_6)$-cycloalkylsulfonyl, arylsulfonyl, $(C_1-C_6)$-alkylsulfinyl, $(C_1-C_6)$-cycloalkylsulfinyl, arylsulfinyl, $(C_1-C_6)$—N,S-dialkylsulfonimidoyl, $(C_1-C_6)$—S-alkylsulfonimidoyl, $(C_1-C_6)$-alkylsulfonylaminocarbonyl, $(C_1-C_6)$-cycloalkylsulfonylaminocarbonyl, $(C_1-C_6)$-cycloalkylaminosulfonyl, $(C_1-C_6)$-arylalkylcarbonylamino, $(C_1-C_6)$-cycloalkylalkylcarbonylamino, heteroarylcarbonylamino, $(C_1-C_{10})$-alkoxyalkylcarbonylamino, $(C_1-C_6)$-hydroxyalkylcarbonylamino, $(C_1-C_6)$-trialkylsilyl, $A^6, A^7, A^8, A^9$ are identical or different and independently of one another represent O, S, N, NH, N-alkyl, alkoxycarbonyl-N,N-aryl, N-heteroaryl or the C—$R^{14}$ moiety, where at most two oxygen or sulfur atoms are present in the heterocycle, and where no oxygen or sulfur atoms are adjacent to one another, and where each $R^{14}$ in the C—$R^{14}$ moiety has identical or different meanings according to the definition below, and $R^{14}$ represents hydrogen, nitro, amino, cyano, thiocyanato, isothiocyanato, halogen, $(C_1-C_6)$-alkyl, $(C_1-C_6)$-cycloalkyl, $(C_1-C_6)$-alkenyl, $(C_1-C_6)$-alkynyl, aryl, aryl-$(C_1-C_6)$-alkyl, $(C_1-C_6)$-alkenylalkyl, $(C_1-C_6)$-alkynylalkyl, aryl-$(C_1-C_6)$-alkoxy, heteroaryl, $(C_1-C_6)$-alkoxyalkyl, $(C_1-C_6)$-hydroxyalkyl, $(C_1-C_6)$-haloalkyl, $(C_1-C_6)$-halocycloalkyl, $(C_1-C_6)$-alkoxy, $(C_1-C_6)$-haloalkoxy, aryloxy, heteroaryloxy, $(C_1-C_6)$-cycloalkyloxy, hydroxy, $(C_1-C_6)$-cycloalkylalkoxy, $(C_1-C_6)$-alkoxycarbonyl, hydroxycarbonyl, aminocarbonyl, $(C_1-C_6)$-alkylaminocarbonyl, $(C_1-C_6)$-cycloalkylaminocarbonyl, $(C_1-C_6)$-cyanoalkylaminocarbonyl, $(C_1-C_6)$-alkenylaminocarbonyl, $(C_1-C_6)$-alkynylaminocarbonyl, $(C_1-C_6)$-alkylamino, $(C_1-C_6)$-alkylthio, $(C_1-C_6)$-haloalkylthio, hydrothio, $(C_1-C_6)$-bisalkylamino, $(C_1-C_6)$-cycloalkylamino, $(C_1-C_6)$-alkylcarbonylamino, $(C_1-C_6)$-cycloalkylcarbonylamino, formylamino, $(C_1-C_6)$-haloalkylcarbonylamino, $(C_1-C_6)$-alkoxycarbonylamino, $(C_1-C_6)$-alkylaminocarbonylamino, $((C_1-C_6)$-alkyl)aminocarbonylamino, $(C_1-C_6)$-alkylsulfonylamino, $(C_1-C_6)$-cycloalkylsulfonylamino, arylsulfonylamino, hetarylsulfonylamino, $(C_1-C_6)$-sulfonylhaloalkylamino, aminosulfonyl, $(C_1-C_6)$-aminoalkylsulfonyl, $(C_1-C_6)$-aminohaloalkylsulfonyl, $(C_1-C_6)$-alkylaminosulfonyl, $(C_1-C_6)$-bisalkylaminosulfonyl, $(C_1-C_6)$-cycloalkylaminosulfonyl, $(C_1-C_6)$-haloalkylaminosulfonyl, arylaminosulfonyl, $(C_1-C_6)$-arylalkylaminosulfonyl, $(C_1-C_6)$-alkylsulfonyl, $(C_1-C_6)$-cycloalkylsulfonyl, arylsulfonyl, $(C_1-C_6)$-alkylsulfinyl, $(C_1-C_6)$-cycloalkylsulfinyl, arylsulfinyl, $(C_1-C_6)$—N,S-dialkylsulfonimidoyl, $(C_1-C_6)$—S-alkylsulfonimidoyl, $(C_1-C_6)$-alkylsulfonylaminocarbonyl, $(C_1-C_6)$-cycloalkylsulfonylaminocarbonyl, $(C_1-C_6)$-cycloalkylaminosulfonyl, $(C_1-C_6)$-arylalkylcarbonylamino, $(C_1-C_6)$-cycloalkylalkylcarbonylamino, heteroarylcarbonylamino, $(C_1-C_{10})$-alkoxyalkylcarbonylamino, $(C_1-C_6)$-hydroxyalkylcarbonylamino, $A^{10}$ represents N—$R^{15}$, oxygen or the C—$R^{15}$ moiety, and where each $R^{15}$ in the N—$R^{15}$ and C—$R^{15}$ moieties has identical or different meanings according to the definition below, $A^{11}$ represents N or the C—$R^{18}$ moiety, and where $R^{18}$ in the C—$R^{18}$ moiety has the meaning according to the definition below, $A^{12}$ represents N—$R^{15}$ or the $C(R^{16})R^{17}$ moiety, and where $R^{16}$ and $R^{17}$ in the $C(R^{16})R^{17}$ moiety are each as defined below, $R^{15}$ represents hydrogen, $(C_1-C_6)$-alkyl, $(C_1-C_6)$-alkenylalkyl, $(C_1-C_6)$-alkoxyalkyl, $(C_1-C_6)$-alkylcarbonyl, arylcarbonyl, heteroarylcarbonyl, $(C_1-C_6)$-cycloalkylcarbonyl, $(C_1-C_6)$-alkoxycarbonyl, $(C_1-C_6)$-allyloxycarbonyl, $(C_1-C_6)$-aryloxyalkyl, $(C_1-C_6)$-arylalkyl, $(C_1-C_6)$-haloalkyl, aryl, $R^{16}$ and $R^{17}$ independently of one another represent hydrogen, halogen, $(C_1-C_6)$-alkyl, $(C_1-C_6)$-alkoxy, $(C_1-C_6)$-haloalkyl, $(C_1-C_6)$-haloalkoxy, aryl, heteroaryl, $(C_1-C_6)$-arylalkyl or together with the atom to which they are attached form a carbonyl group, $R^{18}$ in each case represents hydrogen, nitro, amino, cyano, thiocyanato, isothiocyanato, halogen, $(C_1-C_6)$-alkyl, $(C_1-C_6)$-cycloalkyl, $(C_1-C_6)$-alkenyl, $(C_1-C_6)$-alkynyl, aryl, aryl-$(C_1-C_6)$-alkyl, $(C_1-C_6)$-alkenylalkyl, $(C_1-C_6)$-alkynylalkyl, aryl-$(C_1-C_6)$-alkoxy, heteroaryl, $(C_1-C_6)$-alkoxyalkyl, $(C_1-C_6)$-hydroxyalkyl, $(C_1-C_6)$-haloalkyl, $(C_1-C_6)$-halocycloalkyl, $(C_1-C_6)$-alkoxy, $(C_1-C_6)$-haloalkoxy, aryloxy, heteroaryloxy, $(C_1-C_6)$-cycloalkyloxy, hydroxy, $(C_1-C_6)$-cycloalkylalkoxy, $(C_1-C_6)$-alkoxycarbonyl, hydroxycarbonyl, aminocarbonyl, $(C_1-C_6)$-alkylaminocarbonyl, $(C_1-C_6)$-cycloalkylaminocarbonyl, $(C_1-C_6)$-cyanoalkylaminocarbonyl, $(C_1-C_6)$-alkenylaminocarbonyl, $(C_1-C_6)$-alkynylaminocarbonyl, $(C_1-C_6)$-alkylamino, $(C_1-C_6)$-alkylthio, $(C_1-C_6)$-haloalkylthio, hydrothio, $(C_1-C_6)$-bisalkylamino, $(C_1-C_6)$-cycloalkylamino, $(C_1-C_6)$-alkylcarbonylamino, $(C_1-C_6)$-cycloalkylcarbonylamino, formylamino, $(C_1-C_6)$-haloalkylcarbonylamino, $(C_1-C_6)$-alkoxycarbonylamino, $(C_1-C_6)$-alkylaminocarbonylamino, $((C_1-C_6)$-alkyl)aminocarbonylamino, $(C_1-C_6)$-alkylsulfonylamino, $(C_1-C_6)$-cycloalkylsulfonylamino, arylsulfonylamino, hetarylsulfonylamino, $(C_1-C_6)$-sulfonylhaloalkylamino, aminosulfonyl, $(C_1-C_6)$-aminoalkylsulfonyl, $(C_1-C_6)$-aminohaloalkylsulfonyl, $(C_1-C_6)$-alkylaminosulfonyl, $(C_1-C_6)$-bisalkylaminosulfonyl, $(C_1-C_6)$-cycloalkylaminosulfonyl, $(C_1-C_6)$—$C_6$)-alkylsulfonyl, $(C_1-C_6)$-cycloalkylsulfonyl, arylsulfonyl, $(C_1-C_6)$-alkylsulfinyl, $(C_1-C_6)$-cycloalkylsulfinyl, arylsulfinyl, $(C_1-C_6)$—N,S-dialkylsulfonimidoyl, $(C_1-C_6)$—S-alkylsulfonimidoyl, $(C_1-C_6)$-alkylsulfonylaminocarbonyl, $(C_1-C_6)$-cycloalkylsulfonylaminocarbonyl, $(C_1-C_6)$-cycloalkylaminosulfonyl, $(C_1-C_6)$-arylalkylcarbonylamino, $(C_1-C_6)$-cycloalkylalkylcarbonylamino, heteroarylcarbonylamino, $(C_1-C_{10})$-alkoxyalkylcarbonylamino, $(C_1-C_6)$-hydroxyalkylcarbonylamino, $(C_1-C_6)$-trialkylsilyl, where with very particular preference mention may be made of compounds of the formula (I) in which Q represents

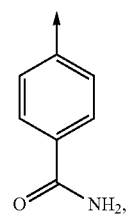

Q-1

-continued
Q-2 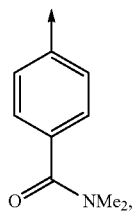
Q-3 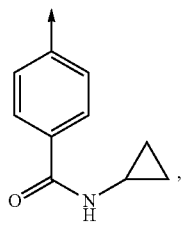
Q-4 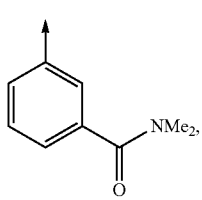
Q-5 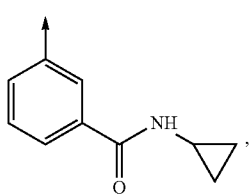
Q-6 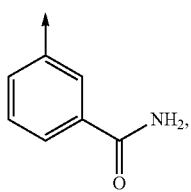
Q-7 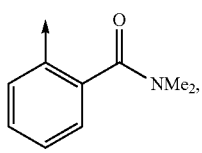
Q-8 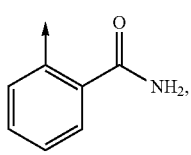
Q-9 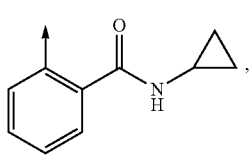
-continued
Q-10 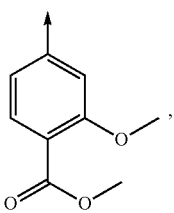
Q-11 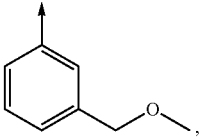
Q-12 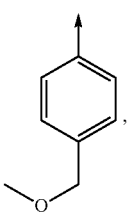
Q-13 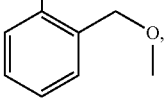
Q-14 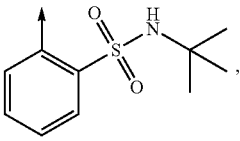
Q-15 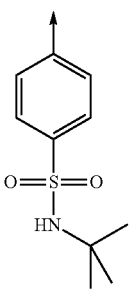
Q-16 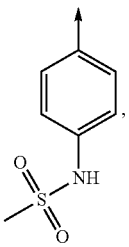
Q-17

Q-18 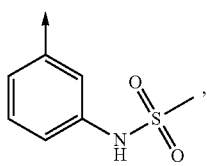
Q-19 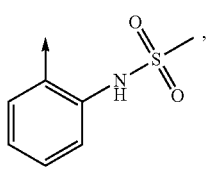
Q-20 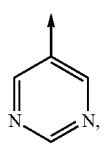
Q-21 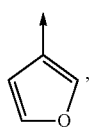
Q-23 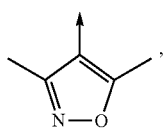
Q-24 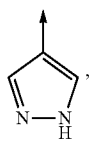
Q-25 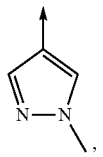
Q-26 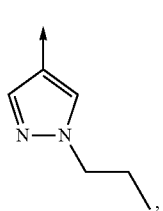
Q-27 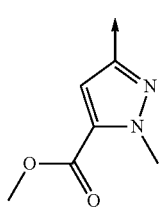
Q-28 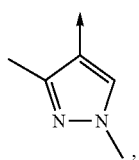
Q-29 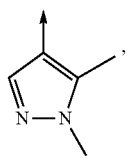
Q-30 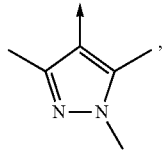
Q-31 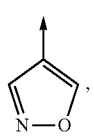
Q-32 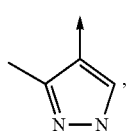
Q-33 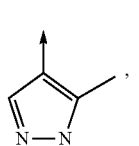
Q-34 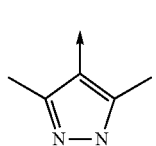
Q-35 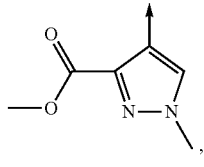
Q-36 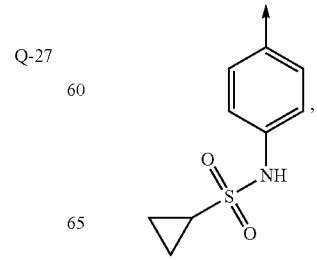

-continued

Q-37 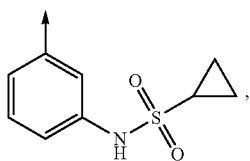

Q-38 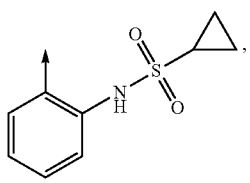

Q-39 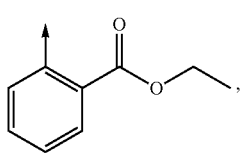

Q-40 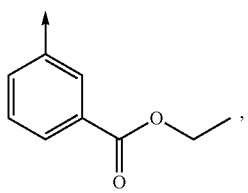

Q-41 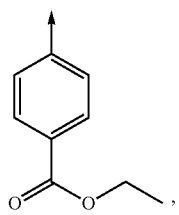

Q-42 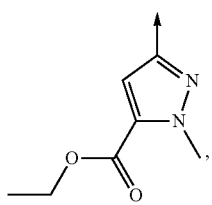

Q-43 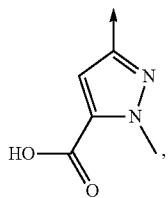

Q-44 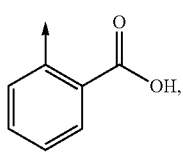

-continued

Q-45 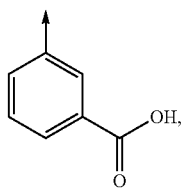

Q-46 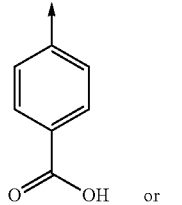 or

Q-47 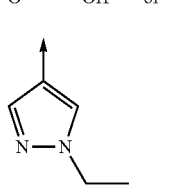

and $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1-C_4)$-alkyl, $(C_1-C_4)$-alkoxy or $(C_1-C_4)$-alkylthio, where each of the three last-mentioned radicals independently of the others is unsubstituted or substituted by one or more radicals from the group consisting of halogen, CN, $(C_1-C_4)$-alkoxy and $(C_1-C_4)$-alkylthio, or more preferably $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1-C_8)$-alkyl or $(C_1-C_4)$-alkoxy, where each of the two last-mentioned radicals independently of the others is unsubstituted or substituted by one or more radicals from the group consisting of halogen, $(C_1-C_3)$-alkoxy and $(C_1-C_3)$-alkylthio, and m represents 1, 2, 3 or 4, preferably 1, 2 or 3, particularly preferably 1 or 2, or more preferably $(R^1)_m$ represents m substituents $R^1$, where in the case that m is the number 1 the radical $R^1$ or, in the case that m is greater than 1, each of the radicals $R^1$ in each case independently of the others represents fluorine, chlorine, bromine, CN, $(C_1-C_3)$-alkyl or $(C_1-C_3)$-alkoxy, where each of the two last-mentioned radicals independently of the others is unsubstituted or substituted by one or more radicals from the group consisting of halogen, preferably fluorine and chlorine, and $(C_1-C_3)$-alkoxy, and m represents 1, 2, 3 or 4, preferably 1, 2 or 3, particularly preferably 1 or 2, or more preferably $(R^1)_m$ represents m substituents $R^1$, where in the case that m is the number 1 the radical $R^1$ or, in the case that m is greater than 1, each of the radicals $R^1$ in each case independently of the others represents fluorine, chlorine, methyl, ethyl, $(C_1-C_2)$-haloalkyl, preferably $(C_1-C_2)$-haloalkyl having one or more halogen atoms from the group consisting of fluorine and chlorine, or $(C_1-C_3)$-alkoxy or $(C_1-C_2)$-haloalkoxy, preferably $(C_1-C_2)$-haloalkoxy having one or more halogen atoms from the group consisting of fluorine and chlorine, and m represents 1, 2 or 3, in particular 1 or 2, or particularly preferably $(R^1)_m$ represents one of the radicals or radical combinations mentioned below (also stated are the positions at the phenyl ring, where the yl-position of the phenyl radical is numbered 1) selected from the group consisting of 2-fluoro, 3-fluoro, 4-fluoro, 2-chloro, 3-chloro, 4-chloro, 2-bromo, 3-bromo, 4-bromo, 2-iodo, 3-iodo, 4-iodo, 2-cyano, 3-cyano, 4-cyano, 2-methoxy, 3-methoxy, 4-methoxy, 2-ethoxy, 3-ethoxy, 4-ethoxy, 2-$CF_3$, 3-$CF_3$, 4-$CF_3$, 2-$CCl_3$, 3-$CCl_3$, 4-$CCl_3$, 2,3-$F_2$, 2,4-$F_2$, 2,5-$F_2$, 2,6-$F_2$, 3,4-$F_2$, 3,5-$F_2$, 2,3-$Cl_2$, 2,4-$Cl_2$, 2,5-$Cl_2$, 2,6-$Cl_2$, 3,4-$Cl_2$, 3,5-$Cl_2$, 2,3-$(OCH_3)_2$, 2,4-$(OCH_3)_2$, 2,5-$(OCH_3)_2$, 2,6-$(OCH_3)_2$, 3,4-$(OCH_3)_2$, 3,5-$(OCH_3)_2$, 2,3,4-$F_3$, 2,3,5-$F_3$, 2,3,6-$F_3$, 2,4,5-$F_3$, 2,3,6-$F_3$, 2,3,4-$F_3$, 3,4,5-$F_3$, 2,3,4-$Cl_3$, 2,3,5-$Cl_3$, 2,3,6-$Cl_3$, 2,4,5-$Cl_3$, 2,3,6-$Cl_3$, 2,3,4-$Cl_3$, 3,4,5-$Cl_3$, 2,3,4-$(OCH_3)_3$, 2,3,5-$(OCH_3)_3$, 2,3,6-$(OCH_3)_3$, 2,4,5-$(OCH_3)_3$, 2,3,6-$(OCH_3)_3$, 2,3,4-$(OCH_3)_3$, 3,4,5-$(OCH_3)_3$, 2-F-3-Cl, 2-F-4-Cl, 2-F-5-Cl, 2-Cl-3-F, 2-Cl-4-F, 2-Cl-5-F, 2-Cl-6-F, 3-Cl-4-F, 4-Cl-3-F, 3-Cl-5-F, 2-F-3-($OCH_3$), 2-F-4-($OCH_3$), 2-F-5-($OCH_3$), 2-F-6-($OCH_3$), 3-F-2-($OCH_3$), 3-F-4-($OCH_3$), 3-F-5-($OCH_3$), 3-F-6-($OCH_3$), 4-F-2-($OCH_3$), 4-F-3-($OCH_3$), $R^2$ represents H, $(C_1-C_6)$-alkyl, $(C_2-C_6)$-alkenyl, $(C_2-C_6)$-alkynyl or $(C_3-C_6)$-cycloalkyl, where each of the 4 last-mentioned radicals is unsubstituted or substituted by one or more radicals from the group consisting of halogen, $(C_1-C_6)$-alkyl, the latter only being a substituent in the case of cyclic parent radicals, $(C_1-C_4)$-alkoxy, $(C_1-C_4)$-alkylthio, $(C_3-C_6)$-cycloalkyl, which is unsubstituted or substituted by one or more radicals from the group consisting of halogen and $(C_1-C_4)$-alkyl, and phenyl which is unsubstituted or substituted by one or more radicals from the group consisting of halogen, $(C_1-C_4)$-alkyl, $(C_1-C_4)$-alkoxy and $(C_1-C_4)$-haloalkyl, and heterocyclyl which is unsubstituted or substituted by one or more radicals from the group consisting of halogen, $(C_1-C_4)$-alkyl, $(C_1-C_4)$-alkoxy, $(C_1-C_4)$-haloalkyl and $(C_1-C_4)$-haloalkoxy, or more preferably $R^2$ represents H, $(C_1-C_4)$-alkyl, $(C_2-C_4)$-alkenyl or $(C_2-C_4)$-alkynyl, where each of the 3 last-mentioned radicals is unsubstituted or substituted by one or more radicals from the group consisting of halogen, $(C_1-C_4)$-alkoxy, $(C_1-C_4)$-alkylthio, cyclopropyl, cyclobutyl, where each of the two last-mentioned radicals is unsubstituted or substituted by one or more radicals from the group consisting of halogen and $(C_1-C_4)$-alkyl, and phenyl which is unsubstituted or substituted by one or more radicals from the group consisting of halogen, $(C_1-C_4)$-alkyl, $(C_1-C_4)$-alkoxy and $(C_1-C_4)$-haloalkyl, and heterocyclyl which is unsubstituted or substituted by one or more radicals from the group consisting of halogen, $(C_1-C_4)$-alkyl, $(C_1-C_4)$-alkoxy and $(C_1-C_4)$-haloalkyl, or more preferably $R^2$ represents a saturated or partially unsaturated heterocyclyl radical having 3 to 6 ring atoms and 1 to 3 ring heteroatoms from the group consisting of N, O and S or a heteroaromatic radical having 5 or 6 ring atoms and 1 to 3 ring heteroatoms from the group consisting of N, O and S, where each of the heterocyclic radicals is unsubstituted or substituted by one or more radicals from the group consisting of halogen, $(C_1-C_4)$-alkyl, $(C_1-C_4)$-haloalkyl, $(C_1-C_4)$-alkoxy and oxo, or particularly preferably $R^2$ represents one of the radicals mentioned below selected from the group consisting of H, methyl, ethyl, n-propyl, isopropyl, phenyl, benzyl, $CH_2$(4-Cl-Ph), $CH_2$(4-F-Ph), $CH_2$(4-OMe-Ph), 2-methoxyethyl, tetrahydrofuran-2-ylmethyl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichlorocyclopropyl)methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclobutylmethyl, cyclopentylmethyl, cyclohexylmethyl or 1-ethyl-5-methyl-1H-pyrazole-4-methyl and very particularly preferably represents H or ethyl.

The definitions of radicals stated above in general terms or in ranges of preference apply both to the end products of the formula (I) and correspondingly to the starting materials or intermediates required in each case for preparation thereof. These radical definitions can be combined with one another as desired, i.e. including combinations between the given preferred ranges.

With regard to the compounds according to the invention, the terms used above and further below will be elucidated. These are familiar to the person skilled in the art and especially have the definitions elucidated hereinafter:

"Alkoxy" is an alkyl radical attached via an oxygen atom, alkenyloxy is an alkenyl radical attached via an oxygen atom, alkynyloxy is an alkynyl radical attached via an oxygen atom, cycloalkyloxy is a cycloalkyl radical attached via an oxygen atom, and cycloalkenyloxy is a cycloalkenyl radical attached via an oxygen atom.

The term "aryl" means an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl".

According to the invention, the expression "heteroaryl" represents heteroaromatic compounds, i.e. fully unsaturated aromatic heterocyclic compounds, preferably 5- to 7-membered rings having 1 to 3, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3- yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl. The heteroaryl groups according to the invention may also be substituted by one or more identical or different radicals. When two adjacent carbon atoms are part of a further aromatic ring, the systems are fused heteroaromatic systems, such as benzofused or polyannulated heteroaromatics. Preference is given, for example, to quinoline; isoquinoline; quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazine; pyridopyrimidine; pyridopyridazine; pteridine; pyrimidopyrimidine.

The term "halogen" means, for example, fluorine, chlorine, bromine or iodine. If the term is used for a radical, "halogen" means, for example, a fluorine, chlorine, bromine or iodine atom.

According to the invention, "alkyl" means a straight-chain or branched open-chain, saturated hydrocarbon radical which is optionally mono- or polysubstituted. Preferred substituents are halogen atoms, alkoxy, haloalkoxy, cyano, alkylthio, haloalkylthio, amino or nitro groups, particular preference being given to methoxy, methyl, fluoroalkyl, cyano, nitro, fluorine, chlorine, bromine or iodine.

"Haloalkyl", "-alkenyl" and "-alkynyl" mean alkyl, alkenyl and alkynyl, respectively, partially or fully substituted by identical or different halogen atoms, for example monohaloalkyl such as, for example, $CH_2CH_2Cl$, $CH_2CH_2Br$, $CHClCH_3$, $CH_2Cl$, $CH_2F$; perhaloalkyl such as, for example, $CCl_3$, $CClF_2$, $CFCl_2$, $CF_2CClF_2$, $CF_2CClFCF_3$; polyhaloalkyl such as, for example, $CH_2CHFC_1$, $CF_2CClFH$, $CF_2CBrFH$, $CH_2CF_3$; here, the term perhaloalkyl also includes the term perfluoroalkyl.

"Fluoroalkyl" means a straight-chain or branched open-chain, saturated and fluorine-substituted hydrocarbon radical, where at least one fluorine atom is at one of the possible positions.

"Perfluoroalkyl" means a straight-chain or branched open-chain, saturated and fully fluorine-substituted hydrocarbon radical, for example $CF_3$, $CF_2CF_3$, $CF_2CF_2CF_3$.

"Partly fluorinated alkyl" means a straight-chain or branched, saturated hydrocarbon which is mono- or polysubstituted by fluorine, where the fluorine atoms in question may be present as substituents on one or more different carbon atoms of the straight-chain or branched hydrocarbyl chain, for example $CHFCH_3$, $CH_2CH_2F$, $CH_2CH_2CF_3$, $OHF_2$, $CH_2F$, $CHFCF_2CF_3$.

"Partly fluorinated haloalkyl" means a straight-chain or branched, saturated hydrocarbon which is substituted by different halogen atoms with at least one fluorine atom, where any other halogen atoms optionally present are selected from the group consisting of fluorine, chlorine or bromine, iodine. The halogen atoms in question may be present as substituents on one or more different carbon atoms of the straight-chain or branched hydrocarbyl chain. Partly fluorinated haloalkyl also includes full substitution of the straight or branched chain by halogen including at least one fluorine atom.

Haloalkoxy is, for example, $OCF_3$, $OCHF_2$, $OCH_2F$, $OCF_2CF_3$, $OCH_2CF_3$ and $OCH_2CH_2Cl$; the situation is equivalent for haloalkenyl and other halogen-substituted radicals.

The expression "$(C_1-C_4)$-alkyl" is a brief notation for alkyl having one to 4 carbon atoms according to the range stated for carbon atoms, i.e. comprises the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, for the hydrocarbon radicals such as alkyl, alkenyl and alkynyl radicals, including in composite radicals, preference is given to the lower carbon skeletons, for example having 1 to 6 carbon atoms, or having 2 to 6 carbon atoms in the case of unsaturated groups. Alkyl radicals, including in composite radicals such as alkoxy, haloalkyl, etc., are, for example, methyl, ethyl, n-propyl or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

Alkenyl especially also includes straight-chain or branched open-chain hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl is, for example, vinyl which may optionally be substituted by further alkyl radicals, for example prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl.

Alkynyl especially also includes straight-chain or branched open-chain hydrocarbon radicals having more than one triple bond, or else having one or more triple bonds and one or more double bonds, for example 1,3-butatrienyl or 3-penten-1-yn-1-yl. $(C_2-C_6)$-alkynyl is, for example, ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

The term "cycloalkyl" means a carbocyclic saturated ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), bicyclo[2.2.2]octan-2-yl, adamantan-1-yl and adamantan-2-yl. The term "$(C_3-C_7)$-cycloalkyl" is a brief notation for cycloalkyl having three to 7 carbon atoms corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

"Cycloalkenyl" means a carbocyclic, nonaromatic, partly unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

The term "alkylidene", for example including in the form of $(C_1-C_{10})$-alkylidene, means the radical of a straight-chain or branched open-chain hydrocarbon radical attached via a double bond. Possible bonding sites for alkylidene are naturally only positions on the base structure where two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$. Cycloalkylidene is a carbocyclic radical attached via a double bond.

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the point of attachment is located at a ring atom. When the heterocyclyl radical or the heterocyclic ring is optionally substituted, it may be fused to other carbocyclic or heterocyclic rings. Optionally substituted heterocyclyl also includes polycyclic systems, such as, for example, 8-aza-bicyclo[3.2.1]octanyl or 1-aza-bicyclo[2.2.1]heptyl. In the case of optionally substituted heterocyclyl, spirocyclic systems are also included, such as, for example, 1-oxa-5-azaspiro[2.3]hexyl. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O and S, though no two oxygen atoms should be directly adjacent, for example with one heteroatom from the group consisting of N, O and S 1- or 2- or 3-pyrrolidinyl, 3,4-dihydro-2H-pyrrol-2- or 3-yl, 2,3-dihydro-1H-pyrrol-1- or 2- or 3- or 4- or 5-yl; 2,5-dihydro-1H-pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetrahydropyridin-1- or 2- or 3- or 4- or 5- or 6-yl; 1,2,3,4-tetrahydropyridin-1- or 2- or 3- or 4- or 5- or 6-yl; 1,4-dihydropyridin-1- or 2- or 3- or 4-yl; 2,3-dihydropyridin-2- or 3- or 4- or 5- or 6-yl; 2,5-dihydropyridin-2- or 3- or 4- or 5- or 6-yl, 1- or 2- or 3- or 4-azepanyl; 2,3,4,5-tetrahydro-1H-azepin-1- or 2- or 3- or 4- or 5- or 6- or 7-yl; 2,3,4,7-tetrahydro-1H-azepin-1- or 2- or 3- or 4- or 5- or 6- or 7-yl; 2,3,6,7-tetrahydro-1H-azepin-1- or 2- or 3- or 4-yl; 3,4,5,6-tetrahydro-2H-azepin-2- or 3- or 4- or 5- or 6- or 7-yl; 4,5-dihydro-1H-azepin-1- or 2- or 3- or 4-yl; 2,5-dihydro-1H-azepin-1- or -2- or 3- or 4- or 5- or 6- or 7-yl; 2,7-dihydro-1H-azepin-1- or -2- or 3- or 4-yl; 2,3-dihydro-1H-azepin-1- or -2- or 3- or 4- or 5- or 6- or 7-yl; 3,4-dihydro-2H-azepin-2- or 3- or 4- or 5- or 6- or 7-yl; 3,6-dihydro-2H-azepin-2- or 3- or 4- or 5- or 6- or 7-yl; 5,6-dihydro-2H-azepin-2- or 3- or 4- or 5- or 6- or 7-yl; 4,5-dihydro-3H-azepin-2- or 3- or 4- or 5- or 6- or 7-yl; 1H-azepin-1- or -2- or 3- or 4- or 5- or 6- or 7-yl; 2H-azepin-2- or 3- or 4- or 5- or 6- or 7-yl; 3H-azepin-2- or 3- or 4- or 5- or 6- or 7-yl; 4H-azepin-2- or 3- or 4- or 5- or 6- or 7-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl.

In the case of a partly or fully saturated nitrogen heterocycle, this may be joined to the remainder of the molecule either via carbon or via the nitrogen.

According to the invention, "arylsulfonyl" represents optionally substituted phenylsulfonyl or optionally substituted polycyclic arylsulfonyl, here especially optionally substituted naphthylsulfonyl, for example substituted by halogen, cyano, nitro, alkyl, haloalkyl, haloalkoxy, amino, alkylamino, alkylcarbonylamino, dialkylamino or alkoxy groups.

According to the invention, "cycloalkylsulfonyl"—alone or as a constituent of a chemical group—represents optionally substituted cycloalkylsulfonyl, preferably having 3 to 6 carbon atoms, for example cyclopropylsulfonyl, cyclobutylsulfonyl, cyclopentylsulfonyl or cyclohexylsulfonyl.

According to the invention, "alkylsulfonyl"—alone or as a constituent of a chemical group—represents straight-chain or branched alkylsulfonyl, preferably having 1 to 8 or having 1 to 6 carbon atoms, for example methylsulfonyl, ethylsulfonyl, n-propylsulfonyl, isopropylsulfonyl, n-butylsulfonyl, isobutylsulfonyl, sec-butylsulfonyl and tert-butylsulfonyl.

According to the invention, "alkylthio"—alone or as a constituent of a chemical group—represents straight-chain or branched S-alkyl, preferably having 1 to 8 or having 1 to 6 carbon atoms, for example methylthio, ethylthio, n-propylthio, isopropylthio, n-butylthio, isobutylthio, sec-butylthio and tert-butylthio. Alkenylthio is an alkenyl radical attached via a sulfur atom, alkynylthio is an alkynyl radical attached via a sulfur atom, cycloalkylthio is a cycloalkyl radical attached via a sulfur atom, and cycloalkenylthio is a cycloalkenyl radical attached via a sulfur atom.

According to the nature and the bonding of the substituents, the compounds of the general formula (I) may be present as stereoisomers. The formula (I) embraces all possible stereoisomers defined by their specific spatial form, such as enantiomers, diastereomers, Z and E isomers. If, for example, one or more alkenyl groups are present, there may be diastereomers (Z and E isomers). If, for example, one or more asymmetric carbon atoms are present, there may be enantiomers and diastereomers. Stereoisomers can be obtained from the mixtures obtained in the preparation by customary separation methods. The chromatographic separation can be effected either on the analytical scale to find the enantiomeric excess or the diastereomeric excess, or on the preparative scale to prepare test specimens for biological testing. It is equally possible to selectively prepare stereoisomers by using stereoselective reactions using optically active starting materials and/or auxiliaries. The invention thus also relates to all stereoisomers which are embraced by the general formula (I) but are not shown in their specific stereomeric form, and to mixtures thereof.

Likewise undisclosed in the prior art and therefore part of the further subject matter of the present invention are compounds of the formula (I)

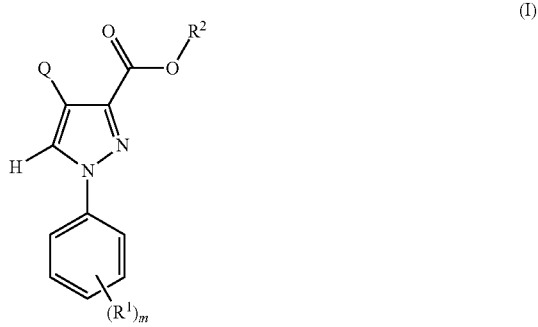

where
Q represents
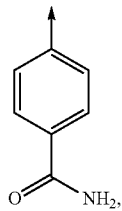 Q-1
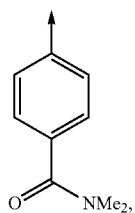 Q-2
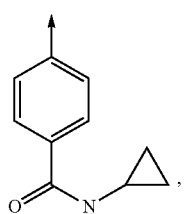 Q-3
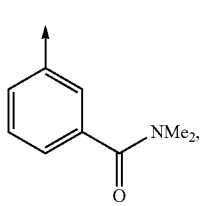 Q-4
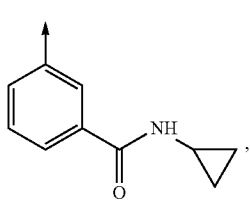 Q-5
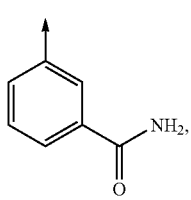 Q-6
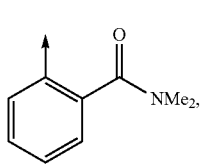 Q-7
-continued
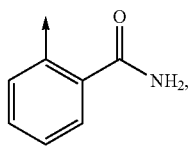 Q-8
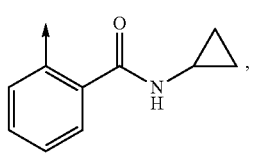 Q-9
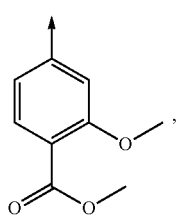 Q-10
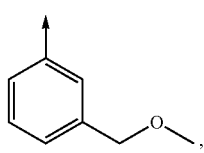 Q-11
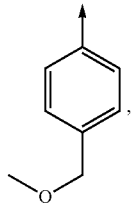 Q-12
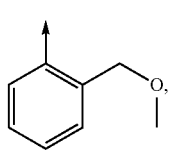 Q-13
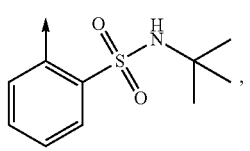 Q-14
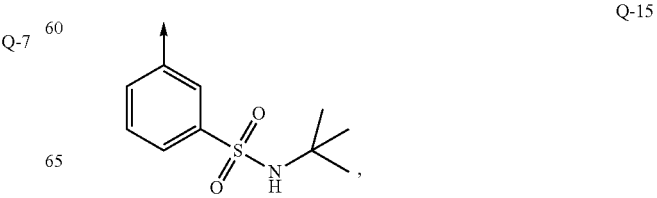 Q-15

Q-16 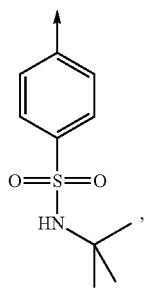
Q-17 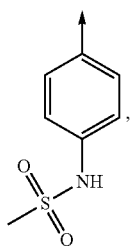
Q-18 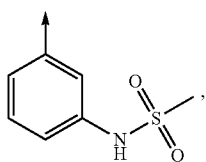
Q-19 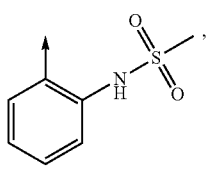
Q-20 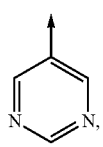
Q-21 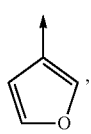
Q-23 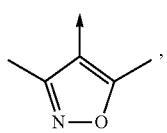
Q-24 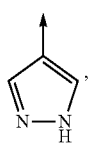
Q-25 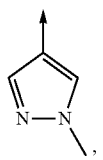
Q-26 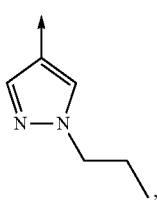
Q-27 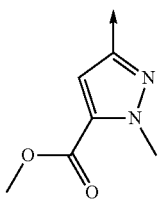
Q-28 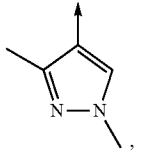
Q-29 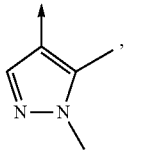
Q-30 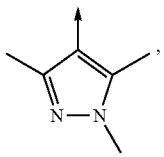
Q-31 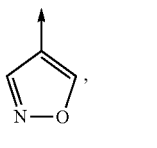
Q-32 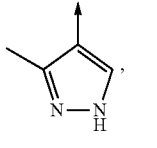
Q-33 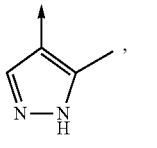
Q-34 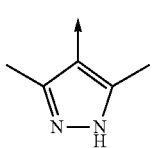

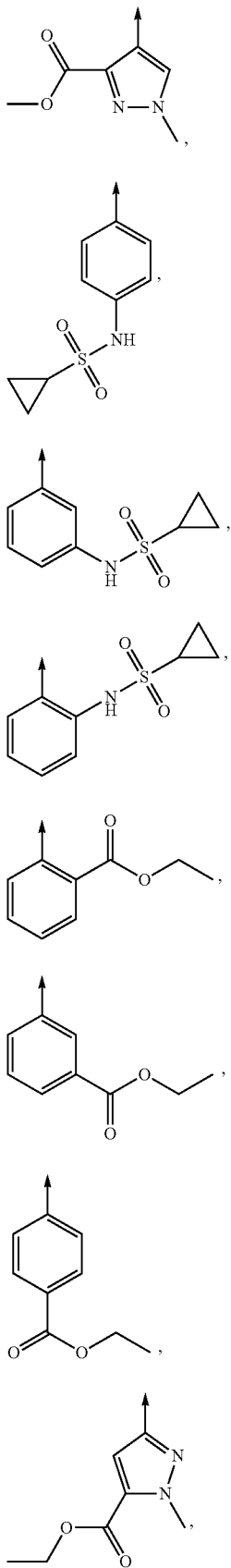
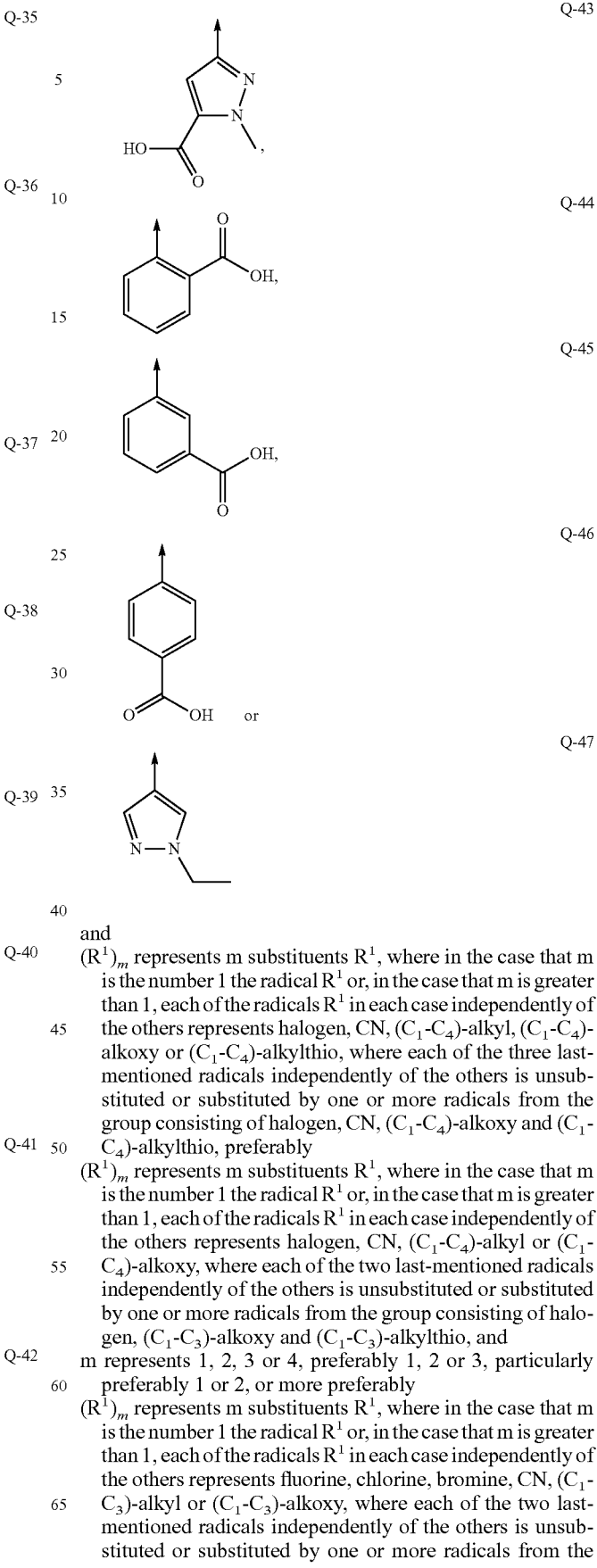

and $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1-C_4)$-alkyl, $(C_1-C_4)$-alkoxy or $(C_1-C_4)$-alkylthio, where each of the three last-mentioned radicals independently of the others is unsubstituted or substituted by one or more radicals from the group consisting of halogen, CN, $(C_1-C_4)$-alkoxy and $(C_1-C_4)$-alkylthio, preferably $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1-C_4)$-alkyl or $(C_1-C_4)$-alkoxy, where each of the two last-mentioned radicals independently of the others is unsubstituted or substituted by one or more radicals from the group consisting of halogen, $(C_1-C_3)$-alkoxy and $(C_1-C_3)$-alkylthio, and m represents 1, 2, 3 or 4, preferably 1, 2 or 3, particularly preferably 1 or 2, or more preferably $(R^1)_m$ represents m substituents $R^1$, where in the case that m is the number 1 the radical $R^1$ or, in the case that m is greater than 1, each of the radicals $R^1$ in each case independently of the others represents fluorine, chlorine, bromine, CN, $(C_1-C_3)$-alkyl or $(C_1-C_3)$-alkoxy, where each of the two last-mentioned radicals independently of the others is unsubstituted or substituted by one or more radicals from the group consisting of halogen, preferably fluorine and chlorine, and $(C_1-C_3)$-alkoxy, and m represents 1, 2, 3 or 4, preferably 1, 2 or 3, particularly preferably 1 or 2, or more preferably $(R^1)_m$ represents m substituents $R^1$, where in the case that m is the number 1 the radical $R^1$ or, in the case that m is greater than 1, each of the radicals $R^1$ in each case independently of the others represents fluorine, chlorine, methyl, ethyl, $(C_1-C_2)$-haloalkyl, preferably $(C_1-C_2)$-haloalkyl having one or more halogen atoms from the group consisting of fluorine and chlorine, or $(C_1-C_3)$-alkoxy or $(C_1-C_2)$-haloalkoxy, preferably $(C_1-C_2)$-haloalkoxy having one or more halogen atoms from the group consisting of fluorine and chlorine, and m represents 1, 2 or 3, in particular 1 or 2, or particularly preferably $(R^1)_m$ represents one of the radicals or radical combinations mentioned below (also stated are the positions at the phenyl ring, where the yl-position of the phenyl radical is numbered 1) selected from the group consisting of 2-fluoro, 3-fluoro, 4-fluoro, 2-chloro, 3-chloro, 4-chloro, 2-bromo, 3-bromo, 4-bromo, 2-iodo, 3-iodo, 4-iodo, 2-cyano, 3-cyano, 4-cyano, 2-methoxy, 3-methoxy, 4-methoxy, 2-ethoxy, 3-ethoxy, 4-ethoxy, 2-$CF_3$, 3-$CF_3$, 4-$CF_3$, 2-$CCl_3$, 3-$CCl_3$, 4-$CCl_3$, 2,3-$F_2$, 2,4-$F_2$, 2,5-$F_2$, 2,6-$F_2$, 3,4-$F_2$, 3,5-$F_2$, 2,3-$Cl_2$, 2,4-$Cl_2$, 2,5-$Cl_2$, 2,6-$Cl_2$, 3,4-$Cl_2$, 3,5-$Cl_2$, 2,3-$(OCH_3)_2$, 2,4-$(OCH_3)_2$, 2,5-$(OCH_3)_2$, 2,6-$(OCH_3)_2$, 3,4-$(OCH_3)_2$, 3,5-$(OCH_3)_2$, 2,3,4-$F_3$, 2,3,5-$F_3$, 2,3,6-$F_3$, 2,4,5-$F_3$, 2,3,6-$F_3$, 2,3,4-$F_3$, 3,4,5-$F_3$, 2,3,4-$Cl_3$, 2,3,5-$Cl_3$, 2,3,6-$Cl_3$, 2,4,5-$Cl_3$, 2,3,6-$Cl_3$, 2,3,4-$Cl_3$, 3,4,5-$Cl_3$, 2,3,4-$(OCH_3)_3$, 2,3,5-$(OCH_3)_3$, 2,3,6-$(OCH_3)_3$, 2,4,5-$(OCH_3)_3$, 2,3,6-$(OCH_3)_3$, 2,3,4-$(OCH_3)_3$, 3,4,5-$(OCH_3)_3$, 2-F-3-Cl, 2-F-4-Cl, 2-F-5-Cl, 2-Cl-3-F, 2-Cl-4-F, 2-Cl-5-F, 2-Cl-6-F, 3-Cl-4-F, 4-Cl-3-F, 3-Cl-5-F, 2-F-3-$(OCH_3)$, 2-F-4-$(OCH_3)$, 2-F-5-$(OCH_3)$, 2-F-6-$(OCH_3)$, 3-F-2-$(OCH_3)$, 3-F-4-$(OCH_3)$, 3-F-5-$(OCH_3)$, 3-F-6-$(OCH_3)$, 4-F-2-$(OCH_3)$, 4-F-3-$(OCH_3)$, and $R^2$ represents H, $(C_1-C_6)$-alkyl, $(C_2-C_6)$-alkenyl, $(C_2-C_6)$-alkynyl or $(C_3-C_6)$-cycloalkyl, where each of the 4 last-mentioned radicals is unsubstituted or substituted by one or more radicals from the group consisting of halogen, $(C_1-C_6)$-alkyl, the latter only being a substituent in the case of cyclic parent radicals, $(C_1-C_4)$-alkoxy, $(C_1-C_4)$-alkylthio, $(C_3-C_6)$-cycloalkyl, which is unsubstituted or substituted by one or more radicals from the group consisting of halogen and $(C_1-C_4)$-alkyl, and phenyl which is unsubstituted or substituted by one or more radicals from the group consisting of halogen, $(C_1-C_4)$-alkyl, $(C_1-C_4)$-alkoxy and $(C_1-C_4)$-haloalkyl, and heterocyclyl which is unsubstituted or substituted by one or more radicals from the group consisting of halogen, $(C_1-C_4)$-alkyl, $(C_1-C_4)$-alkoxy, $(C_1-C_4)$-haloalkyl and $(C_1-C_4)$-haloalkoxy, or preferably $R^2$ represents H, $(C_1-C_4)$-alkyl, $(C_2-C_4)$-alkenyl or $(C_2-C_4)$-alkynyl, where each of the 3 last-mentioned radicals is unsubstituted or substituted by one or more radicals from the group consisting of halogen, $(C_1-C_4)$-alkoxy, $(C_1-C_4)$-alkylthio, cyclopropyl, cyclobutyl, where each of the two last-mentioned radicals is unsubstituted or substituted by one or more radicals from the group consisting of halogen and $(C_1-C_4)$-alkyl, and phenyl which is unsubstituted or substituted by one or more radicals from the group consisting of halogen, $(C_1-C_4)$-alkyl, $(C_1-C_4)$-alkoxy and $(C_1-C_4)$-haloalkyl, and heterocyclyl which is unsubstituted or substituted by one or more radicals from the group consisting of halogen, $(C_1-C_8)$-alkyl, $(C_1-C_4)$-alkoxy and $(C_1-C_4)$-haloalkyl, or more preferably $R^2$ represents a saturated or partially unsaturated heterocyclyl radical having 3 to 6 ring atoms and 1 to 3 ring heteroatoms from the group consisting of N, O and S or a heteroaromatic radical having 5 or 6 ring atoms and 1 to 3 ring heteroatoms from the group consisting of N, O and S, where each of the heterocyclic radicals is unsubstituted or substituted by one or more radicals from the group consisting of halogen, $(C_1-C_4)$-alkyl, $(C_1-C_4)$-haloalkyl, $(C_1-C_4)$-alkoxy and oxo, or particularly preferably $R^2$ represents one of the radicals mentioned below selected from the group consisting of H, methyl, ethyl, n-propyl, isopropyl, phenyl, benzyl, $CH_2$(4-Cl-Ph), $CH_2$(4-F-Ph), $CH_2$(4-OMe-Ph), 2-methoxyethyl, tetrahydrofuran-2-yl-methyl, 2-(dimethylamino)ethyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichlorocyclopropyl)methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclobutylmethyl, cyclopentylmethyl, cyclohexylmethyl or 1-ethyl-5-methyl-1H-pyrazole-4-methyl.

The invention also provides novel processes for preparing the compounds of the general formula (I) or salts thereof.

The compounds of the general formula (I) can be prepared, for example, according to the synthesis scheme below

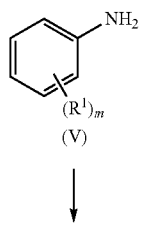
(V)

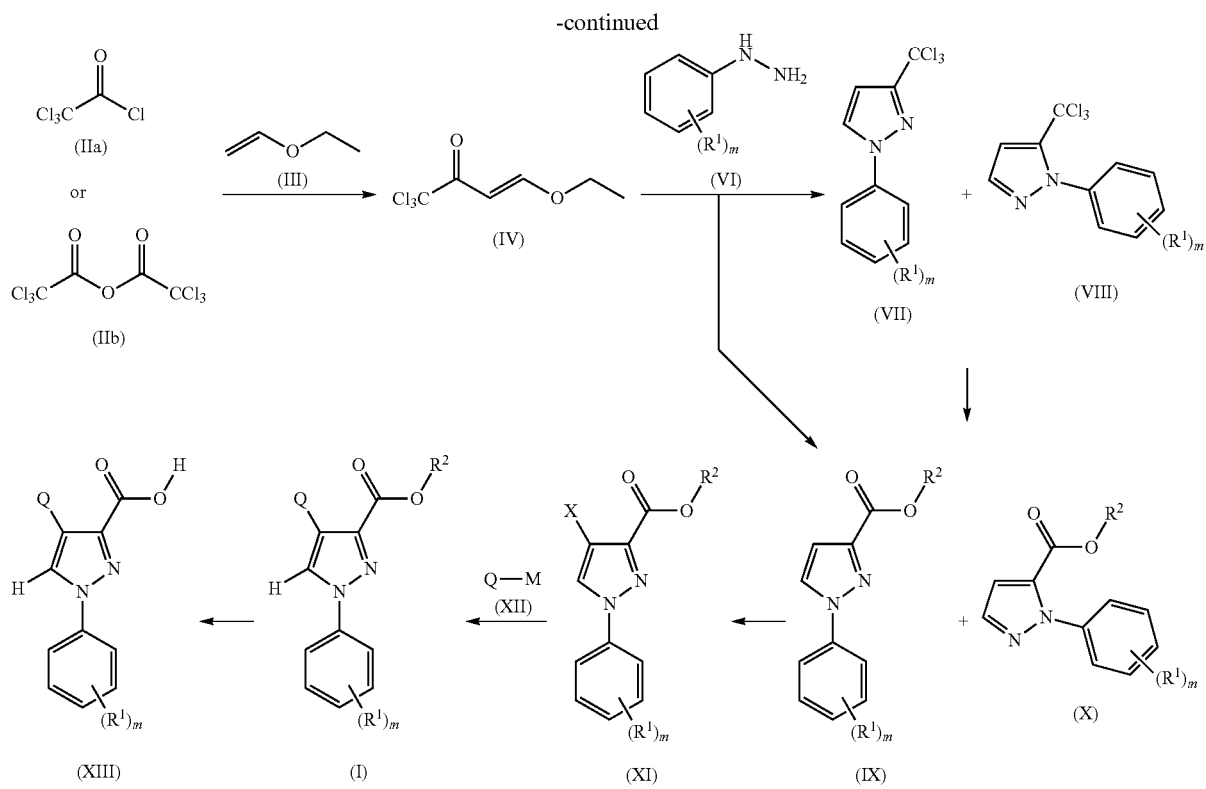

In the reaction scheme, the radicals Q, $(R^1)_m$ and $R^2$ are defined as described above, and $R^2$ preferably represents hydrogen, a methyl or an ethyl group.

A compound of the formula (IV) can be prepared by reacting a compound of the formula (IIa) or (IIb) with bases, for example pyridine, in an adequate solvent such as dichloromethane (e.g. Chemistry Lett. 1976, 499; Chemische Berichte 1982, 115, 2766; Synthesis 1986, 1, 69; Nucleosides, Nucleotides & Nucleic Acids 2006, 25, 243; Synlett, 2008, 11, 1684). The reaction is preferably carried out in the temperature range between −20° C. and 100° C.

The compounds of the general formulae (V) and (VI) are either commercially available or can be prepared by or analogously to methods known to the person skilled in the art (e.g. Heterocycles 22 (1984) 117; J. Med. Chem. 45 (2002) 5397; U.S. Pat. No. 5,624,941; EP 1591443; EP 1698626; U.S. Pat. No. 6,642,237; EP 1548007).

A compound of the formula (VII) can also be prepared by reacting a compound of the formula (IV) and a compound of the formula (VI) in an adequate solvent such as dichloromethane and a Brönsted acid such as trifluoroacetic acid. The reaction is preferably carried out in the temperature range between −10° C. and 100° C. Reaction of the compound of the formula (VII) in an alcohol (methanol or ethanol) as solvent then yields the compound of the formula (IX). The reaction is preferably carried out in the temperature range between −10° C. and 100° C. Alternatively, the compound of the formula (IX) can be obtained by reaction with an alcohol (methanol or ethanol) as solvent. The reaction is preferably carried out in the temperature range between −10° C. and 100° C.

A compound of the formula (XI) can also be prepared by reaction of a compound of the formula (IX) in an organic solvent such as N,N-dimethylformamide or acetic acid with N-halosuccinimide, dihalohydantoin or halogen. The reaction is preferably carried out in the temperature range between −10° C. and 120° C. The radical "X" represents, for example, chlorine, bromine or iodine.

A compound of the formula (I) can be prepared, for example, by reacting a compound of the formula (XI) in a suitable solvent with a Q-M (XII) with addition of an adequate amount of a transition metal catalyst, in particular palladium catalysts such as palladium diacetate or bis(triphenylphosphine)palladium(II) dichloride or nickel catalysts such as nickel(II) acetylacetonate or bis(triphenylphosphine)nickel(II) chloride, preferably at elevated temperature in an organic solvent such as 1,2-dimethoxyethane. The radical "M" represents, for example, Mg—Hal, Zn—Hal, Sn((C$_1$-C$_4$)alkyl)$_3$, lithium, copper or B(OR$^a$)(OR$^b$), where the radicals R$^a$ and R$^b$ independently of one another represent, for example, hydrogen, (C$_1$-C$_4$)-alkyl, or, if the radicals R$^a$ and R$^b$ are attached to one another, together represent ethylene or propylene. Generally suitable are cross-coupling methods described in R. D. Larsen, Organometallics in Process Chemistry 2004 Springer Verlag, in I. Tsuji, Palladium Reagents and Catalysts 2004 Wiley, and in M. Beller, C. Bolm, Transition Metals for Organic Synthesis 2004 VCH-Wiley. Further suitable synthesis methods are described in Chem. Rev. 2006, 106, 2651; Platinum Metals Review, 2009, 53, 183; Platinum Metals Review 2008, 52, 172 and Acc. Chem. Res. 2008, 41, 1486.

The pyrazolecarboxylic acid of the formula (XIII) can be prepared by hydrolysis of the compound of the formula (I) (where $R^2$ is not H) according to or analogously to methods known to the person skilled in the art.

The hydrolysis can be carried out in the presence of a base or a Lewis acid. The base can be a hydroxide salt of an alkali metal (such as, for example, lithium, sodium or potassium), and the hydrolysis reaction is preferably carried out in the temperature range between room temperature and 100° C. The Lewis acid can be boron tribromide, and the reaction can be carried out in a temperature range between −20° C. and 100° C., preferably −5° C. and 50° C.

A variation of the ester of the compounds of the formula (I) can be carried out starting with the pyrazolecarboxylic acid of the formula (XIII) according to or analogously to methods known to the person skilled in the art.

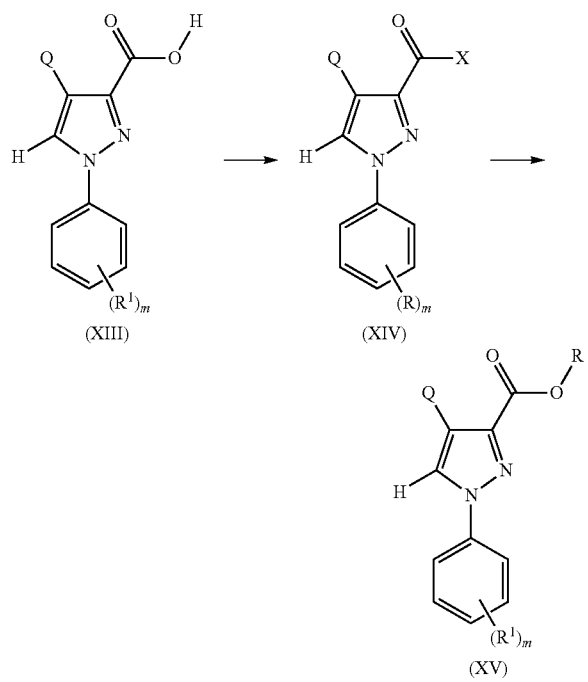

Here, the compound of the formula (XV) corresponds to the formula (I) if R is defined like R2 in the compound of the formula (I) to be prepared.

The conversion into the acid halide of the formula (XIV) using a thionyl halide, oxalyl halide or phosphorus pentahalide can be carried out, for example, in an inert organic solvent in a temperature range between −50° C. and 170° C., preferably −10° C. and 130° C., in an inert organic solvent. Suitable organic solvents are, for example, polar protic solvents or aprotic solvents such as toluene, chlorobenzene, trichloromethane, dichloromethane or 1,2-dichloroethane. The reaction of the acid halide of the formula (XIV) with an alcohol R—OH or R²—OH, where R is a group analogous to R² or R² is directly as defined in the compound of the formula (I) to be prepared, is generally carried out in the presence of an acid binder in an inert organic solvent in a temperature range between 0° C. and 150° C., preferably 0° C. and 50° C. Suitable organic solvents are, for example, polar protic or aprotic solvents such as ethers, for example diethyl ether, tetrahydrofuran and dioxane, or nitriles such as acetonitrile, or amides such as dimethylformamide. Acid binders are, for example, alkali metal or alkaline earth metal carbonates such as, for example, sodium carbonate, potassium carbonate or calcium carbonate, alkali metal or alkaline earth metal hydroxides, such as sodium hydroxide, potassium hydroxide or calcium hydroxide, or alkali metal hydrides or amides, such as sodium hydride or potassium hydride or sodium amide or potassium amide, or else organic bases such as triethylamine, pyridine, dimethylaminopyridine, DBU (1,8-diazabicyclo[5.4.0]-undec-7-ene), DBN (1,5-diazabicyclo[4.3.0]non-5-ene) and 1,4-diazabicyclo[2.2.2]octane.

The compounds of the formula (XII) can optionally be reacted with an alcohol in the presence of a dehydrating agent, for example dicyclohexylcarbodiimide (DCC), to give the compound of the formula (XV). Suitable organic solvents are, for example, polar protic or aprotic solvents such as, for example, dichloromethane, trichloromethane, pyridine, tetrahydrofuran and dioxane, or nitriles such as acetonitrile, or amides such as dimethylformamide, or mixtures thereof, and the reaction is carried out in a temperature range between −20° C. and 50° C., preferably −10° C. and 30° C. Generally suitable are the peptide synthesis methods described in N. Leo Benoiton, Chemistry of Peptide Synthesis 2006 CRC Press.

Alternatively, compounds of the formula (XV) can be prepared by transesterification of esters of the formula (I) (in which R³ is not H) in the presence of a Brönsted acid or a Lewis acid. The Brönsted acid can be sulfuric acid or a hydrogen halide dissolved in an alcohol (such as, for example, methanol, ethanol, n-propanol, 2-propanol or n-butanol). The transesterification is preferably carried out in the temperature range between room temperature and 100° C. The Lewis acid can be titanium tetraisopropoxide, and the reaction can be carried out in a temperature range between 0° C. and 150° C., preferably 0° C. and 100° C.

Accordingly, the invention also provides a process for preparing the compounds of the general formula (I) or salts thereof, characterized in that
a) a compound of the formula (XI)

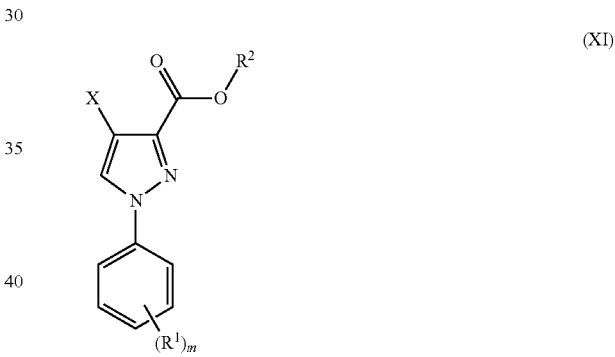

where X corresponds to a halogen, preferably a chlorine, bromine or iodine
is reacted with a compound of the formula (XII)

to give the compound of the formula (I) or a salt thereof, or
b) in the case that R² in formula (I) is different from hydrogen, a compound (I') which corresponds to the compound of the formula (I), but where R² represents hydrogen, is esterified by customary methods to give the compound of the formula (I) in which R² is different from hydrogen, or
c) in the case that R² in formula (I) is different from hydrogen, a compound (I") which corresponds to the compound of the formula (I), but where R² represents a different radical different from hydrogen,
is transesterified by customary methods to give the compound of the formula (I) in which R² is as defined in the compound (I) to be prepared,
d) in the case that R² in formula (I) represents hydrogen or a salt thereof, a compound (I''') which corresponds to the compound of the formula (I) in which R² is different from hydrogen is hydrolyzed by customary methods to give the compound of the formula (I) in which R²=hydrogen, or reacted to a salt thereof, where R², (R¹)$_m$ and m in the formulae (XI), (XII), (I'), (I") and (I"') mentioned are as defined in the compound of the formula (I) to be prepared.

The invention also provides a multi-step process for preparing compounds of the formula (I) or salts thereof, characterized in that e) in a first step (e1)

e1) a compound of the formula (IX)

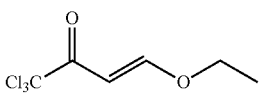
(IV)

is reacted with a substituted phenylhydrazine of the formula (VI)

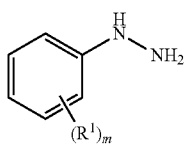
(VI)

to give the compound of the formula (VII)

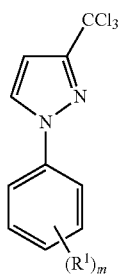
(VII)

and e2) step (e1) a compound of the formula (VII) is reacted with an alcohol to give the compound of the formula (IX)

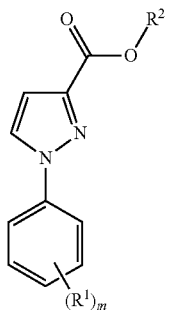
(IX)

and e3) following step (e2) a compound of the formula (IX) is reacted with a halogenating agent to give the compound of the formula (XI)

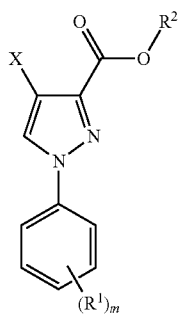
(XI)

where X corresponds to a halogen, preferably a chlorine, bromine or iodine and e4) the compound (III) obtained following step (e3) is reacted with a compound of the formula (XII)

Q-M  (XII)

to give the compound of the formula (I) or a salt thereof, or where R², (R¹)$_m$ and m in the formulae (IX), (XI) and (XII) mentioned are as defined in the compound of the formula (I) to be prepared.

The process procedures and preferred variants for the preparations are described in more detail above.

The invention also provides an alternative multi-step process for preparing compounds of the formula (I) or salts thereof, characterized in that f) in a first step (f1)

f1) a compound of the formula (IX)

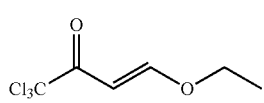
(IV)

is reacted with a substituted phenylhydrazine of the formula (VI)

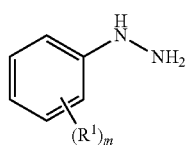
(VI)

in an alcohol to give the compound of the formula (IX)

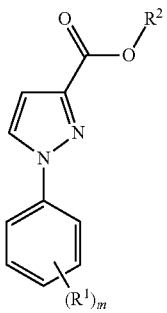

(IX)

and f2) following step (f1) a compound of the formula (IX) is reacted with a halogenating agent to give the compound of the formula (XI)

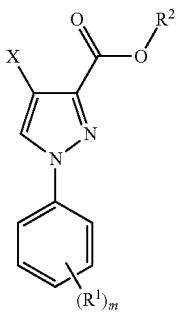

(XI)

where X corresponds to a halogen, preferably a chlorine, bromine or iodine
and
f3) the compound (III) obtained following step (f2) is reacted with a compound of the formula (XII)

Q-M        (XII)

to give the compound of the formula (I) or a salt thereof, or where $R^2$, $(R^1)_m$ and m in the formulae (IX), (XI) and (XII) mentioned are as defined in the compound of the formula (I) to be prepared.

The process procedures and preferred variants for the preparations are described in more detail above.

PREPARATION EXAMPLES

Example A1

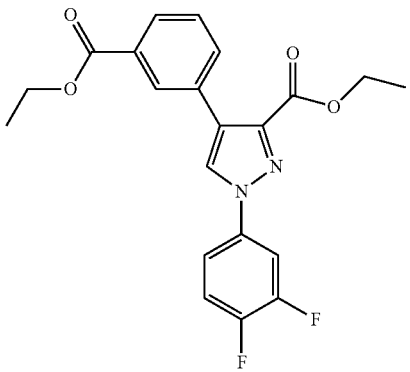 [SMILES: CCOC(=O)c1cccc(-c2cn(-c3ccc(F)c(F)c3)nc2C(=O)OCC)c1]

Ethyl 1-(3,4-difluorophenyl)-4-[3-(ethoxycarbonyl) phenyl]-1H-pyrazole-3-carboxylate A1 1) Ethyl 1-(3,4-difluorophenyl)-1H-pyrazole-3-carboxylate 2 g (9.196 mmol) of (3E)-1,1,1-trichloro-4-ethoxybut-3-en-2-one and 1.993 g (11.036 mmol) of (3,4-difluorophenyl) hydrazine hydrochloride were suspended in 45 ml of ethanol and heated at the boil for 6 hours, with an initial steady evolution of gas. After one hour, the solid went into solution. After cooling, the solvent was removed under reduced pressure and the residue was dissolved in ethyl acetate and saturated sodium bicarbonate solution (evolution of gas!). The phases were separated, the organic phase was dried over magnesium sulfate, the solvent was removed under reduced pressure and the crude product was purified by chromatography (ethyl acetate:n-heptane 1:4). This gave 1.1 g (47%) of the desired product. $^1$H-NMR (400 MHz, CDCl$_3$ δ, ppm) 7.86 (d, 1H); 7.67 (m, 1H); 7.46 (m, 1H); 7.28 (m, 1H); 7.00 (d, 1H); 4.45 (q, 2H); 1.43 (t, 3H)

A1 2) Ethyl 4-bromo-1-(3,4-difluorophenyl)-1H-pyrazole-3-carboxylate 1.1 g (4.36 mmol) of ethyl 1-(3,4-difluorophenyl)-1H-pyrazole-3-carboxylate were suspended in 15 ml of acetic acid, and 0.246 ml (4.797 mmol) of bromine was added. The suspension was heated at 50° C. for 2 h and then at 80° C. for 8 h. After cooling, the solution was poured into 100 ml of water and the resulting precipitate was filtered off with suction and air-dried. This gave 1.13 g (78%) of the desired product. $^1$H-NMR (400 MHz, CDCl$_3$ δ, ppm) 7.94 (s, 1H); 7.63 (m, 1H); 7.42 (m, 1H); 7.28 (m, 1H); 4.47 (q, 2H); 1.45 (t, 3H)

A1 3) Ethyl 1-(3,4-difluorophenyl)-4-[3-(ethoxycarbonyl) phenyl]-1H-pyrazole-3-carboxylate 180 mg (0.54 mmol) of ethyl 4-bromo-1-(3,4-difluorophenyl)-1H-pyrazole-3-carboxylate, 156.7 mg (0.59 mmol) of methyl 3-(4,4,5,5-tetramethyl-1,3,2-dioxaborolan-2-yl)benzoate, 158 mg (1.14 mmol) of potassium carbonate, 5.07 mg (0.011 mmol) of 2,2-dicyclohexylphosphino-2",6"-diisopropoxybiphenyl and 1.22 mg (0.005 mmol) of palladium (II) acetate were suspended in 5 ml of ethanol and heated at the boil for 4 h. After cooling to room temperature, the solvent was removed under reduced pressure, the residue was dissolved in water and dichloromethane, the phases were separated and the organic phase was dried over magnesium sulfate. The crude product was purified by chromatography (ethyl acetate:n-heptane 1:4). This gave 84 mg (37%) of the desired product. $^1$H-NMR (400 MHz, CDCl$_3$ δ, ppm) 8.15 (s, 1H); 8.05 (d, 1H); 7.96 (s, 1H); 7.74-7.69 (m, 2H); 7.53-7.47 (m, 2H); 7.28 (m, 1H); 4.48-4.34 (m, 4H); 1.43 (t, 3H); 1.29 (t, 3H)

Example A2

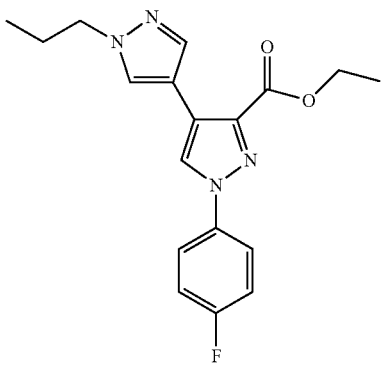 [SMILES: CCCn1cc(-c2cn(-c3ccc(F)cc3)nc2C(=O)OCC)cn1]

Ethyl 1-(4-fluorophenyl)-1-propyl-1H, 1'H-4,4'-bipyrazole-3-carboxylate

A2 1) Ethyl 1-(4-fluorophenyl)-1-propyl-1H, 1'H-4,4'-bipyrazole-3-carboxylate 200 mg (0.639 mmol) of ethyl 4-bromo-1-(4-fluorophenyl)-1H-pyrazole-3-carboxylate, 157 mg (0.766 mmol) of 1-propyl-4-(4,4,5,5-tetramethyl-1,3,2-dioxaborolan-2-yl)-1H-pyrazole, 31 mg (0.045 mmol) of dichlorobis(triphenylphosphine)palladium(II) and 265 mg (1.916 mmol) were suspended in 2.5 ml of 1,2-dimethoxyethane, 0.4 ml of ethanol and 0.5 ml of water. The suspension was heated in a closed vessel in a Biotage Initiator Sixty© microwave at 145° C. for 45 min. After cooling, the reaction mixture was diluted with water and ethyl acetate. The organic phase was dried over magnesium sulfate and the solvent was removed under reduced pressure. The crude product was purified by chromatography (ethyl acetate:n-heptane 1:4). This gave 56 mg (25%) of the desired product. $^1$H-NMR (400 MHz, CDCl$_3$ δ, ppm): 8.08 (s, 1H); 7.99 (s, 1H); 7.75-7.71 (m, 3H); 7.17 (t, 2H); 4.46 (q, 2H); 4.12 (t, 2H); 1.98-1.90 (m, 2H); 1.43 (t, 3H); 0.95 (t, 3H)

Example A3

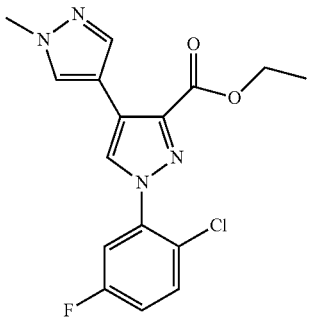 [SMILES: CCOC(=O)c1nn(-c2cc(F)ccc2Cl)cc1-c1cnn(C)c1]

A3 1) Ethyl 1-(5-chloro-2-fluorophenyl)-1'-methyl-1H, 1'H-4,4'-bipyrazole-3-carboxylate 500 mg (1.439 mmol) of ethyl 4-bromo-1-(5-chloro-2-fluorophenyl)-1H-pyrazole-3-carboxylate, 329.0 mg (1.58 mmol) of 1-methyl-4-(4,4,5,5-tetramethyl-1,3,2-dioxaborolan-2-yl)-1H-pyrazole, 604 mg (7.19 mmol) of sodium bicarbonate, 34 mg (0.07 mmol) of 2,2-dicyclohexylphosphino-2', 6'-diisopropoxybiphenyl and 8 mg (0.036 mmol) of palladium (II)acetate were suspended in 5 ml of ethanol and heated at the boil for 6 h. After cooling to room temperature, the solvent was removed under reduced pressure, the residue was dissolved in water and dichloromethane, the phases were separated and the organic phase was dried over magnesium sulfate. The crude product was purified by chromatography (gradient ethyl acetate:n-heptane 10:90 to 100:0). This gave 210 mg (40%) of the desired product. $^1$H-NMR (400 MHz, CDCl$_3$ δ, ppm) 8.11 (s, 1H); 8.02 (m, 2H); 7.72 (s, 1H); 7.32 (m, 1H); 7.23 (m, 2H); 4.47 (m, 2H); 3.98 (s, 3H); 1.45 (t, 3H)

In the Table:
Bu=butyl Et=ethyl
Me=methyl Ph=phenyl
Pr=propyl
i=iso s=secondary
t=tertiary c=cyclo
This applies correspondingly to composite terms such as
iPr=isopropyl
iBu=isobutyl
sBu=sec-butyl
tBu=tert-butyl
cPr=cyclopropyl
cPentyl=cyclopentyl
cHexyl=cyclohexyl If, in the tables, an alkyl radical is listed without further specification, the alkyl radical is a straight-chain alkyl radical, i.e., for example, Bu=n-Bu=n-butyl.

In the table, the number indices in the formulae are not subscript but arranged in the same line height and font size as the atom symbols.

For example, the formula CF3 in the table corresponds to the formula CF$_3$ according to the customary notation with subscript index, or the formula CH2CH(CH2CH3)2 corresponds to the formula CH$_2$CH(CH$_2$CH$_3$)$_2$ with subscript indices.

For example, the formula 2,3-diF in the table corresponds to the formula 2,3-difluoro and the formula 2,5-diCl in the table corresponds to 2,5-dichloro.

TABLE 1

Compounds of the formula (I)

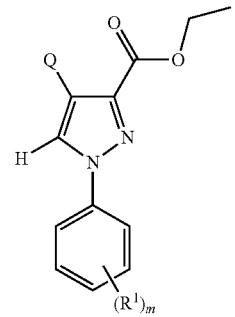

(I)

where the definition in table form below of the radical "Q" corresponds to the definition of the radicals "Q-1" to "Q-47" mentioned above as being very particularly preferred

| Ex. | Q | (R$^1$)$_m$ |
|---|---|---|
| 1-1 | Q-1 | 2-F |
| 1-2 | Q-1 | 3-F |
| 1-3 | Q-1 | 4-F |
| 1-4 | Q-1 | 2,3-diF |
| 1-5 | Q-1 | 2,4-diF |
| 1-6 | Q-1 | 2,5-diF |

TABLE 1-continued

Compounds of the formula (I)

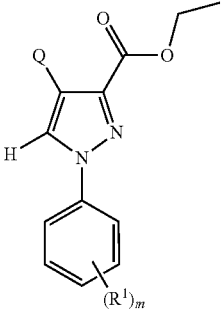

where the definition in table form below of the radical "Q" corresponds to the definition of the radicals "Q-1" to "Q-47" mentioned above as being very particularly preferred

| Ex. | Q | (R¹)ₘ |
|---|---|---|
| 1-7 | Q-1 | 2,6-diF |
| 1-8 | Q-1 | 3,4-diF |
| 1-9 | Q-1 | 3,5-diF |
| 1-10 | Q-1 | 2-F, 4-Cl |
| 1-11 | Q-1 | 2-F, 5-Cl |
| 1-12 | Q-1 | 3-F, 5-Cl |
| 1-13 | Q-1 | 2-Cl |
| 1-14 | Q-1 | 3-Cl |
| 1-15 | Q-1 | 4-Cl |
| 1-16 | Q-1 | 2,3-diCl |
| 1-17 | Q-1 | 2,4-diCl |
| 1-18 | Q-1 | 2,5-diCl |
| 1-19 | Q-1 | 2,6-diCl |
| 1-20 | Q-1 | 3,4-diCl |
| 1-21 | Q-1 | 3,5-diCl |
| 1-22 | Q-1 | 2-Cl, 4-F |
| 1-23 | Q-1 | 2-Cl, 5-F |
| 1-24 | Q-1 | 2-CF3 |
| 1-25 | Q-1 | 3-CF3 |
| 1-26 | Q-1 | 4-CF3 |
| 1-27 | Q-1 | 2-OCF3 |
| 1-28 | Q-1 | 3-OCF3 |
| 1-29 | Q-1 | 4-OCF3 |
| 1-30 | Q-1 | 2-Me |
| 1-31 | Q-1 | 3-Me |
| 1-32 | Q-1 | 4-Me |
| 1-33 | Q-1 | 2-OMe |
| 1-34 | Q-1 | 3-OMe |
| 1-35 | Q-1 | 4-OMe |
| 1-36 | Q-2 | 2-F |
| 1-37 | Q-2 | 3-F |
| 1-38 | Q-2 | 4-F |
| 1-39 | Q-2 | 2,3-diF |
| 1-40 | Q-2 | 2,4-diF |
| 1-41 | Q-2 | 2,5-diF |
| 1-42 | Q-2 | 2,6-diF |
| 1-43 | Q-2 | 3,4-diF |
| 1-44 | Q-2 | 3,5-diF |
| 1-45 | Q-2 | 2-F, 4-Cl |
| 1-46 | Q-2 | 2-F, 5-Cl |
| 1-47 | Q-2 | 3-F, 5-Cl |
| 1-48 | Q-2 | 2-Cl |
| 1-49 | Q-2 | 3-Cl |
| 1-50 | Q-2 | 4-Cl |
| 1-51 | Q-2 | 2,3-diCl |
| 1-52 | Q-2 | 2,4-diCl |
| 1-53 | Q-2 | 2,5-diCl |
| 1-54 | Q-2 | 2,6-diCl |
| 1-55 | Q-2 | 3,4-diCl |
| 1-56 | Q-2 | 3,5-diCl |
| 1-57 | Q-2 | 2-Cl, 4-F |
| 1-58 | Q-2 | 2-Cl, 5-F |
| 1-59 | Q-2 | 2-CF3 |
| 1-60 | Q-2 | 3-CF3 |
| 1-61 | Q-2 | 4-CF3 |
| 1-62 | Q-2 | 2-OCF3 |
| 1-63 | Q-2 | 3-OCF3 |
| 1-64 | Q-2 | 4-OCF3 |
| 1-65 | Q-2 | 2-Me |
| 1-66 | Q-2 | 3-Me |
| 1-67 | Q-2 | 4-Me |
| 1-68 | Q-2 | 2-OMe |
| 1-69 | Q-2 | 3-OMe |
| 1-70 | Q-2 | 4-OMe |
| 1-71 | Q-3 | 2-F |
| 1-72 | Q-3 | 3-F |
| 1-73 | Q-3 | 4-F |
| 1-74 | Q-3 | 2,3-diF |
| 1-75 | Q-3 | 2,4-diF |
| 1-76 | Q-3 | 2,5-diF |
| 1-77 | Q-3 | 2,6-diF |
| 1-78 | Q-3 | 3,4-diF |
| 1-79 | Q-3 | 3,5-diF |
| 1-80 | Q-3 | 2-F, 4-Cl |
| 1-81 | Q-3 | 2-F, 5-Cl |
| 1-82 | Q-3 | 3-F, 5-Cl |
| 1-83 | Q-3 | 2-Cl |
| 1-84 | Q-3 | 3-Cl |
| 1-85 | Q-3 | 4-Cl |
| 1-86 | Q-3 | 2,3-diCl |
| 1-87 | Q-3 | 2,4-diCl |
| 1-88 | Q-3 | 2,5-diCl |
| 1-89 | Q-3 | 2,6-diCl |
| 1-90 | Q-3 | 3,4-diCl |
| 1-91 | Q-3 | 3,5-diCl |
| 1-92 | Q-3 | 2-Cl, 4-F |
| 1-93 | Q-3 | 2-Cl, 5-F |
| 1-94 | Q-3 | 2-CF3 |
| 1-95 | Q-3 | 3-CF3 |
| 1-96 | Q-3 | 4-CF3 |
| 1-97 | Q-3 | 2-OCF3 |
| 1-98 | Q-3 | 3-OCF3 |
| 1-99 | Q-3 | 4-OCF3 |
| 1-100 | Q-3 | 2-Me |
| 1-101 | Q-3 | 3-Me |
| 1-102 | Q-3 | 4-Me |
| 1-103 | Q-3 | 2-OMe |
| 1-104 | Q-3 | 3-OMe |
| 1-105 | Q-3 | 4-OMe |
| 1-106 | Q-4 | 2-F |
| 1-107 | Q-4 | 3-F |
| 1-108 | Q-4 | 4-F |
| 1-109 | Q-4 | 2,3-diF |
| 1-110 | Q-4 | 2,4-diF |
| 1-111 | Q-4 | 2,5-diF |
| 1-112 | Q-4 | 2,6-diF |
| 1-113 | Q-4 | 3,4-diF |
| 1-114 | Q-4 | 3,5-diF |
| 1-115 | Q-4 | 2-F, 4-Cl |
| 1-116 | Q-4 | 2-F, 5-Cl |
| 1-117 | Q-4 | 3-F, 5-Cl |
| 1-118 | Q-4 | 2-Cl |

TABLE 1-continued

Compounds of the formula (I)

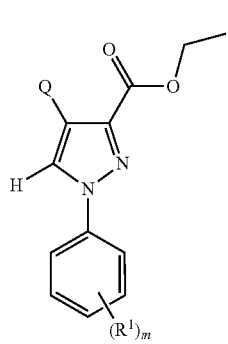

where the definition in table form below of the radical "Q" corresponds to the definition of the radicals "Q-1" to "Q-47" mentioned above as being very particularly preferred

| Ex.   | Q   | (R¹)$_m$   |
|-------|-----|------------|
| 1-119 | Q-4 | 3-Cl       |
| 1-120 | Q-4 | 4-Cl       |
| 1-121 | Q-4 | 2,3-diCl   |
| 1-122 | Q-4 | 2,4-diCl   |
| 1-123 | Q-4 | 2,5-diCl   |
| 1-124 | Q-4 | 2,6-diCl   |
| 1-125 | Q-4 | 3,4-diCl   |
| 1-126 | Q-4 | 3,5-diCl   |
| 1-127 | Q-4 | 2-Cl, 4-F  |
| 1-128 | Q-4 | 2-Cl, 5-F  |
| 1-129 | Q-4 | 2-CF3      |
| 1-130 | Q-4 | 3-CF3      |
| 1-131 | Q-4 | 4-CF3      |
| 1-132 | Q-4 | 2-OCF3     |
| 1-133 | Q-4 | 3-OCF3     |
| 1-134 | Q-4 | 4-OCF3     |
| 1-135 | Q-4 | 2-Me       |
| 1-136 | Q-4 | 3-Me       |
| 1-137 | Q-4 | 4-Me       |
| 1-138 | Q-4 | 2-OMe      |
| 1-139 | Q-4 | 3-OMe      |
| 1-140 | Q-4 | 4-OMe      |
| 1-141 | Q-5 | 2-F        |
| 1-142 | Q-5 | 3-F        |
| 1-143 | Q-5 | 4-F        |
| 1-144 | Q-5 | 2,3-diF    |
| 1-145 | Q-5 | 2,4-diF    |
| 1-146 | Q-5 | 2,5-diF    |
| 1-147 | Q-5 | 2,6-diF    |
| 1-148 | Q-5 | 3,4-diF    |
| 1-149 | Q-5 | 3,5-diF    |
| 1-150 | Q-5 | 2-F, 4-Cl  |
| 1-151 | Q-5 | 2-F, 5-Cl  |
| 1-152 | Q-5 | 3-F, 5-Cl  |
| 1-153 | Q-5 | 2-Cl       |
| 1-154 | Q-5 | 3-Cl       |
| 1-155 | Q-5 | 4-Cl       |
| 1-156 | Q-5 | 2,3-diCl   |
| 1-157 | Q-5 | 2,4-diCl   |
| 1-158 | Q-5 | 2,5-diCl   |
| 1-159 | Q-5 | 2,6-diCl   |
| 1-160 | Q-5 | 3,4-diCl   |
| 1-161 | Q-5 | 3,5-diCl   |
| 1-162 | Q-5 | 2-Cl, 4-F  |
| 1-163 | Q-5 | 2-Cl, 5-F  |
| 1-164 | Q-5 | 2-CF3      |
| 1-165 | Q-5 | 3-CF3      |
| 1-166 | Q-5 | 4-CF3      |
| 1-167 | Q-5 | 2-OCF3     |
| 1-168 | Q-5 | 3-OCF3     |
| 1-169 | Q-5 | 4-OCF3     |
| 1-170 | Q-5 | 2-Me       |
| 1-171 | Q-5 | 3-Me       |
| 1-172 | Q-5 | 4-Me       |
| 1-173 | Q-5 | 2-OMe      |
| 1-174 | Q-5 | 3-OMe      |

TABLE 1-continued

Compounds of the formula (I)

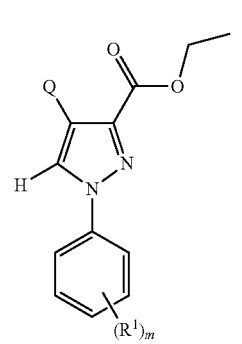

where the definition in table form below of the radical "Q" corresponds to the definition of the radicals "Q-1" to "Q-47" mentioned above as being very particularly preferred

| Ex.   | Q   | (R¹)$_m$   |
|-------|-----|------------|
| 1-175 | Q-5 | 4-OMe      |
| 1-176 | Q-6 | 2-F        |
| 1-177 | Q-6 | 3-F        |
| 1-178 | Q-6 | 4-F        |
| 1-179 | Q-6 | 2,3-diF    |
| 1-180 | Q-6 | 2,4-diF    |
| 1-181 | Q-6 | 2,5-diF    |
| 1-182 | Q-6 | 2,6-diF    |
| 1-183 | Q-6 | 3,4-diF    |
| 1-184 | Q-6 | 3,5-diF    |
| 1-185 | Q-6 | 2-F, 4-Cl  |
| 1-186 | Q-6 | 2-F, 5-Cl  |
| 1-187 | Q-6 | 3-F, 5-Cl  |
| 1-188 | Q-6 | 2-Cl       |
| 1-189 | Q-6 | 3-Cl       |
| 1-190 | Q-6 | 4-Cl       |
| 1-191 | Q-6 | 2,3-diCl   |
| 1-192 | Q-6 | 2,4-diCl   |
| 1-193 | Q-6 | 2,5-diCl   |
| 1-194 | Q-6 | 2,6-diCl   |
| 1-195 | Q-6 | 3,4-diCl   |
| 1-196 | Q-6 | 3,5-diCl   |
| 1-197 | Q-6 | 2-Cl, 4-F  |
| 1-198 | Q-6 | 2-Cl, 5-F  |
| 1-199 | Q-6 | 2-CF3      |
| 1-200 | Q-6 | 3-CF3      |
| 1-201 | Q-6 | 4-CF3      |
| 1-202 | Q-6 | 2-OCF3     |
| 1-203 | Q-6 | 3-OCF3     |
| 1-204 | Q-6 | 4-OCF3     |
| 1-205 | Q-6 | 2-Me       |
| 1-206 | Q-6 | 3-Me       |
| 1-207 | Q-6 | 4-Me       |
| 1-208 | Q-6 | 2-OMe      |
| 1-209 | Q-6 | 3-OMe      |
| 1-210 | Q-6 | 4-OMe      |
| 1-211 | Q-7 | 2-F        |
| 1-212 | Q-7 | 3-F        |
| 1-213 | Q-7 | 4-F        |
| 1-214 | Q-7 | 2,3-diF    |
| 1-215 | Q-7 | 2,4-diF    |
| 1-216 | Q-7 | 2,5-diF    |
| 1-217 | Q-7 | 2,6-diF    |
| 1-218 | Q-7 | 3,4-diF    |
| 1-219 | Q-7 | 3,5-diF    |
| 1-220 | Q-7 | 2-F, 4-Cl  |
| 1-221 | Q-7 | 2-F, 5-Cl  |
| 1-222 | Q-7 | 3-F, 5-Cl  |
| 1-223 | Q-7 | 2-Cl       |
| 1-224 | Q-7 | 3-Cl       |
| 1-225 | Q-7 | 4-Cl       |
| 1-226 | Q-7 | 2,3-diCl   |
| 1-227 | Q-7 | 2,4-diCl   |
| 1-228 | Q-7 | 2,5-diCl   |
| 1-229 | Q-7 | 2,6-diCl   |
| 1-230 | Q-7 | 3,4-diCl   |

TABLE 1-continued

Compounds of the formula (I)

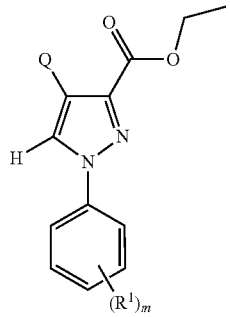

where the definition in table form below of the radical "Q" corresponds to the definition of the radicals "Q-1" to "Q-47" mentioned above as being very particularly preferred

| Ex. | Q | (R¹)$_m$ |
|---|---|---|
| 1-231 | Q-7 | 3,5-diCl |
| 1-232 | Q-7 | 2-Cl, 4-F |
| 1-233 | Q-7 | 2-Cl, 5-F |
| 1-234 | Q-7 | 2-CF3 |
| 1-235 | Q-7 | 3-CF3 |
| 1-236 | Q-7 | 4-CF3 |
| 1-237 | Q-7 | 2-OCF3 |
| 1-238 | Q-7 | 3-OCF3 |
| 1-239 | Q-7 | 4-OCF3 |
| 1-240 | Q-7 | 2-Me |
| 1-241 | Q-7 | 3-Me |
| 1-242 | Q-7 | 4-Me |
| 1-243 | Q-7 | 2-OMe |
| 1-244 | Q-7 | 3-OMe |
| 1-245 | Q-7 | 4-OMe |
| 1-246 | Q-8 | 2-F |
| 1-247 | Q-8 | 3-F |
| 1-248 | Q-8 | 4-F |
| 1-249 | Q-8 | 2,3-diF |
| 1-250 | Q-8 | 2,4-diF |
| 1-251 | Q-8 | 2,5-diF |
| 1-252 | Q-8 | 2,6-diF |
| 1-253 | Q-8 | 3,4-diF |
| 1-254 | Q-8 | 3,5-diF |
| 1-255 | Q-8 | 2-F, 4-Cl |
| 1-256 | Q-8 | 2-F, 5-Cl |
| 1-257 | Q-8 | 3-F, 5-Cl |
| 1-258 | Q-8 | 2-Cl |
| 1-259 | Q-8 | 3-Cl |
| 1-260 | Q-8 | 4-Cl |
| 1-261 | Q-8 | 2,3-diCl |
| 1-262 | Q-8 | 2,4-diCl |
| 1-263 | Q-8 | 2,5-diCl |
| 1-264 | Q-8 | 2,6-diCl |
| 1-265 | Q-8 | 3,4-diCl |
| 1-266 | Q-8 | 3,5-diCl |
| 1-267 | Q-8 | 2-Cl, 4-F |
| 1-268 | Q-8 | 2-Cl, 5-F |
| 1-269 | Q-8 | 2-CF3 |
| 1-270 | Q-8 | 3-CF3 |
| 1-271 | Q-8 | 4-CF3 |
| 1-272 | Q-8 | 2-OCF3 |
| 1-273 | Q-8 | 3-OCF3 |
| 1-274 | Q-8 | 4-OCF3 |
| 1-275 | Q-8 | 2-Me |
| 1-276 | Q-8 | 3-Me |
| 1-277 | Q-8 | 4-Me |
| 1-278 | Q-8 | 2-OMe |
| 1-279 | Q-8 | 3-OMe |
| 1-280 | Q-8 | 4-OMe |
| 1-281 | Q-9 | 2-F |
| 1-282 | Q-9 | 3-F |
| 1-283 | Q-9 | 4-F |
| 1-284 | Q-9 | 2,3-diF |
| 1-285 | Q-9 | 2,4-diF |
| 1-286 | Q-9 | 2,5-diF |

TABLE 1-continued

Compounds of the formula (I)

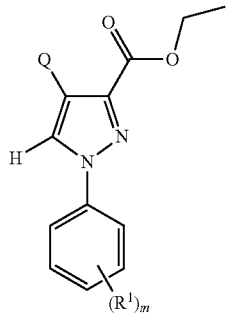

where the definition in table form below of the radical "Q" corresponds to the definition of the radicals "Q-1" to "Q-47" mentioned above as being very particularly preferred

| Ex. | Q | (R¹)$_m$ |
|---|---|---|
| 1-287 | Q-9 | 2,6-diF |
| 1-288 | Q-9 | 3,4-diF |
| 1-289 | Q-9 | 3,5-diF |
| 1-290 | Q-9 | 2-F, 4-Cl |
| 1-291 | Q-9 | 2-F, 5-Cl |
| 1-292 | Q-9 | 3-F, 5-Cl |
| 1-293 | Q-9 | 2-Cl |
| 1-294 | Q-9 | 3-Cl |
| 1-295 | Q-9 | 4-Cl |
| 1-296 | Q-9 | 2,3-diCl |
| 1-297 | Q-9 | 2,4-diCl |
| 1-298 | Q-9 | 2,5-diCl |
| 1-299 | Q-9 | 2,6-diCl |
| 1-300 | Q-9 | 3,4-diCl |
| 1-301 | Q-9 | 3,5-diCl |
| 1-302 | Q-9 | 2-Cl, 4-F |
| 1-303 | Q-9 | 2-Cl, 5-F |
| 1-304 | Q-9 | 2-CF3 |
| 1-305 | Q-9 | 3-CF3 |
| 1-306 | Q-9 | 4-CF3 |
| 1-307 | Q-9 | 2-OCF3 |
| 1-308 | Q-9 | 3-OCF3 |
| 1-309 | Q-9 | 4-OCF3 |
| 1-310 | Q-9 | 2-Me |
| 1-311 | Q-9 | 3-Me |
| 1-312 | Q-9 | 4-Me |
| 1-313 | Q-9 | 2-OMe |
| 1-314 | Q-9 | 3-OMe |
| 1-315 | Q-9 | 4-OMe |
| 1-316 | Q-10 | 2-F |
| 1-317 | Q-10 | 3-F |
| 1-318 | Q-10 | 4-F |
| 1-319 | Q-10 | 2,3-diF |
| 1-320 | Q-10 | 2,4-diF |
| 1-321 | Q-10 | 2,5-diF |
| 1-322 | Q-10 | 2,6-diF |
| 1-323 | Q-10 | 3,4-diF |
| 1-324 | Q-10 | 3,5-diF |
| 1-325 | Q-10 | 2-F, 4-Cl |
| 1-326 | Q-10 | 2-F, 5-Cl |
| 1-327 | Q-10 | 3-F, 5-Cl |
| 1-328 | Q-10 | 2-Cl |
| 1-329 | Q-10 | 3-Cl |
| 1-330 | Q-10 | 4-Cl |
| 1-331 | Q-10 | 2,3-diCl |
| 1-332 | Q-10 | 2,4-diCl |
| 1-333 | Q-10 | 2,5-diCl |
| 1-334 | Q-10 | 2,6-diCl |
| 1-335 | Q-10 | 3,4-diCl |
| 1-336 | Q-10 | 3,5-diCl |
| 1-337 | Q-10 | 2-Cl, 4-F |
| 1-338 | Q-10 | 2-Cl, 5-F |
| 1-339 | Q-10 | 2-CF3 |
| 1-340 | Q-10 | 3-CF3 |
| 1-341 | Q-10 | 4-CF3 |
| 1-342 | Q-10 | 2-OCF3 |

TABLE 1-continued

Compounds of the formula (I)

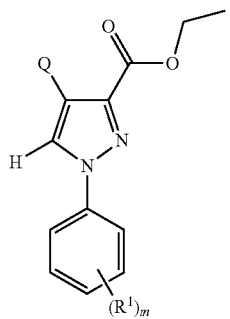

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-343 | Q-10 | 3-OCF3 |
| 1-344 | Q-10 | 4-OCF3 |
| 1-345 | Q-10 | 2-Me |
| 1-346 | Q-10 | 3-Me |
| 1-347 | Q-10 | 4-Me |
| 1-348 | Q-10 | 2-OMe |
| 1-349 | Q-10 | 3-OMe |
| 1-350 | Q-10 | 4-OMe |
| 1-351 | Q-11 | 2-F |
| 1-352 | Q-11 | 3-F |
| 1-353 | Q-11 | 4-F |
| 1-354 | Q-11 | 2,3-diF |
| 1-355 | Q-11 | 2,4-diF |
| 1-356 | Q-11 | 2,5-diF |
| 1-357 | Q-11 | 2,6-diF |
| 1-358 | Q-11 | 3,4-diF |
| 1-359 | Q-11 | 3,5-diF |
| 1-360 | Q-11 | 2-F, 4-Cl |
| 1-361 | Q-11 | 2-F, 5-Cl |
| 1-362 | Q-11 | 3-F, 5-Cl |
| 1-363 | Q-11 | 2-Cl |
| 1-364 | Q-11 | 3-Cl |
| 1-365 | Q-11 | 4-Cl |
| 1-366 | Q-11 | 2,3-diCl |
| 1-367 | Q-11 | 2,4-diCl |
| 1-368 | Q-11 | 2,5-diCl |
| 1-369 | Q-11 | 2,6-diCl |
| 1-370 | Q-11 | 3,4-diCl |
| 1-371 | Q-11 | 3,5-diCl |
| 1-372 | Q-11 | 2-Cl, 4-F |
| 1-373 | Q-11 | 2-Cl, 5-F |
| 1-374 | Q-11 | 2-CF3 |
| 1-375 | Q-11 | 3-CF3 |
| 1-376 | Q-11 | 4-CF3 |
| 1-377 | Q-11 | 2-OCF3 |
| 1-378 | Q-11 | 3-OCF3 |
| 1-379 | Q-11 | 4-OCF3 |
| 1-380 | Q-11 | 2-Me |
| 1-381 | Q-11 | 3-Me |
| 1-382 | Q-11 | 4-Me |
| 1-383 | Q-11 | 2-OMe |
| 1-384 | Q-11 | 3-OMe |
| 1-385 | Q-11 | 4-OMe |
| 1-386 | Q-12 | 2-F |
| 1-387 | Q-12 | 3-F |
| 1-388 | Q-12 | 4-F |
| 1-389 | Q-12 | 2,3-diF |
| 1-390 | Q-12 | 2,4-diF |
| 1-391 | Q-12 | 2,5-diF |
| 1-392 | Q-12 | 2,6-diF |
| 1-393 | Q-12 | 3,4-diF |
| 1-394 | Q-12 | 3,5-diF |
| 1-395 | Q-12 | 2-F, 4-Cl |
| 1-396 | Q-12 | 2-F, 5-Cl |
| 1-397 | Q-12 | 3-F, 5-Cl |
| 1-398 | Q-12 | 2-Cl |
| 1-399 | Q-12 | 3-Cl |
| 1-400 | Q-12 | 4-Cl |
| 1-401 | Q-12 | 2,3-diCl |
| 1-402 | Q-12 | 2,4-diCl |
| 1-403 | Q-12 | 2,5-diCl |
| 1-404 | Q-12 | 2,6-diCl |
| 1-405 | Q-12 | 3,4-diCl |
| 1-406 | Q-12 | 3,5-diCl |
| 1-407 | Q-12 | 2-Cl, 4-F |
| 1-408 | Q-12 | 2-Cl, 5-F |
| 1-409 | Q-12 | 2-CF3 |
| 1-410 | Q-12 | 3-CF3 |
| 1-411 | Q-12 | 4-CF3 |
| 1-412 | Q-12 | 2-OCF3 |
| 1-413 | Q-12 | 3-OCF3 |
| 1-414 | Q-12 | 4-OCF3 |
| 1-415 | Q-13 | 2-Me |
| 1-416 | Q-13 | 3-Me |
| 1-417 | Q-13 | 4-Me |
| 1-418 | Q-13 | 2-OMe |
| 1-419 | Q-13 | 3-OMe |
| 1-420 | Q-13 | 4-OMe |
| 1-421 | Q-13 | 2-F |
| 1-422 | Q-13 | 3-F |
| 1-423 | Q-13 | 4-F |
| 1-424 | Q-13 | 2,3-diF |
| 1-425 | Q-13 | 2,4-diF |
| 1-426 | Q-13 | 2,5-diF |
| 1-427 | Q-13 | 2,6-diF |
| 1-428 | Q-13 | 3,4-diF |
| 1-429 | Q-13 | 3,5-diF |
| 1-430 | Q-13 | 2-F, 4-Cl |
| 1-431 | Q-13 | 2-F, 5-Cl |
| 1-432 | Q-13 | 3-F, 5-Cl |
| 1-433 | Q-13 | 2-Cl |
| 1-434 | Q-13 | 3-Cl |
| 1-435 | Q-13 | 4-Cl |
| 1-436 | Q-13 | 2,3-diCl |
| 1-437 | Q-13 | 2,4-diCl |
| 1-438 | Q-13 | 2,5-diCl |
| 1-439 | Q-13 | 2,6-diCl |
| 1-440 | Q-13 | 3,4-diCl |
| 1-441 | Q-13 | 3,5-diCl |
| 1-442 | Q-13 | 2-Cl, 4-F |
| 1-443 | Q-13 | 2-Cl, 5-F |
| 1-444 | Q-13 | 2-CF3 |
| 1-445 | Q-13 | 3-CF3 |
| 1-446 | Q-13 | 4-CF3 |
| 1-447 | Q-13 | 2-OCF3 |
| 1-448 | Q-13 | 3-OCF3 |
| 1-449 | Q-13 | 4-OCF3 |
| 1-450 | Q-13 | 2-Me |
| 1-451 | Q-13 | 3-Me |
| 1-452 | Q-13 | 4-Me |
| 1-453 | Q-13 | 2-OMe |
| 1-454 | Q-13 | 3OMe |

TABLE 1-continued

Compounds of the formula (I)

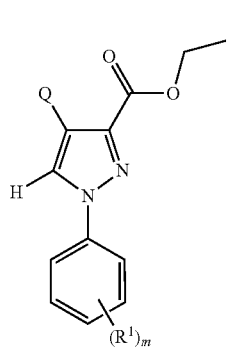

where the definition in table form below of the radical "Q" corresponds to the definition of the radicals "Q-1" to "Q-47" mentioned above as being very particularly preferred

| Ex. | Q | (R¹)$_m$ |
|---|---|---|
| 1-455 | Q-13 | 4-OMe |
| 1-456 | Q-14 | 2-F |
| 1-457 | Q-14 | 3-F |
| 1-458 | Q-14 | 4-F |
| 1-459 | Q-14 | 2,3-diF |
| 1-460 | Q-14 | 2,4-diF |
| 1-461 | Q-14 | 2,5-diF |
| 1-462 | Q-14 | 2,6-diF |
| 1-463 | Q-14 | 3,4-diF |
| 1-464 | Q-14 | 3,5-diF |
| 1-465 | Q-14 | 2-F, 4-Cl |
| 1-466 | Q-14 | 2-F, 5-Cl |
| 1-467 | Q-14 | 3-F, 5-Cl |
| 1-468 | Q-14 | 2-Cl |
| 1-469 | Q-14 | 3-Cl |
| 1-470 | Q-14 | 4-Cl |
| 1-471 | Q-14 | 2,3-diCl |
| 1-472 | Q-14 | 2,4-diCl |
| 1-473 | Q-14 | 2,5-diCl |
| 1-474 | Q-14 | 2,6-diCl |
| 1-475 | Q-14 | 3,4-diCl |
| 1-476 | Q-14 | 3,5-diCl |
| 1-477 | Q-14 | 2-Cl, 4-F |
| 1-478 | Q-14 | 2-Cl, 5-F |
| 1-479 | Q-14 | 2-CF3 |
| 1-480 | Q-14 | 3-CF3 |
| 1-481 | Q-14 | 4-CF3 |
| 1-482 | Q-14 | 2-OCF3 |
| 1-483 | Q-14 | 3-OCF3 |
| 1-484 | Q-14 | 4-OCF3 |
| 1-485 | Q-14 | 2-Me |
| 1-486 | Q-14 | 3-Me |
| 1-487 | Q-14 | 4-Me |
| 1-488 | Q-14 | 2-OMe |
| 1-489 | Q-14 | 3-OMe |
| 1-490 | Q-14 | 4-OMe |
| 1-491 | Q-15 | 2-F |
| 1-492 | Q-15 | 3-F |
| 1-493 | Q-15 | 4-F |
| 1-494 | Q-15 | 2,3-diF |
| 1-495 | Q-15 | 2,4-diF |
| 1-496 | Q-15 | 2,5-diF |
| 1-497 | Q-15 | 2,6-diF |
| 1-498 | Q-15 | 3,4-diF |
| 1-499 | Q-15 | 3,5-diF |
| 1-500 | Q-15 | 2-F, 4-Cl |
| 1-501 | Q-15 | 2-F, 5-Cl |
| 1-502 | Q-15 | 3-F, 5-Cl |
| 1-503 | Q-15 | 2-Cl |
| 1-504 | Q-15 | 3-Cl |
| 1-505 | Q-15 | 4-Cl |
| 1-506 | Q-15 | 2,3-diCl |
| 1-507 | Q-15 | 2,4-diCl |
| 1-508 | Q-15 | 2,5-diCl |
| 1-509 | Q-15 | 2,6-diCl |
| 1-510 | Q-15 | 3,4-diCl |
| 1-511 | Q-15 | 3,5-diCl |
| 1-512 | Q-15 | 2-Cl, 4-F |
| 1-513 | Q-15 | 2-Cl, 5-F |
| 1-514 | Q-15 | 2-CF3 |
| 1-515 | Q-15 | 3-CF3 |
| 1-516 | Q-15 | 4-CF3 |
| 1-517 | Q-15 | 2-OCF3 |
| 1-518 | Q-15 | 3-OCF3 |
| 1-519 | Q-15 | 4-OCF3 |
| 1-520 | Q-15 | 2-Me |
| 1-521 | Q-15 | 3-Me |
| 1-522 | Q-15 | 4-Me |
| 1-523 | Q-15 | 2-OMe |
| 1-524 | Q-15 | 3-OMe |
| 1-525 | Q-15 | 4-OMe |
| 1-526 | Q-16 | 2-F |
| 1-527 | Q-16 | 3-F |
| 1-528 | Q-16 | 4-F |
| 1-529 | Q-16 | 2,3-diF |
| 1-530 | Q-16 | 2,4-diF |
| 1-531 | Q-16 | 2,5-diF |
| 1-532 | Q-16 | 2,6-diF |
| 1-533 | Q-16 | 3,4-diF |
| 1-534 | Q-16 | 3,5-diF |
| 1-535 | Q-16 | 2-F, 4-Cl |
| 1-536 | Q-16 | 2-F, 5-Cl |
| 1-537 | Q-16 | 3-F, 5-Cl |
| 1-538 | Q-16 | 2-Cl |
| 1-539 | Q-16 | 3-Cl |
| 1-540 | Q-16 | 4-Cl |
| 1-541 | Q-16 | 2,3-diCl |
| 1-542 | Q-16 | 2,4-diCl |
| 1-543 | Q-16 | 2,5-diCl |
| 1-544 | Q-16 | 2,6-diCl |
| 1-545 | Q-16 | 3,4-diCl |
| 1-546 | Q-16 | 3,5-diCl |
| 1-547 | Q-16 | 2-Cl, 4-F |
| 1-548 | Q-16 | 2-Cl, 5-F |
| 1-549 | Q-16 | 2-CF3 |
| 1-550 | Q-16 | 3-CF3 |
| 1-551 | Q-16 | 4-CF3 |
| 1-552 | Q-16 | 2-OCF3 |
| 1-553 | Q-16 | 3-OCF3 |
| 1-554 | Q-16 | 4-OCF3 |
| 1-555 | Q-16 | 2-Me |
| 1-556 | Q-16 | 3-Me |
| 1-557 | Q-16 | 4-Me |
| 1-558 | Q-16 | 2-OMe |
| 1-559 | Q-16 | 3-OMe |
| 1-560 | Q-16 | 4-OMe |
| 1-561 | Q-17 | 2-F |
| 1-562 | Q-17 | 3-F |
| 1-563 | Q-17 | 4-F |
| 1-564 | Q-17 | 2,3-diF |
| 1-565 | Q-17 | 2,4-diF |
| 1-566 | Q-17 | 2,5-diF |

TABLE 1-continued

Compounds of the formula (I)

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-567 | Q-17 | 2,6-diF |
| 1-568 | Q-17 | 3,4-diF |
| 1-569 | Q-17 | 3,5-diF |
| 1-570 | Q-17 | 2-F, 4-Cl |
| 1-571 | Q-17 | 2-F, 5-Cl |
| 1-572 | Q-17 | 3-F, 5-Cl |
| 1-573 | Q-17 | 2-Cl |
| 1-574 | Q-17 | 3-Cl |
| 1-575 | Q-17 | 4-Cl |
| 1-576 | Q-17 | 2,3-diCl |
| 1-577 | Q-17 | 2,4-diCl |
| 1-578 | Q-17 | 2,5-diCl |
| 1-579 | Q-17 | 2,6-diCl |
| 1-580 | Q-17 | 3,4-diCl |
| 1-581 | Q-17 | 3,5-diCl |
| 1-582 | Q-17 | 2-Cl, 4-F |
| 1-583 | Q-17 | 2-Cl, 5-F |
| 1-584 | Q-17 | 2-CF3 |
| 1-585 | Q-17 | 3-CF3 |
| 1-586 | Q-17 | 4-CF3 |
| 1-587 | Q-17 | 2-OCF3 |
| 1-588 | Q-17 | 3-OCF3 |
| 1-589 | Q-17 | 4-OCF3 |
| 1-590 | Q-17 | 2-Me |
| 1-591 | Q-17 | 3-Me |
| 1-592 | Q-17 | 4-Me |
| 1-593 | Q-17 | 2-OMe |
| 1-594 | Q-17 | 3-OMe |
| 1-595 | Q-17 | 4-OMe |
| 1-596 | Q-18 | 2-F |
| 1-597 | Q-18 | 3-F |
| 1-598 | Q-18 | 4-F |
| 1-599 | Q-18 | 2,3-diF |
| 1-600 | Q-18 | 2,4-diF |
| 1-601 | Q-18 | 2,5-diF |
| 1-602 | Q-18 | 2,6-diF |
| 1-603 | Q-18 | 3,4-diF |
| 1-604 | Q-18 | 3,5-diF |
| -1605 | Q-18 | 2-F, 4-Cl |
| -1606 | Q-18 | 2-F, 5-Cl |
| 1-607 | Q-18 | 3-F, 5-Cl |
| 1-608 | Q-18 | 2-Cl |
| 1-609 | Q-18 | 3-Cl |
| 1-610 | Q-18 | 4-Cl |
| 1-611 | Q-18 | 2,3-diCl |
| 1-612 | Q-18 | 2,4-diCl |
| 1-613 | Q-18 | 2,5-diCl |
| 1-614 | Q-18 | 2,6-diCl |
| 1-615 | Q-18 | 3,4-diCl |
| 1-616 | Q-18 | 3,5-diCl |
| 1-617 | Q-18 | 2-Cl, 4-F |
| 1-618 | Q-18 | 2-Cl, 5-F |
| 1-619 | Q-18 | 2-CF3 |
| 1-620 | Q-18 | 3-CF3 |
| 1-621 | Q-18 | 4-CF3 |
| 1-622 | Q-18 | 2-OCF3 |
| 1-623 | Q-18 | 3-OCF3 |
| 1-624 | Q-18 | 4-OCF3 |
| 1-625 | Q-18 | 2-Me |
| 1-626 | Q-18 | 3-Me |
| 1-627 | Q-18 | 4-Me |
| 1-628 | Q-18 | 2-OMe |
| 1-629 | Q-18 | 3-OMe |
| 1-630 | Q-18 | 4-OMe |
| 1-631 | Q-19 | 2-F |
| 1-632 | Q-19 | 3-F |
| 1-633 | Q-19 | 4-F |
| 1-634 | Q-19 | 2,3-diF |
| 1-635 | Q-19 | 2,4-diF |
| 1-636 | Q-19 | 2,5-diF |
| 1-637 | Q-19 | 2,6-diF |
| 1-638 | Q-19 | 3,4-diF |
| 1-639 | Q-19 | 3,5-diF |
| 1-640 | Q-19 | 2-F, 4-Cl |
| 1-641 | Q-19 | 2-F, 5-Cl |
| 1-642 | Q-19 | 3-F, 5-Cl |
| 1-643 | Q-19 | 2-Cl |
| 1-644 | Q-19 | 3-Cl |
| 1-645 | Q-19 | 4-Cl |
| 1-646 | Q-19 | 2,3-diCl |
| 1-647 | Q-19 | 2,4-diCl |
| 1-648 | Q-19 | 2,5-diCl |
| 1-649 | Q-19 | 2,6-diCl |
| 1-650 | Q-19 | 3,4-diCl |
| 1-651 | Q-19 | 3,5-diCl |
| 1-652 | Q-19 | 2-Cl, 4-F |
| 1-653 | Q-19 | 2-Cl, 5-F |
| 1-654 | Q-19 | 2-CF3 |
| 1-655 | Q-19 | 3-CF3 |
| 1-656 | Q-19 | 4-CF3 |
| 1-657 | Q-19 | 2-OCF3 |
| 1-658 | Q-19 | 3-OCF3 |
| 1-659 | Q-19 | 4-OCF3 |
| 1-660 | Q-19 | 2-Me |
| 1-661 | Q-19 | 3-Me |
| 1-662 | Q-19 | 4-Me |
| 1-663 | Q-19 | 2-OMe |
| 1-664 | Q-19 | 3-OMe |
| 1-665 | Q-19 | 4-OMe |
| 1-666 | Q-20 | 2-F |
| 1-667 | Q-20 | 3-F |
| 1-668 | Q-20 | 4-F |
| 1-669 | Q-20 | 2,3-diF |
| 1-670 | Q-20 | 2,4-diF |
| 1-671 | Q-20 | 2,5-diF |
| 1-672 | Q-20 | 2,6-diF |
| 1-673 | Q-20 | 3,4-diF |
| 1-674 | Q-20 | 3,5-diF |
| 1-675 | Q-20 | 2-F, 4-Cl |
| 1-676 | Q-20 | 2-F, 5-Cl |
| 1-677 | Q-20 | 3-F, 5-Cl |
| 1-678 | Q-20 | 2-Cl |

TABLE 1-continued

Compounds of the formula (I)

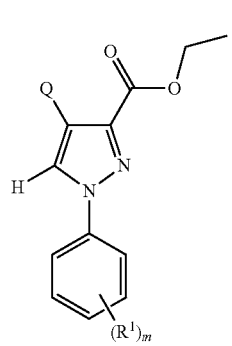

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-679 | Q-20 | 3-Cl |
| 1-680 | Q-20 | 4-Cl |
| 1-681 | Q-20 | 2,3-diCl |
| 1-682 | Q-20 | 2,4-diCl |
| 1-683 | Q-20 | 2,5-diCl |
| 1-684 | Q-20 | 2,6-diCl |
| 1-685 | Q-20 | 3,4-diCl |
| 1-686 | Q-20 | 3,5-diCl |
| 1-687 | Q-20 | 2-Cl, 4-F |
| 1-688 | Q-20 | 2-Cl, 5-F |
| 1-689 | Q-20 | 2-CF3 |
| 1-690 | Q-20 | 3-CF3 |
| 1-691 | Q-20 | 4-CF3 |
| 1-692 | Q-20 | 2-OCF3 |
| 1-693 | Q-20 | 3-OCF3 |
| 1-694 | Q-20 | 4-OCF3 |
| 1-695 | Q-20 | 2-Me |
| 1-696 | Q-20 | 3-Me |
| 1-697 | Q-20 | 4-Me |
| 1-698 | Q-20 | 2-OMe |
| 1-699 | Q-20 | 3-OMe |
| 1-700 | Q-20 | 4-OMe |
| 1-701 | Q-21 | 2-F |
| 1-702 | Q-21 | 3-F |
| 1-703 | Q-21 | 4-F |
| 1-704 | Q-21 | 2,3-diF |
| 1-705 | Q-21 | 2,4-diF |
| 1-706 | Q-21 | 2,5-diF |
| 1-707 | Q-21 | 2,6-diF |
| 1-708 | Q-21 | 3,4-diF |
| 1-709 | Q-21 | 3,5-diF |
| 1-710 | Q-21 | 2-F, 4-Cl |
| 1-711 | Q-21 | 2-F, 5-Cl |
| 1-712 | Q-21 | 3-F, 5-Cl |
| 1-713 | Q-21 | 2-Cl |
| 1-714 | Q-21 | 3-Cl |
| 1-715 | Q-21 | 4-Cl |
| 1-716 | Q-21 | 2,3-diCl |
| 1-717 | Q-21 | 2,4-diCl |
| 1-718 | Q-21 | 2,5-diCl |
| 1-719 | Q-21 | 2,6-diCl |
| 1-720 | Q-21 | 3,4-diCl |
| 1-721 | Q-21 | 3,5-diCl |
| 1-722 | Q-21 | 2-Cl, 4-F |
| 1-723 | Q-21 | 2-Cl, 5-F |
| 1-724 | Q-21 | 2-CF3 |
| 1-725 | Q-21 | 3-CF3 |
| 1-726 | Q-21 | 4-CF3 |
| 1-727 | Q-21 | 2-OCF3 |
| 1-728 | Q-21 | 3-OCF3 |
| 1-729 | Q-21 | 4-OCF3 |
| 1-730 | Q-21 | 2-Me |
| 1-731 | Q-21 | 3-Me |
| 1-732 | Q-21 | 4-Me |
| 1-733 | Q-21 | 2-OMe |
| 1-734 | Q-21 | 3-OMe |
| 1-735 | Q-21 | 4-OMe |
| 1-736 | Q-22 | 2-F |
| 1-737 | Q-22 | 3-F |
| 1-738 | Q-22 | 4-F |
| 1-739 | Q-22 | 2,3-diF |
| 1-740 | Q-22 | 2,4-diF |
| 1-741 | Q-22 | 2,5-diF |
| 1-742 | Q-22 | 2,6-diF |
| 1-743 | Q-22 | 3,4-diF |
| 1-744 | Q-22 | 3,5-diF |
| 1-745 | Q-22 | 2-F, 4-Cl |
| 1-746 | Q-22 | 2-F, 5-Cl |
| 1-747 | Q-22 | 3-F, 5-Cl |
| 1-748 | Q-22 | 2-Cl |
| 1-749 | Q-22 | 3-Cl |
| 1-750 | Q-22 | 4-Cl |
| 1-751 | Q-22 | 2,3-diCl |
| 1-752 | Q-22 | 2,4-diCl |
| 1-753 | Q-22 | 2,5-diCl |
| 1-754 | Q-22 | 2,6-diCl |
| 1-755 | Q-22 | 3,4-diCl |
| 1-756 | Q-22 | 3,5-diCl |
| 1-757 | Q-22 | 2-Cl, 4-F |
| 1-758 | Q-22 | 2-Cl, 5-F |
| 1-759 | Q-22 | 2-CF3 |
| 1-760 | Q-22 | 3-CF3 |
| 1-761 | Q-22 | 4-CF3 |
| 1-762 | Q-22 | 2-OCF3 |
| 1-763 | Q-22 | 3-OCF3 |
| 1-764 | Q-22 | 4-OCF3 |
| 1-765 | Q-22 | 2-Me |
| 1-766 | Q-22 | 3-Me |
| 1-767 | Q-22 | 4-Me |
| 1-768 | Q-22 | 2-OMe |
| 1-769 | Q-22 | 3-OMe |
| 1-770 | Q-22 | 4-OMe |
| 1-771 | Q-23 | 2-F |
| 1-772 | Q-23 | 3-F |
| 1-773 | Q-23 | 4-F |
| 1-774 | Q-23 | 2,3-diF |
| 1-775 | Q-23 | 2,4-diF |
| 1-776 | Q-23 | 2,5-diF |
| 1-777 | Q-23 | 2,6-diF |
| 1-778 | Q-23 | 3,4-diF |
| 1-779 | Q-23 | 3,5-diF |
| 1-780 | Q-23 | 2-F, 4-Cl |
| 1-781 | Q-23 | 2-F, 5-Cl |
| 1-782 | Q-23 | 3-F, 5-Cl |
| 1-783 | Q-23 | 2-Cl |
| 1-784 | Q-23 | 3-Cl |
| 1-785 | Q-23 | 4-Cl |
| 1-786 | Q-23 | 2,3-diCl |
| 1-787 | Q-23 | 2,4-diCl |
| 1-788 | Q-23 | 2,5-diCl |
| 1-789 | Q-23 | 2,6-diCl |
| 1-790 | Q-23 | 3,4-diCl |

TABLE 1-continued

Compounds of the formula (I)

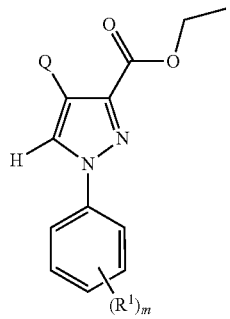

(I)

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-791 | Q-23 | 3,5-diCl |
| 1-792 | Q-23 | 2-Cl, 4-F |
| 1-793 | Q-23 | 2-Cl, 5-F |
| 1-794 | Q-23 | 2-CF3 |
| 1-795 | Q-23 | 3-CF3 |
| 1-796 | Q-23 | 4-CF3 |
| 1-797 | Q-23 | 2-OCF3 |
| 1-798 | Q-23 | 3-OCF3 |
| 1-799 | Q-23 | 4-OCF3 |
| 1-800 | Q-23 | 2-Me |
| 1-801 | Q-23 | 3-Me |
| 1-802 | Q-23 | 4-Me |
| 1-803 | Q-23 | 2-OMe |
| 1-804 | Q-23 | 3-OMe |
| 1-805 | Q-23 | 4-OMe |
| 1-806 | Q-24 | 2-F |
| 1-807 | Q-24 | 3-F |
| 1-808 | Q-24 | 4-F |
| 1-809 | Q-24 | 2,3-diF |
| 1-810 | Q-24 | 2,4-diF |
| 1-811 | Q-24 | 2,5-diF |
| 1-812 | Q-24 | 2,6-diF |
| 1-813 | Q-24 | 3,4-diF |
| 1-814 | Q-24 | 3,5-diF |
| 1-815 | Q-24 | 2-F, 4-Cl |
| 1-816 | Q-24 | 2-F, 5-Cl |
| 1-817 | Q-24 | 3-F, 5-Cl |
| 1-818 | Q-24 | 2-Cl |
| 1-819 | Q-24 | 3-Cl |
| 1-820 | Q-24 | 4-Cl |
| 1-821 | Q-24 | 2,3-diCl |
| 1-822 | Q-24 | 2,4-diCl |
| 1-823 | Q-24 | 2,5-diCl |
| 1-824 | Q-24 | 2,6-diCl |
| 1-825 | Q-24 | 3,4-diCl |
| 1-826 | Q-24 | 3,5-diCl |
| 1-827 | Q-24 | 2-Cl, 4-F |
| 1-828 | Q-24 | 2-Cl, 5-F |
| 1-829 | Q-24 | 2-CF3 |
| 1-830 | Q-24 | 3-CF3 |
| 1-831 | Q-24 | 4-CF3 |
| 1-832 | Q-24 | 2-OCF3 |
| 1-833 | Q-24 | 3-OCF3 |
| 1-834 | Q-24 | 4-OCF3 |
| 1-835 | Q-24 | 2-Me |
| 1-836 | Q-24 | 3-Me |
| 1-837 | Q-24 | 4-Me |
| 1-838 | Q-24 | 2-OMe |
| 1-839 | Q-24 | 3-OMe |
| 1-840 | Q-24 | 4-OMe |
| 1-841 | Q-25 | 2-F |
| 1-842 | Q-25 | 3-F |
| 1-843 | Q-25 | 4-F |
| 1-844 | Q-25 | 2,3-diF |
| 1-845 | Q-25 | 2,4-diF |
| 1-846 | Q-25 | 2,5-diF |

TABLE 1-continued

Compounds of the formula (I)

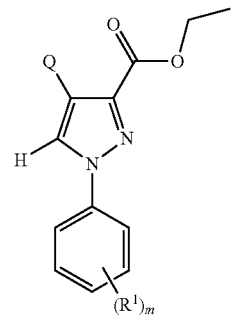

(I)

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-847 | Q-25 | 2,6-diF |
| 1-848 | Q-25 | 3,4-diF |
| 1-849 | Q-25 | 3,5-diF |
| 1-850 | Q-25 | 2-F, 4-Cl |
| 1-851 | Q-25 | 2-F, 5-Cl |
| 1-852 | Q-25 | 3-F, 5-Cl |
| 1-853 | Q-25 | 2-Cl |
| 1-854 | Q-25 | 3-Cl |
| 1-855 | Q-25 | 4-Cl |
| 1-856 | Q-25 | 2,3-diCl |
| 1-857 | Q-25 | 2,4-diCl |
| 1-858 | Q-25 | 2,5-diCl |
| 1-859 | Q-25 | 2,6-diCl |
| 1-860 | Q-25 | 3,4-diCl |
| 1-861 | Q-25 | 3,5-diCl |
| 1-862 | Q-25 | 2-Cl, 4-F |
| 1-863 | Q-25 | 2-Cl, 5-F |
| 1-864 | Q-25 | 2-CF3 |
| 1-865 | Q-25 | 3-CF3 |
| 1-866 | Q-25 | 4-CF3 |
| 1-867 | Q-25 | 2-OCF3 |
| 1-868 | Q-25 | 3-OCF3 |
| 1-869 | Q-25 | 4-OCF3 |
| 1-870 | Q-25 | 2-Me |
| 1-871 | Q-25 | 3-Me |
| 1-872 | Q-25 | 4-Me |
| 1-873 | Q-25 | 2-OMe |
| 1-874 | Q-25 | 3-OMe |
| 1-875 | Q-25 | 4-OMe |
| 1-876 | Q-26 | 2-F |
| 1-877 | Q-26 | 3-F |
| 1-878 | Q-26 | 4-F |
| 1-879 | Q-26 | 2,3-diF |
| 1-880 | Q-26 | 2,4-diF |
| 1-881 | Q-26 | 2,5-diF |
| 1-882 | Q-26 | 2,6-diF |
| 1-883 | Q-26 | 3,4-diF |
| 1-884 | Q-26 | 3,5-diF |
| 1-885 | Q-26 | 2-F, 4-Cl |
| 1-886 | Q-26 | 2-F, 5-Cl |
| 1-887 | Q-26 | 3-F, 5-Cl |
| 1-888 | Q-26 | 2-Cl |
| 1-889 | Q-26 | 3-Cl |
| 1-890 | Q-26 | 4-Cl |
| 1-891 | Q-26 | 2,3-diCl |
| 1-892 | Q-26 | 2,4-diCl |
| 1-893 | Q-26 | 2,5-diCl |
| 1-894 | Q-26 | 2,6-diCl |
| 1-895 | Q-26 | 3,4-diCl |
| 1-896 | Q-26 | 3,5-diCl |
| 1-897 | Q-26 | 2-Cl, 4-F |
| 1-898 | Q-26 | 2-Cl, 5-F |
| 1-899 | Q-26 | 2-CF3 |
| 1-900 | Q-26 | 3-CF3 |
| 1-901 | Q-26 | 4-CF3 |
| 1-902 | Q-26 | 2-OCF3 |

TABLE 1-continued

Compounds of the formula (I)

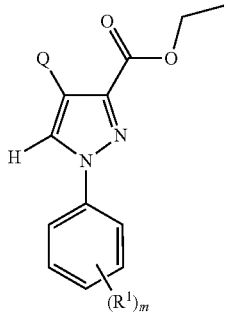

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-903 | Q-26 | 3-OCF3 |
| 1-904 | Q-26 | 4-OCF3 |
| 1-905 | Q-26 | 2-Me |
| 1-906 | Q-26 | 3-Me |
| 1-907 | Q-26 | 4-Me |
| 1-908 | Q-26 | 2-OMe |
| 1-909 | Q-26 | 3-OMe |
| 1-910 | Q-26 | 4-OMe |
| 1-911 | Q-27 | 2-F |
| 1-912 | Q-27 | 3-F |
| 1-913 | Q-27 | 4-F |
| 1-914 | Q-27 | 2,3-diF |
| 1-915 | Q-27 | 2,4-diF |
| 1-916 | Q-27 | 2,5-diF |
| 1-917 | Q-27 | 2,6-diF |
| 1-918 | Q-27 | 3,4-diF |
| 1-919 | Q-27 | 3,5-diF |
| 1-920 | Q-27 | 2-F, 4-Cl |
| 1-921 | Q-27 | 2-F, 5-Cl |
| 1-922 | Q-27 | 3-F, 5-Cl |
| 1-923 | Q-27 | 2-Cl |
| 1-924 | Q-27 | 3-Cl |
| 1-925 | Q-27 | 4-Cl |
| 1-926 | Q-27 | 2,3-diCl |
| 1-927 | Q-27 | 2,4-diCl |
| 1-928 | Q-27 | 2,5-diCl |
| 1-929 | Q-27 | 2,6-diCl |
| 1-930 | Q-27 | 3,4-diCl |
| 1-931 | Q-27 | 3,5-diCl |
| 1-932 | Q-27 | 2-Cl, 4-F |
| 1-933 | Q-27 | 2-Cl, 5-F |
| 1-934 | Q-27 | 2-CF3 |
| 1-935 | Q-27 | 3-CF3 |
| 1-936 | Q-27 | 4-CF3 |
| 1-937 | Q-27 | 2-OCF3 |
| 1-938 | Q-27 | 3-OCF3 |
| 1-939 | Q-27 | 4-OCF3 |
| 1-940 | Q-27 | 2-Me |
| 1-941 | Q-27 | 3-Me |
| 1-942 | Q-27 | 4-Me |
| 1-943 | Q-27 | 2-OMe |
| 1-944 | Q-27 | 3-OMe |
| 1-945 | Q-27 | 4-OMe |
| 1-946 | Q-28 | 2-F |
| 1-947 | Q-28 | 3-F |
| 1-948 | Q-28 | 4-F |
| 1-949 | Q-28 | 2,3-diF |
| 1-950 | Q-28 | 2,4-diF |
| 1-951 | Q-28 | 2,5-diF |
| 1-952 | Q-28 | 2,6-diF |
| 1-953 | Q-28 | 3,4-diF |
| 1-954 | Q-28 | 3,5-diF |
| 1-955 | Q-28 | 2-F, 4-Cl |
| 1-956 | Q-28 | 2-F, 5-Cl |
| 1-957 | Q-28 | 3-F, 5-Cl |
| 1-958 | Q-28 | 2-Cl |
| 1-959 | Q-28 | 3-Cl |
| 1-960 | Q-28 | 4-Cl |
| 1-961 | Q-28 | 2,3-diCl |
| 1-962 | Q-28 | 2,4-diCl |
| 1-963 | Q-28 | 2,5-diCl |
| 1-964 | Q-28 | 2,6-diCl |
| 1-965 | Q-28 | 3,4-diCl |
| 1-966 | Q-28 | 3,5-diCl |
| 1-967 | Q-28 | 2-Cl, 4-F |
| 1-968 | Q-28 | 2-Cl, 5-F |
| 1-969 | Q-28 | 2-CF3 |
| 1-970 | Q-28 | 3-CF3 |
| 1-971 | Q-28 | 4-CF3 |
| 1-972 | Q-28 | 2-OCF3 |
| 1-973 | Q-28 | 3-OCF3 |
| 1-974 | Q-28 | 4-OCF3 |
| 1-975 | Q-28 | 2-Me |
| 1-976 | Q-28 | 3-Me |
| 1-977 | Q-28 | 4-Me |
| 1-978 | Q-28 | 2-OMe |
| 1-979 | Q-28 | 3-OMe |
| 1-980 | Q-28 | 4-OMe |
| 1-981 | Q-29 | 2-F |
| 1-982 | Q-29 | 3-F |
| 1-983 | Q-29 | 4-F |
| 1-984 | Q-29 | 2,3-diF |
| 1-985 | Q-29 | 2,4-diF |
| 1-986 | Q-29 | 2,5-diF |
| 1-987 | Q-29 | 2,6-diF |
| 1-988 | Q-29 | 3,4-diF |
| 1-989 | Q-29 | 3,5-diF |
| 1-990 | Q-29 | 2-F, 4-Cl |
| 1-991 | Q-29 | 2-F, 5-Cl |
| 1-992 | Q-29 | 3-F, 5-Cl |
| 1-993 | Q-29 | 2-Cl |
| 1-994 | Q-29 | 3-Cl |
| 1-995 | Q-29 | 4-Cl |
| 1-996 | Q-29 | 2,3-diCl |
| 1-997 | Q-29 | 2,4-diCl |
| 1-998 | Q-29 | 2,5-diCl |
| 1-999 | Q-29 | 2,6-diCl |
| 1-1000 | Q-29 | 3,4-diCl |
| 1-1001 | Q-29 | 3,5-diCl |
| 1-1002 | Q-29 | 2-Cl, 4-F |
| 1-1003 | Q-29 | 2-Cl, 5-F |
| 1-1004 | Q-29 | 2-CF3 |
| 1-1005 | Q-29 | 3-CF3 |
| 1-1006 | Q-29 | 4-CF3 |
| 1-1007 | Q-29 | 2-OCF3 |
| 1-1008 | Q-29 | 3-OCF3 |
| 1-1009 | Q-29 | 4-OCF3 |
| 1-1010 | Q-29 | 2-Me |
| 1-1011 | Q-29 | 3-Me |
| 1-1012 | Q-29 | 4-Me |
| 1-1013 | Q-29 | 2-OMe |
| 1-1014 | Q-29 | 3-OMe |

TABLE 1-continued

Compounds of the formula (I)

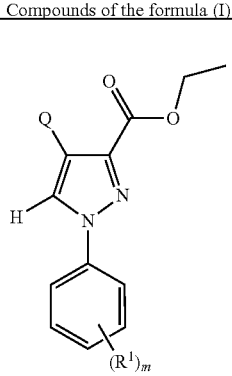

where the definition in table form below of the radical "Q" corresponds to the definition of the radicals "Q-1" to "Q-47" mentioned above as being very particularly preferred

| Ex. | Q | (R¹)$_m$ |
|---|---|---|
| 1-1015 | Q-29 | 4-OMe |
| 1-1016 | Q-30 | 2-F |
| 1-1017 | Q-30 | 3-F |
| 1-1018 | Q-30 | 4-F |
| 1-1019 | Q-30 | 2,3-diF |
| 1-1020 | Q-30 | 2,4-diF |
| 1-1021 | Q-30 | 2,5-diF |
| 1-1022 | Q-30 | 2,6-diF |
| 1-1023 | Q-30 | 3,4-diF |
| 1-1024 | Q-30 | 3,5-diF |
| 1-1025 | Q-30 | 2-F, 4-Cl |
| 1-1026 | Q-30 | 2-F, 5-Cl |
| 1-1027 | Q-30 | 3-F, 5-Cl |
| 1-1028 | Q-30 | 2-Cl |
| 1-1029 | Q-30 | 3-Cl |
| 1-1030 | Q-30 | 4-Cl |
| 1-1031 | Q-30 | 2,3-diCl |
| 1-1032 | Q-30 | 2,4-diCl |
| 1-1033 | Q-30 | 2,5-diCl |
| 1-1034 | Q-30 | 2,6-diCl |
| 1-1035 | Q-30 | 3,4-diCl |
| 1-1036 | Q-30 | 3,5-diCl |
| 1-1037 | Q-30 | 2-Cl, 4-F |
| 1-1038 | Q-30 | 2-Cl, 5-F |
| 1-1039 | Q-30 | 2-CF3 |
| 1-1040 | Q-30 | 3-CF3 |
| 1-1041 | Q-30 | 4-CF3 |
| 1-1042 | Q-30 | 2-OCF3 |
| 1-1043 | Q-30 | 3-OCF3 |
| 1-1044 | Q-30 | 4-OCF3 |
| 1-1045 | Q-30 | 2-Me |
| 1-1046 | Q-30 | 3-Me |
| 1-1047 | Q-30 | 4-Me |
| 1-1048 | Q-30 | 2-OMe |
| 1-1049 | Q-30 | 3-OMe |
| 1-1050 | Q-30 | 4-OMe |
| 1-1051 | Q-31 | 2-F |
| 1-1052 | Q-31 | 3-F |
| 1-1053 | Q-31 | 4-F |
| 1-1054 | Q-31 | 2,3-diF |
| 1-1055 | Q-31 | 2,4-diF |
| 1-1056 | Q-31 | 2,5-diF |
| 1-1057 | Q-31 | 2,6-diF |
| 1-1058 | Q-31 | 3,4-diF |
| 1-1059 | Q-31 | 3,5-diF |
| 1-1060 | Q-31 | 2-F, 4-Cl |
| 1-1061 | Q-31 | 2-F, 5-Cl |
| 1-1062 | Q-31 | 3-F, 5-Cl |
| 1-1063 | Q-31 | 2-Cl |
| 1-1064 | Q-31 | 3-Cl |
| 1-1065 | Q-31 | 4-Cl |
| 1-1066 | Q-31 | 2,3-diCl |
| 1-1067 | Q-31 | 2,4-diCl |
| 1-1068 | Q-31 | 2,5-diCl |
| 1-1069 | Q-31 | 2,6-diCl |
| 1-1070 | Q-31 | 3,4-diCl |
| 1-1071 | Q-31 | 3,5-diCl |
| 1-1072 | Q-31 | 2-Cl, 4-F |
| 1-1073 | Q-31 | 2-Cl, 5-F |
| 1-1074 | Q-31 | 2-CF3 |
| 1-1075 | Q-31 | 3-CF3 |
| 1-1076 | Q-31 | 4-CF3 |
| 1-1077 | Q-31 | 2-OCF3 |
| 1-1078 | Q-31 | 3-OCF3 |
| 1-1079 | Q-31 | 4-OCF3 |
| 1-1080 | Q-31 | 2-Me |
| 1-1081 | Q-31 | 3-Me |
| 1-1082 | Q-31 | 4-Me |
| 1-1083 | Q-31 | 2-OMe |
| 1-1084 | Q-31 | 3-OMe |
| 1-1085 | Q-31 | 4-OMe |
| 1-1086 | Q-32 | 2-F |
| 1-1087 | Q-32 | 3-F |
| 1-1088 | Q-32 | 4-F |
| 1-1089 | Q-32 | 2,3-diF |
| 1-1090 | Q-32 | 2,4-diF |
| 1-1091 | Q-32 | 2,5-diF |
| 1-1092 | Q-32 | 2,6-diF |
| 1-1093 | Q-32 | 3,4-diF |
| 1-1094 | Q-32 | 3,5-diF |
| 1-1095 | Q-32 | 2-F, 4-Cl |
| 1-1096 | Q-32 | 2-F, 5-Cl |
| 1-1097 | Q-32 | 3-F, 5-Cl |
| 1-1098 | Q-32 | 2-Cl |
| 1-1099 | Q-32 | 3-Cl |
| 1-1100 | Q-32 | 4-Cl |
| 1-1101 | Q-32 | 2,3-diCl |
| 1-1102 | Q-32 | 2,4-diCl |
| 1-1103 | Q-32 | 2,5-diCl |
| 1-1104 | Q-32 | 2,6-diCl |
| 1-1105 | Q-32 | 3,4-diCl |
| 1-1106 | Q-32 | 3,5-diCl |
| 1-1107 | Q-32 | 2-Cl, 4-F |
| 1-1108 | Q-32 | 2-Cl, 5-F |
| 1-1109 | Q-32 | 2-CF3 |
| 1-1110 | Q-32 | 3-CF3 |
| 1-1111 | Q-32 | 4-CF3 |
| 1-1112 | Q-32 | 2-OCF3 |
| 1-1113 | Q-32 | 3-OCF3 |
| 1-1114 | Q-32 | 4-OCF3 |
| 1-1115 | Q-32 | 2-Me |
| 1-1116 | Q-32 | 3-Me |
| 1-1117 | Q-32 | 4-Me |
| 1-1118 | Q-32 | 2-OMe |
| 1-1119 | Q-32 | 3-OMe |
| 1-1120 | Q-32 | 4-OMe |
| 1-1121 | Q-33 | 2-F |
| 1-1122 | Q-33 | 3-F |
| 1-1123 | Q-33 | 4-F |
| 1-1124 | Q-33 | 2,3-diF |
| 1-1125 | Q-33 | 2,4-diF |
| 1-1126 | Q-33 | 2,5-diF |

TABLE 1-continued

Compounds of the formula (I)

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-1127 | Q-33 | 2,6-diF |
| 1-1128 | Q-33 | 3,4-diF |
| 1-1129 | Q-33 | 3,5-diF |
| 1-1130 | Q-33 | 2-F, 4-Cl |
| 1-1131 | Q-33 | 2-F, 5-Cl |
| 1-1132 | Q-33 | 3-F, 5-Cl |
| 1-1133 | Q-33 | 2-Cl |
| 1-1134 | Q-33 | 3-Cl |
| 1-1135 | Q-33 | 4-Cl |
| 1-1136 | Q-33 | 2,3-diCl |
| 1-1137 | Q-33 | 2,4-diCl |
| 1-1138 | Q-33 | 2,5-diCl |
| 1-1139 | Q-33 | 2,6-diCl |
| 1-1140 | Q-33 | 3,4-diCl |
| 1-1141 | Q-33 | 3,5-diCl |
| 1-1142 | Q-33 | 2-Cl, 4-F |
| 1-1143 | Q-33 | 2-Cl, 5-F |
| 1-1144 | Q-33 | 2-CF3 |
| 1-1145 | Q-33 | 3-CF3 |
| 1-1146 | Q-33 | 4-CF3 |
| 1-1147 | Q-33 | 2-OCF3 |
| 1-1148 | Q-33 | 3-OCF3 |
| 1-1149 | Q-33 | 4-OCF3 |
| 1-1150 | Q-33 | 2-Me |
| 1-1151 | Q-33 | 3-Me |
| 1-1152 | Q-33 | 4-Me |
| 1-1153 | Q-33 | 2-OMe |
| 1-1154 | Q-33 | 3-OMe |
| 1-1155 | Q-33 | 4-OMe |
| 1-1156 | Q-34 | 2-F |
| 1-1157 | Q-34 | 3-F |
| 1-1158 | Q-34 | 4-F |
| 1-1159 | Q-34 | 2,3-diF |
| 1-1160 | Q-34 | 2,4-diF |
| 1-1161 | Q-34 | 2,5-diF |
| 1-1162 | Q-34 | 2,6-diF |
| 1-1163 | Q-34 | 3,4-diF |
| 1-1164 | Q-34 | 3,5-diF |
| 1-1165 | Q-34 | 2-F, 4-Cl |
| 1-1166 | Q-34 | 2-F, 5-Cl |
| 1-1167 | Q-34 | 3-F, 5-Cl |
| 1-1168 | Q-34 | 2-Cl |
| 1-1169 | Q-34 | 3-Cl |
| 1-1170 | Q-34 | 4-Cl |
| 1-1171 | Q-34 | 2,3-diCl |
| 1-1172 | Q-34 | 2,4-diCl |
| 1-1173 | Q-34 | 2,5-diCl |
| 1-1174 | Q-34 | 2,6-diCl |
| 1-1175 | Q-34 | 3,4-diCl |
| 1-1176 | Q-34 | 3,5-diCl |
| 1-1177 | Q-34 | 2-Cl, 4-F |
| 1-1178 | Q-34 | 2-Cl, 5-F |
| 1-1179 | Q-34 | 2-CF3 |
| 1-1180 | Q-34 | 3-CF3 |
| 1-1181 | Q-34 | 4-CF3 |
| 1-1182 | Q-34 | 2-OCF3 |
| 1-1183 | Q-34 | 3-OCF3 |
| 1-1184 | Q-34 | 4-OCF3 |
| 1-1185 | Q-34 | 2-Me |
| 1-1186 | Q-34 | 3-Me |
| 1-1187 | Q-34 | 4-Me |
| 1-1188 | Q-34 | 2-OMe |
| 1-1189 | Q-34 | 3-OMe |
| 1-1190 | Q-34 | 4-OMe |
| 1-1191 | Q-35 | 2-F |
| 1-1192 | Q-35 | 3-F |
| 1-1193 | Q-35 | 4-F |
| 1-1194 | Q-35 | 2,3-diF |
| 1-1195 | Q-35 | 2,4-diF |
| 1-1196 | Q-35 | 2,5-diF |
| 1-1197 | Q-35 | 2,6-diF |
| 1-1198 | Q-35 | 3,4-diF |
| 1-1199 | Q-35 | 3,5-diF |
| 1-1200 | Q-35 | 2-F, 4-Cl |
| 1-1201 | Q-35 | 2-F, 5-Cl |
| 1-1202 | Q-35 | 3-F, 5-Cl |
| 1-1203 | Q-35 | 2-Cl |
| 1-1204 | Q-35 | 3-Cl |
| 1-1205 | Q-35 | 4-Cl |
| 1-1206 | Q-35 | 2,3-diCl |
| 1-1207 | Q-35 | 2,4-diCl |
| 1-1208 | Q-35 | 2,5-diCl |
| 1-1209 | Q-35 | 2,6-diCl |
| 1-1210 | Q-35 | 3,4-diCl |
| 1-1211 | Q-35 | 3,5-diCl |
| 1-1212 | Q-35 | 2-Cl, 4-F |
| 1-1213 | Q-35 | 2-Cl, 5-F |
| 1-1214 | Q-35 | 2-CF3 |
| 1-1215 | Q-35 | 3-CF3 |
| 1-1216 | Q-35 | 4-CF3 |
| 1-1217 | Q-35 | 2-OCF3 |
| 1-1218 | Q-35 | 3-OCF3 |
| 1-1219 | Q-35 | 4-OCF3 |
| 1-1220 | Q-35 | 2-Me |
| 1-1221 | Q-35 | 3-Me |
| 1-1222 | Q-35 | 4-Me |
| 1-1223 | Q-35 | 2-OMe |
| 1-1224 | Q-35 | 3-OMe |
| 1-1225 | Q-35 | 4-OMe |
| 1-1226 | Q-36 | 2-F |
| 1-1227 | Q-36 | 3-F |
| 1-1228 | Q-36 | 4-F |
| 1-1229 | Q-36 | 2,3-diF |
| 1-1230 | Q-36 | 2,4-diF |
| 1-1231 | Q-36 | 2,5-diF |
| 1-1232 | Q-36 | 2,6-diF |
| 1-1233 | Q-36 | 3,4-diF |
| 1-1234 | Q-36 | 3,5-diF |
| 1-1235 | Q-36 | 2-F, 4-Cl |
| 1-1236 | Q-36 | 2-F, 5-Cl |
| 1-1237 | Q-36 | 3-F, 5-Cl |
| 1-1238 | Q-36 | 2-Cl |

TABLE 1-continued

Compounds of the formula (I)

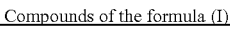

where the definition in table form below of the radical "Q" corresponds to the definition of the radicals "Q-1" to "Q-47" mentioned above as being very particularly preferred

| Ex. | Q | (R¹)$_m$ |
|---|---|---|
| 1-1239 | Q-36 | 3-Cl |
| 1-1240 | Q-36 | 4-Cl |
| 1-1241 | Q-36 | 2,3-diCl |
| 1-1242 | Q-36 | 2,4-diCl |
| 1-1243 | Q-36 | 2,5-diCl |
| 1-1244 | Q-36 | 2,6-diCl |
| 1-1245 | Q-36 | 3,4-diCl |
| 1-1246 | Q-36 | 3,5-diCl |
| 1-1247 | Q-36 | 2-Cl, 4-F |
| 1-1248 | Q-36 | 2-Cl, 5-F |
| 1-1249 | Q-36 | 2-CF3 |
| 1-1250 | Q-36 | 3-CF3 |
| 1-1251 | Q-36 | 4-CF3 |
| 1-1252 | Q-36 | 2-OCF3 |
| 1-1253 | Q-36 | 3-OCF3 |
| 1-1254 | Q-36 | 4-OCF3 |
| 1-1255 | Q-36 | 2-Me |
| 1-1256 | Q-36 | 3-Me |
| 1-1257 | Q-36 | 4-Me |
| 1-1258 | Q-36 | 2-OMe |
| 1-1259 | Q-36 | 3-OMe |
| 1-1260 | Q-36 | 4-OMe |
| 1-1261 | Q-37 | 2-F |
| 1-1262 | Q-37 | 3-F |
| 1-1263 | Q-37 | 4-F |
| 1-1264 | Q-37 | 2,3-diF |
| 1-1265 | Q-37 | 2,4-diF |
| 1-1266 | Q-37 | 2,5-diF |
| 1-1267 | Q-37 | 2,6-diF |
| 1-1268 | Q-37 | 3,4-diF |
| 1-1269 | Q-37 | 3,5-diF |
| 1-1270 | Q-37 | 2-F, 4-Cl |
| 1-1271 | Q-37 | 2-F, 5-Cl |
| 1-1272 | Q-37 | 3-F, 5-Cl |
| 1-1273 | Q-37 | 2-Cl |
| 1-1274 | Q-37 | 3-Cl |
| 1-1275 | Q-37 | 4-Cl |
| 1-1276 | Q-37 | 2,3-diCl |
| 1-1277 | Q-37 | 2,4-diCl |
| 1-1278 | Q-37 | 2,5-diCl |
| 1-1279 | Q-37 | 2,6-diCl |
| 1-1280 | Q-37 | 3,4-diCl |
| 1-1281 | Q-37 | 3,5-diCl |
| 1-1282 | Q-37 | 2-Cl, 4-F |
| 1-1283 | Q-37 | 2-Cl, 5-F |
| 1-1284 | Q-37 | 2-CF3 |
| 1-1285 | Q-37 | 3-CF3 |
| 1-1286 | Q-37 | 4-CF3 |
| 1-1287 | Q-37 | 2-OCF3 |
| 1-1288 | Q-37 | 3-OCF3 |
| 1-1289 | Q-37 | 4-OCF3 |
| 1-1290 | Q-37 | 2-Me |
| 1-1291 | Q-37 | 3-Me |
| 1-1292 | Q-37 | 4-Me |
| 1-1293 | Q-37 | 2-OMe |
| 1-1294 | Q-37 | 3-OMe |

TABLE 1-continued

Compounds of the formula (I)

where the definition in table form below of the radical "Q" corresponds to the definition of the radicals "Q-1" to "Q-47" mentioned above as being very particularly preferred

| Ex. | Q | (R¹)$_m$ |
|---|---|---|
| 1-1295 | Q-37 | 4-OMe |
| 1-1296 | Q-38 | 2-F |
| 1-1297 | Q-38 | 3-F |
| 1-1298 | Q-38 | 4-F |
| 1-1299 | Q-38 | 2,3-diF |
| 1-1300 | Q-38 | 2,4-diF |
| 1-1301 | Q-38 | 2,5-diF |
| 1-1302 | Q-38 | 2,6-diF |
| 1-1303 | Q-38 | 3,4-diF |
| 1-1304 | Q-38 | 3,5-diF |
| 1-1305 | Q-38 | 2-F, 4-Cl |
| 1-1306 | Q-38 | 2-F, 5-Cl |
| 1-1307 | Q-38 | 3-F, 5-Cl |
| 1-1308 | Q-38 | 2-Cl |
| 1-1309 | Q-38 | 3-Cl |
| 1-1310 | Q-38 | 4-Cl |
| 1-1311 | Q-38 | 2,3-diCl |
| 1-1312 | Q-38 | 2,4-diCl |
| 1-1313 | Q-38 | 2,5-diCl |
| 1-1314 | Q-38 | 2,6-diCl |
| 1-1315 | Q-38 | 3,4-diCl |
| 1-1316 | Q-38 | 3,5-diCl |
| 1-1317 | Q-38 | 2-Cl, 4-F |
| 1-1318 | Q-38 | 2-Cl, 5-F |
| 1-1319 | Q-38 | 2-CF3 |
| 1-1320 | Q-38 | 3-CF3 |
| 1-1321 | Q-38 | 4-CF3 |
| 1-1322 | Q-38 | 2-OCF3 |
| 1-1323 | Q-38 | 3-OCF3 |
| 1-1324 | Q-38 | 4-OCF3 |
| 1-1325 | Q-38 | 2-Me |
| 1-1326 | Q-38 | 3-Me |
| 1-1327 | Q-38 | 4-Me |
| 1-1328 | Q-38 | 2-OMe |
| 1-1329 | Q-38 | 3-OMe |
| 1-1330 | Q-38 | 4-OMe |
| 1-1331 | Q-39 | 2-F |
| 1-1332 | Q-39 | 3-F |
| 1-1333 | Q-39 | 4-F |
| 1-1334 | Q-39 | 2,3-diF |
| 1-1335 | Q-39 | 2,4-diF |
| 1-1336 | Q-39 | 2,5-diF |
| 1-1337 | Q-39 | 2,6-diF |
| 1-1338 | Q-39 | 3,4-diF |
| 1-1339 | Q-39 | 3,5-diF |
| 1-1340 | Q-39 | 2-F, 4-Cl |
| 1-1341 | Q-39 | 2-F, 5-Cl |
| 1-1342 | Q-39 | 3-F, 5-Cl |
| 1-1343 | Q-39 | 2-Cl |
| 1-1344 | Q-39 | 3-Cl |
| 1-1345 | Q-39 | 4-Cl |
| 1-1346 | Q-39 | 2,3-diCl |
| 1-1347 | Q-39 | 2,4-diCl |
| 1-1348 | Q-39 | 2,5-diCl |
| 1-1349 | Q-39 | 2,6-diCl |
| 1-1350 | Q-39 | 3,4-diCl |

TABLE 1-continued

Compounds of the formula (I)

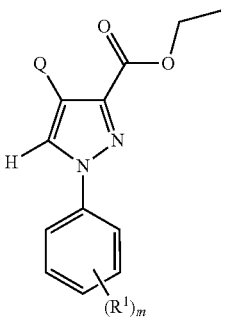

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-1351 | Q-39 | 3,5-diCl |
| 1-1352 | Q-39 | 2-Cl, 4-F |
| 1-1353 | Q-39 | 2-Cl, 5-F |
| 1-1354 | Q-39 | 2-CF3 |
| 1-1355 | Q-39 | 3-CF3 |
| 1-1356 | Q-39 | 4-CF3 |
| 1-1357 | Q-39 | 2-OCF3 |
| 1-1358 | Q-39 | 3-OCF3 |
| 1-1359 | Q-39 | 4-OCF3 |
| 1-1360 | Q-39 | 2-Me |
| 1-1361 | Q-39 | 3-Me |
| 1-1362 | Q-39 | 4-Me |
| 1-1363 | Q-39 | 2-OMe |
| 1-1364 | Q-39 | 3-OMe |
| 1-1365 | Q-39 | 4-OMe |
| 1-1366 | Q-40 | 2-F |
| 1-1367 | Q-40 | 3-F |
| 1-1368 | Q-40 | 4-F |
| 1-1369 | Q-40 | 2,3-diF |
| 1-1370 | Q-40 | 2,4-diF |
| 1-1371 | Q-40 | 2,5-diF |
| 1-1372 | Q-40 | 2,6-diF |
| 1-1373 | Q-40 | 3,4-diF |
| 1-1374 | Q-40 | 3,5-diF |
| 1-1375 | Q-40 | 2-F, 4-Cl |
| 1-1376 | Q-40 | 2-F, 5-Cl |
| 1-1377 | Q-40 | 3-F, 5-Cl |
| 1-1378 | Q-40 | 2-Cl |
| 1-1379 | Q-40 | 3-Cl |
| 1-1380 | Q-40 | 4-Cl |
| 1-1381 | Q-40 | 2,3-diCl |
| 1-1382 | Q-40 | 2,4-diCl |
| 1-1383 | Q-40 | 2,5-diCl |
| 1-1384 | Q-40 | 2,6-diCl |
| 1-1385 | Q-40 | 3,4-diCl |
| 1-1386 | Q-40 | 3,5-diCl |
| 1-1387 | Q-40 | 2-Cl, 4-F |
| 1-1388 | Q-40 | 2-Cl, 5-F |
| 1-1389 | Q-40 | 2-CF3 |
| 1-1390 | Q-40 | 3-CF3 |
| 1-1391 | Q-40 | 4-CF3 |
| 1-1392 | Q-40 | 2-OCF3 |
| 1-1393 | Q-40 | 3-OCF3 |
| 1-1394 | Q-40 | 4-OCF3 |
| 1-1395 | Q-40 | 2-Me |
| 1-1396 | Q-40 | 3-Me |
| 1-1397 | Q-40 | 4-Me |
| 1-1398 | Q-40 | 2-OMe |
| 1-1399 | Q-40 | 3-OMe |
| 1-1400 | Q-40 | 4-OMe |
| 1-1401 | Q-41 | 2-F |
| 1-1402 | Q-41 | 3-F |
| 1-1403 | Q-41 | 4-F |
| 1-1404 | Q-41 | 2,3-diF |
| 1-1405 | Q-41 | 2,4-diF |
| 1-1406 | Q-41 | 2,5-diF |

TABLE 1-continued

Compounds of the formula (I)

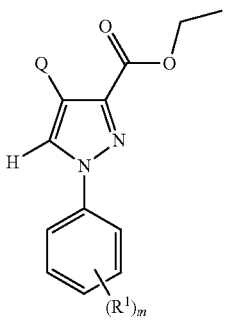

where the definition in table form below of the radical "Q" corresponds to the definition of the radicals "Q-1" to "Q-47" mentioned above as being very particularly preferred

| Ex. | Q | $(R^1)_m$ |
|---|---|---|
| 1-1407 | Q-41 | 2,6-diF |
| 1-1408 | Q-41 | 3,4-diF |
| 1-1409 | Q-41 | 3,5-diF |
| 1-1410 | Q-41 | 2-F, 4-Cl |
| 1-1411 | Q-41 | 2-F, 5-Cl |
| 1-1412 | Q-41 | 3-F, 5-Cl |
| 1-1413 | Q-41 | 2-Cl |
| 1-1414 | Q-41 | 3-Cl |
| 1-1415 | Q-41 | 4-Cl |
| 1-1416 | Q-41 | 2,3-diCl |
| 1-1417 | Q-41 | 2,4-diCl |
| 1-1418 | Q-41 | 2,5-diCl |
| 1-1419 | Q-41 | 2,6-diCl |
| 1-1420 | Q-41 | 3,4-diCl |
| 1-1421 | Q-41 | 3,5-diCl |
| 1-1422 | Q-41 | 2-Cl, 4-F |
| 1-1423 | Q-41 | 2-Cl, 5-F |
| 1-1424 | Q-41 | 2-CF3 |
| 1-1425 | Q-41 | 3-CF3 |
| 1-1426 | Q-41 | 4-CF3 |
| 1-1427 | Q-41 | 2-OCF3 |
| 1-1428 | Q-41 | 3-OCF3 |
| 1-1429 | Q-41 | 4-OCF3 |
| 1-1430 | Q-41 | 2-Me |
| 1-1431 | Q-41 | 3-Me |
| 1-1432 | Q-41 | 4-Me |
| 1-1433 | Q-41 | 2-OMe |
| 1-1434 | Q-41 | 3-OMe |
| 1-1435 | Q-41 | 4-OMe |
| 1-1436 | Q-42 | 2-F |
| 1-1437 | Q-42 | 3-F |
| 1-1438 | Q-42 | 4-F |
| 1-1439 | Q-42 | 2,3-diF |
| 1-1440 | Q-42 | 2,4-diF |
| 1-1441 | Q-42 | 2,5-diF |
| 1-1442 | Q-42 | 2,6-diF |
| 1-1443 | Q-42 | 3,4-diF |
| 1-1444 | Q-42 | 3,5-diF |
| 1-1445 | Q-42 | 2-F, 4-Cl |
| 1-1446 | Q-42 | 2-F, 5-Cl |
| 1-1447 | Q-42 | 3-F, 5-Cl |
| 1-1448 | Q-42 | 2-Cl |
| 1-1449 | Q-42 | 3-Cl |
| 1-1450 | Q-42 | 4-Cl |
| 1-1451 | Q-42 | 2,3-diCl |
| 1-1452 | Q-42 | 2,4-diCl |
| 1-1453 | Q-42 | 2,5-diCl |
| 1-1454 | Q-42 | 2,6-diCl |
| 1-1455 | Q-42 | 3,4-diCl |
| 1-1456 | Q-42 | 3,5-diCl |
| 1-1457 | Q-42 | 2-Cl, 4-F |
| 1-1458 | Q-42 | 2-Cl, 5-F |
| 1-1459 | Q-42 | 2-CF3 |
| 1-1460 | Q-42 | 3-CF3 |
| 1-1461 | Q-42 | 4-CF3 |
| 1-1462 | Q-42 | 2-OCF3 |

TABLE 1-continued

Compounds of the formula (I)

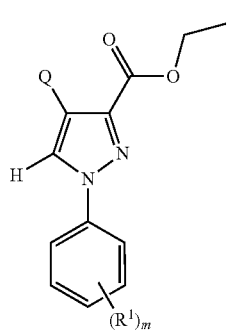

(I)

where the definition in table form below of the radical "Q" corresponds to the definition of the radicals "Q-1" to "Q-47" mentioned above as being very particularly preferred

| Ex.    | Q    | (R¹)ₘ     |
|--------|------|-----------|
| 1-1463 | Q-42 | 3-OCF3    |
| 1-1464 | Q-42 | 4-OCF3    |
| 1-1465 | Q-42 | 2-Me      |
| 1-1466 | Q-42 | 3-Me      |
| 1-1467 | Q-42 | 4-Me      |
| 1-1468 | Q-42 | 2-OMe     |
| 1-1469 | Q-42 | 3-OMe     |
| 1-1470 | Q-42 | 4-OMe     |
| 1-1471 | Q-43 | 2-F       |
| 1-1472 | Q-43 | 3-F       |
| 1-1473 | Q-43 | 4-F       |
| 1-1474 | Q-43 | 2,3-diF   |
| 1-1475 | Q-43 | 2,4-diF   |
| 1-1476 | Q-43 | 2,5-diF   |
| 1-1477 | Q-43 | 2,6-diF   |
| 1-1478 | Q-43 | 3,4-diF   |
| 1-1479 | Q-43 | 3,5-diF   |
| 1-1480 | Q-43 | 2-F, 4-Cl |
| 1-1481 | Q-43 | 2-F, 5-Cl |
| 1-1482 | Q-43 | 3-F, 5-Cl |
| 1-1483 | Q-43 | 2-Cl      |
| 1-1484 | Q-43 | 3-Cl      |
| 1-1485 | Q-43 | 4-Cl      |
| 1-1486 | Q-43 | 2,3-diCl  |
| 1-1487 | Q-43 | 2,4-diCl  |
| 1-1488 | Q-43 | 2,5-diCl  |
| 1-1489 | Q-43 | 2,6-diCl  |
| 1-1490 | Q-43 | 3,4-diCl  |
| 1-1491 | Q-43 | 3,5-diCl  |
| 1-1492 | Q-43 | 2-Cl, 4-F |
| 1-1493 | Q-43 | 2-Cl, 5-F |
| 1-1494 | Q-43 | 2-CF3     |
| 1-1495 | Q-43 | 3-CF3     |
| 1-1496 | Q-43 | 4-CF3     |
| 1-1497 | Q-43 | 2-OCF3    |
| 1-1498 | Q-43 | 3-OCF3    |
| 1-1499 | Q-43 | 4-OCF3    |
| 1-1500 | Q-43 | 2-Me      |
| 1-1501 | Q-43 | 3-Me      |
| 1-1502 | Q-43 | 4-Me      |
| 1-1503 | Q-43 | 2-OMe     |
| 1-1504 | Q-43 | 3-OMe     |
| 1-1505 | Q-43 | 4-OMe     |
| 1-1506 | Q-44 | 2-F       |
| 1-1507 | Q-44 | 3-F       |
| 1-1508 | Q-44 | 4-F       |
| 1-1509 | Q-44 | 2,3-diF   |
| 1-1510 | Q-44 | 2,4-diF   |
| 1-1511 | Q-44 | 2,5-diF   |
| 1-1512 | Q-44 | 2,6-diF   |
| 1-1513 | Q-44 | 3,4-diF   |
| 1-1514 | Q-44 | 3,5-diF   |
| 1-1515 | Q-44 | 2-F, 4-Cl |
| 1-1516 | Q-44 | 2-F, 5-Cl |
| 1-1517 | Q-44 | 3-F, 5-Cl |
| 1-1518 | Q-44 | 2-Cl      |
| 1-1519 | Q-44 | 3-Cl      |
| 1-1520 | Q-44 | 4-Cl      |
| 1-1521 | Q-44 | 2,3-diCl  |
| 1-1522 | Q-44 | 2,4-diCl  |
| 1-1523 | Q-44 | 2,5-diCl  |
| 1-1524 | Q-44 | 2,6-diCl  |
| 1-1525 | Q-44 | 3,4-diCl  |
| 1-1526 | Q-44 | 3,5-diCl  |
| 1-1527 | Q-44 | 2-Cl, 4-F |
| 1-1528 | Q-44 | 2-Cl, 5-F |
| 1-1529 | Q-44 | 2-CF3     |
| 1-1530 | Q-44 | 3-CF3     |
| 1-1531 | Q-44 | 4-CF3     |
| 1-1532 | Q-44 | 2-OCF3    |
| 1-1533 | Q-44 | 3-OCF3    |
| 1-1534 | Q-44 | 4-OCF3    |
| 1-1535 | Q-44 | 2-Me      |
| 1-1536 | Q-44 | 3-Me      |
| 1-1537 | Q-44 | 4-Me      |
| 1-1538 | Q-44 | 2-OMe     |
| 1-1539 | Q-44 | 3-OMe     |
| 1-1540 | Q-44 | 4-OMe     |
| 1-1541 | Q-45 | 2-F       |
| 1-1542 | Q-45 | 3-F       |
| 1-1543 | Q-45 | 4-F       |
| 1-1544 | Q-45 | 2,3-diF   |
| 1-1545 | Q-45 | 2,4-diF   |
| 1-1546 | Q-45 | 2,5-diF   |
| 1-1547 | Q-45 | 2,6-diF   |
| 1-1548 | Q-45 | 3,4-diF   |
| 1-1549 | Q-45 | 3,5-diF   |
| 1-1550 | Q-45 | 2-F, 4-Cl |
| 1-1551 | Q-45 | 2-F, 5-Cl |
| 1-1552 | Q-45 | 3-F, 5-Cl |
| 1-1553 | Q-45 | 2-Cl      |
| 1-1554 | Q-45 | 3-Cl      |
| 1-1555 | Q-45 | 4-Cl      |
| 1-1556 | Q-45 | 2,3-diCl  |
| 1-1557 | Q-45 | 2,4-diCl  |
| 1-1558 | Q-45 | 2,5-diCl  |
| 1-1559 | Q-45 | 2,6-diCl  |
| 1-1560 | Q-45 | 3,4-diCl  |
| 1-1561 | Q-45 | 3,5-diCl  |
| 1-1562 | Q-45 | 2-Cl, 4-F |
| 1-1563 | Q-45 | 2-Cl, 5-F |
| 1-1564 | Q-45 | 2-CF3     |
| 1-1565 | Q-45 | 3-CF3     |
| 1-1566 | Q-45 | 4-CF3     |
| 1-1567 | Q-45 | 2-OCF3    |
| 1-1568 | Q-45 | 3-OCF3    |
| 1-1569 | Q-45 | 4-OCF3    |
| 1-1570 | Q-45 | 2-Me      |
| 1-1571 | Q-45 | 3-Me      |
| 1-1572 | Q-45 | 4-Me      |
| 1-1573 | Q-45 | 2-OMe     |
| 1-1574 | Q-45 | 3-OMe     |

TABLE 1-continued

Compounds of the formula (I)

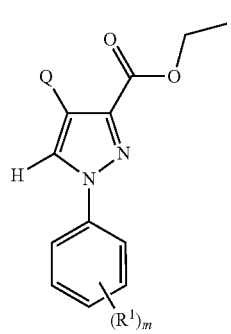

where the definition in table form below of the radical "Q" corresponds to the definition of the radicals "Q-1" to "Q-47" mentioned above as being very particularly preferred

| Ex. | Q | (R¹)ₘ |
|---|---|---|
| 1-1575 | Q-45 | 4-OMe |
| 1-1576 | Q-46 | 2-F |
| 1-1577 | Q-46 | 3-F |
| 1-1578 | Q-46 | 4-F |
| 1-1579 | Q-46 | 2,3-diF |
| 1-1580 | Q-46 | 2,4-diF |
| 1-1581 | Q-46 | 2,5-diF |
| 1-1582 | Q-46 | 2,6-diF |
| 1-1583 | Q-46 | 3,4-diF |
| 1-1584 | Q-46 | 3,5-diF |
| 1-1585 | Q-46 | 2-F, 4-Cl |
| 1-1586 | Q-46 | 2-F, 5-Cl |
| 1-1587 | Q-46 | 3-F, 5-Cl |
| 1-1588 | Q-46 | 2-Cl |
| 1-1589 | Q-46 | 3-Cl |
| 1-1590 | Q-46 | 4-Cl |
| 1-1591 | Q-46 | 2,3-diCl |
| 1-1592 | Q-46 | 2,4-diCl |
| 1-1593 | Q-46 | 2,5-diCl |
| 1-1594 | Q-46 | 2,6-diCl |
| 1-1595 | Q-46 | 3,4-diCl |
| 1-1596 | Q-46 | 3,5-diCl |
| 1-1597 | Q-46 | 2-Cl, 4-F |
| 1-1598 | Q-46 | 2-Cl, 5-F |
| 1-1599 | Q-46 | 2-CF3 |
| 1-1600 | Q-46 | 3-CF3 |
| 1-1601 | Q-46 | 4-CF3 |
| 1-1602 | Q-46 | 2-OCF3 |
| 1-1603 | Q-46 | 3-OCF3 |
| 1-1604 | Q-46 | 4-OCF3 |
| 1-1605 | Q-46 | 2-Me |
| 1-1606 | Q-46 | 3-Me |
| 1-1607 | Q-46 | 4-Me |
| 1-1608 | Q-46 | 2-OMe |
| 1-1609 | Q-46 | 3-OMe |
| 1-1610 | Q-46 | 4-OMe |
| 1-1611 | Q-47 | 2-F |
| 1-1612 | Q-47 | 3-F |
| 1-1613 | Q-47 | 4-F |
| 1-1614 | Q-47 | 2,3-diF |
| 1-1615 | Q-47 | 2,4-diF |
| 1-1616 | Q-47 | 2,5-diF |
| 1-1617 | Q-47 | 2,6-diF |
| 1-1618 | Q-47 | 3,4-diF |
| 1-1619 | Q-47 | 3,5-diF |
| 1-1620 | Q-47 | 2-F, 4-Cl |
| 1-1621 | Q-47 | 2-F, 5-Cl |
| 1-1622 | Q-47 | 3-F, 5-Cl |
| 1-1623 | Q-47 | 2-Cl |
| 1-1624 | Q-47 | 3-Cl |
| 1-1625 | Q-47 | 4-Cl |
| 1-1626 | Q-47 | 2,3-diCl |
| 1-1627 | Q-47 | 2,4-diCl |
| 1-1628 | Q-47 | 2,5-diCl |
| 1-1629 | Q-47 | 2,6-diCl |
| 1-1630 | Q-47 | 3,4-diCl |

TABLE 1-continued

Compounds of the formula (I)

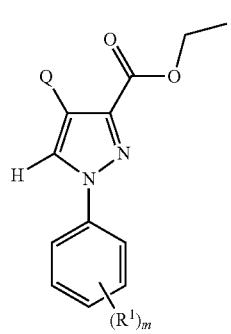

where the definition in table form below of the radical "Q" corresponds to the definition of the radicals "Q-1" to "Q-47" mentioned above as being very particularly preferred

| Ex. | Q | (R¹)ₘ |
|---|---|---|
| 1-1631 | Q-47 | 3,5-diCl |
| 1-1632 | Q-47 | 2-Cl, 4-F |
| 1-1633 | Q-47 | 2-Cl, 5-F |
| 1-1634 | Q-47 | 2-CF3 |
| 1-1635 | Q-47 | 3-CF3 |
| 1-1636 | Q-47 | 4-CF3 |
| 1-1637 | Q-47 | 2-OCF3 |
| 1-1638 | Q-47 | 3-OCF3 |
| 1-1639 | Q-47 | 4-OCF3 |
| 1-1640 | Q-47 | 2-Me |
| 1-1641 | Q-47 | 3-Me |
| 1-1642 | Q-47 | 4-Me |
| 1-1643 | Q-47 | 2-OMe |
| 1-1644 | Q-47 | 3-OMe |
| 1-1645 | Q-47 | 4-OMe |

TABLE 2

Compounds of the formula (I)

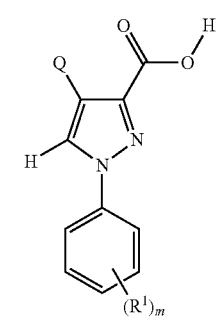

where the definition in table form below of the radical "Q" corresponds to the definition of the radicals "Q-1" to "Q-47" mentioned above as being very particularly preferred

| Ex. | Q | (R¹)ₘ |
|---|---|---|
| 2-1 | Q-1 | 2-F |
| 2-2 | Q-1 | 3-F |
| 2-3 | Q-1 | 4-F |
| 2-4 | Q-1 | 2,3-diF |
| 2-5 | Q-1 | 2,4-diF |
| 2-6 | Q-1 | 2,5-diF |
| 2-7 | Q-1 | 2,6-diF |
| 2-8 | Q-1 | 3,4-diF |
| 2-9 | Q-1 | 3,5-diF |
| 2-10 | Q-1 | 2-F, 4-Cl |
| 2-11 | Q-1 | 2-F, 5-Cl |

TABLE 2-continued

Compounds of the formula (I)

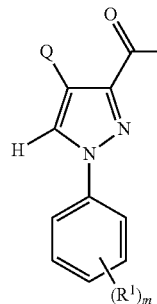

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-12 | Q-1 | 3-F, 5-Cl |
| 2-13 | Q-1 | 2-Cl |
| 2-14 | Q-1 | 3-Cl |
| 2-15 | Q-1 | 4-Cl |
| 2-16 | Q-1 | 2,3-diCl |
| 2-17 | Q-1 | 2,4-diCl |
| 2-18 | Q-1 | 2,5-diCl |
| 2-19 | Q-1 | 2,6-diCl |
| 2-20 | Q-1 | 3,4-diCl |
| 2-21 | Q-1 | 3,5-diCl |
| 2-22 | Q-1 | 2-Cl, 4-F |
| 2-23 | Q-1 | 2-Cl, 5-F |
| 2-24 | Q-1 | 2-CF3 |
| 2-25 | Q-1 | 3-CF3 |
| 2-26 | Q-1 | 4-CF3 |
| 2-27 | Q-1 | 2-OCF3 |
| 2-28 | Q-1 | 3-OCF3 |
| 2-29 | Q-1 | 4-OCF3 |
| 2-30 | Q-1 | 2-Me |
| 2-31 | Q-1 | 3-Me |
| 2-32 | Q-1 | 4-Me |
| 2-33 | Q-1 | 2-OMe |
| 2-34 | Q-1 | 3-OMe |
| 2-35 | Q-1 | 4-OMe |
| 2-36 | Q-2 | 2-F |
| 2-37 | Q-2 | 3-F |
| 2-38 | Q-2 | 4-F |
| 2-39 | Q-2 | 2,3-diF |
| 2-40 | Q-2 | 2,4-diF |
| 2-41 | Q-2 | 2,5-diF |
| 2-42 | Q-2 | 2,6-diF |
| 2-43 | Q-2 | 3,4-diF |
| 2-44 | Q-2 | 3,5-diF |
| 2-45 | Q-2 | 2-F, 4-Cl |
| 2-46 | Q-2 | 2-F, 5-Cl |
| 2-47 | Q-2 | 3-F, 5-Cl |
| 2-48 | Q-2 | 2-Cl |
| 2-49 | Q-2 | 3-Cl |
| 2-50 | Q-2 | 4-Cl |
| 2-51 | Q-2 | 2,3-diCl |
| 2-52 | Q-2 | 2,4-diCl |
| 2-53 | Q-2 | 2,5-diCl |
| 2-54 | Q-2 | 2,6-diCl |
| 2-55 | Q-2 | 3,4-diCl |
| 2-56 | Q-2 | 3,5-diCl |
| 2-57 | Q-2 | 2-Cl, 4-F |
| 2-58 | Q-2 | 2-Cl, 5-F |
| 2-59 | Q-2 | 2-CF3 |
| 2-60 | Q-2 | 3-CF3 |
| 2-61 | Q-2 | 4-CF3 |
| 2-62 | Q-2 | 2-OCF3 |
| 2-63 | Q-2 | 3-OCF3 |
| 2-64 | Q-2 | 4-OCF3 |
| 2-65 | Q-2 | 2-Me |
| 2-66 | Q-2 | 3-Me |

TABLE 2-continued

Compounds of the formula (I)

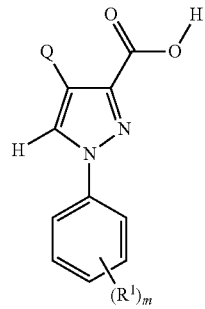

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-67 | Q-2 | 4-Me |
| 2-68 | Q-2 | 2-OMe |
| 2-69 | Q-2 | 3-OMe |
| 2-70 | Q-2 | 4-OMe |
| 2-71 | Q-3 | 2-F |
| 2-72 | Q-3 | 3-F |
| 2-73 | Q-3 | 4-F |
| 2-74 | Q-3 | 2,3-diF |
| 2-75 | Q-3 | 2,4-diF |
| 2-76 | Q-3 | 2,5-diF |
| 2-77 | Q-3 | 2,6-diF |
| 2-78 | Q-3 | 3,4-diF |
| 2-79 | Q-3 | 3,5-diF |
| 2-80 | Q-3 | 2-F, 4-Cl |
| 2-81 | Q-3 | 2-F, 5-Cl |
| 2-82 | Q-3 | 3-F, 5-Cl |
| 2-83 | Q-3 | 2-Cl |
| 2-84 | Q-3 | 3-Cl |
| 2-85 | Q-3 | 4-Cl |
| 2-86 | Q-3 | 2,3-diCl |
| 2-87 | Q-3 | 2,4-diCl |
| 2-88 | Q-3 | 2,5-diCl |
| 2-89 | Q-3 | 2,6-diCl |
| 2-90 | Q-3 | 3,4-diCl |
| 2-91 | Q-3 | 3,5-diCl |
| 2-92 | Q-3 | 2-Cl, 4-F |
| 2-93 | Q-3 | 2-Cl, 5-F |
| 2-94 | Q-3 | 2-CF3 |
| 2-95 | Q-3 | 3-CF3 |
| 2-96 | Q-3 | 4-CF3 |
| 2-97 | Q-3 | 2-OCF3 |
| 2-98 | Q-3 | 3-OCF3 |
| 2-99 | Q-3 | 4-OCF3 |
| 2-100 | Q-3 | 2-Me |
| 2-101 | Q-3 | 3-Me |
| 2-102 | Q-3 | 4-Me |
| 2-103 | Q-3 | 2-OMe |
| 2-104 | Q-3 | 3-OMe |
| 2-105 | Q-3 | 4-OMe |
| 2-106 | Q-4 | 2-F |
| 2-107 | Q-4 | 3-F |
| 2-108 | Q-4 | 4-F |
| 2-109 | Q-4 | 2,3-diF |
| 2-110 | Q-4 | 2,4-diF |
| 2-111 | Q-4 | 2,5-diF |
| 2-112 | Q-4 | 2,6-diF |
| 2-113 | Q-4 | 3,4-diF |
| 2-114 | Q-4 | 3,5-diF |
| 2-115 | Q-4 | 2-F, 4-Cl |
| 2-116 | Q-4 | 2-F, 5-Cl |
| 2-117 | Q-4 | 3-F, 5-Cl |
| 2-118 | Q-4 | 2-Cl |
| 2-119 | Q-4 | 3-Cl |
| 2-120 | Q-4 | 4-Cl |
| 2-121 | Q-4 | 2,3-diCl |

TABLE 2-continued

Compounds of the formula (I)

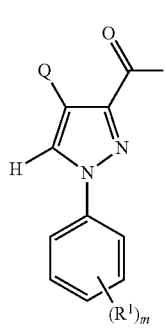

(I)

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-122 | Q-4 | 2,4-diCl |
| 2-123 | Q-4 | 2,5-diCl |
| 2-124 | Q-4 | 2,6-diCl |
| 2-125 | Q-4 | 3,4-diCl |
| 2-126 | Q-4 | 3,5-diCl |
| 2-127 | Q-4 | 2-Cl, 4-F |
| 2-128 | Q-4 | 2-Cl, 5-F |
| 2-129 | Q-4 | 2-CF3 |
| 2-130 | Q-4 | 3-CF3 |
| 2-131 | Q-4 | 4-CF3 |
| 2-132 | Q-4 | 2-OCF3 |
| 2-133 | Q-4 | 3-OCF3 |
| 2-134 | Q-4 | 4-OCF3 |
| 2-135 | Q-4 | 2-Me |
| 2-136 | Q-4 | 3-Me |
| 2-137 | Q-4 | 4-Me |
| 2-138 | Q-4 | 2-OMe |
| 2-139 | Q-4 | 3-OMe |
| 2-140 | Q-4 | 4-OMe |
| 2-141 | Q-5 | 2-F |
| 2-142 | Q-5 | 3-F |
| 2-143 | Q-5 | 4-F |
| 2-144 | Q-5 | 2,3-diF |
| 2-145 | Q-5 | 2,4-diF |
| 2-146 | Q-5 | 2,5-diF |
| 2-147 | Q-5 | 2,6-diF |
| 2-148 | Q-5 | 3,4-diF |
| 2-149 | Q-5 | 3,5-diF |
| 2-150 | Q-5 | 2-F, 4-Cl |
| 2-151 | Q-5 | 2-F, 5-Cl |
| 2-152 | Q-5 | 3-F, 5-Cl |
| 2-153 | Q-5 | 2-Cl |
| 2-154 | Q-5 | 3-Cl |
| 2-155 | Q-5 | 4-Cl |
| 2-156 | Q-5 | 2,3-diCl |
| 2-157 | Q-5 | 2,4-diCl |
| 2-158 | Q-5 | 2,5-diCl |
| 2-159 | Q-5 | 2,6-diCl |
| 2-160 | Q-5 | 3,4-diCl |
| 2-161 | Q-5 | 3,5-diCl |
| 2-162 | Q-5 | 2-Cl, 4-F |
| 2-163 | Q-5 | 2-Cl, 5-F |
| 2-164 | Q-5 | 2-CF3 |
| 2-165 | Q-5 | 3-CF3 |
| 2-166 | Q-5 | 4-CF3 |
| 2-167 | Q-5 | 2-OCF3 |
| 2-168 | Q-5 | 3-OCF3 |
| 2-169 | Q-5 | 4-OCF3 |
| 2-170 | Q-5 | 2-Me |
| 2-171 | Q-5 | 3-Me |
| 2-172 | Q-5 | 4-Me |
| 2-173 | Q-5 | 2-OMe |
| 2-174 | Q-5 | 3-OMe |
| 2-175 | Q-5 | 4-OMe |
| 2-176 | Q-6 | 2-F |

TABLE 2-continued

Compounds of the formula (I)

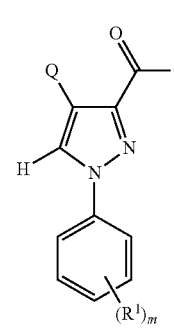

(I)

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-177 | Q-6 | 3-F |
| 2-178 | Q-6 | 4-F |
| 2-179 | Q-6 | 2,3-diF |
| 2-180 | Q-6 | 2,4-diF |
| 2-181 | Q-6 | 2,5-diF |
| 2-182 | Q-6 | 2,6-diF |
| 2-183 | Q-6 | 3,4-diF |
| 2-184 | Q-6 | 3,5-diF |
| 2-185 | Q-6 | 2-F, 4-Cl |
| 2-186 | Q-6 | 2-F, 5-Cl |
| 2-187 | Q-6 | 3-F, 5-Cl |
| 2-188 | Q-6 | 2-Cl |
| 2-189 | Q-6 | 3-Cl |
| 2-190 | Q-6 | 4-Cl |
| 2-191 | Q-6 | 2,3-diCl |
| 2-192 | Q-6 | 2,4-diCl |
| 2-193 | Q-6 | 2,5-diCl |
| 2-194 | Q-6 | 2,6-diCl |
| 2-195 | Q-6 | 3,4-diCl |
| 2-196 | Q-6 | 3,5-diCl |
| 2-197 | Q-6 | 2-Cl, 4-F |
| 2-198 | Q-6 | 2-Cl, 5-F |
| 2-199 | Q-6 | 2-CF3 |
| 2-200 | Q-6 | 3-CF3 |
| 2-201 | Q-6 | 4-CF3 |
| 2-202 | Q-6 | 2-OCF3 |
| 2-203 | Q-6 | 3-OCF3 |
| 2-204 | Q-6 | 4-OCF3 |
| 2-205 | Q-6 | 2-Me |
| 2-206 | Q-6 | 3-Me |
| 2-207 | Q-6 | 4-Me |
| 2-208 | Q-6 | 2-OMe |
| 2-209 | Q-6 | 3-OMe |
| 2-210 | Q-6 | 4-OMe |
| 2-211 | Q-7 | 2-F |
| 2-212 | Q-7 | 3-F |
| 2-213 | Q-7 | 4-F |
| 2-214 | Q-7 | 2,3-diF |
| 2-215 | Q-7 | 2,4-diF |
| 2-216 | Q-7 | 2,5-diF |
| 2-217 | Q-7 | 2,6-diF |
| 2-218 | Q-7 | 3,4-diF |
| 2-219 | Q-7 | 3,5-diF |
| 2-220 | Q-7 | 2-F, 4-Cl |
| 2-221 | Q-7 | 2-F, 5-Cl |
| 2-222 | Q-7 | 3-F, 5-Cl |
| 2-223 | Q-7 | 2-Cl |
| 2-224 | Q-7 | 3-Cl |
| 2-225 | Q-7 | 4-Cl |
| 2-226 | Q-7 | 2,3-diCl |
| 2-227 | Q-7 | 2,4-diCl |
| 2-228 | Q-7 | 2,5-diCl |
| 2-229 | Q-7 | 2,6-diCl |
| 2-230 | Q-7 | 3,4-diCl |
| 2-231 | Q-7 | 3,5-diCl |

TABLE 2-continued

Compounds of the formula (I)

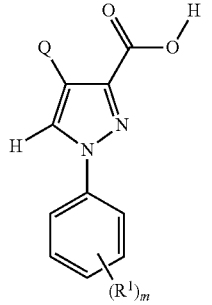

where the definition in table form below of the radical "Q" corresponds to the definition of the radicals "Q-1" to "Q-47" mentioned above as being very particularly preferred

| Ex. | Q | (R¹)$_m$ |
|---|---|---|
| 2-232 | Q-7 | 2-Cl, 4-F |
| 2-233 | Q-7 | 2-Cl, 5-F |
| 2-234 | Q-7 | 2-CF3 |
| 2-235 | Q-7 | 3-CF3 |
| 2-236 | Q-7 | 4-CF3 |
| 2-237 | Q-7 | 2-OCF3 |
| 2-238 | Q-7 | 3-OCF3 |
| 2-239 | Q-7 | 4-OCF3 |
| 2-240 | Q-7 | 2-Me |
| 2-241 | Q-7 | 3-Me |
| 2-242 | Q-7 | 4-Me |
| 2-243 | Q-7 | 2-OMe |
| 2-244 | Q-7 | 3-OMe |
| 2-245 | Q-7 | 4-OMe |
| 2-246 | Q-8 | 2-F |
| 2-247 | Q-8 | 3-F |
| 2-248 | Q-8 | 4-F |
| 2-249 | Q-8 | 2,3-diF |
| 2-250 | Q-8 | 2,4-diF |
| 2-251 | Q-8 | 2,5-diF |
| 2-252 | Q-8 | 2,6-diF |
| 2-253 | Q-8 | 3,4-diF |
| 2-254 | Q-8 | 3,5-diF |
| 2-255 | Q-8 | 2-F, 4-Cl |
| 2-256 | Q-8 | 2-F, 5-Cl |
| 2-257 | Q-8 | 3-F, 5-Cl |
| 2-258 | Q-8 | 2-Cl |
| 2-259 | Q-8 | 3-Cl |
| 2-260 | Q-8 | 4-Cl |
| 2-261 | Q-8 | 2,3-diCl |
| 2-262 | Q-8 | 2,4-diCl |
| 2-263 | Q-8 | 2,5-diCl |
| 2-264 | Q-8 | 2,6-diCl |
| 2-265 | Q-8 | 3,4-diCl |
| 2-266 | Q-8 | 3,5-diCl |
| 2-267 | Q-8 | 2-Cl, 4-F |
| 2-268 | Q-8 | 2-Cl, 5-F |
| 2-269 | Q-8 | 2-CF3 |
| 2-270 | Q-8 | 3-CF3 |
| 2-271 | Q-8 | 4-CF3 |
| 2-272 | Q-8 | 2-OCF3 |
| 2-273 | Q-8 | 3-OCF3 |
| 2-274 | Q-8 | 4-OCF3 |
| 2-275 | Q-8 | 2-Me |
| 2-276 | Q-8 | 3-Me |
| 2-277 | Q-8 | 4-Me |
| 2-278 | Q-8 | 2-OMe |
| 2-279 | Q-8 | 3-OMe |
| 2-280 | Q-8 | 4-OMe |
| 2-281 | Q-9 | 2-F |
| 2-282 | Q-9 | 3-F |
| 2-283 | Q-9 | 4-F |
| 2-284 | Q-9 | 2,3-diF |
| 2-285 | Q-9 | 2,4-diF |
| 2-286 | Q-9 | 2,5-diF |

TABLE 2-continued

Compounds of the formula (I)

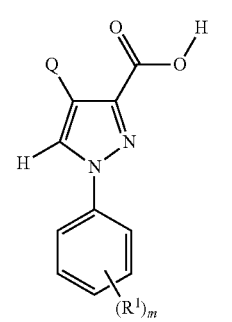

where the definition in table form below of the radical "Q" corresponds to the definition of the radicals "Q-1" to "Q-47" mentioned above as being very particularly preferred

| Ex. | Q | (R¹)$_m$ |
|---|---|---|
| 2-287 | Q-9 | 2,6-diF |
| 2-288 | Q-9 | 3,4-diF |
| 2-289 | Q-9 | 3,5-diF |
| 2-290 | Q-9 | 2-F, 4-Cl |
| 2-291 | Q-9 | 2-F, 5-Cl |
| 2-292 | Q-9 | 3-F, 5-Cl |
| 2-293 | Q-9 | 2-Cl |
| 2-294 | Q-9 | 3-Cl |
| 2-295 | Q-9 | 4-Cl |
| 2-296 | Q-9 | 2,3-diCl |
| 2-297 | Q-9 | 2,4-diCl |
| 2-298 | Q-9 | 2,5-diCl |
| 2-299 | Q-9 | 2,6-diCl |
| 2-300 | Q-9 | 3,4-diCl |
| 2-301 | Q-9 | 3,5-diCl |
| 2-302 | Q-9 | 2-Cl, 4-F |
| 2-303 | Q-9 | 2-Cl, 5-F |
| 2-304 | Q-9 | 2-CF3 |
| 2-305 | Q-9 | 3-CF3 |
| 2-306 | Q-9 | 4-CF3 |
| 2-307 | Q-9 | 2-OCF3 |
| 2-308 | Q-9 | 3-OCF3 |
| 2-309 | Q-9 | 4-OCF3 |
| 2-310 | Q-9 | 2-Me |
| 2-311 | Q-9 | 3-Me |
| 2-312 | Q-9 | 4-Me |
| 2-313 | Q-9 | 2-OMe |
| 2-314 | Q-9 | 3-OMe |
| 2-315 | Q-9 | 4-OMe |
| 2-316 | Q-10 | 2-F |
| 2-317 | Q-10 | 3-F |
| 2-318 | Q-10 | 4-F |
| 2-319 | Q-10 | 2,3-diF |
| 2-320 | Q-10 | 2,4-diF |
| 2-321 | Q-10 | 2,5-diF |
| 2-322 | Q-10 | 2,6-diF |
| 2-323 | Q-10 | 3,4-diF |
| 2-324 | Q-10 | 3,5-diF |
| 2-325 | Q-10 | 2-F, 4-Cl |
| 2-326 | Q-10 | 2-F, 5-Cl |
| 2-327 | Q-10 | 3-F, 5-Cl |
| 2-328 | Q-10 | 2-Cl |
| 2-329 | Q-10 | 3-Cl |
| 2-330 | Q-10 | 4-Cl |
| 2-331 | Q-10 | 2,3-diCl |
| 2-332 | Q-10 | 2,4-diCl |
| 2-333 | Q-10 | 2,5-diCl |
| 2-334 | Q-10 | 2,6-diCl |
| 2-335 | Q-10 | 3,4-diCl |
| 2-336 | Q-10 | 3,5-diCl |
| 2-337 | Q-10 | 2-Cl, 4-F |
| 2-338 | Q-10 | 2-Cl, 5-F |
| 2-339 | Q-10 | 2-CF3 |
| 2-340 | Q-10 | 3-CF3 |
| 2-341 | Q-10 | 4-CF3 |

TABLE 2-continued

Compounds of the formula (I)

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-342 | Q-10 | 2-OCF3 |
| 2-343 | Q-10 | 3-OCF3 |
| 2-344 | Q-10 | 4-OCF3 |
| 2-345 | Q-10 | 2-Me |
| 2-346 | Q-10 | 3-Me |
| 2-347 | Q-10 | 4-Me |
| 2-348 | Q-10 | 2-OMe |
| 2-349 | Q-10 | 3-OMe |
| 2-350 | Q-10 | 4-OMe |
| 2-351 | Q-11 | 2-F |
| 2-352 | Q-11 | 3-F |
| 2-353 | Q-11 | 4-F |
| 2-354 | Q-11 | 2,3-diF |
| 2-355 | Q-11 | 2,4-diF |
| 2-356 | Q-11 | 2,5-diF |
| 2-357 | Q-11 | 2,6-diF |
| 2-358 | Q-11 | 3,4-diF |
| 2-359 | Q-11 | 3,5-diF |
| 2-360 | Q-11 | 2-F, 4-Cl |
| 2-361 | Q-11 | 2-F, 5-Cl |
| 2-362 | Q-11 | 3-F, 5-Cl |
| 2-363 | Q-11 | 2-Cl |
| 2-364 | Q-11 | 3-Cl |
| 2-365 | Q-11 | 4-Cl |
| 2-366 | Q-11 | 2,3-diCl |
| 2-367 | Q-11 | 2,4-diCl |
| 2-368 | Q-11 | 2,5-diCl |
| 2-369 | Q-11 | 2,6-diCl |
| 2-370 | Q-11 | 3,4-diCl |
| 2-371 | Q-11 | 3,5-diCl |
| 2-372 | Q-11 | 2-Cl, 4-F |
| 2-373 | Q-11 | 2-Cl, 5-F |
| 2-374 | Q-11 | 2-CF3 |
| 2-375 | Q-11 | 3-CF3 |
| 2-376 | Q-11 | 4-CF3 |
| 2-377 | Q-11 | 2-OCF3 |
| 2-378 | Q-11 | 3-OCF3 |
| 2-379 | Q-11 | 4-OCF3 |
| 2-380 | Q-11 | 2-Me |
| 2-381 | Q-11 | 3-Me |
| 2-382 | Q-11 | 4-Me |
| 2-383 | Q-11 | 2-OMe |
| 2-384 | Q-11 | 3-OMe |
| 2-385 | Q-11 | 4-OMe |
| 2-386 | Q-12 | 2-F |
| 2-387 | Q-12 | 3-F |
| 2-388 | Q-12 | 4-F |
| 2-389 | Q-12 | 2,3-diF |
| 2-390 | Q-12 | 2,4-diF |
| 2-391 | Q-12 | 2,5-diF |
| 2-392 | Q-12 | 2,6-diF |
| 2-393 | Q-12 | 3,4-diF |
| 2-394 | Q-12 | 3,5-diF |
| 2-395 | Q-12 | 2-F, 4-Cl |
| 2-396 | Q-12 | 2-F, 5-Cl |
| 2-397 | Q-12 | 3-F, 5-Cl |
| 2-398 | Q-12 | 2-Cl |
| 2-399 | Q-12 | 3-Cl |
| 2-400 | Q-12 | 4-Cl |
| 2-401 | Q-12 | 2,3-diCl |
| 2-402 | Q-12 | 2,4-diCl |
| 2-403 | Q-12 | 2,5-diCl |
| 2-404 | Q-12 | 2,6-diCl |
| 2-405 | Q-12 | 3,4-diCl |
| 2-406 | Q-12 | 3,5-diCl |
| 2-407 | Q-12 | 2-Cl, 4-F |
| 2-408 | Q-12 | 2-Cl, 5-F |
| 2-409 | Q-12 | 2-CF3 |
| 2-410 | Q-12 | 3-CF3 |
| 2-411 | Q-12 | 4-CF3 |
| 2-412 | Q-12 | 2-OCF3 |
| 2-413 | Q-12 | 3-OCF3 |
| 2-414 | Q-12 | 4-OCF3 |
| 2-415 | Q-13 | 2-Me |
| 2-416 | Q-13 | 3-Me |
| 2-417 | Q-13 | 4-Me |
| 2-418 | Q-13 | 2-OMe |
| 2-419 | Q-13 | 3-OMe |
| 2-420 | Q-13 | 4-OMe |
| 2-421 | Q-13 | 2-F |
| 2-422 | Q-13 | 3-F |
| 2-423 | Q-13 | 4-F |
| 2-424 | Q-13 | 2,3-diF |
| 2-425 | Q-13 | 2,4-diF |
| 2-426 | Q-13 | 2,5-diF |
| 2-427 | Q-13 | 2,6-diF |
| 2-428 | Q-13 | 3,4-diF |
| 2-429 | Q-13 | 3,5-diF |
| 2-430 | Q-13 | 2-F, 4-Cl |
| 2-431 | Q-13 | 2-F, 5-Cl |
| 2-432 | Q-13 | 3-F, 5-Cl |
| 2-433 | Q-13 | 2-Cl |
| 2-434 | Q-13 | 3-Cl |
| 2-435 | Q-13 | 4-Cl |
| 2-436 | Q-13 | 2,3-diCl |
| 2-437 | Q-13 | 2,4-diCl |
| 2-438 | Q-13 | 2,5-diCl |
| 2-439 | Q-13 | 2,6-diCl |
| 2-440 | Q-13 | 3,4-diCl |
| 2-441 | Q-13 | 3,5-diCl |
| 2-442 | Q-13 | 2-Cl, 4-F |
| 2-443 | Q-13 | 2-Cl, 5-F |
| 2-444 | Q-13 | 2-CF3 |
| 2-445 | Q-13 | 3-CF3 |
| 2-446 | Q-13 | 4-CF3 |
| 2-447 | Q-13 | 2-OCF3 |
| 2-448 | Q-13 | 3-OCF3 |
| 2-449 | Q-13 | 4-OCF3 |
| 2-450 | Q-13 | 2-Me |
| 2-451 | Q-13 | 3-Me |

TABLE 2-continued

Compounds of the formula (I)

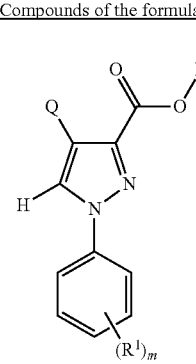

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-452 | Q-13 | 4-Me |
| 2-453 | Q-13 | 2-OMe |
| 2-454 | Q-13 | 3-OMe |
| 2-455 | Q-13 | 4-OMe |
| 2-456 | Q-14 | 2-F |
| 2-457 | Q-14 | 3-F |
| 2-458 | Q-14 | 4-F |
| 2-459 | Q-14 | 2,3-diF |
| 2-460 | Q-14 | 2,4-diF |
| 2-461 | Q-14 | 2,5-diF |
| 2-462 | Q-14 | 2,6-diF |
| 2-463 | Q-14 | 3,4-diF |
| 2-464 | Q-14 | 3,5-diF |
| 2-465 | Q-14 | 2-F, 4-Cl |
| 2-466 | Q-14 | 2-F, 5-Cl |
| 2-467 | Q-14 | 3-F, 5-Cl |
| 2-468 | Q-14 | 2-Cl |
| 2-469 | Q-14 | 3-Cl |
| 2-470 | Q-14 | 4-Cl |
| 2-471 | Q-14 | 2,3-diCl |
| 2-472 | Q-14 | 2,4-diCl |
| 2-473 | Q-14 | 2,5-diCl |
| 2-474 | Q-14 | 2,6-diCl |
| 2-475 | Q-14 | 3,4-diCl |
| 2-476 | Q-14 | 3,5-diCl |
| 2-477 | Q-14 | 2-Cl, 4-F |
| 2-478 | Q-14 | 2-Cl, 5-F |
| 2-479 | Q-14 | 2-CF3 |
| 2-480 | Q-14 | 3-CF3 |
| 2-481 | Q-14 | 4-CF3 |
| 2-482 | Q-14 | 2-OCF3 |
| 2-483 | Q-14 | 3-OCF3 |
| 2-484 | Q-14 | 4-OCF3 |
| 2-485 | Q-14 | 2-Me |
| 2-486 | Q-14 | 3-Me |
| 2-487 | Q-14 | 4-Me |
| 2-488 | Q-14 | 2-OMe |
| 2-489 | Q-14 | 3-OMe |
| 2-490 | Q-14 | 4-OMe |
| 2-491 | Q-15 | 2-F |
| 2-492 | Q-15 | 3-F |
| 2-493 | Q-15 | 4-F |
| 2-494 | Q-15 | 2,3-diF |
| 2-495 | Q-15 | 2,4-diF |
| 2-496 | Q-15 | 2,5-diF |
| 2-497 | Q-15 | 2,6-diF |
| 2-498 | Q-15 | 3,4-diF |
| 2-499 | Q-15 | 3,5-diF |
| 2-500 | Q-15 | 2-F, 4-Cl |
| 2-501 | Q-15 | 2-F, 5-Cl |
| 2-502 | Q-15 | 3-F, 5-Cl |
| 2-503 | Q-15 | 2-Cl |
| 2-504 | Q-15 | 3-Cl |
| 2-505 | Q-15 | 4-Cl |
| 2-506 | Q-15 | 2,3-diCl |
| 2-507 | Q-15 | 2,4-diCl |
| 2-508 | Q-15 | 2,5-diCl |
| 2-509 | Q-15 | 2,6-diCl |
| 2-510 | Q-15 | 3,4-diCl |
| 2-511 | Q-15 | 3,5-diCl |
| 2-512 | Q-15 | 2-Cl, 4-F |
| 2-513 | Q-15 | 2-Cl, 5-F |
| 2-514 | Q-15 | 2-CF3 |
| 2-515 | Q-15 | 3-CF3 |
| 2-516 | Q-15 | 4-CF3 |
| 2-517 | Q-15 | 2-OCF3 |
| 2-518 | Q-15 | 3-OCF3 |
| 2-519 | Q-15 | 4-OCF3 |
| 2-520 | Q-15 | 2-Me |
| 2-521 | Q-15 | 3-Me |
| 2-522 | Q-15 | 4-Me |
| 2-523 | Q-15 | 2-OMe |
| 2-524 | Q-15 | 3-OMe |
| 2-525 | Q-15 | 4-OMe |
| 2-526 | Q-16 | 2-F |
| 2-527 | Q-16 | 3-F |
| 2-528 | Q-16 | 4-F |
| 2-529 | Q-16 | 2,3-diF |
| 2-530 | Q-16 | 2,4-diF |
| 2-531 | Q-16 | 2,5-diF |
| 2-532 | Q-16 | 2,6-diF |
| 2-533 | Q-16 | 3,4-diF |
| 2-534 | Q-16 | 3,5-diF |
| 2-535 | Q-16 | 2-F, 4-Cl |
| 2-536 | Q-16 | 2-F, 5-Cl |
| 2-537 | Q-16 | 3-F, 5-Cl |
| 2-538 | Q-16 | 2-Cl |
| 2-539 | Q-16 | 3-Cl |
| 2-540 | Q-16 | 4-Cl |
| 2-541 | Q-16 | 2,3-diCl |
| 2-542 | Q-16 | 2,4-diCl |
| 2-543 | Q-16 | 2,5-diCl |
| 2-544 | Q-16 | 2,6-diCl |
| 2-545 | Q-16 | 3,4-diCl |
| 2-546 | Q-16 | 3,5-diCl |
| 2-547 | Q-16 | 2-Cl, 4-F |
| 2-548 | Q-16 | 2-Cl, 5-F |
| 2-549 | Q-16 | 2-CF3 |
| 2-550 | Q-16 | 3-CF3 |
| 2-551 | Q-16 | 4-CF3 |
| 2-552 | Q-16 | 2-OCF3 |
| 2-553 | Q-16 | 3-OCF3 |
| 2-554 | Q-16 | 4-OCF3 |
| 2-555 | Q-16 | 2-Me |
| 2-556 | Q-16 | 3-Me |
| 2-557 | Q-16 | 4-Me |
| 2-558 | Q-16 | 2-OMe |
| 2-559 | Q-16 | 3-OMe |
| 2-560 | Q-16 | 4-OMe |
| 2-561 | Q-17 | 2-F |

TABLE 2-continued

Compounds of the formula (I)

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-562 | Q-17 | 3-F |
| 2-563 | Q-17 | 4-F |
| 2-564 | Q-17 | 2,3-diF |
| 2-565 | Q-17 | 2,4-diF |
| 2-566 | Q-17 | 2,5-diF |
| 2-567 | Q-17 | 2,6-diF |
| 2-568 | Q-17 | 3,4-diF |
| 2-569 | Q-17 | 3,5-diF |
| 2-570 | Q-17 | 2-F, 4-Cl |
| 2-571 | Q-17 | 2-F, 5-Cl |
| 2-572 | Q-17 | 3-F, 5-Cl |
| 2-573 | Q-17 | 2-Cl |
| 2-574 | Q-17 | 3-Cl |
| 2-575 | Q-17 | 4-Cl |
| 2-576 | Q-17 | 2,3-diCl |
| 2-577 | Q-17 | 2,4-diCl |
| 2-578 | Q-17 | 2,5-diCl |
| 2-579 | Q-17 | 2,6-diCl |
| 2-580 | Q-17 | 3,4-diCl |
| 2-581 | Q-17 | 3,5-diCl |
| 2-582 | Q-17 | 2-Cl, 4-F |
| 2-583 | Q-17 | 2-Cl, 5-F |
| 2-584 | Q-17 | 2-CF3 |
| 2-585 | Q-17 | 3-CF3 |
| 2-586 | Q-17 | 4-CF3 |
| 2-587 | Q-17 | 2-OCF3 |
| 2-588 | Q-17 | 3-OCF3 |
| 2-589 | Q-17 | 4-OCF3 |
| 2-590 | Q-17 | 2-Me |
| 2-591 | Q-17 | 3-Me |
| 2-592 | Q-17 | 4-Me |
| 2-593 | Q-17 | 2-OMe |
| 2-594 | Q-17 | 3-OMe |
| 2-595 | Q-17 | 4-OMe |
| 2-596 | Q-18 | 2-F |
| 2-597 | Q-18 | 3-F |
| 2-598 | Q-18 | 4-F |
| 2-599 | Q-18 | 2,3-diF |
| 2-600 | Q-18 | 2,4-diF |
| 2-601 | Q-18 | 2,5-diF |
| 2-602 | Q-18 | 2,6-diF |
| 2-603 | Q-18 | 3,4-diF |
| 2-604 | Q-18 | 3,5-diF |
| 2-605 | Q-18 | 2-F, 4-Cl |
| 2-606 | Q-18 | 2-F, 5-Cl |
| 2-607 | Q-18 | 3-F, 5-Cl |
| 2-608 | Q-18 | 2-Cl |
| 2-609 | Q-18 | 3-Cl |
| 2-610 | Q-18 | 4-Cl |
| 2-611 | Q-18 | 2,3-diCl |
| 2-612 | Q-18 | 2,4-diCl |
| 2-613 | Q-18 | 2,5-diCl |
| 2-614 | Q-18 | 2,6-diCl |
| 2-615 | Q-18 | 3,4-diCl |
| 2-616 | Q-18 | 3,5-diCl |
| 2-617 | Q-18 | 2-Cl, 4-F |
| 2-618 | Q-18 | 2-Cl, 5-F |
| 2-619 | Q-18 | 2-CF3 |
| 2-620 | Q-18 | 3-CF3 |
| 2-621 | Q-18 | 4-CF3 |
| 2-622 | Q-18 | 2-OCF3 |
| 2-623 | Q-18 | 3-OCF3 |
| 2-624 | Q-18 | 4-OCF3 |
| 2-625 | Q-18 | 2-Me |
| 2-626 | Q-18 | 3-Me |
| 2-627 | Q-18 | 4-Me |
| 2-628 | Q-18 | 2-OMe |
| 2-629 | Q-18 | 3-OMe |
| 2-630 | Q-18 | 4-OMe |
| 2-631 | Q-19 | 2-F |
| 2-632 | Q-19 | 3-F |
| 2-633 | Q-19 | 4-F |
| 2-634 | Q-19 | 2,3-diF |
| 2-635 | Q-19 | 2,4-diF |
| 2-636 | Q-19 | 2,5-diF |
| 2-637 | Q-19 | 2,6-diF |
| 2-638 | Q-19 | 3,4-diF |
| 2-639 | Q-19 | 3,5-diF |
| 2-640 | Q-19 | 2-F, 4-Cl |
| 2-641 | Q-19 | 2-F, 5-Cl |
| 2-642 | Q-19 | 3-F, 5-Cl |
| 2-643 | Q-19 | 2-Cl |
| 2-644 | Q-19 | 3-Cl |
| 2-645 | Q-19 | 4-Cl |
| 2-646 | Q-19 | 2,3-diCl |
| 2-647 | Q-19 | 2,4-diCl |
| 2-648 | Q-19 | 2,5-diCl |
| 2-649 | Q-19 | 2,6-diCl |
| 2-650 | Q-19 | 3,4-diCl |
| 2-651 | Q-19 | 3,5-diCl |
| 2-652 | Q-19 | 2-Cl, 4-F |
| 2-653 | Q-19 | 2-Cl, 5-F |
| 2-654 | Q-19 | 2-CF3 |
| 2-655 | Q-19 | 3-CF3 |
| 2-656 | Q-19 | 4-CF3 |
| 2-657 | Q-19 | 2-OCF3 |
| 2-658 | Q-19 | 3-OCF3 |
| 2-659 | Q-19 | 4-OCF3 |
| 2-660 | Q-19 | 2-Me |
| 2-661 | Q-19 | 3-Me |
| 2-662 | Q-19 | 4-Me |
| 2-663 | Q-19 | 2-OMe |
| 2-664 | Q-19 | 3-OMe |
| 2-665 | Q-19 | 4-OMe |
| 2-666 | Q-20 | 2-F |
| 2-667 | Q-20 | 3-F |
| 2-668 | Q-20 | 4-F |
| 2-669 | Q-20 | 2,3-diF |
| 2-670 | Q-20 | 2,4-diF |
| 2-671 | Q-20 | 2,5-diF |

TABLE 2-continued

Compounds of the formula (I)

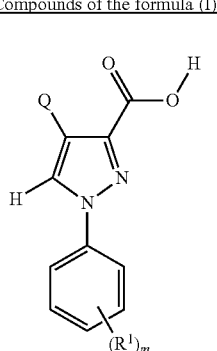

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-672 | Q-20 | 2,6-diF |
| 2-673 | Q-20 | 3,4-diF |
| 2-674 | Q-20 | 3,5-diF |
| 2-675 | Q-20 | 2-F, 4-Cl |
| 2-676 | Q-20 | 2-F, 5-Cl |
| 2-677 | Q-20 | 3-F, 5-Cl |
| 2-678 | Q-20 | 2-Cl |
| 2-679 | Q-20 | 3-Cl |
| 2-680 | Q-20 | 4-Cl |
| 2-681 | Q-20 | 2,3-diCl |
| 2-682 | Q-20 | 2,4-diCl |
| 2-683 | Q-20 | 2,5-diCl |
| 2-684 | Q-20 | 2,6-diCl |
| 2-685 | Q-20 | 3,4-diCl |
| 2-686 | Q-20 | 3,5-diCl |
| 2-687 | Q-20 | 2-Cl, 4-F |
| 2-688 | Q-20 | 2-Cl, 5-F |
| 2-689 | Q-20 | 2-CF3 |
| 2-690 | Q-20 | 3-CF3 |
| 2-691 | Q-20 | 4-CF3 |
| 2-692 | Q-20 | 2-OCF3 |
| 2-693 | Q-20 | 3-OCF3 |
| 2-694 | Q-20 | 4-OCF3 |
| 2-695 | Q-20 | 2-Me |
| 2-696 | Q-20 | 3-Me |
| 2-697 | Q-20 | 4-Me |
| 2-698 | Q-20 | 2-OMe |
| 2-699 | Q-20 | 3-OMe |
| 2-700 | Q-20 | 4-OMe |
| 2-701 | Q-21 | 2-F |
| 2-702 | Q-21 | 3-F |
| 2-703 | Q-21 | 4-F |
| 2-704 | Q-21 | 2,3-diF |
| 2-705 | Q-21 | 2,4-diF |
| 2-706 | Q-21 | 2,5-diF |
| 2-707 | Q-21 | 2,6-diF |
| 2-708 | Q-21 | 3,4-diF |
| 2-709 | Q-21 | 3,5-diF |
| 2-710 | Q-21 | 2-F, 4-Cl |
| 2-711 | Q-21 | 2-F, 5-Cl |
| 2-712 | Q-21 | 3-F, 5-Cl |
| 2-713 | Q-21 | 2-Cl |
| 2-714 | Q-21 | 3-Cl |
| 2-715 | Q-21 | 4-Cl |
| 2-716 | Q-21 | 2,3-diCl |
| 2-717 | Q-21 | 2,4-diCl |
| 2-718 | Q-21 | 2,5-diCl |
| 2-719 | Q-21 | 2,6-diCl |
| 2-720 | Q-21 | 3,4-diCl |
| 2-721 | Q-21 | 3,5-diCl |
| 2-722 | Q-21 | 2-Cl, 4-F |
| 2-723 | Q-21 | 2-Cl, 5-F |
| 2-724 | Q-21 | 2-CF3 |
| 2-725 | Q-21 | 3-CF3 |
| 2-726 | Q-21 | 4-CF3 |

TABLE 2-continued

Compounds of the formula (I)

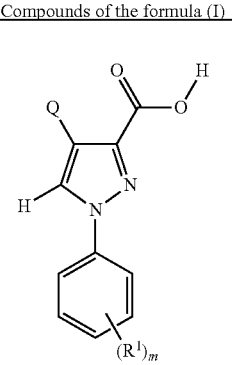

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-727 | Q-21 | 2-OCF3 |
| 2-728 | Q-21 | 3-OCF3 |
| 2-729 | Q-21 | 4-OCF3 |
| 2-730 | Q-21 | 2-Me |
| 2-731 | Q-21 | 3-Me |
| 2-732 | Q-21 | 4-Me |
| 2-733 | Q-21 | 2-OMe |
| 2-734 | Q-21 | 3-OMe |
| 2-735 | Q-21 | 4-OMe |
| 2-736 | Q-22 | 2-F |
| 2-737 | Q-22 | 3-F |
| 2-738 | Q-22 | 4-F |
| 2-739 | Q-22 | 2,3-diF |
| 2-740 | Q-22 | 2,4-diF |
| 2-741 | Q-22 | 2,5-diF |
| 2-742 | Q-22 | 2,6-diF |
| 2-743 | Q-22 | 3,4-diF |
| 2-744 | Q-22 | 3,5-diF |
| 2-745 | Q-22 | 2-F, 4-Cl |
| 2-746 | Q-22 | 2-F, 5-Cl |
| 2-747 | Q-22 | 3-F, 5-Cl |
| 2-748 | Q-22 | 2-Cl |
| 2-749 | Q-22 | 3-Cl |
| 2-750 | Q-22 | 4-Cl |
| 2-751 | Q-22 | 2,3-diCl |
| 2-752 | Q-22 | 2,4-diCl |
| 2-753 | Q-22 | 2,5-diCl |
| 2-754 | Q-22 | 2,6-diCl |
| 2-755 | Q-22 | 3,4-diCl |
| 2-756 | Q-22 | 3,5-diCl |
| 2-757 | Q-22 | 2-Cl, 4-F |
| 2-758 | Q-22 | 2-Cl, 5-F |
| 2-759 | Q-22 | 2-CF3 |
| 2-760 | Q-22 | 3-CF3 |
| 2-761 | Q-22 | 4-CF3 |
| 2-762 | Q-22 | 2-OCF3 |
| 2-763 | Q-22 | 3-OCF3 |
| 2-764 | Q-22 | 4-OCF3 |
| 2-765 | Q-22 | 2-Me |
| 2-766 | Q-22 | 3-Me |
| 2-767 | Q-22 | 4-Me |
| 2-768 | Q-22 | 2-OMe |
| 2-769 | Q-22 | 3-OMe |
| 2-770 | Q-22 | 4-OMe |
| 2-771 | Q-23 | 2-F |
| 2-772 | Q-23 | 3-F |
| 2-773 | Q-23 | 4-F |
| 2-774 | Q-23 | 2,3-diF |
| 2-775 | Q-23 | 2,4-diF |
| 2-776 | Q-23 | 2,5-diF |
| 2-777 | Q-23 | 2,6-diF |
| 2-778 | Q-23 | 3,4-diF |
| 2-779 | Q-23 | 3,5-diF |
| 2-780 | Q-23 | 2-F, 4-Cl |
| 2-781 | Q-23 | 2-F, 5-Cl |

TABLE 2-continued

Compounds of the formula (I)

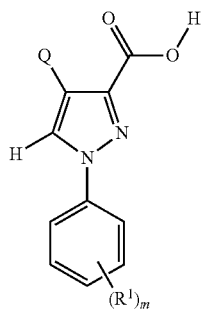

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-782 | Q-23 | 3-F, 5-Cl |
| 2-783 | Q-23 | 2-Cl |
| 2-784 | Q-23 | 3-Cl |
| 2-785 | Q-23 | 4-Cl |
| 2-786 | Q-23 | 2,3-diCl |
| 2-787 | Q-23 | 2,4-diCl |
| 2-788 | Q-23 | 2,5-diCl |
| 2-789 | Q-23 | 2,6-diCl |
| 2-790 | Q-23 | 3,4-diCl |
| 2-791 | Q-23 | 3,5-diCl |
| 2-792 | Q-23 | 2-Cl, 4-F |
| 2-793 | Q-23 | 2-Cl, 5-F |
| 2-794 | Q-23 | 2-CF3 |
| 2-795 | Q-23 | 3-CF3 |
| 2-796 | Q-23 | 4-CF3 |
| 2-797 | Q-23 | 2-OCF3 |
| 2-798 | Q-23 | 3-OCF3 |
| 2-799 | Q-23 | 4-OCF3 |
| 2-800 | Q-23 | 2-Me |
| 2-801 | Q-23 | 3-Me |
| 2-802 | Q-23 | 4-Me |
| 2-803 | Q-23 | 2-OMe |
| 2-804 | Q-23 | 3-OMe |
| 2-805 | Q-23 | 4-OMe |
| 2-806 | Q-24 | 2-F |
| 2-807 | Q-24 | 3-F |
| 2-808 | Q-24 | 4-F |
| 2-809 | Q-24 | 2,3-diF |
| 2-810 | Q-24 | 2,4-diF |
| 2-811 | Q-24 | 2,5-diF |
| 2-812 | Q-24 | 2,6-diF |
| 2-813 | Q-24 | 3,4-diF |
| 2-814 | Q-24 | 3,5-diF |
| 2-815 | Q-24 | 2-F, 4-Cl |
| 2-816 | Q-24 | 2-F, 5-Cl |
| 2-817 | Q-24 | 3-F, 5-Cl |
| 2-818 | Q-24 | 2-Cl |
| 2-819 | Q-24 | 3-Cl |
| 2-820 | Q-24 | 4-Cl |
| 2-821 | Q-24 | 2,3-diCl |
| 2-822 | Q-24 | 2,4-diCl |
| 2-823 | Q-24 | 2,5-diCl |
| 2-824 | Q-24 | 2,6-diCl |
| 2-825 | Q-24 | 3,4-diCl |
| 2-826 | Q-24 | 3,5-diCl |
| 2-827 | Q-24 | 2-Cl, 4-F |
| 2-828 | Q-24 | 2-Cl, 5-F |
| 2-829 | Q-24 | 2-CF3 |
| 2-830 | Q-24 | 3-CF3 |
| 2-831 | Q-24 | 4-CF3 |
| 2-832 | Q-24 | 2-OCF3 |
| 2-833 | Q-24 | 3-OCF3 |
| 2-834 | Q-24 | 4-OCF3 |
| 2-835 | Q-24 | 2-Me |
| 2-836 | Q-24 | 3-Me |

TABLE 2-continued

Compounds of the formula (I)

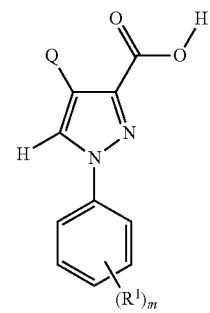

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-837 | Q-24 | 4-Me |
| 2-838 | Q-24 | 2-OMe |
| 2-839 | Q-24 | 3-OMe |
| 2-840 | Q-24 | 4-OMe |
| 2-841 | Q-25 | 2-F |
| 2-842 | Q-25 | 3-F |
| 2-843 | Q-25 | 4-F |
| 2-844 | Q-25 | 2,3-diF |
| 2-845 | Q-25 | 2,4-diF |
| 2-846 | Q-25 | 2,5-diF |
| 2-847 | Q-25 | 2,6-diF |
| 2-848 | Q-25 | 3,4-diF |
| 2-849 | Q-25 | 3,5-diF |
| 2-850 | Q-25 | 2-F, 4-Cl |
| 2-851 | Q-25 | 2-F, 5-Cl |
| 2-852 | Q-25 | 3-F, 5-Cl |
| 2-853 | Q-25 | 2-Cl |
| 2-854 | Q-25 | 3-Cl |
| 2-855 | Q-25 | 4-Cl |
| 2-856 | Q-25 | 2,3-diCl |
| 2-857 | Q-25 | 2,4-diCl |
| 2-858 | Q-25 | 2,5-diCl |
| 2-859 | Q-25 | 2,6-diCl |
| 2-860 | Q-25 | 3,4-diCl |
| 2-861 | Q-25 | 3,5-diCl |
| 2-862 | Q-25 | 2-Cl, 4-F |
| 2-863 | Q-25 | 2-Cl, 5-F |
| 2-864 | Q-25 | 2-CF3 |
| 2-865 | Q-25 | 3-CF3 |
| 2-866 | Q-25 | 4-CF3 |
| 2-867 | Q-25 | 2-OCF3 |
| 2-868 | Q-25 | 3-OCF3 |
| 2-869 | Q-25 | 4-OCF3 |
| 2-870 | Q-25 | 2-Me |
| 2-871 | Q-25 | 3-Me |
| 2-872 | Q-25 | 4-Me |
| 2-873 | Q-25 | 2-OMe |
| 2-874 | Q-25 | 3-OMe |
| 2-875 | Q-25 | 4-OMe |
| 2-876 | Q-26 | 2-F |
| 2-877 | Q-26 | 3-F |
| 2-878 | Q-26 | 4-F |
| 2-879 | Q-26 | 2,3-diF |
| 2-880 | Q-26 | 2,4-diF |
| 2-881 | Q-26 | 2,5-diF |
| 2-882 | Q-26 | 2,6-diF |
| 2-883 | Q-26 | 3,4-diF |
| 2-884 | Q-26 | 3,5-diF |
| 2-885 | Q-26 | 2-F, 4-Cl |
| 2-886 | Q-26 | 2-F, 5-Cl |
| 2-887 | Q-26 | 3-F, 5-Cl |
| 2-888 | Q-26 | 2-Cl |
| 2-889 | Q-26 | 3-Cl |
| 2-890 | Q-26 | 4-Cl |
| 2-891 | Q-26 | 2,3-diCl |

TABLE 2-continued

Compounds of the formula (I)

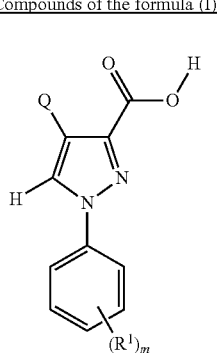

where the definition in table form below of the radical "Q" corresponds to the definition of the radicals "Q-1" to "Q-47" mentioned above as being very particularly preferred

| Ex. | Q | (R¹)$_m$ |
|---|---|---|
| 2-892 | Q-26 | 2,4-diCl |
| 2-893 | Q-26 | 2,5-diCl |
| 2-894 | Q-26 | 2,6-diCl |
| 2-895 | Q-26 | 3,4-diCl |
| 2-896 | Q-26 | 3,5-diCl |
| 2-897 | Q-26 | 2-Cl, 4-F |
| 2-898 | Q-26 | 2-Cl, 5-F |
| 2-899 | Q-26 | 2-CF3 |
| 2-900 | Q-26 | 3-CF3 |
| 2-901 | Q-26 | 4-CF3 |
| 2-902 | Q-26 | 2-OCF3 |
| 2-903 | Q-26 | 3-OCF3 |
| 2-904 | Q-26 | 4-OCF3 |
| 2-905 | Q-26 | 2-Me |
| 2-906 | Q-26 | 3-Me |
| 2-907 | Q-26 | 4-Me |
| 2-908 | Q-26 | 2-OMe |
| 2-909 | Q-26 | 3-OMe |
| 2-910 | Q-26 | 4-OMe |
| 2-911 | Q-27 | 2-F |
| 2-912 | Q-27 | 3-F |
| 2-913 | Q-27 | 4-F |
| 2-914 | Q-27 | 2,3-diF |
| 2-915 | Q-27 | 2,4-diF |
| 2-916 | Q-27 | 2,5-diF |
| 2-917 | Q-27 | 2,6-diF |
| 2-918 | Q-27 | 3,4-diF |
| 2-919 | Q-27 | 3,5-diF |
| 2-920 | Q-27 | 2-F, 4-Cl |
| 2-921 | Q-27 | 2-F, 5-Cl |
| 2-922 | Q-27 | 3-F, 5-Cl |
| 2-923 | Q-27 | 2-Cl |
| 2-924 | Q-27 | 3-Cl |
| 2-925 | Q-27 | 4-Cl |
| 2-926 | Q-27 | 2,3-diCl |
| 2-927 | Q-27 | 2,4-diCl |
| 2-928 | Q-27 | 2,5-diCl |
| 2-929 | Q-27 | 2,6-diCl |
| 2-930 | Q-27 | 3,4-diCl |
| 2-931 | Q-27 | 3,5-diCl |
| 2-932 | Q-27 | 2-Cl, 4-F |
| 2-933 | Q-27 | 2-Cl, 5-F |
| 2-934 | Q-27 | 2-CF3 |
| 2-935 | Q-27 | 3-CF3 |
| 2-936 | Q-27 | 4-CF3 |
| 2-937 | Q-27 | 2-OCF3 |
| 2-938 | Q-27 | 3-OCF3 |
| 2-939 | Q-27 | 4-OCF3 |
| 2-940 | Q-27 | 2-Me |
| 2-941 | Q-27 | 3-Me |
| 2-942 | Q-27 | 4-Me |
| 2-943 | Q-27 | 2-OMe |
| 2-944 | Q-27 | 3-OMe |
| 2-945 | Q-27 | 4-OMe |
| 2-946 | Q-28 | 2-F |

TABLE 2-continued

Compounds of the formula (I)

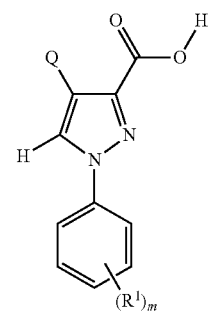

where the definition in table form below of the radical "Q" corresponds to the definition of the radicals "Q-1" to "Q-47" mentioned above as being very particularly preferred

| Ex. | Q | (R¹)$_m$ |
|---|---|---|
| 2-947 | Q-28 | 3-F |
| 2-948 | Q-28 | 4-F |
| 2-949 | Q-28 | 2,3-diF |
| 2-950 | Q-28 | 2,4-diF |
| 2-951 | Q-28 | 2,5-diF |
| 2-952 | Q-28 | 2,6-diF |
| 2-953 | Q-28 | 3,4-diF |
| 2-954 | Q-28 | 3,5-diF |
| 2-955 | Q-28 | 2-F, 4-Cl |
| 2-956 | Q-28 | 2-F, 5-Cl |
| 2-957 | Q-28 | 3-F, 5-Cl |
| 2-958 | Q-28 | 2-Cl |
| 2-959 | Q-28 | 3-Cl |
| 2-960 | Q-28 | 4-Cl |
| 2-961 | Q-28 | 2,3-diCl |
| 2-962 | Q-28 | 2,4-diCl |
| 2-963 | Q-28 | 2,5-diCl |
| 2-964 | Q-28 | 2,6-diCl |
| 2-965 | Q-28 | 3,4-diCl |
| 2-966 | Q-28 | 3,5-diCl |
| 2-967 | Q-28 | 2-Cl, 4-F |
| 2-968 | Q-28 | 2-Cl, 5-F |
| 2-969 | Q-28 | 2-CF3 |
| 2-970 | Q-28 | 3-CF3 |
| 2-971 | Q-28 | 4-CF3 |
| 2-972 | Q-28 | 2-OCF3 |
| 2-973 | Q-28 | 3-OCF3 |
| 2-974 | Q-28 | 4-OCF3 |
| 2-975 | Q-28 | 2-Me |
| 2-976 | Q-28 | 3-Me |
| 2-977 | Q-28 | 4-Me |
| 2-978 | Q-28 | 2-OMe |
| 2-979 | Q-28 | 3-OMe |
| 2-980 | Q-28 | 4-OMe |
| 2-981 | Q-29 | 2-F |
| 2-982 | Q-29 | 3-F |
| 2-983 | Q-29 | 4-F |
| 2-984 | Q-29 | 2,3-diF |
| 2-985 | Q-29 | 2,4-diF |
| 2-986 | Q-29 | 2,5-diF |
| 2-987 | Q-29 | 2,6-diF |
| 2-988 | Q-29 | 3,4-diF |
| 2-989 | Q-29 | 3,5-diF |
| 2-990 | Q-29 | 2-F, 4-Cl |
| 2-991 | Q-29 | 2-F, 5-Cl |
| 2-992 | Q-29 | 3-F, 5-Cl |
| 2-993 | Q-29 | 2-Cl |
| 2-994 | Q-29 | 3-Cl |
| 2-995 | Q-29 | 4-Cl |
| 2-996 | Q-29 | 2,3-diCl |
| 2-997 | Q-29 | 2,4-diCl |
| 2-998 | Q-29 | 2,5-diCl |
| 2-999 | Q-29 | 2,6-diCl |
| 2-1000 | Q-29 | 3,4-diCl |
| 2-1001 | Q-29 | 3,5-diCl |

TABLE 2-continued

Compounds of the formula (I)

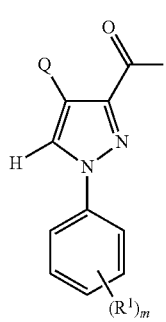

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1002 | Q-29 | 2-Cl, 4-F |
| 2-1003 | Q-29 | 2-Cl, 5-F |
| 2-1004 | Q-29 | 2-CF3 |
| 2-1005 | Q-29 | 3-CF3 |
| 2-1006 | Q-29 | 4-CF3 |
| 2-1007 | Q-29 | 2-OCF3 |
| 2-1008 | Q-29 | 3-OCF3 |
| 2-1009 | Q-29 | 4-OCF3 |
| 2-1010 | Q-29 | 2-Me |
| 2-1011 | Q-29 | 3-Me |
| 2-1012 | Q-29 | 4-Me |
| 2-1013 | Q-29 | 2-OMe |
| 2-1014 | Q-29 | 3-OMe |
| 2-1015 | Q-29 | 4-OMe |
| 2-1016 | Q-30 | 2-F |
| 2-1017 | Q-30 | 3-F |
| 2-1018 | Q-30 | 4-F |
| 2-1019 | Q-30 | 2,3-diF |
| 2-1020 | Q-30 | 2,4-diF |
| 2-1021 | Q-30 | 2,5-diF |
| 2-1022 | Q-30 | 2,6-diF |
| 2-1023 | Q-30 | 3,4-diF |
| 2-1024 | Q-30 | 3,5-diF |
| 2-1025 | Q-30 | 2-F, 4-Cl |
| 2-1026 | Q-30 | 2-F, 5-Cl |
| 2-1027 | Q-30 | 3-F, 5-Cl |
| 2-1028 | Q-30 | 2-Cl |
| 2-1029 | Q-30 | 3-Cl |
| 2-1030 | Q-30 | 4-Cl |
| 2-1031 | Q-30 | 2,3-diCl |
| 2-1032 | Q-30 | 2,4-diCl |
| 2-1033 | Q-30 | 2,5-diCl |
| 2-1034 | Q-30 | 2,6-diCl |
| 2-1035 | Q-30 | 3,4-diCl |
| 2-1036 | Q-30 | 3,5-diCl |
| 2-1037 | Q-30 | 2-Cl, 4-F |
| 2-1038 | Q-30 | 2-Cl, 5-F |
| 2-1039 | Q-30 | 2-CF3 |
| 2-1040 | Q-30 | 3-CF3 |
| 2-1041 | Q-30 | 4-CF3 |
| 2-1042 | Q-30 | 2-OCF3 |
| 2-1043 | Q-30 | 3-OCF3 |
| 2-1044 | Q-30 | 4-OCF3 |
| 2-1045 | Q-30 | 2-Me |
| 2-1046 | Q-30 | 3-Me |
| 2-1047 | Q-30 | 4-Me |
| 2-1048 | Q-30 | 2-OMe |
| 2-1049 | Q-30 | 3-OMe |
| 2-1050 | Q-30 | 4-OMe |
| 2-1051 | Q-31 | 2-F |
| 2-1052 | Q-31 | 3-F |
| 2-1053 | Q-31 | 4-F |
| 2-1054 | Q-31 | 2,3-diF |
| 2-1055 | Q-31 | 2,4-diF |
| 2-1056 | Q-31 | 2,5-diF |

TABLE 2-continued

Compounds of the formula (I)

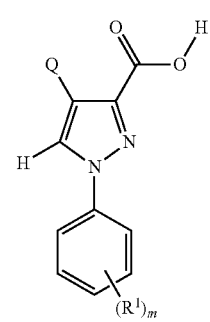

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1057 | Q-31 | 2,6-diF |
| 2-1058 | Q-31 | 3,4-diF |
| 2-1059 | Q-31 | 3,5-diF |
| 2-1060 | Q-31 | 2-F, 4-Cl |
| 2-1061 | Q-31 | 2-F, 5-Cl |
| 2-1062 | Q-31 | 3-F, 5-Cl |
| 2-1063 | Q-31 | 2-Cl |
| 2-1064 | Q-31 | 3-Cl |
| 2-1065 | Q-31 | 4-Cl |
| 2-1066 | Q-31 | 2,3-diCl |
| 2-1067 | Q-31 | 2,4-diCl |
| 2-1068 | Q-31 | 2,5-diCl |
| 2-1069 | Q-31 | 2,6-diCl |
| 2-1070 | Q-31 | 3,4-diCl |
| 2-1071 | Q-31 | 3,5-diCl |
| 2-1072 | Q-31 | 2-Cl, 4-F |
| 2-1073 | Q-31 | 2-Cl, 5-F |
| 2-1074 | Q-31 | 2-CF3 |
| 2-1075 | Q-31 | 3-CF3 |
| 2-1076 | Q-31 | 4-CF3 |
| 2-1077 | Q-31 | 2-OCF3 |
| 2-1078 | Q-31 | 3-OCF3 |
| 2-1079 | Q-31 | 4-OCF3 |
| 2-1080 | Q-31 | 2-Me |
| 2-1081 | Q-31 | 3-Me |
| 2-1082 | Q-31 | 4-Me |
| 2-1083 | Q-31 | 2-OMe |
| 2-1084 | Q-31 | 3-OMe |
| 2-1085 | Q-31 | 4-OMe |
| 2-1086 | Q-32 | 2-F |
| 2-1087 | Q-32 | 3-F |
| 2-1088 | Q-32 | 4-F |
| 2-1089 | Q-32 | 2,3-diF |
| 2-1090 | Q-32 | 2,4-diF |
| 2-1091 | Q-32 | 2,5-diF |
| 2-1092 | Q-32 | 2,6-diF |
| 2-1093 | Q-32 | 3,4-diF |
| 2-1094 | Q-32 | 3,5-diF |
| 2-1095 | Q-32 | 2-F, 4-Cl |
| 2-1096 | Q-32 | 2-F, 5-Cl |
| 2-1097 | Q-32 | 3-F, 5-Cl |
| 2-1098 | Q-32 | 2-Cl |
| 2-1099 | Q-32 | 3-Cl |
| 2-1100 | Q-32 | 4-Cl |
| 2-1101 | Q-32 | 2,3-diCl |
| 2-1102 | Q-32 | 2,4-diCl |
| 2-1103 | Q-32 | 2,5-diCl |
| 2-1104 | Q-32 | 2,6-diCl |
| 2-1105 | Q-32 | 3,4-diCl |
| 2-1106 | Q-32 | 3,5-diCl |
| 2-1107 | Q-32 | 2-Cl, 4-F |
| 2-1108 | Q-32 | 2-Cl, 5-F |
| 2-1109 | Q-32 | 2-CF3 |
| 2-1110 | Q-32 | 3-CF3 |
| 2-1111 | Q-32 | 4-CF3 |

TABLE 2-continued

Compounds of the formula (I)

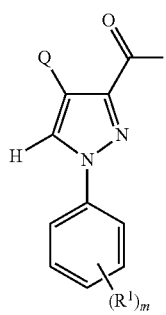

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1112 | Q-32 | 2-OCF3 |
| 2-1113 | Q-32 | 3-OCF3 |
| 2-1114 | Q-32 | 4-OCF3 |
| 2-1115 | Q-32 | 2-Me |
| 2-1116 | Q-32 | 3-Me |
| 2-1117 | Q-32 | 4-Me |
| 2-1118 | Q-32 | 2-OMe |
| 2-1119 | Q-32 | 3-OMe |
| 2-1120 | Q-32 | 4-OMe |
| 2-1121 | Q-33 | 2-F |
| 2-1122 | Q-33 | 3-F |
| 2-1123 | Q-33 | 4-F |
| 2-1124 | Q-33 | 2,3-diF |
| 2-1125 | Q-33 | 2,4-diF |
| 2-1126 | Q-33 | 2,5-diF |
| 2-1127 | Q-33 | 2,6-diF |
| 2-1128 | Q-33 | 3,4-diF |
| 2-1129 | Q-33 | 3,5-diF |
| 2-1130 | Q-33 | 2-F, 4-Cl |
| 2-1131 | Q-33 | 2-F, 5-Cl |
| 2-1132 | Q-33 | 3-F, 5-Cl |
| 2-1133 | Q-33 | 2-Cl |
| 2-1134 | Q-33 | 3-Cl |
| 2-1135 | Q-33 | 4-Cl |
| 2-1136 | Q-33 | 2,3-diCl |
| 2-1137 | Q-33 | 2,4-diCl |
| 2-1138 | Q-33 | 2,5-diCl |
| 2-1139 | Q-33 | 2,6-diCl |
| 2-1140 | Q-33 | 3,4-diCl |
| 2-1141 | Q-33 | 3,5-diCl |
| 2-1142 | Q-33 | 2-Cl, 4-F |
| 2-1143 | Q-33 | 2-Cl, 5-F |
| 2-1144 | Q-33 | 2-CF3 |
| 2-1145 | Q-33 | 3-CF3 |
| 2-1146 | Q-33 | 4-CF3 |
| 2-1147 | Q-33 | 2-OCF3 |
| 2-1148 | Q-33 | 3-OCF3 |
| 2-1149 | Q-33 | 4-OCF3 |
| 2-1150 | Q-33 | 2-Me |
| 2-1151 | Q-33 | 3-Me |
| 2-1152 | Q-33 | 4-Me |
| 2-1153 | Q-33 | 2-OMe |
| 2-1154 | Q-33 | 3-OMe |
| 2-1155 | Q-33 | 4-OMe |
| 2-1156 | Q-34 | 2-F |
| 2-1157 | Q-34 | 3-F |
| 2-1158 | Q-34 | 4-F |
| 2-1159 | Q-34 | 2,3-diF |
| 2-1160 | Q-34 | 2,4-diF |
| 2-1161 | Q-34 | 2,5-diF |
| 2-1162 | Q-34 | 2,6-diF |
| 2-1163 | Q-34 | 3,4-diF |
| 2-1164 | Q-34 | 3,5-diF |
| 2-1165 | Q-34 | 2-F, 4-Cl |
| 2-1166 | Q-34 | 2-F, 5-Cl |

TABLE 2-continued

Compounds of the formula (I)

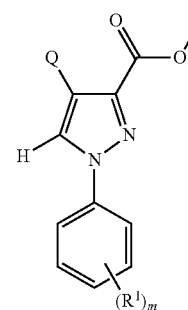

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1167 | Q-34 | 3-F, 5-Cl |
| 2-1168 | Q-34 | 2-Cl |
| 2-1169 | Q-34 | 3-Cl |
| 2-1170 | Q-34 | 4-Cl |
| 2-1171 | Q-34 | 2,3-diCl |
| 2-1172 | Q-34 | 2,4-diCl |
| 2-1173 | Q-34 | 2,5-diCl |
| 2-1174 | Q-34 | 2,6-diCl |
| 2-1175 | Q-34 | 3,4-diCl |
| 2-1176 | Q-34 | 3,5-diCl |
| 2-1177 | Q-34 | 2-Cl, 4-F |
| 2-1178 | Q-34 | 2-Cl, 5-F |
| 2-1179 | Q-34 | 2-CF3 |
| 2-1180 | Q-34 | 3-CF3 |
| 2-1181 | Q-34 | 4-CF3 |
| 2-1182 | Q-34 | 2-OCF3 |
| 2-1183 | Q-34 | 3-OCF3 |
| 2-1184 | Q-34 | 4-OCF3 |
| 2-1185 | Q-34 | 2-Me |
| 2-1186 | Q-34 | 3-Me |
| 2-1187 | Q-34 | 4-Me |
| 2-1188 | Q-34 | 2-OMe |
| 2-1189 | Q-34 | 3-OMe |
| 2-1190 | Q-34 | 4-OMe |
| 2-1191 | Q-35 | 2-F |
| 2-1192 | Q-35 | 3-F |
| 2-1193 | Q-35 | 4-F |
| 2-1194 | Q-35 | 2,3-diF |
| 2-1195 | Q-35 | 2,4-diF |
| 2-1196 | Q-35 | 2,5-diF |
| 2-1197 | Q-35 | 2,6-diF |
| 2-1198 | Q-35 | 3,4-diF |
| 2-1199 | Q-35 | 3,5-diF |
| 2-1200 | Q-35 | 2-F, 4-Cl |
| 2-1201 | Q-35 | 2-F, 5-Cl |
| 2-1202 | Q-35 | 3-F, 5-Cl |
| 2-1203 | Q-35 | 2-Cl |
| 2-1204 | Q-35 | 3-Cl |
| 2-1205 | Q-35 | 4-Cl |
| 2-1206 | Q-35 | 2,3-diCl |
| 2-1207 | Q-35 | 2,4-diCl |
| 2-1208 | Q-35 | 2,5-diCl |
| 2-1209 | Q-35 | 2,6-diCl |
| 2-1210 | Q-35 | 3,4-diCl |
| 2-1211 | Q-35 | 3,5-diCl |
| 2-1212 | Q-35 | 2-Cl, 4-F |
| 2-1213 | Q-35 | 2-Cl, 5-F |
| 2-1214 | Q-35 | 2-CF3 |
| 2-1215 | Q-35 | 3-CF3 |
| 2-1216 | Q-35 | 4-CF3 |
| 2-1217 | Q-35 | 2-OCF3 |
| 2-1218 | Q-35 | 3-OCF3 |
| 2-1219 | Q-35 | 4-OCF3 |
| 2-1220 | Q-35 | 2-Me |
| 2-1221 | Q-35 | 3-Me |

TABLE 2-continued

Compounds of the formula (I)

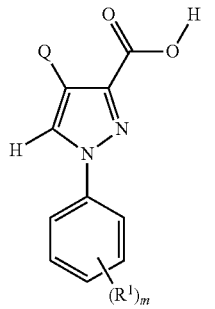

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1222 | Q-35 | 4-Me |
| 2-1223 | Q-35 | 2-OMe |
| 2-1224 | Q-35 | 3-OMe |
| 2-1225 | Q-35 | 4-OMe |
| 2-1226 | Q-36 | 2-F |
| 2-1227 | Q-36 | 3-F |
| 2-1228 | Q-36 | 4-F |
| 2-1229 | Q-36 | 2,3-diF |
| 2-1230 | Q-36 | 2,4-diF |
| 2-1231 | Q-36 | 2,5-diF |
| 2-1232 | Q-36 | 2,6-diF |
| 2-1233 | Q-36 | 3,4-diF |
| 2-1234 | Q-36 | 3,5-diF |
| 2-1235 | Q-36 | 2-F, 4-Cl |
| 2-1236 | Q-36 | 2-F, 5-Cl |
| 2-1237 | Q-36 | 3-F, 5-Cl |
| 2-1238 | Q-36 | 2-Cl |
| 2-1239 | Q-36 | 3-Cl |
| 2-1240 | Q-36 | 4-Cl |
| 2-1241 | Q-36 | 2,3-diCl |
| 2-1242 | Q-36 | 2,4-diCl |
| 2-1243 | Q-36 | 2,5-diCl |
| 2-1244 | Q-36 | 2,6-diCl |
| 2-1245 | Q-36 | 3,4-diCl |
| 2-1246 | Q-36 | 3,5-diCl |
| 2-1247 | Q-36 | 2-Cl, 4-F |
| 2-1248 | Q-36 | 2-Cl, 5-F |
| 2-1249 | Q-36 | 2-CF3 |
| 2-1250 | Q-36 | 3-CF3 |
| 2-1251 | Q-36 | 4-CF3 |
| 2-1252 | Q-36 | 2-OCF3 |
| 2-1253 | Q-36 | 3-OCF3 |
| 2-1254 | Q-36 | 4-OCF3 |
| 2-1255 | Q-36 | 2-Me |
| 2-1256 | Q-36 | 3-Me |
| 2-1257 | Q-36 | 4-Me |
| 2-1258 | Q-36 | 2-OMe |
| 2-1259 | Q-36 | 3-OMe |
| 2-1260 | Q-36 | 4-OMe |
| 2-1261 | Q-37 | 2-F |
| 2-1262 | Q-37 | 3-F |
| 2-1263 | Q-37 | 4-F |
| 2-1264 | Q-37 | 2,3-diF |
| 2-1265 | Q-37 | 2,4-diF |
| 2-1266 | Q-37 | 2,5-diF |
| 2-1267 | Q-37 | 2,6-diF |
| 2-1268 | Q-37 | 3,4-diF |
| 2-1269 | Q-37 | 3,5-diF |
| 2-1270 | Q-37 | 2-F, 4-Cl |
| 2-1271 | Q-37 | 2-F, 5-Cl |
| 2-1272 | Q-37 | 3-F, 5-Cl |
| 2-1273 | Q-37 | 2-Cl |
| 2-1274 | Q-37 | 3-Cl |
| 2-1275 | Q-37 | 4-Cl |
| 2-1276 | Q-37 | 2,3-diCl |

TABLE 2-continued

Compounds of the formula (I)

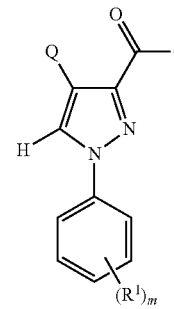

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1277 | Q-37 | 2,4-diCl |
| 2-1278 | Q-37 | 2,5-diCl |
| 2-1279 | Q-37 | 2,6-diCl |
| 2-1280 | Q-37 | 3,4-diCl |
| 2-1281 | Q-37 | 3,5-diCl |
| 2-1282 | Q-37 | 2-Cl, 4-F |
| 2-1283 | Q-37 | 2-Cl, 5-F |
| 2-1284 | Q-37 | 2-CF3 |
| 2-1285 | Q-37 | 3-CF3 |
| 2-1286 | Q-37 | 4-CF3 |
| 2-1287 | Q-37 | 2-OCF3 |
| 2-1288 | Q-37 | 3-OCF3 |
| 2-1289 | Q-37 | 4-OCF3 |
| 2-1290 | Q-37 | 2-Me |
| 2-1291 | Q-37 | 3-Me |
| 2-1292 | Q-37 | 4-Me |
| 2-1293 | Q-37 | 2-OMe |
| 2-1294 | Q-37 | 3-OMe |
| 2-1295 | Q-37 | 4-OMe |
| 2-1296 | Q-38 | 2-F |
| 2-1297 | Q-38 | 3-F |
| 2-1298 | Q-38 | 4-F |
| 2-1299 | Q-38 | 2,3-diF |
| 2-1300 | Q-38 | 2,4-diF |
| 2-1301 | Q-38 | 2,5-diF |
| 2-1302 | Q-38 | 2,6-diF |
| 2-1303 | Q-38 | 3,4-diF |
| 2-1304 | Q-38 | 3,5-diF |
| 2-1305 | Q-38 | 2-F, 4-Cl |
| 2-1306 | Q-38 | 2-F, 5-Cl |
| 2-1307 | Q-38 | 3-F, 5-Cl |
| 2-1308 | Q-38 | 2-Cl |
| 2-1309 | Q-38 | 3-Cl |
| 2-1310 | Q-38 | 4-Cl |
| 2-1311 | Q-38 | 2,3-diCl |
| 2-1312 | Q-38 | 2,4-diCl |
| 2-1313 | Q-38 | 2,5-diCl |
| 2-1314 | Q-38 | 2,6-diCl |
| 2-1315 | Q-38 | 3,4-diCl |
| 2-1316 | Q-38 | 3,5-diCl |
| 2-1317 | Q-38 | 2-Cl, 4-F |
| 2-1318 | Q-38 | 2-Cl, 5-F |
| 2-1319 | Q-38 | 2-CF3 |
| 2-1320 | Q-38 | 3-CF3 |
| 2-1321 | Q-38 | 4-CF3 |
| 2-1322 | Q-38 | 2-OCF3 |
| 2-1323 | Q-38 | 3-OCF3 |
| 2-1324 | Q-38 | 4-OCF3 |
| 2-1325 | Q-38 | 2-Me |
| 2-1326 | Q-38 | 3-Me |
| 2-1327 | Q-38 | 4-Me |
| 2-1328 | Q-38 | 2-OMe |
| 2-1329 | Q-38 | 3-OMe |
| 2-1330 | Q-38 | 4-OMe |
| 2-1331 | Q-39 | 2-F |

TABLE 2-continued

Compounds of the formula (I)

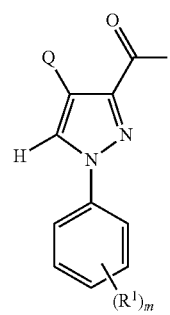

where the definition in table form below of the radical "Q" corresponds to the definition of the radicals "Q-1" to "Q-47" mentioned above as being very particularly preferred

| Ex. | Q | (R¹)$_m$ |
|---|---|---|
| 2-1332 | Q-39 | 3-F |
| 2-1333 | Q-39 | 4-F |
| 2-1334 | Q-39 | 2,3-diF |
| 2-1335 | Q-39 | 2,4-diF |
| 2-1336 | Q-39 | 2,5-diF |
| 2-1337 | Q-39 | 2,6-diF |
| 2-1338 | Q-39 | 3,4-diF |
| 2-1339 | Q-39 | 3,5-diF |
| 2-1340 | Q-39 | 2-F, 4-Cl |
| 2-1341 | Q-39 | 2-F, 5-Cl |
| 2-1342 | Q-39 | 3-F, 5-Cl |
| 2-1343 | Q-39 | 2-Cl |
| 2-1344 | Q-39 | 3-Cl |
| 2-1345 | Q-39 | 4-Cl |
| 2-1346 | Q-39 | 2,3-diCl |
| 2-1347 | Q-39 | 2,4-diCl |
| 2-1348 | Q-39 | 2,5-diCl |
| 2-1349 | Q-39 | 2,6-diCl |
| 2-1350 | Q-39 | 3,4-diCl |
| 2-1351 | Q-39 | 3,5-diCl |
| 2-1352 | Q-39 | 2-Cl, 4-F |
| 2-1353 | Q-39 | 2-Cl, 5-F |
| 2-1354 | Q-39 | 2-CF3 |
| 2-1355 | Q-39 | 3-CF3 |
| 2-1356 | Q-39 | 4-CF3 |
| 2-1357 | Q-39 | 2-OCF3 |
| 2-1358 | Q-39 | 3-OCF3 |
| 2-1359 | Q-39 | 4-OCF3 |
| 2-1360 | Q-39 | 2-Me |
| 2-1361 | Q-39 | 3-Me |
| 2-1362 | Q-39 | 4-Me |
| 2-1363 | Q-39 | 2-OMe |
| 2-1364 | Q-39 | 3-OMe |
| 2-1365 | Q-39 | 4-OMe |
| 2-1366 | Q-40 | 2-F |
| 2-1367 | Q-40 | 3-F |
| 2-1368 | Q-40 | 4-F |
| 2-1369 | Q-40 | 2,3-diF |
| 2-1370 | Q-40 | 2,4-diF |
| 2-1371 | Q-40 | 2,5-diF |
| 2-1372 | Q-40 | 2,6-diF |
| 2-1373 | Q-40 | 3,4-diF |
| 2-1374 | Q-40 | 3,5-diF |
| 2-1375 | Q-40 | 2-F, 4-Cl |
| 2-1376 | Q-40 | 2-F, 5-Cl |
| 2-1377 | Q-40 | 3-F, 5-Cl |
| 2-1378 | Q-40 | 2-Cl |
| 2-1379 | Q-40 | 3-Cl |
| 2-1380 | Q-40 | 4-Cl |
| 2-1381 | Q-40 | 2,3-diCl |
| 2-1382 | Q-40 | 2,4-diCl |
| 2-1383 | Q-40 | 2,5-diCl |
| 2-1384 | Q-40 | 2,6-diCl |
| 2-1385 | Q-40 | 3,4-diCl |
| 2-1386 | Q-40 | 3,5-diCl |

TABLE 2-continued

Compounds of the formula (I)

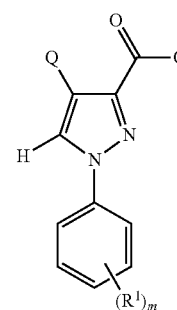

where the definition in table form below of the radical "Q" corresponds to the definition of the radicals "Q-1" to "Q-47" mentioned above as being very particularly preferred

| Ex. | Q | (R¹)$_m$ |
|---|---|---|
| 2-1387 | Q-40 | 2-Cl, 4-F |
| 2-1388 | Q-40 | 2-Cl, 5-F |
| 2-1389 | Q-40 | 2-CF3 |
| 2-1390 | Q-40 | 3-CF3 |
| 2-1391 | Q-40 | 4-CF3 |
| 2-1392 | Q-40 | 2-OCF3 |
| 2-1393 | Q-40 | 3-OCF3 |
| 2-1394 | Q-40 | 4-OCF3 |
| 2-1395 | Q-40 | 2-Me |
| 2-1396 | Q-40 | 3-Me |
| 2-1397 | Q-40 | 4-Me |
| 2-1398 | Q-40 | 2-OMe |
| 2-1399 | Q-40 | 3-OMe |
| 2-1400 | Q-40 | 4-OMe |
| 2-1401 | Q-41 | 2-F |
| 2-1402 | Q-41 | 3-F |
| 2-1403 | Q-41 | 4-F |
| 2-1404 | Q-41 | 2,3-diF |
| 2-1405 | Q-41 | 2,4-diF |
| 2-1406 | Q-41 | 2,5-diF |
| 2-1407 | Q-41 | 2,6-diF |
| 2-1408 | Q-41 | 3,4-diF |
| 2-1409 | Q-41 | 3,5-diF |
| 2-1410 | Q-41 | 2-F, 4-Cl |
| 2-1411 | Q-41 | 2-F, 5-Cl |
| 2-1412 | Q-41 | 3-F, 5-Cl |
| 2-1413 | Q-41 | 2-Cl |
| 2-1414 | Q-41 | 3-Cl |
| 2-1415 | Q-41 | 4-Cl |
| 2-1416 | Q-41 | 2,3-diCl |
| 2-1417 | Q-41 | 2,4-diCl |
| 2-1418 | Q-41 | 2,5-diCl |
| 2-1419 | Q-41 | 2,6-diCl |
| 2-1420 | Q-41 | 3,4-diCl |
| 2-1421 | Q-41 | 3,5-diCl |
| 2-1422 | Q-41 | 2-Cl, 4-F |
| 2-1423 | Q-41 | 2-Cl, 5-F |
| 2-1424 | Q-41 | 2-CF3 |
| 2-1425 | Q-41 | 3-CF3 |
| 2-1426 | Q-41 | 4-CF3 |
| 2-1427 | Q-41 | 2-OCF3 |
| 2-1428 | Q-41 | 3-OCF3 |
| 2-1429 | Q-41 | 4-OCF3 |
| 2-1430 | Q-41 | 2-Me |
| 2-1431 | Q-41 | 3-Me |
| 2-1432 | Q-41 | 4-Me |
| 2-1433 | Q-41 | 2-OMe |
| 2-1434 | Q-41 | 3-OMe |
| 2-1435 | Q-41 | 4-OMe |
| 2-1436 | Q-42 | 2-F |
| 2-1437 | Q-42 | 3-F |
| 2-1438 | Q-42 | 4-F |
| 2-1439 | Q-42 | 2,3-diF |
| 2-1440 | Q-42 | 2,4-diF |
| 2-1441 | Q-42 | 2,5-diF |

TABLE 2-continued

Compounds of the formula (I)

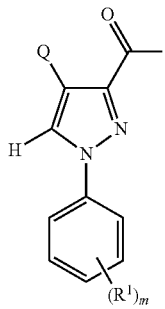

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1442 | Q-42 | 2,6-diF |
| 2-1443 | Q-42 | 3,4-diF |
| 2-1444 | Q-42 | 3,5-diF |
| 2-1445 | Q-42 | 2-F, 4-Cl |
| 2-1446 | Q-42 | 2-F, 5-Cl |
| 2-1447 | Q-42 | 3-F, 5-Cl |
| 2-1448 | Q-42 | 2-Cl |
| 2-1449 | Q-42 | 3-Cl |
| 2-1450 | Q-42 | 4-Cl |
| 2-1451 | Q-42 | 2,3-diCl |
| 2-1452 | Q-42 | 2,4-diCl |
| 2-1453 | Q-42 | 2,5-diCl |
| 2-1454 | Q-42 | 2,6-diCl |
| 2-1455 | Q-42 | 3,4-diCl |
| 2-1456 | Q-42 | 3,5-diCl |
| 2-1457 | Q-42 | 2-Cl, 4-F |
| 2-1458 | Q-42 | 2-Cl, 5-F |
| 2-1459 | Q-42 | 2-CF3 |
| 2-1460 | Q-42 | 3-CF3 |
| 2-1461 | Q-42 | 4-CF3 |
| 2-1462 | Q-42 | 2-OCF3 |
| 2-1463 | Q-42 | 3-OCF3 |
| 2-1464 | Q-42 | 4-OCF3 |
| 2-1465 | Q-42 | 2-Me |
| 2-1466 | Q-42 | 3-Me |
| 2-1467 | Q-42 | 4-Me |
| 2-1468 | Q-42 | 2-OMe |
| 2-1469 | Q-42 | 3-OMe |
| 2-1470 | Q-42 | 4-OMe |
| 2-1471 | Q-43 | 2-F |
| 2-1472 | Q-43 | 3-F |
| 2-1473 | Q-43 | 4-F |
| 2-1474 | Q-43 | 2,3-diF |
| 2-1475 | Q-43 | 2,4-diF |
| 2-1476 | Q-43 | 2,5-diF |
| 2-1477 | Q-43 | 2,6-diF |
| 2-1478 | Q-43 | 3,4-diF |
| 2-1479 | Q-43 | 3,5-diF |
| 2-1480 | Q-43 | 2-F, 4-Cl |
| 2-1481 | Q-43 | 2-F, 5-Cl |
| 2-1482 | Q-43 | 3-F, 5-Cl |
| 2-1483 | Q-43 | 2-Cl |
| 2-1484 | Q-43 | 3-Cl |
| 2-1485 | Q-43 | 4-Cl |
| 2-1486 | Q-43 | 2,3-diCl |
| 2-1487 | Q-43 | 2,4-diCl |
| 2-1488 | Q-43 | 2,5-diCl |
| 2-1489 | Q-43 | 2,6-diCl |
| 2-1490 | Q-43 | 3,4-diCl |
| 2-1491 | Q-43 | 3,5-diCl |
| 2-1492 | Q-43 | 2-Cl, 4-F |
| 2-1493 | Q-43 | 2-Cl, 5-F |
| 2-1494 | Q-43 | 2-CF3 |
| 2-1495 | Q-43 | 3-CF3 |
| 2-1496 | Q-43 | 4-CF3 |
| 2-1497 | Q-43 | 2-OCF3 |
| 2-1498 | Q-43 | 3-OCF3 |
| 2-1499 | Q-43 | 4-OCF3 |
| 2-1500 | Q-43 | 2-Me |
| 2-1501 | Q-43 | 3-Me |
| 2-1502 | Q-43 | 4-Me |
| 2-1503 | Q-43 | 2-OMe |
| 2-1504 | Q-43 | 3-OMe |
| 2-1505 | Q-43 | 4-OMe |
| 2-1506 | Q-44 | 2-F |
| 2-1507 | Q-44 | 3-F |
| 2-1508 | Q-44 | 4-F |
| 2-1509 | Q-44 | 2,3-diF |
| 2-1510 | Q-44 | 2,4-diF |
| 2-1511 | Q-44 | 2,5-diF |
| 2-1512 | Q-44 | 2,6-diF |
| 2-1513 | Q-44 | 3,4-diF |
| 2-1514 | Q-44 | 3,5-diF |
| 2-1515 | Q-44 | 2-F, 4-Cl |
| 2-1516 | Q-44 | 2-F, 5-Cl |
| 2-1517 | Q-44 | 3-F, 5-Cl |
| 2-1518 | Q-44 | 2-Cl |
| 2-1519 | Q-44 | 3-Cl |
| 2-1520 | Q-44 | 4-Cl |
| 2-1521 | Q-44 | 2,3-diCl |
| 2-1522 | Q-44 | 2,4-diCl |
| 2-1523 | Q-44 | 2,5-diCl |
| 2-1524 | Q-44 | 2,6-diCl |
| 2-1525 | Q-44 | 3,4-diCl |
| 2-1526 | Q-44 | 3,5-diCl |
| 2-1527 | Q-44 | 2-Cl, 4-F |
| 2-1528 | Q-44 | 2-Cl, 5-F |
| 2-1529 | Q-44 | 2-CF3 |
| 2-1530 | Q-44 | 3-CF3 |
| 2-1531 | Q-44 | 4-CF3 |
| 2-1532 | Q-44 | 2-OCF3 |
| 2-1533 | Q-44 | 3-OCF3 |
| 2-1534 | Q-44 | 4-OCF3 |
| 2-1535 | Q-44 | 2-Me |
| 2-1536 | Q-44 | 3-Me |
| 2-1537 | Q-44 | 4-Me |
| 2-1538 | Q-44 | 2-OMe |
| 2-1539 | Q-44 | 3-OMe |
| 2-1540 | Q-44 | 4-OMe |
| 2-1541 | Q-45 | 2-F |
| 2-1542 | Q-45 | 3-F |
| 2-1543 | Q-45 | 4-F |
| 2-1544 | Q-45 | 2,3-diF |
| 2-1545 | Q-45 | 2,4-diF |
| 2-1546 | Q-45 | 2,5-diF |
| 2-1547 | Q-45 | 2,6-diF |
| 2-1548 | Q-45 | 3,4-diF |
| 2-1549 | Q-45 | 3,5-diF |
| 2-1550 | Q-45 | 2-F, 4-Cl |
| 2-1551 | Q-45 | 2-F, 5-Cl |

TABLE 2-continued

Compounds of the formula (I)

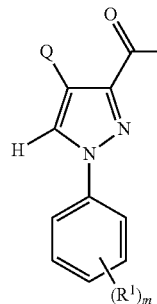

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1552 | Q-45 | 3-F, 5-Cl |
| 2-1553 | Q-45 | 2-Cl |
| 2-1554 | Q-45 | 3-Cl |
| 2-1555 | Q-45 | 4-Cl |
| 2-1556 | Q-45 | 2,3-diCl |
| 2-1557 | Q-45 | 2,4-diCl |
| 2-1558 | Q-45 | 2,5-diCl |
| 2-1559 | Q-45 | 2,6-diCl |
| 2-1560 | Q-45 | 3,4-diCl |
| 2-1561 | Q-45 | 3,5-diCl |
| 2-1562 | Q-45 | 2-Cl, 4-F |
| 2-1563 | Q-45 | 2-Cl, 5-F |
| 2-1564 | Q-45 | 2-CF3 |
| 2-1565 | Q-45 | 3-CF3 |
| 2-1566 | Q-45 | 4-CF3 |
| 2-1567 | Q-45 | 2-OCF3 |
| 2-1568 | Q-45 | 3-OCF3 |
| 2-1569 | Q-45 | 4-OCF3 |
| 2-1570 | Q-45 | 2-Me |
| 2-1571 | Q-45 | 3-Me |
| 2-1572 | Q-45 | 4-Me |
| 2-1573 | Q-45 | 2-OMe |
| 2-1574 | Q-45 | 3-OMe |
| 2-1575 | Q-45 | 4-OMe |
| 2-1576 | Q-46 | 2-F |
| 2-1577 | Q-46 | 3-F |
| 2-1578 | Q-46 | 4-F |
| 2-1579 | Q-46 | 2,3-diF |
| 2-1580 | Q-46 | 2,4-diF |
| 2-1581 | Q-46 | 2,5-diF |
| 2-1582 | Q-46 | 2,6-diF |
| 2-1583 | Q-46 | 3,4-diF |
| 2-1584 | Q-46 | 3,5-diF |
| 2-1585 | Q-46 | 2-F, 4-Cl |
| 2-1586 | Q-46 | 2-F, 5-Cl |
| 2-1587 | Q-46 | 3-F, 5-Cl |
| 2-1588 | Q-46 | 2-Cl |
| 2-1589 | Q-46 | 3-Cl |
| 2-1590 | Q-46 | 4-Cl |
| 2-1591 | Q-46 | 2,3-diCl |
| 2-1592 | Q-46 | 2,4-diCl |
| 2-1593 | Q-46 | 2,5-diCl |
| 2-1594 | Q-46 | 2,6-diCl |
| 2-1595 | Q-46 | 3,4-diCl |
| 2-1596 | Q-46 | 3,5-diCl |
| 2-1597 | Q-46 | 2-Cl, 4-F |
| 2-1598 | Q-46 | 2-Cl, 5-F |
| 2-1599 | Q-46 | 2-CF3 |
| 2-1600 | Q-46 | 3-CF3 |
| 2-1601 | Q-46 | 4-CF3 |
| 2-1602 | Q-46 | 2-OCF3 |
| 2-1603 | Q-46 | 3-OCF3 |
| 2-1604 | Q-46 | 4-OCF3 |
| 2-1605 | Q-46 | 2-Me |
| 2-1606 | Q-46 | 3-Me |

TABLE 2-continued

Compounds of the formula (I)

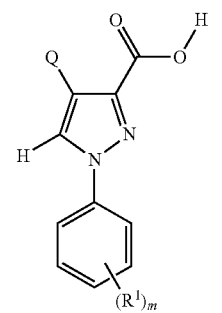

where the definition in table form below of the radical "Q" corresponds to the definition of the radicals "Q-1" to "Q-47" mentioned above as being very particularly preferred

| Ex. | Q | $(R^1)_m$ |
|---|---|---|
| 2-1607 | Q-46 | 4-Me |
| 2-1608 | Q-46 | 2-OMe |
| 2-1609 | Q-46 | 3-OMe |
| 2-1610 | Q-46 | 4-OMe |
| 2-1611 | Q-47 | 2-F |
| 2-1612 | Q-47 | 3-F |
| 2-1613 | Q-47 | 4-F |
| 2-1614 | Q-47 | 2,3-diF |
| 2-1615 | Q-47 | 2,4-diF |
| 2-1616 | Q-47 | 2,5-diF |
| 2-1617 | Q-47 | 2,6-diF |
| 2-1618 | Q-47 | 3,4-diF |
| 2-1619 | Q-47 | 3,5-diF |
| 2-1620 | Q-47 | 2-F, 4-Cl |
| 2-1621 | Q-47 | 2-F, 5-Cl |
| 2-1622 | Q-47 | 3-F, 5-Cl |
| 2-1623 | Q-47 | 2-Cl |
| 2-1624 | Q-47 | 3-Cl |
| 2-1625 | Q-47 | 4-Cl |
| 2-1626 | Q-47 | 2,3-diCl |
| 2-1627 | Q-47 | 2,4-diCl |
| 2-1628 | Q-47 | 2,5-diCl |
| 2-1629 | Q-47 | 2,6-diCl |
| 2-1630 | Q-47 | 3,4-diCl |
| 2-1631 | Q-47 | 3,5-diCl |
| 2-1632 | Q-47 | 2-Cl, 4-F |
| 2-1633 | Q-47 | 2-Cl, 5-F |
| 2-1634 | Q-47 | 2-CF3 |
| 2-1635 | Q-47 | 3-CF3 |
| 2-1636 | Q-47 | 4-CF3 |
| 2-1637 | Q-47 | 2-OCF3 |
| 2-1638 | Q-47 | 3-OCF3 |
| 2-1639 | Q-47 | 4-OCF3 |
| 2-1640 | Q-47 | 2-Me |
| 2-1641 | Q-47 | 3-Me |
| 2-1642 | Q-47 | 4-Me |
| 2-1643 | Q-47 | 2-OMe |
| 2-1644 | Q-47 | 3-OMe |
| 2-1645 | Q-47 | 4-OMe |

TABLE 3

Compounds of the formula (I) where Q = "Q-25", according to the above definition

| Ex. | (R¹)$_m$ | R² |
|---|---|---|
| 3-1 | 4-F | Me |
| 3-2 | 4-F | isopropyl |
| 3-3 | 4-F | n-propyl |
| 3-4 | 4-F | n-butyl |
| 3-5 | 2,5-diF | Me |

TABLE 4

Compounds of the formula(I)

(XI)

| Ex. | X | (R¹)$_m$ |
|---|---|---|
| 4-1 | Cl | 2-F |
| 4-2 | Cl | 3-F |
| 4-3 | Cl | 4-F |
| 4-4 | Cl | 2,3-diF |
| 4-5 | Cl | 2,4-diF |
| 4-6 | Cl | 2,5-diF |
| 4-7 | Cl | 2,6-diF |
| 4-8 | Cl | 3,4-diF |
| 4-9 | Cl | 3,5-diF |
| 4-10 | Cl | 2-F, 4-Cl |
| 4-11 | Cl | 2-F, 5-Cl |
| 4-12 | Cl | 3-F, 5-Cl |
| 4-13 | Cl | 2-Cl |
| 4-14 | Cl | 3-Cl |
| 4-15 | Cl | 4-Cl |
| 4-16 | Cl | 2,3-diCl |
| 4-17 | Cl | 2,4-diCl |
| 4-18 | Cl | 2,5-diCl |
| 4-19 | Cl | 2,6-diCl |
| 4-20 | Cl | 3,4-diCl |
| 4-21 | Cl | 3,5-diCl |
| 4-22 | Cl | 2-Cl, 4-F |
| 4-23 | Cl | 2-Cl, 5-F |
| 4-24 | Cl | 2-CF3 |
| 4-25 | Cl | 3-CF3 |
| 4-26 | Cl | 4-CF3 |
| 4-27 | Cl | 2-OCF3 |
| 4-28 | Cl | 3-OCF3 |
| 4-29 | Cl | 4-OCF3 |
| 4-30 | Cl | 2-Me |
| 4-31 | Cl | 3-Me |
| 4-32 | Cl | 4-Me |
| 4-33 | Cl | 2-OMe |
| 4-34 | Cl | 3-OMe |
| 4-35 | Cl | 4-OMe |
| 4-36 | Br | 2-F |
| 4-37 | Br | 3-F |
| 4-38 | Br | 4-F |
| 4-39 | Br | 2,3-diF |
| 4-40 | Br | 2,4-diF |
| 4-41 | Br | 2,5-diF |
| 4-42 | Br | 2,6-diF |
| 4-43 | Br | 3,4-diF |
| 4-44 | Br | 3,5-diF |
| 4-45 | Br | 2-F, 4-Cl |
| 4-46 | Br | 2-F, 5-Cl |
| 4-47 | Br | 3-F, 5-Cl |
| 4-48 | Br | 2-Cl |
| 4-49 | Br | 3-Cl |
| 4-50 | Br | 4-Cl |
| 4-51 | Br | 2,3-diCl |
| 4-52 | Br | 2,4-diCl |
| 4-53 | Br | 2,5-diCl |
| 4-54 | Br | 2,6-diCl |
| 4-55 | Br | 3,4-diCl |
| 4-56 | Br | 3,5-diCl |
| 4-57 | Br | 2-Cl, 4-F |
| 4-58 | Br | 2-Cl, 5-F |
| 4-59 | Br | 2-CF3 |
| 4-60 | Br | 3-CF3 |
| 4-61 | Br | 4-CF3 |
| 4-62 | Br | 2-OCF3 |
| 4-63 | Br | 3-OCF3 |
| 4-64 | Br | 4-OCF3 |
| 4-65 | Br | 2-Me |
| 4-66 | Br | 3-Me |
| 4-67 | Br | 4-Me |
| 4-68 | Br | 2-OMe |
| 4-69 | Br | 3-OMe |
| 4-70 | Br | 4-OMe |
| 4-71 | I | 2-F |
| 4-72 | I | 3-F |
| 4-73 | I | 4-F |
| 4-74 | I | 2,3-diF |
| 4-75 | I | 2,4-diF |
| 4-76 | I | 2,5-diF |
| 4-77 | I | 2,6-diF |
| 4-78 | I | 3,4-diF |
| 4-79 | I | 3,5-diF |
| 4-80 | I | 2-F, 4-Cl |
| 4-81 | I | 2-F, 5-Cl |
| 4-82 | I | 3-F, 5-Cl |
| 4-83 | I | 2-Cl |
| 4-84 | I | 3-Cl |
| 4-85 | I | 4-Cl |
| 4-86 | I | 2,3-diCl |
| 4-87 | I | 2,4-diCl |

TABLE 4-continued

Compounds of the formula(I)

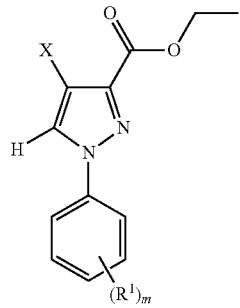

(XI)

| Ex. | X | (R¹)$_m$ |
|---|---|---|
| 4-88 | I | 2,5-diCl |
| 4-89 | I | 2,6-diCl |
| 4-90 | I | 3,4-diCl |
| 4-91 | I | 3,5-diCl |
| 4-92 | I | 2-Cl, 4-F |
| 4-93 | I | 2-Cl, 5-F |
| 4-94 | I | 2-CF3 |
| 4-95 | I | 3-CF3 |
| 4-96 | I | 4-CF3 |
| 4-97 | I | 2-OCF3 |
| 4-98 | I | 3-OCF3 |
| 4-99 | I | 4-OCF3 |
| 4-100 | I | 2-Me |
| 4-101 | I | 3-Me |
| 4-102 | I | 4-Me |
| 4-103 | I | 2-OMe |
| 4-104 | I | 3-OMe |
| 4-105 | I | 4-OMe |

The $^1$H NMR and $^{13}$C NMR spectroscopic data which are reported for the chemical examples described in the paragraphs which follow (400 MHz for $^1$H NMR and 150 MHz for $^{13}$C NMR, solvent: CDCl$_3$, CD$_3$OD or d$_6$-DMSO, internal standard: tetramethylsilane δ=0.00 ppm) were obtained on a Bruker instrument, and the signals listed have the meanings given below: br=broad; s=singlet, d=doublet, t=triplet, dd=doublet of doublets, ddd=doublet of a doublet of doublets, m=multiplet, q=quartet, quint=quintet, sext=sextet, sept=septet, t=triplet, dq=doublet of quartets, dt=doublet of triplets.

Selected spectroscopic data of the chemical examples mentioned above according to Tables 1 to 4:

TABLE 5

| Ex. | $^1$H NMR |
|---|---|
| 1-3 | [DMSO]: 8.88 (s, 1H); 8.03 (bs, 1H); 8.00-7.98 (m, 2H); 7.91 (d, 2H); 7.64 (d, 2H); 7.46-7.41 (m, 3H); 4.29 (q, 2H); 1.25 (t, 3H) |
| 1-5 | [DMSO]: 8.57 (s, 1H); 8.03 (bs, 1H); 7.90 (d, 2H); 7.67 (m, 1H); 7.63-7.54 (m, 3H); 7.40 (bs, 1H); 7.34 (m, 1H); 4.28 (q, 2H); 1.23 (t, 3H) |
| 1-10 | [DMSO]: 8.60 (s, 1H); 8.03 (bs, 1H); 7.91-7.88 (m, 3H); 7.85 (d, 1H); 7.61 (d, 2H); 7.54 (m, 1H); 7.41 (bs, 1H); 4.28 (q, 2H); 1.23 (t, 3H) |
| 1-11 | [DMSO]: 8.61 (s, 1H); 7.99-7.95 (m, 2H); 7.91 (d, 2H); 7.64-7.59 (m, 4H); 7.36 (bs, 1H); 4.28 (q, 2H); 1.24 (t, 3H) |
| 1-14 | [CDCl$_3$]: 8.01 (s, 1H); 7.86-7.73 (m, 4H); 7.62 (d, 2H); 7.48-7.36 (m, 3H); 6.08 (bs, 1H); 5.60 (bs, 1H); 4.39 (q, 1H); 1.36 (t, 3H) |
| 1-15 | [DMSO]: 8.92 (s, 1H); 8.01-7.98 (m, 3H); 7.92 (d, 2H); 7.66-7.63 (m, 4H); 7.36 (bs, 1H); 4.29 (q, 2H); 1.23 (t, 3H) |
| 1-17 | [CDCl$_3$]: 7.95 (s, 1H); 7.88 (d, 2H); 7.69-7.62 (m, 3H); 7.58-7.43 (m, 2H); 6.08 (bs, 1H); 5.59 (bs, 1H); 4.40 (q, 2H); 1.33 (t, 3H) |
| 1-22 | [DMSO]: 8.51 (s, 1H); 7.98 (bs, 1H); 7.90 (d, 2H); 7.83-7.79 (m, 2H); 7.61 (d, 2H); 7.48 (m, 1H); 7.35 (bs, 1H); 4.27 (q, 2H); 1.23 (t, 3H) |

TABLE 5-continued

| Ex. | $^1$H NMR |
|---|---|
| 1-23 | [DMSO]: 8.57 (s, 1H); 7.98 (bs, 1H); 7.90 (d, 2H); 7.81 (dd, 1H); 7.75 (dd, 1H); 7.60 (d, 2H); 7.53 (m, 1H); 7.36 (bs, 1H); 4.28 (q, 2H); 1.23 (t, 3H) |
| 1-38 | [DMSO]: 8.86 (s, 1H); 8.00-7.96 (m, 2H); 7.63 (d, 2H); 7.46-7.40 (m, 4H); 4.28 (q, 2H); 2.98 (bs, 6H); 1.24 (t, 3H) |
| 1-40 | [DMSO]: 8.54 (s, 1H); 7.90 (m, 1H); 7.65 (m, 1H); 7.59 (d, 2H); 7.43 (d, 2H); 7.33 (m, 1H); 4.27 (q, 2H); 3.00 (bs, 6H); 1.26 (t, 3H) |
| 1-41 | [DMSO]: 8.59 (s, 1H); 7.78 (m, 1H); 7.66-7.58 (m, 3H); 7.49-7.40 (m, 3H); 4.28 (q, 2H); 2.97 (bs, 6H); 1.23 (t, 3H) |
| 1-45 | [DMSO]: 8.55 (s, 1H); 7.90 (t, 1H); 7.83 (dd, 1H); 7.58 (d, 2H); 7.53 (d, 1H); 7.44 (d, 2H); 4.27 (q, 2H); 2.97 (bs, 6H); 1.25 (t, 3H) |
| 1-46 | [DMSO]: 8.59 (d, 1H); 7.97 (m, 1H); 7.64-7.58 (m, 4H); 7.44 (d, 2H); 4.28 (q, 2H); 2.98 (bd, 6H); 1.23 (t, 3H) |
| 1-52 | [DMSO]: 8.53 (s, 1H); 7.96 (d, 1H); 7.77 (d, 1H); 7.67 (dd, 1H); 7.58 (d, 2H); 7.44 (d, 2H); 4.27 (q, 2H); 2.97 (bs, 6H); 1.24 (t, 3H) |
| 1-57 | [DMSO]: 8.52 (s, 1H); 7.83-7.80 (m, 2H); 7.58 (d, 2H); 7.49 (m, 1H); 7.44 (d, 2H); 4.26 (q, 2H); 2.98 (bd, 6H); 1.22 (t, 3H) |
| 1-58 | [DMSO]: 8.56 (s, 1H); 7.83-7.74 (m, 2H); 7.58 (d, 2H); 7.52 (m, 1H); 7.44 (d, 2H); 4.27 (q, 2H); 2.97 (bs, 6H); 1.23 (t, 3H) |
| 1-108 | [DMSO]: 8.85 (s, 1H); 8.01-7.96 (m, 2H); 7.64-7.57 (m, 2H); 7.50-7.36 (m, 4H); 4.27 (q, 2H); 2.98 (bd, 6H); 1.24 (t, 3H) |
| 1-111 | [DMSO]: 8.59 (s, 1H); 7.78 (m, 1H); 7.65-7.55 (m, 3H); 7.50-7.37 (m, 3H); 4.27 (q, 2H); 2.97 (bd, 6H); 1.23 (t, 3H) |
| 1-115 | [DMSO]: 8.56 (s, 1H); 7.90 (t, 1H); 7.82 (dd, 1H); 7.61-7.46 (m, 4H); 7.38 (d, 1H); 4.26 (q, 2H); 2.97 (bd, 6H); 1.23 (t, 3H) |
| 1-116 | [DMSO]: 8.56 (s, 1H); 7.90 (t, 1H); 7.85 (dd, 1H); 7.61-7.46 (m, 4H); 7.38 (d, 1H); 4.27 (q, 2H); 2.97 (bd, 6H); 1.23 (t, 3H) |
| 1-122 | [DMSO]: 8.53 (s, 1H); 7.96 (d, 1H); 7.77 (d, 1H); 7.66 (dd, 1H); 7.59 (d, 1H); 7.54 (s, 1H); 7.47 (t, 1H); 7.36 (d, 1H); 4.26 (q, 2H); 2.97 (bd, 6H); 1.22 (t, 3H) |
| 1-127 | [DMSO]: 8.50 (s, 1H); 7.83-7.80 (m, 2H); 7.59 (d, 1H); 7.54 (s, 1H); 7.49-7.43 (m, 2H); 7.36 (d, 1H); 4.25 (q, 2H); 2.97 (bd, 6H); 1.22 (t, 3H) |
| 1-128 | [DMSO]: 8.56 (s, 1H); 7.83-7.76 (m, 2H); 7.61-7.46 (m, 4H); 7.37 (d, 1H); 4.26 (q, 2H); 2.97 (bd, 6H); 1.22 (t, 3H) |
| 1-141 | [CDCl$_3$]: 8.08 (s, 1H); 7.99 (t, 1H); 7.90 (s, 1H); 7.74-7.67 (m, 2H); 7.48 (t, 1H); 7.37-7.26 (m, 3H); 6.24 (bs, 1H); 4.38 (q, 2H); 2.92 (m, 2H); 1.32 (t, 3H); 0.90-0.87 (m, 2H); 0.64-0.61 (m, 2H) |
| 1-143 | [CDCl$_3$]: 7.97 (s, 1H); 7.91 (s, 1H); 7.77-7.74 (m, 2H); 7.70-7.66 (m, 2H); 7.47 (t, 1H); 7.20 (t, 2H); 6.25 (bs, 1H); 4.38 (q, 2H); 2.92 (m, 1H); 1.32 (t, 3H); 0.92-0.88 (m, 2H); 0.65-0.61 (m, 2H) |
| 1-146 | [DMSO]: 8.58 (s, 1H); 8.43 (bs, 1H); 7.95 (s, 1H); 7.80-7.76 (m, 2H); 7.67-7.59 (m, 2H); 7.50-7.41 (m, 2H); 4.25 (q, 2H); 2.86 (m, 1H); 1.20 (t, 3H); 0.73-0.68 (m, 2H); 0.59-0.55 (m, 2H) |
| 1-149 | [CDCl$_3$]: 8.00 (s, 1H); 7.90 (m, 1H); 7.72-7.65 (m, 2H); 7.47 (t, 1H); 7.41-7.38 (m, 2H); 6.83 (m, 1H); 6.26 (bs, 1H); 4.38 (q, 2H); 2.92 (m, 1H); 1.32 (t, 3H); 0.91-0.87 (m, 2H); 0.65-0.61 (m, 2H) |
| 1-150 | [DMSO]: 8.54 (s, 1H); 8.42 (d, 1H); 7.94-7.78 (m, 4H); 7.65 (d, 1H); 7.55-7.46 (m, 2H); 4.25 (q, 2H); 2.85 (m, 1H); 1.20 (t, 3H); 0.73-0.68 (m, 2H); 0.59-0.55 (m, 2H) |
| 1-151 | [DMSO]: 8.53 (s, 1H); 8.43 (bs, 1H); 7.95 (s, 1H); 7.83-7.74 (m, 3H); 7.66 (m, 1H); 7.55-7.46 (m, 2H); 4.24 (q, 2H); 2.85 (m, 1H); 1.20 (t, 3H); 0.71-0.68 (m, 2H); 0.58-0.56 (m, 2H) |
| 1-154 | [CDCl$_3$]: 8.01 (s, 1H); 7.90 (t, 1H); 7.85 (t, 1H); 7.69 (d, 1H); 7.65 (d, 2H); 7.47-7.38 (m, 2H); 7.35 (m, 1H); 6.32 (bs, 1H); 4.38 (q, 2H); 2.93 (m, 1H); 1.32 (t; 3H); 0.91-0.86 (m, 2H); 0.65-0.61 (m, 2H) |
| 1-155 | [DMSO]: 8.90 (s, 1H); 8.42 (bd, 1H); 7.98 (d, 2H); 7.80 (m, 1H); 7.68-7.63 (m, 3H); 7.51-7.45 (m, 2H); 4.26 (q, 2H); 2.87 (m, 1H); 1.21 (t, 3H); 0.73-0.69 (m, 2H); 0.59-0.57 (m, 2H) |
| 1-157 | [CDCl$_3$]: 7.93 (s, 1H); 7.91 (s, 1H); 7.73-7.62 (m, 3H); 7.57 (d, 1H); 7.52-7.43 (m, 2H); 6.25 (bs, 1H); 4.37 (q, 2H); 2.92 (m, 1H); 1.32 (t, 3H); 0.90-0.86 (m, 2H); 0.64-0.61 (m, 2H) |
| 1-158 | [CDCl$_3$]: 7.99 (s, 1H); 7.92 (s, 1H); 7.74-7.65 (m, 3H); 7.48-7.43 (m, 3H); 7.36 (m, 1H); 4.38 (q, 2H); 2.93 (m, 1H); 1.32 (t; 3H); 0.91-0.84 (m, 2H); 0.65-0.61 (m, 2H) |
| 1-160 | [CDCl$_3$]: 8.00 (s, 1H); 7.97 (d, 1H); 7.90 (m, 1H); 7.69-7.63 (m, 3H); 7.54 (d, 1H); 7.46 (t, 1H); 6.25 (bs, 1H); 4.38 (q, 2H); 2.93 (m, 1H); 1.33 (t; 3H); 0.90-0.87 (m, 2H); 0.65-0.61 (m, 2H) |
| 1-163 | [DMSO]: 8.53 (s, 1H); 8.43 (bd, 1H); 7.95 (s, 1H); 7.83-7.74 (m, 3H); 7.65 (d, 1H); 7.55-7.46 (m, 2H); 4.24 (q, 2H); 2.86 (m, 1H); 1.21 (t, 3H); 0.71-0.68 (m, 2H); 0.59-0.57 (m, 2H) |
| 1-169 | [CDCl$_3$]: 8.00 (s, 1H); 7.91 (m, 1H); 7.82 (d, 2H); 7.71-7.64 (m, 2H); 7.46 (t, 1H); 7.35 (d, 2H); 6.26 (bs, 1H); 4.37 (q, 2H); 2.92 (m, 1H); 1.32 (t; 3H); 0.89-0.84 (m, 2H); 0.64-0.59 (m, 2H) |

TABLE 5-continued

| Ex. | ¹H NMR |
|---|---|
| 1-173 | [CDCl₃]: 8.09 (s, 1H); 7.91 (m, 1H); 7.80 (dd, 1H); 7.73-7.67 (m, 3H); 7.45 (m, 1H); 7.09-7.05 (m, 2H); 6.26 (bs, 1H); 4.39 (q, 2H); 3.90 (s, 3H); 2.93 (m, 2H); 1.32 (t, 3H); 0.91-0.87 (m, 2H); 0.67-0.62 (m, 2H) |
| 1-176 | [CDCl₃]: 8.09 (s, 1H); 8.03-7.97 (m, 2H); 7.84-7.78 (m, 2H); 7.71 (m, 1H); 7.52-7.46 (m, 2H); 7.32 (m, 1H); 6.08 (bs, 1H); 5.55 (bs, 1H); 4.38 (q, 2H); 1.33 (t, 3H) |
| 1-178 | [DMSO]: 8.85 (s, 1H); 8.06 (bs, 1H); 8.01-7.96 (m, 3H); 7.85 (m, 1H); 7.60 (m, 1H); 7.51-7.37 (m, 4H); 4.26 (q, 2H); 1.21 (t, 3H) |
| 1-181 | [DMSO]: 8.59 (s, 1H); 8.03 (s, 1H); 7.98 (bs, 1H); 7.85 (d, 1H); 7.79 (m, 1H); 7.68-7.38 (m, 5H); 4.26 (q, 2H); 1.21 (t, 3H) |
| 1-184 | [CDCl₃]: 8.03 (s, 1H); 7.83-7.79 (m, 2H); 7.69 (m, 1H); 7.53-7.39 (m, 4H); 6.08 (bs, 1H); 5.53 (bs, 1H); 4.38 (q, 2H); 1.33 (t, 3H) |
| 1-185 | [DMSO]: 8.58 (s, 1H); 8.03-8.01 (m, 2H); 7.91 (t, 1H); 7.87-7.85 (m, 2H); 7.67 (m, 1H); 7.53 (m, 1H); 7.50 (t, 1H); 7.43 (bs, 1H); 4.26 (q, 2H); 1.20 (t, 3H) |
| 1-186 | [DMSO]: 8.59 (s, 1H); 8.03 (s, 1H); 7.99-7.96 (m, 2H); 7.85 (d, 1H); 7.67 (d, 1H); 7.63 (d, 2H); 7.49 (t, 1H); 7.37 (bs, 1H); 4.26 (q, 2H); 1.21 (t, 3H) |
| 1-188 | [CDCl₃]: 8.04 (s, 1H); 7.97 (s, 1H); 7.82-7.67 (m, 3H); 7.54-7.41 (m, 4H); 6.11 (bs, 1H); 5.58 (bs, 1H); 4.38 (q, 2H); 1.32 (t, 3H) |
| 1-189 | [CDCl₃]: 8.03 (s, 1H); 7.83-7.76 (m, 2H); 7.72-7.64 (m, 2H); 7.52-7.34 (m, 4H); 6.15 (bs, 1H); 5.61 (bs, 1H); 4.39 (q, 2H); 1.33 (t, 3H) |
| 1-190 | [DMSO]: 8.90 (s, 1H); 8.06 (m, 1H); 8.00-7.98 (m, 3H); 7.85 (dd, 1H); 7.69 (dd, 1H); 7.64 (d, 2H); 7.50 (t, 1H); 7.38 (bs, 1H); 4.27 (q, 2H); 1.22 (t, 3H) |
| 1-192 | [CDCl₃]: 8.03 (s, 1H); 7.83-7.79 (m, 2H); 7.72-7.68 (m, 2H); 7.56-7.49 (m, 3H); 6.04 (bs, 1H); 5.54 (bs, 1H); 4.38 (q, 2H); 1.32 (t, 3H) |
| 1-195 | [CDCl₃]: 8.03-7.97 (m, 3H); 7.81-7.44 (m, 5H); 6.09 (bs, 1H); 5.57 (bs, 1H); 4.42 (q, 2H); 1.33 (t; 3H) |
| 1-197 | [DMSO]: 8.48 (s, 1H); 8.02 (s, 1H); 7.97 (bs, 1H); 7.85-7.79 (m, 3H); 7.66 (d, 1H); 7.50-7.45 (m, 2H); 7.36 (bs, 1H); 4.24 (q, 2H); 1.20 (t, 3H) |
| 1-198 | [DMSO]: 8.54 (s, 1H); 8.03 (s, 1H); 7.98 (bs, 1H); 7.86-7.80 (m, 2H); 7.75 (dd, 1H); 7.55-7.47 (m, 2H); 7.37 (bs, 1H); 4.25 (q, 2H); 1.22 (t, 3H) |
| 1-204 | [CDCl₃]: 8.03 (s, 1H); 7.82-7.79 (m, 2H); 7.70 (m, 1H); 7.54-7.48 (m, 1H); 7.37 (d, 2H); 6.11 (bs, 1H); 5.58 (bs, 1H); 4.39 (q, 2H); 1.33 (t, 3H) |
| 1-316 | [CDCl₃]: 8.09 (d, 1H); 7.99 (dt, 1H); 7.84 (d, 1H); 7.38 (m, 1H); 7.31-7.24 (m, 3H); 7.13 (d, 1H); 4.39 (q, 2H); 3.95 (s, 3H); 3.91 (s, 3H); 1.33 (t, 3H) |
| 1-318 | [DMSO]: 8.93 (s, 1H); 8.01-7.98 (m, 1H); 7.70 (d, 1H); 7.44 (t, 1H); 7.38 (s, 1H); 7.21 (d, 2H); 4.30 (q, 2H); 3.87 (s, 3H); 3.80 (s, 3H); 1.25 (t, 3H) |
| 1-320 | [DMSO]: 8.62 (s, 1H); 7.90 (m, 1H); 7.69-7.63 (m, 2H); 7.37-7.32 (m, 2H); 7.17 (dd, 1H); 4.28 (q, 2H); 3.86 (s, 3H); 3.80 (s, 3H); 1.25 (t, 3H) |
| 1-321 | [DMSO]: 8.67 (s, 1H); 7.77 (m, 1H); 7.70-7.60 (m, 2H); 7.43 (m, 1H); 7.34 (s, 1H); 7.18 (dd, 1H); 4.29 (q, 2H); 3.86 (s, 3H); 3.80 (s, 3H); 1.24 (t, 3H) |
| 1-325 | [DMSO]: 8.65 (s, 1H); 7.91-7.82 (m, 2H); 7.68 (d, 1H); 7.53 (d, 1H); 7.34 (s, 1H); 7.17 (dd, 1H); 4.29 (q, 2H); 3.86 (s, 3H); 3.80 (s, 3H); 1.23 (t, 3H) |
| 1-326 | [DMSO]: 8.68 (s, 1H); 7.97 (m, 1H); 7.69 (d, 1H); 7.65-7.60 (m, 2H); 7.35 (s, 1H); 7.18 (dd, 1H); 4.29 (q, 2H); 3.86 (s, 3H); 3.80 (s, 3H); 1.24 (t, 3H) |
| 1-329 | [CDCl₃]: 8.02 (s, 1H); 7.86-7.84 (m, 2H); 7.67 (dd, 1H); 7.42 (t, 1H); 7.35 (dd, 1H); 7.23 (m, 1H); 7.12 (d, 1H); 4.38 (q, 2H); 3.96 (s, 3H); 3.90 (s, 3H); 1.32 (t, 3H) |
| 1-338 | [DMSO]: 8.64 (s, 1H); 7.81 (dd, 1H); 7.76 (dd, 1H); 7.68 (d, 1H); 7.53 (m, 1H); 7.34 (s, 1H); 7.18 (dd, 1H); 4.28 (q, 2H); 3.86 (s, 3H); 3.80 (s, 3H); 1.24 (t, 3H) |
| 1-344 | [CDCl₃]: 8.01 (s, 1H); 7.87-7.82 (m, 3H); 7.38 (d, 2H); 7.23 (s, 1H); 7.12 (d, 1H); 4.39 (q, 2H); 3.95 (s, 3H); 3.91 (s, 3H); 1.32 (t; 3H) |
| 1-356 | [DMSO]: 8.55 (s, 1H); 7.79 (m, 1H); 7.62 (m, 1H); 7.47-7.38 (m, 4H); 7.32 (m, 1H); 4.45 (s, 2H); 4.26 (q, 2H); 3.32 (s, 3H); 1.22 (t, 3H) |
| 1-360 | [DMSO]: 8.50 (s, 1H); 7.90 (t, 1H); 7.82 (dd, 1H); 7.52 (d, 1H); 7.46-7.37 (m, 3H); 7.30 (d, 1H); 4.45 (s, 2H); 4.26 (q, 2H); 2.53 (s, 3H); 1.22 (t, 3H) |
| 1-361 | [DMSO]: 8.54 (s, 1H); 7.96 (m, 1H); 7.62 (d, 2H); 7.49-7.37 (m, 2H); 7.30 (d, 2H); 4.45 (s, 2H); 4.27 (q, 2H); 2.52 (s, 3H); 1.22 (t, 3H) |
| 1-372 | [DMSO]: 8.43 (s, 1H); 7.82-7.78 (m, 2H); 7.49-7.37 (m, 4H); 7.28 (d, 1H); 4.44 (s, 2H); 4.25 (q, 2H); 2.52 (s, 3H); 1.21 (t, 3H) |
| 1-373 | [DMSO]: 8.49 (s, 1H); 7.80 (dd, 1H); 7.74 (dd, 1H); 7.54-7.37 (m, 4H); 7.29 (d, 1H); 4.45 (s, 2H); 4.25 (q, 2H); 2.52 (s, 3H); 1.32 (t, 3H) |
| 1-457 | [CDCl₃]: 8.22 (s, 1H); 7.90-7.88 (m, 2H); 7.58-7.45 (m, 4H); 7.10 (m, 2H); 4.30 (q, 2H); 1.22 (t, 3H); 1.10 (s, 9H) |
| 1-458 | [CDCl₃]: 8.19 (s, 1H); 7.78-7.75 (m, 2H); 7.57-7.49 (m, 3H); 7.40 (d, 1H); 7.19 (t, 2H); 4.30 (q, 2H); 1.23 (t, 3H); 1.10 (s, 9H) |
| 1-469 | [CDCl₃]: 8.19 (d, 1H); 8.12 (s, 1H); 7.90-7.88 (m, 2H); 7.66 (dd, 1H); 7.54-7.39 (m, 4H); 4.30 (q, 2H); 1.22 (t, 3H); 1.10 (s, 9H) |
| 1-566 | [DMSO]: 9.81 (bs, 1H); 8.49 (s, 1H); 7.76 (m, 1H); 7.62 (m, 1H); 7.59 (d, 2H); 7.42 (m, 1H); 7.24 (d, 2H); 4.27 (q, 2H); 3.02 (s, 3H); 1.23 (t, 3H) |
| 1-570 | [DMSO]: 9.81 (bs, 1H); 8.46 (s, 1H); 7.91-7.78 (m, 2H); 7.53-7.48 (m, 3H); 7.24 (d, 2H); 4.27 (q, 2H); 3.02 (s, 3H); 1.23 (t, 3H) |
| 1-571 | [DMSO]: 9.81 (bs, 1H); 8.49 (s, 1H); 7.95 (m, 1H); 7.62-7.58 (m, 2H); 7.49 (d, 2H); 7.24 (d, 2H); 4.27 (q, 2H); 3.02 (s, 3H); 1.24 (t, 3H) |
| 1-582 | [DMSO]: 9.82 (bs, 1H); 8.39 (s, 1H); 7.80-7.77 (m, 2H); 7.50-7.48 (m, 3H); 7.23 (d, 2H); 4.25 (q, 2H); 3.02 (s, 3H); 1.23 (t, 3H) |
| 1-583 | [DMSO]: 9.81 (bs, 1H); 8.45 (s, 1H); 7.80 (m, 1H); 7.75 (m, 1H); 7.53-7.48 (m, 3H); 7.23 (d, 2H); 4.26 (q, 2H); 3.02 (s, 3H); 1.21 (t, 3H) |
| 1-601 | [DMSO]: 9.80 (bs, 1H); 8.52 (s, 1H); 7.77 (m, 1H); 7.63 (m, 1H); 7.46-7.34 (m, 3H); 7.23 (d, 2H); 7.19 (d, 1H); 4.28 (q, 2H); 3.03 (s, 3H); 1.23 (t, 3H) |
| 1-605 | [DMSO]: 9.80 (bs, 1H); 8.49 (s, 1H); 7.89 (t, 1H); 7.82 (dd, 1H); 7.52 (dd, 1H); 7.39-7.34 (m, 2H); 7.22 (d, 1H); 7.19 (d, 1H); 4.27 (q, 2H); 3.03 (s, 3H); 1.23 (t, 3H) |
| 1-606 | [DMSO]: 9.80 (bs, 1H); 8.53 (s, 1H); 7.96 (m, 1H); 7.63-7.58 (m, 2H); 7.40-7.34 (m, 2H); 7.24 (d, 1H); 7.19 (d, 1H); 4.28 (q, 2H); 3.03 (s, 3H); 1.23 (t, 3H) |
| 1-617 | [DMSO]: 9.79 (bs, 1H); 8.43 (s, 1H); 7.83-7.78 (m, 2H); 7.47 (m, 1H); 7.38-7.35 (m, 2H); 7.23 (d, 1H); 7.18 (d, 1H); 4.25 (q, 2H); 3.03 (s, 3H); 1.23 (t, 3H) |
| 1-618 | [DMSO]: 9.80 (bs, 1H); 8.49 (s, 1H); 7.83-7.74 (m, 2H); 7.52 (m, 1H); 7.39-7.35 (m, 2H); 7.20 (dd, 1H); 7.18 (dd, 1H); 4.26 (q, 2H); 3.03 (s, 3H); 1.23 (t, 3H) |
| 1-670 | [DMSO]: 9.17 (s, 1H); 9.00 (s, 1H); 8.73 (s, 1H); 7.91 (m, 1H); 7.69 (m, 1H); 7.37 (m, 1H); 4.27 (q, 2H); 1.22 (t, 3H) |
| 1-674 | [CDCl₃]: 9.21 (s, 1H); 8.90 (s, 2H); 8.03 (s, 1H); 7.41-7.38 (m, 2H); 6.88 (m, 1H); 4.39 (q, 2H); 1.35 (t, 3H) |
| 1-675 | [DMSO]: 9.16 (s, 1H); 8.99 (s, 2H); 8.74 (s, 1H); 7.92-7.84 (m, 2H); 7.54 (m, 1H); 4.28 (q, 2H); 1.23 (t, 3H) |
| 1-679 | [CDCl₃]: 9.20 (s, 1H); 8.91 (s, 2H); 8.06 (s, 1H); 7.87 (t, 1H); 7.68 (dd, 1H); 7.44 (t, 1H); 7.39 (dd, 1H); 4.39 (q, 2H); 1.36 (t, 3H) |
| 1-688 | [DMSO]: 9.16 (s, 1H); 8.99 (s, 2H); 8.73 (s, 1H); 7.83 (dd, 1H); 7.76 (dd, 1H); 7.55 (m, 1H); 4.28 (q, 2H); 1.25 (t, 3H) |
| 1-703 | [CDCl₃]: 8.07 (d, 1H); 7.94 (s, 1H); 7.76-7.70 (m, 2H); 7.47 (m, 1H); 7.18 (t, 2H); 6.65 (d, 1H); 4.45 (q, 2H); 1.43 (t, 3H) |
| 1-705 | [CDCl₃]: 8.04 (d, 1H); 8.00 (s, 1H); 7.91 (m, 1H); 7.48 (t, 1H); 7.06-7.02 (m, 2H); 6.64 (d, 1H); 4.45 (q, 2H); 1.43 (t, 3H) |
| 1-706 | [DMSO]: 8.64 (d, 1H); 8.16 (s, 1H); 7.77-7.72 (m, 2H); 7.62 (m, 1H); 7.43 (m, 1H); 6.90 (d, 1H); 4.35 (q, 2H); 1.32 (t, 3H) |
| 1-709 | [CDCl₃]: 8.06 (d, 1H); 7.98 (s, 1H); 7.48 (m, 1H); 7.37-7.34 (m, 2H); 6.82 (m, 1H); 6.64 (d, 1H); 4.44 (q, 2H); 1.43 (t, 3H) |
| 1-710 | [DMSO]: 8.61 (d, 1H); 8.16 (s, 1H); 7.89-7.81 (m, 2H); 7.72 (d, 1H); 7.52 (dd, 1H); 6.89 (d, 1H); 4.34 (q, 2H); 1.31 (t, 3H) |
| 1-711 | [DMSO]: 8.65 (d, 1H); 8.16 (s, 1H); 7.93 (m, 1H); 7.73 (d, 1H); 7.64-7.59 (m, 2H); 6.90 (m, 1H); 4.35 (q, 2H); 1.32 (t, 3H) |
| 1-713 | [CDCl₃]: 8.08 (s, 1H); 7.95 (s, 1H); 7.62 (m, 1H); 7.52 (m, 1H); 7.48 (m, 1H); 7.42-7.38 (m, 2H); 6.67 (d, 1H); 4.43 (q, 2H); 1.41 (t, 3H) |
| 1-718 | [CDCl₃]: 8.08 (d, 1H); 7.98 (s, 1H); 7.69 (m, 1H); 7.47-7.45 (m, 2H); 7.37 (m, 1H); 6.64 (m, 1H); 4.45 (q, 2H); 1.43 (t, 3H) |
| 1-722 | [DMSO]: 8.55 (s, 1H); 8.16 (d, 1H); 7.81-7.76 (m, 2H); 7.72 (t, 1H); 7.47 (m, 1H); 4.32 (q, 2H); 1.30 (t, 3H) |
| 1-723 | [DMSO]: 9.00 (s, 1H); 8.16 (m, 1H); 7.80 (m, 1H); 7.75-7.72 (m, 2H); 7.52 (m, 1H); 6.87 (d, 1H); 4.34 (q, 2H); 1.32 (t, 3H) |
| 1-729 | [CDCl₃]: 8.05 (d, 1H); 7.99 (s, 1H); 7.82-7.78 (m, 2H); 7.47 (d, 1H); 7.34 (d, 2H); 6.66 (d, 1H); 4.44 (q, 2H); 1.42 (t, 3H) |
| 1-733 | [CDCl₃]: 8.05 (s, 1H); 7.72 (m, 2H); 7.51 (m, 1H); 7.45 (m, 1H); 7.06 (m, 1H); 7.01-6.97 (m, 2H); 6.68 (d, 1H); 4.45 (q, 2H); 3.90 (s, 3H); 1.42 (t, 3H) |
| 1-808 | [CDCl₃]: 8.05 (s, 2H); 8.01 (s, 1H); 7.75-7.72 (m, 2H); 7.19 (t, 2H); 4.46 (q, 2H); 1.42 (t, 3H) |

TABLE 5-continued

| Ex. | ¹H NMR |
|---|---|
| 1-810 | [CDCl₃]: 8.07-8.01 (m, 3H); 7.91 (m, 1H); 7.06-6.99 (m, 2H); 4.45 (q, 2H); 1.41 (t, 3H) |
| 1-822 | [CDCl₃]: 8.05 (bs, 2H); 7.98 (s, 1H); 7.64-7.58 (m, 3H); 7.39 (dd, 1H); 4.43 (q, 2H); 1.38 (t, 3H) |
| 1-834 | [CDCl₃]: 8.08-8.04 (m, 3H); 7.81 (d, 2H); 7.36 (d, 2H); 4.45 (q, 2H); 1.42 (t, 3H) |
| 1-841 | [CDCl₃]: 8.09 (s, 1H); 8.03 (s, 1H); 7.94 (dd, 1H); 7.73 (s, 1H); 7.37-7.23 (m, 4H), 4.46 (m, 2H); 3.98 (s, 3H); 1.45 (t, 3H) |
| 1-842 | [CDCl₃]: 7.99 (s, 1H); 7.87 (s, 1H); 7.81 (s, 1H); 7.65-7.46 (m, 4H); 4.46 (q, 2H); 3.98 (s, 3H); 1.45 (t, 3H) |
| 1-843 | [CDCl₃]: 8.05 (s, 1H); 7.98 (s, 1H); 7.75-7.71 (m, 3H); 7.20-7.18 (m, 2H); 4.45 (q, 2H); 3.95 (s, 3H); 1.44 (t, 3H) |
| 1-845 | [CDCl₃]: 8.03-8.00 (m, 2H); 7.90 (m, 1H); 7.71 (s, 1H); 7.03-6.98 (m, 2H); 4.44 (q, 2H); 3.95 (s, 3H); 1.43 (t, 3H) |
| 1-846 | [CDCl₃]: 8.15 (s, 1H); 8.03 (m, 1H); 8.03 (m, 1H); 7.76 (m, 1H); 7.73 (s, 1H), 7.22 (m, 1H); 7.05 (m, 1H); 4.47 (m, 2H); 3.99(s, 3H); 1.45 (t, 3H) |
| 1-848 | [CDCl₃]: 8.05 (s, 1H); 7.98 (s, 1H); 7.72-7.66 (m, 2H); 7.48 (m, 1H); 7.28 (m, 1H); 4.46 (q, 2H); 3.95 (s, 3H); 1.44 (t, 3H) |
| 1-851 | [CDCl₃]: 8.11 (s, 1H); 8.02 (m, 2H); 7.72 (s, 1H); 7.32 (m, 1H); 7.23 (m, 2H), 4.47 (m, 2H); 3.98 (s, 3H); 1.45 (t, 3H) |
| 1-853 | [CDCl₃]: 8.06 (s, 1H); 7.97 (s, 1H); 7.72 (s, 1H); 7.63 (m, 1H); 7.53 (m, 1H); 7.42-7.39 (m, 2H); 4.45 (q, 2H); 3.96 (s, 3H); 1.42 (t, 3H) |
| 1-854 | [CDCl₃]: 8.06 (s, 1H); 8.02 (s, 1H); 7.81 (t, 1H); 7.72 (s, 1H); 7.65 (dd, 1H); 7.40 (t, 1H); 7.33 (dd, 1H); 4.47 (q, 2H); 3.96 (s, 3H); 1.43 (t, 3H) |
| 1-857 | [DMSO]: 8.51 (s, 1H); 8.10 (s, 1H); 7.97 (d, 1H); 7.78 (s, 1H); 7.74 (d, 1H); 7.65 (dd, 1H); 4.31 (q, 2H); 3.87 (s, 3H); 1.30 (t, 3H) |
| 1-858 | [CDCl₃]: 8.03 (s, 1H); 7.97 (s, 1H); 7.70 (m, 1H); 7.47-7.44 (m, 2H); 7.36 (dd, 1H); 4.46 (q, 2H); 3.96 (s, 3H); 1.43 (t, 3H) |
| 1-860 | [CDCl₃]: 8.04 (s, 1H); 8.01 (m, 1H); 7.94 (d, 1H); 7.72 (s, 1H); 7.63 (dd, 1H); 7.56 (d, 1H); 7.46 (q, 2H); 3.96 (s, 3H); 1.45 (t, 3H) |
| 1-862 | [CDCl₃]: 8.06 (s, 1H); 7.90 (s, 1H); 7.72 (s, 1H); 7.61 (m, 1H); 7.29 (m, 1H); 7.13 (m, 1H); 4.45 (m, 2H); 3.96 (s, 3H); 1.42 (t, 3H) |
| 1-863 | [CDCl₃]: 8.05 (s, 1H); 8.03 (s, 1H); 7.51 (m, 1H); 7.47 (m, 1H); 7.13 (m, 1H); 4.46 (m, 2H); 3.98 (s, 3H); 1.43 (t, 3H) |
| 1-865 | [CDCl₃]: 8.10 (s, 1H); 8.06 (m, 2H); 7.98 (m, 1H); 7.75 (s, 1H); 7.64 (d, 1H); 4.47 (q, 2H); 3.96 (s, 3H); 1.46 (t, 3H) |
| 1-873 | [CDCl₃]: 8.11 (s, 1H); 8.05 (s, 1H); 7.83-7.72 (m, 2H); 7.35 (m, 1H); 7.09-7.03 (m, 2H); 4.43 (q, 2H); 3.93 (s, 3H); 3.88 (s, 3H); 1.42 (t, 3H) |
| 1-876 | [CDCl₃]: 8.10 (d, 1H); 8.05 (s, 1H); 7.94 (t, 1H); 7.75 (s, 1H); 7.36 (m, 1H); 7.32-7.27 (m, 2H); 4.47 (q, 2H); 4.12 (t, 2H); 1.94 (m, 2H); 1.42 (t, 3H); 0.97 (t, 3H) |
| 1-877 | [CDCl₃]: 8.05 (s, 1H); 7.89 (s, 1H); 7.75 (s, 1H); 7.66-7.51 (m, 2H); 7.45 (m, 1H); 7.08 (m, 1H); 4.46 (q, 2H); 4.14 (t, 2H); 1.95 (m, 2H); 1.45 (t, 3H); 0.96 (t, 3H) |
| 1-878 | [DMSO]: 8.85 (s, 1H); 8.13 (s, 1H); 7.97-7.90 (m, 2H); 7.83 (s, 1H); 7.44 (t, 2H); 4.35 (q, 2H); 4.10 (t, 2H); 1.86-1.77 (m, 2H); 1.34 (t, 3H); 0.86 (t, 3H) |
| 1-880 | [DMSO]: 9.51 (s, 1H); 8.13 (s, 1H); 7.90-7.82 (m, 2H); 7.64 (m, 1H); 7.32 (m, 1H); 4.33 (q, 2H); 4.09 (t, 2H); 1.85-1.76 (m, 2H); 1.31 (t, 3H); 0.86 (t, 3H) |
| 1-886 | [CDCl₃]: 8.12 (s, 1H); 8.06 (m, 1H); 8.03 (m, 1H); 7.76 (s, 1H); 7.32 (m, 1H); 7.22 (m, 2H); 4.47 (q, 2H); 4.14 (t, 2H); 1.95 (m, 2H); 1.45 (t, 3H); 0.96 (t, 3H) |
| 1-892 | [DMSO]: 8.51 (s, 1H); 8.13 (s, 1H); 7.97 (d, 1H); 7.80 (s, 1H); 7.74 (d, 1H); 7.65 (dd, 1H); 4.32 (q, 2H); 4.09 (t, 2H); 1.80 (m, 2H); 1.30 (t, 3H); 0.85 (t, 3H) |
| 1-895 | [CDCl₃]: 8.07 (s, 1H); 8.02 (s, 1H); 7.94 (d, 1H); 7.72 (s, 1H); 7.62 (dd, 1H); 7.55 (d, 1H); 7.47 (q, 2H); 4.12 (t, 2H); 1.93 (m, 2H); 1.43 (t, 3H); 0.96 (t, 3H) |
| 1-898 | [CDCl₃]: 8.07 (s, 1H); 8.04 (s, 1H); 7.73 (s, 1H); 7.49 (m, 1H); 7.44 (m, 1H); 7.13 (m, 1H); 4.46 (q, 2H); 4.13 (t, 2H); 1.94 (m, 2H); 1.44 (t, 3H); 0.95 (t, 3H) |
| 1-904 | [CDCl₃]: 8.08 (s, 1H); 8.03 (s, 1H); 7.81 (d, 2H); 7.75 (s, 1H); 7.33 (d, 2H); 4.47 (q, 2H); 4.13 (t, 2H); 1.93 (m, 2H); 1.43 (t, 3H); 0.97 (t, 3H) |
| 1-913 | [CDCl₃]: 8.30 (s, 1H); 7.77-7.73 (m, 2H); 7.51 (s, 1H); 7.18 (dd, 2H); 4.48 (q, 2H); 4.21 (s, 3H); 3.90 (s, 3H); 1.43 (t, 3H) |
| 1-915 | [CDCl₃]: 8.31 (m, 1H); 7.89 (m, 1H); 7.47 (s, 1H); 7.04-7.00 (m, 2H); 4.47 (q, 2H); 4.21 (s, 3H); 3.90 (s, 3H); 1.42 (t, 3H) |
| 1-1371 | [CDCl₃]: 8.17 (s, 1H); 8.14 (s, 1H); 8.06 (m, 1H); 7.83 (m, 1H); 7.72 (m, 1H); 7.50 (m, 1H); 7.25 (m, 1H); 7.05 (m, 1H); 4.41 (m, 4H); 1.41 (t, 3H); 1.32 (t, 3H) |
| 1-1441 | [CDCl₃]: 8.44 (s, 1H); 7.77 (m, 1H); 7.46 (s, 1H); 7.21 (m, 1H); 7.06 (m, 1H); 4.49 (m, 2H); 4.39 (m, 2H); 1.43 (m, 3H); 1.40 (t, 3H) |
| 2-10 | [DMSO]: 13.15 (bs, 1H); 8.56 (s, 1H); 8.02 (bs, 1H); 7.92-7.89 (m, 3H); 7.84 (d, 1H); 7.62 (d, 2H); 7.54 (m, 1H); 7.40 (bs, 1H) |
| 2-11 | [DMSO]: 8.57 (s, 1H); 7.98-7.95 (m, 2H); 7.89 (d, 2H); 7.65-7.59 (m, 4H); 7.42 (m, 1H) |
| 2-22 | [DMSO]: 13.00 (bs, 1H); 8.48 (s, 1H); 7.97 (bs, 1H); 7.88 (d, 2H); 7.82-7.78 (m, 2H); 7.62 (d, 2H); 7.47 (m, 1H); 7.33 (bs, 1H) |
| 2-23 | [DMSO]: 8.54 (s, 1H); 7.98 (bs, 1H); 7.89 (d, 2H); 7.81 (m, 1H); 7.74 (m, 1H); 7.62 (d, 2H); 7.51 (m, 1H); 7.34 (bs, 1H) |
| 2-41 | [DMSO]: 8.54 (s, 1H); 7.77 (m, 1H); 7.64-7.58 (m, 3H); 7.44-7.37 (m, 3H); 2.98 (bs, 6H) |
| 2-45 | [DMSO]: 13.11 (bs, 1H); 8.53 (s, 1H); 7.90 (t, 1H); 7.82 (dd, 1H); 7.60 (d, 2H); 7.51 (dd, 1H); 7.43 (d, 2H); 2.98 (bs, 6H) |
| 2-46 | [DMSO]: 13.15 (bs, 1H); 8.57 (s, 1H); 7.98 (bs, 1H); 7.63-7.60 (m, 4H); 7.43 (d, 2H); 3.30 (bd, 6H) |
| 2-52 | [DMSO]: 8.46 (s, 1H); 7.94 (d, 1H); 7.74 (d, 1H); 7.66-7.63 (m, 3H); 7.40 (d, 2H); 2.98 (bs, 6H) |
| 2-57 | [DMSO]: 13.10 (bs, 1H); 8.47 (s, 1H); 7.82-7.77 (m, 2H); 7.61 (d, 1H); 7.49-7.41 (m, 3H); 2.98 (bs, 6H) |
| 2-58 | [DMSO]: 13.07 (bs, 1H); 8.53 (s, 1H); 7.81 (m, 1H); 7.74 (m, 1H); 7.61 (d, 2H); 7.51 (m, 1H); 7.43 (d, 2H); 2.98 (bs, 6H) |
| 2-111 | [DMSO]: 8.56 (s, 1H); 7.78 (m, 1H); 7.65-7.54 (m, 3H); 7.49-7.35 (m, 3H); 2.97 (bd, 6H) |
| 2-115 | [DMSO]: 8.52 (s, 1H); 7.90 (t, 1H); 7.81 (dd, 1H); 7.61-7.44 (m, 4H); 7.36 (d, 1H); 2.97 (bd, 6H) |
| 2-116 | [DMSO]: 13.12 (bs, 1H); 8.53 (s, 1H); 7.90 (t, 1H); 7.81 (dd, 1H); 7.61 (d, 1H); 7.57 (s, 1H); 7.52 (m, 1H); 7.47 (t, 1H); 7.35 (d, 1H); 2.97 (bd, 6H) |
| 2-127 | [DMSO]: 13.00 (s, 1H); 8.49 (s, 1H); 7.82-7.79 (m, 2H); 7.60 (d, 1H); 7.56 (s, 1H); 7.48-7.45 (m, 2H); 7.35 (m, 1H); 3.16 (bd, 6H) |
| 2-141 | [CDCl₃]: 7.98 (s, 1H); 7.74-7.65 (m, 3H); 7.56-7.48 (m, 3H); 7.30-7.27 (m, 2H); 6.26 (bs, 1H); 2.96 (m, 1H); 0.93-0.88 (m, 2H); 0.67-0.64 (m, 2H) |
| 2-150 | [DMSO]: 13.10 (bs, 1H); 8.52 (s, 1H); 8.44 (s, 1H); 7.95 (s, 1H); 7.90 (t, 1H); 7.84 (dd, 1H); 7.77 (m, 1H); 7.68 (m, 1H); 7.53 (m, 1H); 7.47 (t, 1H); 2.84 (m, 1H); 0.73-0.69 (m, 2H); 0.57-0.55 (m, 2H) |
| 2-162 | [DMSO]: 12.95 (bs, 1H); 8.43-8.41 (m, 2H); 7.95 (s, 1H); 7.81-7.75 (m, 3H); 7.65 (d, 1H); 7.50-7.44 (m, 2H); 2.85 (m, 1H); 0.72-0.67 (m, 2H); 0.58-0.54 (m, 2H) |
| 2-181 | [DMSO]: 13.05 (bs, 1H); 8.54 (d, 1H); 8.02 (s, 1H); 7.97 (bs, 1H); 7.84-7.76 (m, 2H); 7.76 (m, 1H); 7.63 (m, 1H); 7.50 (t, 1H); 7.43-7.37 (m, 2H) |
| 2-185 | [DMSO]: 8.44 (s, 1H); 8.05 (s, 1H); 7.94-7.89 (m, 2H); 7.80-7.76 (m, 3H); 7.49 (dd, 1H); 7.44 (t, 1H); 7.34 (bs, 1H) |
| 2-186 | [DMSO]: 13.13 (bs, 1H); 8.55 (s, 1H); 8.03 (s, 1H); 7.99-7.97 (m, 2H); 7.82 (d, 1H); 7.69 (d, 1H); 7.63-7.60 (m, 2H); 7.48 (t, 1H); 7.37 (bs, 1H) |
| 2-192 | [DMSO]: 8.06 (s, 1H); 7.82-7.75 (m, 2H); 7.62 (d, 1H); 7.55-7.50 (m, 2H); 7.48-7.40 (m, 2H); 6.04 (bs, 1H); 5.56 (bs, 1H) |
| 2-197 | [DMSO]: 8.41 (s, 1H); 8.03 (s, 1H); 7.94 (bs, 1H); 7.79-7.73 (m, 4H); 7.48-7.43 (m, 2H); 7.34 (bs, 1H) |
| 2-198 | [DMSO]: 8.50 (s, 1H); 8.04 (s, 1H); 7.98 (bs, 1H); 7.83-7.76 (m, 2H); 7.74-7.70 (m, 2H); 7.52-7.45 (m, 2H); 7.36 (bs, 1H) |
| 2-201 | [DMSO]: 8.04 (s, 1H); 7.82-7.75 (m, 3H); 7.61 (d, 1H); 7.55-7.45 (m, 4H); 6.09 (bs, 1H); 5.57 (bs, 1H) |
| 2-356 | [DMSO]: 13.15 (bs, 1H); 8.49 (s, 1H); 7.77 (m, 1H); 7.59 (m, 1H); 7.48-7.37 (m, 4H); 7.28 (d, 1H); 4.44 (s, 2H); 2.53 (s, 3H) |
| 2-360 | [DMSO]: 13.10 (bs, 1H); 8.47 (s, 1H); 7.90 (t, 1H); 7.83 (dd, 1H); 7.52 (dd, 1H); 7.48-7.46 (m, 2H); 7.38 (t, 1H); 7.28 (d, 1H); 4.44 (s, 2H); 3.31 (s, 3H) |
| 2-361 | [DMSO]: 8.48 (s, 1H); 7.96 (m, 1H); 7.60-7.57 (m, 2H); 7.50-7.47 (m, 2H); 7.38 (t, 1H); 7.27 (d, 1H); 4.44 (s, 2H); 2.52 (s, 3H) |
| 2-372 | [DMSO]: 13.00 (bs, 1H); 8.41 (s, 1H); 7.81-7.79 (m, 2H); 7.49-7.45 (m, 3H); 7.38 (t, 1H); 7.26 (d, 1H); 4.44 (s, 2H); 3.30 (s, 3H) |
| 2-373 | [DMSO]: 13.00 (bs, 1H); 8.45 (s, 1H); 7.80 (dd, 1H); 7.73 (dd, 1H); 7.51-7.45 (m, 3H); 7.38 (t, 1H); 7.27 (d, 1H); 4.44 (s, 2H); 3.31 (s, 3H) |
| 2-566 | [DMSO]: 9.80 (bs, 1H); 8.45 (s, 1H); 7.77 (m, 1H); 7.62 (m, 1H); 7.51 (d, 2H); 7.42 (m, 1H); 7.23 (d, 2H); 3.03 (s, 3H) |
| 2-570 | [DMSO]: 9.80 (bs, 1H); 8.42 (s, 1H); 7.89 (t, 1H); 7.80 (dd, 1H); 7.51 (d, 2H); 7.22 (d, 2H); 3.02 (s, 3H) |
| 2-571 | [DMSO]: 9.85 (bs, 1H); 8.42 (s, 1H); 7.93 (m, 1H); 7.58-7.54 (m, 4H); 7.52 (d, 2H); 3.01 (s, 3H) |
| 2-583 | [DMSO]: 12.90 (bs, 1H); 9.78 (bs, 1H); 8.42 (s, 1H); 7.78 (dd, 1H); 7.71 (dd, 1H); 7.52-7.47 (m, 3H); 7.22 (d, 2H); 3.02 (s, 3H) |

TABLE 5-continued

| Ex. | $^1$H NMR |
|---|---|
| 2-601 | [DMSO]: 13.15 (bs, 1H); 8.47 (d, 1H); 7.77 (m, 1H); 7.63 (m, 1H); 7.44-7.34 (m, 3H); 7.25 (d, 1H); 7.15 (d, 1H) 3.03 (s, 3H) |
| 2-605 | [DMSO]: 9.78 (bs, 1H); 8.44 (s, 1H); 7.89 (t, 1H); 7.81 (dd, 1H); 7.51 (dd, 1H); 7.41 (t, 1H); 7.36 (t, 1H); 7.25 (d, 1H); 7.15 (d, 1H); 3.03 (s, 3H) |
| 2-606 | [DMSO]: 13.10 (bs, 1H); 9.78 (bs, 1H); 8.48 (d, 1H); 7.96 (m, 1H); 7.62-7.59 (m, 2H); 7.41-7.34 (m, 2H); 7.25 (d, 1H); 7.15 (dd, 1H); 3.03 (s, 3H) |
| 2-617 | [DMSO]: 13.00 (bs, 1H); 9.77 (bs, 1H); 8.39 (s, 1H); 7.82-7.77 (m, 2H); 7.47 (m, 1H); 7.42 (m, 1H); 7.35 (t, 1H); 7.23 (d, 1H); 7.15 (d, 1H); 3.03 (s, 3H) |
| 2-618 | [DMSO]: 9.78 (bs, 1H); 8.44 (s, 1H); 7.80 (dd, 1H); 7.73 (dd, 1H); 7.50 (m, 1H); 7.42 (s, 1H); 7.36 (t, 1H); 7.24 (d, 1H); 7.15 (d, 1H); 3.03 (s, 3H) |
| 2-687 | [DMSO]: 9.10 (s, 1H); 9.01 (s, 1H); 8.47 (s, 1H); 7.75-7.71 (m, 2H); 7.64-7.61 (m, 2H); 7.44 (m, 1H) |
| 2-706 | [DMSO]: 13.14 (bs, 1H); 8.62 (d, 1H); 8.19 (s, 1H); 7.76 (m, 1H); 7.71 (s, 1H); 7.62 (m, 1H); 7.41 (m, 1H); 6.92 (d, 1H) |
| 2-710 | [DMSO]: 13.11 (bs, 1H); 8.59 (d, 1H); 8.19 (d, 1H); 7.90-7.80 (m, 2H); 7.71 (d, 1H); 7.53 (dd, 1H); 6.91 (d, 1H) |
| 2-711 | [DMSO]: 13.15 (bs, 1H); 8.63 (d, 1H); 8.20 (s, 1H); 7.94 (dd, 1H); 7.71 (t, 1H); 7.64-7.60 (m, 2H); 6.92 (d, 1H) |
| 2-723 | [DMSO]: 13.10 (bs, 1H); 8.58 (s, 1H); 8.19 (s, 1H); 7.80 (dd, 1H); 7.73-7.70 (m, 2H); 7.51 (m, 1H); 6.88 (d, 1H) |
| 2-775 | [DMSO]: 13.05 (bs, 1H); 8.42 (s, 1H); 7.91 (m, 1H); 7.64 (m, 1H); 7.33 (m, 1H); 2.28 (s, 3H); 2.11 (s, 3H) |
| 2-841 | [DMSO]: 13.0 (bs, 1H); 8.53 (s, 1H); 8.13 (s, 1H); 7.83 (m, 2H); 7.81 (s, 1H); 7.53 (m, 2H); 7.41 (m, 1H); 3.87 (s, 3H) |
| 2-843 | [CDCl$_3$]: 8.14 (s, 1H); 8.05 (s, 1H); 7.77-7.71 (m, 3H); 7.21 (dd, 2H); 3.96 (s, 3H) |
| 2-845 | [DMSO]: 12.95 (bs, 1H); 8.49 (s, 1H); 8.10 (s, 1H); 7.87 (m, 1H); 7.81 (s, 1H); 7.63 (m, 1H); 7.32 (m, 1H); 3.86 (s, 3H) |
| 2-846 | [DMSO]: 12.90 (bs, 1H); 8.55 (s, 1H); 8.12 (s, 1H); 7.83 (m, 1H); 7.75 (m, 1H); 7.62 (m, 1H); 7.39 (m, 1H); 3.86 (s, 3H); |
| 2-851 | [DMSO]: 8.56 (s, 1H); 8.12 (s, 1H); 7.93 (m, 1H); 7.83 (s, 1H); 7.60 (m, 2H); 3.87 (s, 3H) |
| 2-857 | [DMSO]: 12.95 (bs, 1H); 8.46 (s, 1H); 8.10 (s, 1H); 7.94 (d, 1H); 7.79 (s, 1H); 7.72 (d, 1H); 7.65 (dd, 1H); 3.86 (s, 3H) |
| 2-863 | [CDCl$_3$]: 8.30 (s, 1H); 8.20 (s, 1H); 7.90 (s, 1H); 7.55 (m, 1H); 7.42 (m, 1H); 7.20 (m, 1H); 4.08 (s, 3H) |
| 2-878 | [DMSO]: 12.90 (bs, 1H); 8.87 (s, 1H); 8.13 (s, 1H); 7.96-7.93 (m, 2H); 7.85 (s, 1H); 7.43 (t, 2H); 4.09 (t, 2H); 1.83-1.78 (m, 2H); 0.88 (t, 3H) |
| 2-892 | [DMSO]: 8.46 (s, 1H); 8.13 (s, 1H); 7.94 (d, 1H); 7.81 (s, 1H); 7.72 (d, 1H); 7.64 (dd, 1H); 4.07 (q, 2H); 1.82-1.77 (m, 2H); 0.83 (t, 3H) |
| 2-1476 | [DMSO]: 8.58 (s, 1H); 7.78 (m, 1H); 7.60 (m, 1H); 7.40 (m, 1H); 7.34 (s, 1H); 4.12 (s, 3H) |
| 2-1581 | [DMSO]: 13.06 (bs, 1H); 8.58 (s, 1H); 8.11 (s, 1H); 7.91 (d, 1H); 7.78 (m, 1H); 7.62 (m, 1H); 7.54 (t, 1H); 7.40 (m, 1H) |
| 3-1 | [CDCl$_3$]: 8.08 (s, 1H); 7.99 (s, 1H); 7.73-7.69 (m, 3H); 7.20-7.14 (m, 2H); 3.98 (s, 3H); 3.96 (s, 3H) |
| 3-2 | [CDCl$_3$]: 8.03 (s, 1H); 7.97 (s, 1H); 7.75-7.69 (m, 3H); 7.18-7.15 (m, 2H); 5.30 (m, 1H); 3.96 (s, 3H); 1.42 (d, 6H) |
| 3-3 | [DMSO]: 8.86 (s, 1H); 8.10 (s, 1H); 7.95-7.92 (m, 2H); 7.81 (s, 1H); 7.45-7.40 (m, 2H); 4.26 (t, 2H); 3.88 (s, 3H); 1.75-1.70 (m, 2H); 0.94 (t, 3H) |
| 3-4 | [DMSO]: 8.85 (s, 1H); 8.09 (s, 1H); 7.95-7.92 (m, 2H); 7.80 (s, 1H); 7.42 (t, 2H); 4.30 (t, 2H); 3.88 (s, 3H); 1.69 (m, 2H); 1.38 (m, 2H); 0.93 (t, 3H) |
| 3-5 | [DMSO]: 8.61 (s, 1H); 8.13 (s, 1H); 7.83 (s, 1H); 7.75 (m, 1H); 7.62 (m, 1H); 7.42 (m, 1H); 3.88 (s, 6H); |
| 4-36 | [CDCl$_3$]: 8.06 (s, 1 H); 7.91 (m, 1 H); 7.37 (m, 1 H); 7.31-7.20 (m, 2 H); 4.47 (q, 2 H); 1.43 (t, 3 H) |
| 4-37 | [CDCl$_3$]: 8.06 (s, 1 H); 8.00 (m, 1 H); 7.92 (m, 1 H); 7.65-7.60 (m, 2 H); 4.48 (q, 2 H); 1.45 (t, 3 H) |
| 4-38 | [CDCl$_3$]: 7.93 (s, 1 H); 7.69-7.65 (m, 2 H); 7.20-7.15 (m, 2 H); 4.46 (q, 2 H); 1.43 (t, 3 H) |
| 4-40 | [CDCl$_3$]: 7.99 (s, 1 H); 7.88 (m, 1 H); 7.05-6.98 (m, 2 H); 4.46 (q, 2 H); 1.43 (t, 3 H) |
| 4-41 | [CDCl$_3$]: 8.11 (s, 1 H); 7.73 (m, 1 H); 7.23 (m, 1 H); 7.06 (m, 1 H); 4.47 (q, 2 H); 1.45 (t, 3 H) |
| 4-43 | [CDCl$_3$]: 7.94 (s, 1 H); 7.63 (m, 1 H); 7.42 (m, 1 H); 7.24 (m, 1 H); 4.47 (q, 2 H); 1.44 (t, 3 H) |
| 4-44 | [CDCl$_3$]: 7.99 (s, 1 H); 7.33-7.27 (m, 2 H); 6.83 (m, 1 H); 4.48 (q, 2 H); 1.43 (t, 3 H) |
| 4-46 | [CDCl$_3$]: 8.08 (s, 1 H); 8.01 (dd, 1 H); 7.33 (m, 1 H); 7.20 (dd, 1 H); 4.48 (q, 2 H); 1.45 (t, 3 H) |
| 4-48 | [CDCl$_3$]: 7.92 (s, 1 H); 7.59 (m, 1 H); 7.43-7.38 (m, 2 H); 4.45 (q, 2 H); 1.43 (t, 3 H) |
| 4-53 | [CDCl$_3$]: 7.97 (s, 1 H); 7.67 (d, 1 H); 7.47 (d, 1 H); 7.69 (dd, 1 H); 4.48 (q, 2 H); 1.43 (t, 3 H) |
| 4-55 | [CDCl$_3$]: 7.98 (s; 1 H); 7.89 (s, 1 H); 7.56 (d, 2 H); 4.47 (q, 2 H); 1.43 (t, 3 H) |
| 4-57 | [CDCl$_3$]: 7.87 (s, 1 H); 7.57 (dd, 1 H); 7.28 (dd, 1 H); 7.13 (dt, 1 H); 4.46 (q, 2 H); 1.43 (t, 3 H) |
| 4-58 | [CDCl$_3$]: 8.00 (s, 1 H); 7.50 (dd, 1 H); 7.41 (dd, 1 H); 7.15 (m, 1 H); 4.47 (q, 2 H); 1.44 (t, 3 H) |
| 4-61 | [CDCl$_3$]: 8.07 (s, 1 H); 7.87 (d, 2 H); 7.76 (d, 2 H); 4.48 (q, 2 H); 1.43 (t, 3 H) |
| 4-64 | [CDCl$_3$]: 7.98 (s, 1 H); 7.73 (d, 2 H); 7.32 (d, 2 H); 4.46 (q, 2 H); 1.43 (t, 3 H) |

The present invention accordingly provides for the use of at least one compound selected from the group consisting of 4-substituted 1-phenylpyrazole-3-carboxylic acid derivatives of the general formula (I) or salts thereof, and of any mixtures of 4-substituted 1-phenylpyrazole-3-carboxylic acid derivatives of the general formula (I) or salts thereof with agrochemically active compounds corresponding to the definition below, for increasing the resistance of plants to abiotic stress factors, preferably to cold stress or drought stress, particularly preferably to drought stress, and for enhancing plant growth and/or for increasing plant yield.

The present invention further provides a spray solution for treatment of plants, comprising an amount, effective for enhancement of the resistance of plants to abiotic stress factors, of at least one compound selected from the group consisting of 4-substituted 1-phenylpyrazole-3-carboxylic acid derivatives of the general formula (I) or salts thereof. The abiotic stress conditions which can be relativized may include, for example, heat, drought, cold and aridity stress (stress caused by aridity and/or lack of water), osmotic stress, waterlogging, elevated soil salinity, elevated exposure to minerals, ozone conditions, strong light conditions, limited availability of nitrogen nutrients, limited availability of phosphorus nutrients.

In one embodiment, it is possible, for example, that the compounds envisaged in accordance with the invention, i.e. the appropriate 1,4-substituted 3-pyrazolecarboxylic acid derivatives of the general formula (I) or salts thereof, are applied by spray application to appropriate plants or plant parts to be treated. The compounds (I) according to the invention are used as envisaged in accordance with the invention preferably with a dosage between 0.00005 and 3 kg/ha, more preferably between 0.0001 and 2 kg/ha, especially preferably between 0.0005 and 1 kg/ha. If, in the context of the present invention, abscisic acid is used simultaneously with 1,4-substituted 3-pyrazolecarboxylic acid derivatives of the general formula (I) or salts thereof, for example in the context of a combined preparation or formulation, the addition of abscisic acid is preferably carried out in a dosage between 0.001 and 3 kg/ha, particularly preferably between 0.005 and 2 kg/ha, especially preferably between 0.01 and 1 kg/ha.

The term "resistance to abiotic stress" is understood in the context of the present invention to mean various kinds of advantages for plants. Such advantageous properties are manifested, for example, in the following improved plant characteristics: improved root growth with regard to surface area and depth, increased stolon or tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibers, better fiber quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soils and water, enhanced tolerance to ozone stress, improved compatibility with respect to herbicides and other plant treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

More particularly, the inventive use exhibits the advantages described in spray application to plants and plant parts. Combinations of the corresponding 4-substituted 1-phenylpyrazole-3-carboxylic acid derivatives of the general formula (I) or salts thereof with substances including insecticides, attractants, acaricides, fungicides, nematicides, herbicides, growth regulators, safeners, substances which influence plant maturity, and bactericides can likewise be employed in the control of plant disorders in the context of the present invention. In addition, the combined use of corresponding 4-substituted 1-phenylpyrazole-3-carboxylic acid derivatives of the general formula (I) or salts thereof with genetically modified cultivars with a view to increased tolerance to abiotic stress is likewise possible.

As is known, the various advantages for plants, which have been mentioned further above, can be combined in part, and generally applicable terms can be used to describe them. Such terms are, for example, the following names: phytotonic effect, resistance to stress factors, less plant stress, plant health, healthy plants, plant fitness, plant wellness, plant concept, vigor effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is quite familiar.

In the context of the present invention, a good effect on the resistance to abiotic stress is understood as meaning, but not by limitation,
at least an emergence improved by generally 3%, especially more than 5%, more preferably more than 10%,
at least a yield enhanced by generally 3%, especially more than 5%, more preferably more than 10%,
at least a root development improved by generally 3%, especially more than 5%, more preferably more than 10%,
at least a shoot size rising by generally 3%, especially more than 5%, more preferably more than 10%,
at least a leaf area increased by generally 3%, especially more than 5%, more preferably more than 10%,
at least a photosynthesis performance improved by generally 3%, especially more than 5%, more preferably more than 10%, and/or
at least a flower formation improved by generally 3%, especially more than 5%, more preferably more than 10%,
and the effects may occur individually or else in any combination of two or more effects.

The present invention further provides a spray solution for treatment of plants, comprising an amount, effective for enhancement of the resistance of plants to abiotic stress factors, of at least one compound of the formula (I) or salts thereof. The spray solution may comprise other customary constituents, such as solvents, formulation aids, especially water. Further constituents may include agrochemically active compounds which are described further below.

The present invention further provides for the use of corresponding spray solutions for enhancing the resistance of plants to abiotic stress factors. The remarks which follow apply both to the use according to the invention of the compounds of the formula (I) or salts thereof per se and to the corresponding spray solutions.

In accordance with the invention, it has additionally been found that the application, to plants or in their environment, of the compounds of the general formula (I) or salts thereof in combination with at least one fertilizer as defined below is possible.

Fertilizers which can be used in accordance with the invention together with the compounds of the general formula (I) or salts thereof elucidated in detail above are generally organic and inorganic nitrogen-containing compounds, for example ureas, urea/formaldehyde condensation products, amino acids, ammonium salts and ammonium nitrates, potassium salts (preferably chlorides, sulfates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonium nitrate sulfate (general formula $(NR_4)_2SO_4 \ NH_4NO_3$), ammonium phosphate and ammonium sulfate. These fertilizers are generally known to the person skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may also contain salts of micronutrients (preferably calcium, sulfur, boron, manganese, magnesium, iron, boron, copper, zinc, molybdenum and cobalt) and phytohormones (for example vitamin B1 and indole-(III)-acetic acid) or mixtures of these. Fertilizers used in accordance with the invention may also contain other salts such as monoammonium phosphate (MAP), diammonium phosphate (DAP), potassium sulfate, potassium chloride, magnesium sulfate. Suitable amounts of the secondary nutrients, or trace elements, are amounts of from 0.5 to 5% by weight, based on the totality of the fertilizer. Further possible ingredients are crop protection compositions, insecticides or fungicides, growth regulators or mixtures thereof. This will be explained in more detail further below.

The fertilizers can be used, for example, in the form of powders, granules, prills or compactates. However, the fertilizers can also be used in liquid form, dissolved in an aqueous medium. In this case, dilute aqueous ammonia can also be used as a nitrogen fertilizer. Further possible ingredients for fertilizers are described, for example, in Ullmann's Encyclopedia of Industrial Chemistry, 5th edition, 1987, volume A 10, pages 363 to 401, DE-A 41 28 828, DE-A 19 05 834 and DE-A 196 31 764. The general composition of the fertilizers which, within the context of the present invention, may take the form of straight and/or compound fertilizers, for example composed of nitrogen, potassium or phosphorus, may vary within a wide range. In general, a content of from 1 to 30% by weight of nitrogen (preferably from 5 to 20% by weight), from 1 to 20% by weight of potassium (preferably from 3 to 15% by weight) and a content of from 1 to 20% by weight of phosphorus (preferably from 3 to 10% by weight) is advantageous. The microelement content is usually in the ppm order of magnitude, preferably in the order of magnitude of from 1 to 1000 ppm.

In the context of the present invention, the fertilizer and the compounds of the general formula (I) or salts thereof may be administered simultaneously, i.e. synchronously. However, it is also possible first to apply the fertilizer and then a compound of the general formula (I), or first to apply a compound of the general formula (I) and then the fertilizer. In the case of nonsynchronous application of a compound of the general formula (I) or salts thereof and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, the compound of the formula (I) according to the invention and the fertilizer are applied within a time frame of less than 1 hour, preferably less than 30 minutes, more preferably less than 15 minutes.

The active ingredients of the general formula (I) or salts thereof to be used in accordance with the invention, if appropriate in combination with fertilizers, can preferably be used on the following plants, though the enumeration which follows is not limiting.

Preferred plants are those from the group of the useful plants, ornamentals, turfs, generally used trees which are employed as ornamentals in the public and domestic sectors, and forestry trees. Forestry trees include trees for the production of timber, cellulose, paper and products made from parts of the trees. The term "useful plants" as used here refers to crop plants which are employed as plants for obtaining foods, animal feeds, fuels or for industrial purposes.

The useful plants include, for example, the following types of plants: triticale, durum (hard wheat), turf, vines, cereals, for example wheat, barley, rye, oats, rice, corn and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cocoa beans and peanuts; cucurbits, for example pumpkin/squash, cucumbers and melons; fiber plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, eggplant, sugar cane, tea, pepper, grapevines, hops, bananas, latex plants and ornamentals, for example flowers, shrubs, deciduous trees and coniferous trees. This enumeration does not constitute a limitation.

The following plants are considered to be particularly suitable target crops for applying the method according to the invention: oats, rye, triticale, durum, cotton, egg-plant, turf, pome fruit, stone fruit, soft fruit, corn, wheat, barley, cucumber, tobacco, vines, rice, cereals, pears, pepper, beans, soybeans, oilseed rape, tomato, bell pepper, melons, cabbage, potatoes and apples.

Examples of trees which can be improved in accordance with the method according to the invention include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the method according to the invention are: from the tree species *Aesculus*: *A. hippocastanum*, *A. pariflora*, *A. carnea*; from the tree species *Platanus*: *P. aceriflora*, *P. occidentalis*, *P. racemosa*; from the tree species *Picea*: *P. abies*; from the tree species *Pinus*: *P. radiate*, *P. ponderosa*, *P. contorta*, *P. sylvestre*, *P. elliottii*, *P. montecola*, *P. albicaulis*, *P. resinosa*, *P. palustris*, *P. taeda*, *P. flexilis*, *P. jeffregi*, *P. baksiana*, *P. strobes*; from the tree species *Eucalyptus*: *E. grandis*, *E. globulus*, *E. camadentis*, *E. nitens*, *E. obliqua*, *E. regnans*, *E. pilularus*.

Particularly preferred trees which can be improved in accordance with the method according to the invention are: from the tree species *Pinus*: *P. radiate*, *P. ponderosa*, *P. contorta*, *P. sylvestre*, *P. strobes*; from the tree species *Eucalyptus*: *E. grandis*, *E. globulus* and *E. camadentis*.

Particularly preferred trees which can be improved in accordance with the method according to the invention are: horse chestnut, *Platanaceae*, linden tree and maple tree.

The present invention can also be applied to any turfgrasses, including cool-season turfgrasses and warm-season turfgrasses. Examples of cool-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra* commutata Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm-season turfgrasses are Bermuda grass (*Cynodon* spp. L. C. Rich), *zoysia* grass (*Zoysia* spp. Willd.), St. Augustine grass (*Stenotaphrum secundatum* Walt Kuntze), centipede grass (*Eremochloa ophiuroides* Munro Hack.), carpet grass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.)). Cool-season turfgrasses are generally preferred for the use according to the invention. Especially preferred are bluegrass, bentgrass and redtop, fescues and ryegrasses. Bentgrass is especially preferred.

The invention is used with particular preference to treat plants according to the invention of the respective commercially customary cultivars or those that are in use. Plant cultivars are to be understood as meaning plants having new properties ("traits") and which have been obtained by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant cultivars which are protectable or non-protectable by plant breeders' rights.

The treatment method according to the invention can thus also be used for the treatment of genetically modified organisms (GMOs), for example plants or seeds. Genetically modified plants (or transgenic plants) are plants in which a heterologous gene has been stably integrated into the genome. The expression "heterologous gene" essentially means a gene which is provided or assembled outside the plant and when introduced into the nuclear, chloroplastic or hypochondrial genome gives the transformed plant new or improved agronomic or other properties by expressing a protein or polypeptide of interest or by downregulating or silencing (an)other gene(s) which is/are present in the plant (using for example antisense technology, cosuppression technology or RNAi technology [RNA interference]). A heterologous gene that is located in the genome is also referred to as a transgene. A transgene that is defined by its particular location in the plant genome is called a transformation or transgenic event.

Plants and plant cultivars which are preferably treated according to the invention include all plants which have genetic material which imparts particularly advantageous, useful traits to these plants (whether obtained by breeding and/or biotechnological means).

Plants and plant cultivars which may also be treated according to the invention are those plants which are resistant to one or more abiotic stress factors. Abiotic stress conditions may include, for example, heat, drought, cold and aridity stress, osmotic stress, waterlogging, increased soil salinity, increased exposure to minerals, ozone conditions, strong light conditions, limited availability of nitrogen nutrients, limited availability of phosphorus nutrients or shade avoidance.

Plants and plant cultivars which can likewise be treated in accordance with the invention are those plants which are characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may also be treated according to the invention are hybrid plants that already express the characteristics of heterosis, or hybrid vigor, which results in generally higher yield, vigor, health and resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (e.g. in corn) be produced by detasseling (i.e. mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species (WO 92/005251, WO 95/009910, WO 98/27806, WO 05/002324, WO 06/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 91/002069).

Plants or plant cultivars (obtained by plant biotechnology methods such as genetic engineering) which may also be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an *Eleusine* EPSPS (WO 01/66704). It can also be a mutated EPSPS, as described, for example, in EP-A 0837944, WO 00/066746, WO 00/066747 or WO 02/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyltransferase enzyme as described, for example, in WO 02/036782, WO 03/092360, WO 05/012515 and WO 07/024,782. Glyphosate-tolerant plants can also be obtained by selecting plants containing naturally occurring mutations of the above-mentioned genes as described, for example, in WO 01/024615 or WO 03/013226.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase are described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme according to WO 96/038567, WO 99/024585 and WO 99/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 99/034008 and WO 02/36787. Tolerance of plants to HPPD inhibitors can also be improved by transforming plants with a gene encoding a prephenate dehydrogenase enzyme in addition to a gene encoding an HPPD-tolerant enzyme, as described in WO 04/024928.

Further herbicide-resistant plants are plants that have been made tolerant to acetolactate synthase (ALS) inhibitors. Known ALS inhibitors include, for example, sulfonylurea, imidazolinone, triazolopyrimidines, pyrimidinyl oxy(thio) benzoates and/or sulfonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright, Weed Science (2002), 50, 700-712, and also in U.S. Pat. No. 5,605,011, U.S. Pat. No. 5,378,824, U.S. Pat. No. 5,141,870 and U.S. Pat. No. 5,013,659. The production of sulfonylurea-tolerant plants and imidazolinone-tolerant plants has been described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and also in the international publication WO 96/033270. Further imidazolinone-tolerant plants have also been described, for example, in WO 04/040012, WO 04/106529, WO 05/020673, WO 05/093093, WO 06/007373, WO 06/015376, WO 06/024351 and WO 06/060634. Further sulfonylurea- and imidazolinone-tolerant plants are also described, for example, in WO 07/024,782.

Further plants tolerant to ALS inhibitors, in particular to imidazolinones, sulfonylureas and/or sulfamoylcarbonyltriazolinones, can be obtained by induced mutagenesis, by selection in cell cultures in the presence of the herbicide or by mutation breeding, as described, for example, for soybeans in U.S. Pat. No. 5,084,082, for rice in WO 97/41218, for sugar beet in U.S. Pat. No. 5,773,702 and WO 99/057965 and WO 2012/049268, for lettuce in U.S. Pat. No. 5,198,599 or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled by Crickmore et al., Microbiology and Molecular Biology Reviews (1998), 62, 807-813, updated by Crickmore et al. (2005) in the *Bacillus thuringiensis* toxin nomenclature (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein than *Bacillus thuringiensis* or a portion thereof which is insecticidal in the presence of a second, other crystal protein than *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising portions of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 07/027,777); or 4) a protein of any one of points 1) to 3) above wherein some, particularly 1 to 10, amino acids have been replaced by another amino acid to obtain a higher insecticidal activity to a target insect species, and/or to expand the range of the target insect species affected, and/or because of changes induced in the encoding DNA during cloning or transformation, such as the Cry3Bb1 protein in corn events MON863 or MON88017, or the Cry3A protein in corn event MI R604; or 5) an insecticidal secreted protein from *Bacillus thuringiensis* or *Bacillus cereus*, or an insecticidal portion thereof, such as the vegetative insecticidal proteins (VIPs) listed under the following link, for example proteins from the VIP3Aa protein class: http://www.lifesci.sussex.ac.uk/Home/Neil_Crickmore/Bt/vip.html; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising portions from different secreted proteins from *Bacillus thuringiensis* or *Bacillus cereus*, such as a hybrid of the proteins of 1) above or a hybrid of the proteins of 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of the target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants, as described in WO 00/004173 or EP 04077984.5 or EP 06009836.5;
b. plants which contain a stress tolerance-enhancing transgene capable of reducing the expression and/or the activity of the PARG-encoding genes of the plants or plant cells, as described, for example, in WO 04/090140;
c. plants which contain a stress tolerance-enhancing transgene encoding a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, for example, in EP 04077624.7 or WO 06/133827 or PCT/EP07/002,433.

Plants or plant cultivars (obtained by plant biotechnology methods such as genetic engineering) which may also be treated according to the invention show altered quantity, quality and/or storage stability in the harvested product and/or altered properties of specific components of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 95/004826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/008184, WO 00/008185, WO 00/28052, WO 00/77229, WO 01/12782, WO 01/12826, WO 02/101059, WO 03/071860, WO 04/056999, WO 05/030942, WO 05/030941, WO 05/095632, WO 05/095617, WO 05/095619, WO 05/095618, WO 05/123927, WO 06/018319, WO 06/103107, WO 06/108702, WO 07/009, 823, WO 00/22140, WO 06/063862, WO 06/072603, WO 02/034923, EP 06090134.5, EP 06090228.5, EP 06090227.7, EP 07090007.1, EP 07090009.7, WO 01/14569, WO 02/79410, WO 03/33540, WO 04/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 05/002359, U.S. Pat. No. 5,824,790, U.S. Pat. No. 6,013, 861, WO 94/004693, WO 94/009144, WO 94/11520, WO 95/35026 and WO 97/20936.

2) Transgenic plants which synthesize non-starch carbohydrate polymers or which synthesize non-starch carbohydrate polymers with altered properties in comparison to wild-type plants without genetic modification. Examples are plants producing polyfructose, especially of the inulin and levan type, as described in EP 0663956, WO 96/001904, WO 96/021023, WO 98/039460 and WO 99/024593, plants producing alpha-1,4-glucans, as described in WO 95/031553, US 2002/031826, U.S. Pat. No. 6,284,479, U.S. Pat. No. 5,712,107, WO 97/047806, WO 97/047807, WO 97/047808 and WO 00/14249, plants producing alpha-1,6-branched alpha-1,4-glucans, as described in WO 2000/73422, and plants producing alternan, as described in WO 00/047727, EP 06077301.7, U.S. Pat. No. 5,908,975 and EP 0728213.

3) Transgenic plants which produce hyaluronan, as described for example in WO 06/032538, WO 07/039,314, WO 07/039,315, WO 07/039,316, JP 2006/304779 and WO 05/012529.

Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes, as described in WO 98/000549;
b) plants, such as cotton plants, which contain an altered form of rsw2 or rsw3 homologous nucleic acids, as described in WO 04/053219;
c) plants, such as cotton plants, with an increased expression of sucrose phosphate synthase, as described in WO 01/017333;
d) plants, such as cotton plants, with an increased expression of sucrose synthase, as described in WO 02/45485;
e) plants, such as cotton plants, wherein the timing of the plasmodesmatal gating at the basis of the fiber cell is altered, for example through downregulation of fiber-selective β-1,3-glucanase as described in WO 05/017157;
f) plants, such as cotton plants, which have fibers with altered reactivity, for example through expression of the N-acetylglucosamine transferase gene including nodC and chitin synthase genes, as described in WO 06/136351.

Plants or plant cultivars (obtained by plant biotechnology methods such as genetic engineering) which may also be treated according to the invention are plants, such as oilseed rape or related *Brassica* plants, with altered oil composition characteristics. Such plants can be obtained by genetic transformation, or by selection of plants containing a mutation imparting such altered oil characteristics, and include:

a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;

b) plants, such as oilseed rape plants, which produce oil having a low linolenic acid content, as described in U.S. Pat. No. 6,270,828, U.S. Pat. No. 6,169,190 or U.S. Pat. No. 5,965,755;
c) plants, such as oilseed rape plants, which produce oil having a low level of saturated fatty acids, as described, for example, in U.S. Pat. No. 5,434,283.

Particularly useful transgenic plants which may be treated according to the invention are plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which may be mentioned are corn varieties, cotton varieties and soybean varieties which are available under the following trade names: Roundup Ready® (tolerance to glyphosates, for example corn, cotton, soybeans), Liberty Link® (tolerance to phosphinothricin, for example oilseed rape), IMI® (tolerance to imidazolinone) and SCS® (tolerance to sulfonylurea, for example corn). Herbicide-resistant plants (plants bred in a conventional manner for herbicide tolerance) which should be mentioned include the varieties sold under the Clearfield® name (for example corn).

Particularly useful transgenic plants which may be treated according to the invention are plants containing transformation events, or a combination of transformation events, and that are listed for example in the databases of various national or regional regulatory agencies.

The compounds of the formula (I) or salts thereof to be used in accordance with the invention can be converted to customary formulations, such as solutions, emulsions, wettable powders, water- and oil-based suspensions, powders, dusts, pastes, soluble powders, soluble granules, granules for broadcasting, suspoemulsion concentrates, natural substances impregnated with active compound, synthetic substances impregnated with active compound, fertilizers, and also microencapsulations in polymeric substances. In the context of the present invention, it is especially preferred when the compounds of the general formula (I) or salts thereof are used in the form of a spray formulation.

The present invention therefore additionally also relates to a spray formulation for enhancing the resistance of plants to abiotic stress. A spray formulation is described in detail hereinafter:

The formulations for spray application are produced in a known manner, for example by mixing the compounds of the general formula (I) or salts thereof for use in accordance with the invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are produced either in suitable production plants or else before or during application.

The auxiliaries used may be those substances which are suitable for imparting, to the composition itself and/or to preparations derived therefrom (for example spray liquors), particular properties such as particular technical properties and/or else special biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Suitable wetting agents which may be present in the formulations which can be used in accordance with the invention are all substances which promote wetting and which are conventionally used for the formulation of agrochemically active compounds. Preference is given to using alkyl naphthalenesulfonates, such as diisopropyl or diisobutyl naphthalenesulfonates.

Suitable dispersants and/or emulsifiers which may be present in the formulations which can be used in accordance with the invention are all nonionic, anionic and cationic dispersants conventionally used for the formulation of agrochemically active compounds. Usable with preference are nonionic or anionic dispersants or mixtures of nonionic or anionic dispersants. Suitable nonionic dispersants are especially ethylene oxide/propylene oxide block polymers, alkylphenol polyglycol ether and tristyrylphenol polyglycol ether, and the phosphated or sulfated derivatives thereof. Suitable anionic dispersants are, in particular, lignosulfonates, polyacrylic acid salts and arylsulfonate/formaldehyde condensates.

Suitable antifoams which may be present in the formulations which can be used in accordance with the invention are all foam-inhibiting substances conventionally used for the formulation of agrochemically active compounds. Silicone antifoams and magnesium stearate can preferably be used.

Suitable preservatives which may be present in the formulations which can be used in accordance with the invention are all substances usable for such purposes in agrochemical compositions. Dichlorophene and benzyl alcohol hemiformal may be mentioned by way of example.

Suitable secondary thickeners which may be present in the formulations which can be used in accordance with the invention are all substances usable for such purposes in agrochemical compositions. Cellulose derivatives, acrylic acid derivatives, xanthan, modified clays and finely divided silica are preferred.

Suitable stickers which may be present in the formulations which can be used in accordance with the invention include all customary binders usable in seed-dressing products. Polyvinylpyrrolidone, polyvinyl acetate, polyvinyl alcohol and tylose may be mentioned as being preferred. Suitable gibberellins which may be present in the formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, pp. 401-412).

Other possible additives are perfumes, mineral or vegetable oils which are optionally modified, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations contain generally between 0.01 and 98% by weight, preferably between 0.5 and 90%, of the compound of the general formula (I) or salts thereof.

The active compound according to the invention can be present in its commercially available formulations and in the use forms, prepared from these formulations, as a mixture with other active compounds, such as insecticides, attractants, sterilants, bactericides, acaricides, nematicides, fungicides, growth-regulating substances, herbicides, safeners, fertilizers or semiochemicals.

In addition, the described positive effect of the compounds of the formula (I) or salts thereof on the plants' own defenses can be supported by an additional treatment with insecticidally, fungicidally or bactericidally active compounds.

Preferred times for the application of compounds of the general formula (I) or salts thereof for enhancing resistance to abiotic stress are treatments of the soil, stems and/or leaves with the approved application rates.

The active compounds of the general formula (I) or salts thereof may generally additionally be present in their commercially available formulations formulations and in the use forms prepared from these formulations in mixtures with other active compounds, such as insecticides, attractants, sterilants, acaricides, nematicides, fungicides, bactericides, growth-regulating substances, substances which influence plant maturity, safeners or herbicides. Particularly favorable mixing partners are, for example, the active compounds of the different classes, specified below in groups, without any preference resulting from the sequence thereof:

Fungicides:

F1) nucleic acid synthesis inhibitors, for example benalaxyl, benalaxyl-M, bupirimate, chiralaxyl, clozylacon, dimethirimol, ethirimol, furalaxyl, hymexazole, metalaxyl, metalaxyl-M, ofurace, oxadixyl, oxolinic acid;

F2) mitosis and cell division inhibitors, for example benomyl, carbendazim, diethofencarb, fuberidazole, fluopicolid, pencycuron, thiabendazole, thiophanate-methyl, zoxamide and chloro-7-(4-methylpiperidin-1-yl)-6-(2,4,6-trifluorophenyl)[1,2,4]triazolo[1,5-a]pyrimidine;

F3) respiratory chain complex I/II inhibitors, for example diflumetorim, bixafen, boscalid, carboxin, diflumethorim, fenfuram, fluopyram, flutolanil, furametpyr, mepronil, oxycarboxin, penflufen, penthiopyrad, thifluzamid, N-[2-(1,3-dimethylbutyl)phenyl]-5-fluoro-1,3-dimethyl-1H-pyrazole-4-carboxamide, isopyrazam, sedaxan, 3-(difluoromethyl)-1-methyl-N-(3',4',5'-trifluorobiphenyl-2-yl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide and corresponding salts;

F4) respiratory chain complex III inhibitors, for example amisulbrom, azoxystrobin, cyazofamid, dimoxystrobin, enestrobin, famoxadon, fenamidon, fluoxastrobin, kresoxim-methyl, metominostrobin, orysastrobin, pyraclostrobin, pyribencarb, picoxystrobin, trifloxystrobin, (2E)-2-(2-{[(6-(3-chloro-2-methylphenoxy)-5-fluoropyrimidin-4-yl]oxy}phenyl)-2-(methoxyimino)-N-methylethanamide, (2E)-2-(ethoxyimino)-N-methyl-2-(2-{[({(1E)-1-[3-(trifluoromethyl)phenyl]ethylidene}amino)oxy]methyl}phenyl)ethanamide and corresponding salts, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, 2-methyl-{2[({cyclopropyl[(4-methoxyphenyl)imino]methyl}sulfanyl)methyl]phenyl}-3-methoxyacrylate, N-(3-ethyl-3,5,5-trimethylcyclohexyl)-3-(formylamino)-2-hydroxybenzamide and corresponding salts;

F5) decouplers, for example dinocap, fluazinam;

F6) ATP production inhibitors, for example fentin acetate, fentin chloride, fentin hydroxide, silthiofam F7) amino acid and protein biosynthesis inhibitors, for example andoprim, blasticidin-S, cyprodinil, kasugamycin, kasugamycin hydrochloride hydrate, mepanipyrim, pyrimethanil F8) signal transduction inhibitors, for example fenpiclonil, fludioxonil, quinoxyfen F9) lipid and membrane synthesis inhibitors, for example chlozolinate, iprodione, procymidone, vinclozolin, ampropylfos, potassium-ampropylfos, edifenphos, iprobenfos (IBP), isoprothiolane, pyrazophos, tolclofos-methyl, biphenyl, iodocarb, propamocarb, propamocarb hydrochloride F10) ergosterol biosynthesis inhibitors, for example fenhexamid, azaconazole, bitertanol, bromuconazole, diclobutrazole, difenoconazole, diniconazole, diniconazole-M, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, spiroxamine, tebuconazole, triadimefon, triadimenol, triticonazole, uniconazole, voriconazole, imazalil, imazalil sulfate, oxpoconazole, fenarimol, flurprimidol, nuarimol, pyrifenox, triforin, pefurazoate, prochloraz, triflumizole, viniconazole, aldimorph, dodemorph, dodemorph acetate, fenpropimorph, tridemorph, fenpropidin, naftifin, pyributicarb, terbinafin, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-{1-[(4-methoxyphenoxy)methyl]2,2-dimethylpropyl}-1H-imidazole-1-carbothioate;

F11) cell wall synthesis inhibitors, for example benthiavalicarb, bialaphos, dimethomorph, flumorph, iprovalicarb, polyoxins, polyoxorim, validamycin A;

F12) melanine biosynthesis inhibitors, for example capropamide, diclocymet, fenoxanil, phthalide, pyroquilon, tricyclazole F13) resistance induction, for example acibenzolar-5-methyl, probenazole, tiadinil F14) multisite, for example captafol, captan, chlorothalonil, copper salts such as: copper hydroxide, copper naphthenate, copper oxychloride, copper sulfate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations containing calcium polysulfide, thiram, tolylfluanid, zineb, ziram;

F15) unknown mechanism, for example amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulfate, diphenylamine, ethaboxam, ferimzone, flumetover, flusulfamide, fluopicolid, fluoroimid, fosatyl-Al, hexachlorobenzene, 8-hydroxyquinoline sulfate, iprodione, irumamycin, isotianil, methasulfocarb, metrafenone, methyl isothiocyanate, mildiomycin, natamycin, nickel dimethyl dithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrroInitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene] amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl] ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4] triazolo[1,5-a]pyrimidine, 5-chloro-6-(2,4,6-trifluorophenyl)-N-[(1R)-1,2,2-trimethylpropyl][1,2,4] triazolo[1,5-a]pyrimidine-7-amine, 5-chloro-N-[(1R)-1,2-dimethylpropyl]-6-(2,4,6-trifluorophenyl)[1,2,4]triazolo[1, 5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene] amino]oxy]methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{([6-(3-chloro-2-methylphenoxy)-5-fluoropyrimidin-4-yl]oxy}phenyl)-2-(methoxyimino)-N-methylacetamide.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:

I1) acetylcholine esterase (AChE) inhibitors, a) from the substance group of the carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, fenoxycarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate, b) from the group of the organophosphates, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion I2) sodium channel modulators/voltage-dependent sodium channel blockers, a) from the group of the pyrethroids, for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, eflusilanate, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, pyrethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum), b) DDT, c) oxadiazines, for example indoxacarb, d) semicarbazones, for example metaflumizone (BAS3201)

I3) acetylcholine receptor agonists/antagonists, a) from the group of the chloronicotinyls,
for example acetamiprid, AKD 1022, clothianidin, dinotefuran, imidacloprid, imidaclothiz, nitenpyram, nithiazine, thiacloprid, thiamethoxam, b) nicotine, bensultap, cartap; c) sulfoxaflor (N-[methyloxido[1-[6-(trifluoromethyl)-3-pyridinyl]ethyl]-λ4-sulfanylidene]cyanamide)

I4) acetylcholine receptor modulators from the group of the spinosyns, for example spinosad I5) GABA-gated chloride channel antagonists, a) from the group of the organochlorines, for example camphechlor, chlordane, endosulfan, gamma-HCH, HCH, heptachlor, lindane, methoxychlor, b) fiproles, for example acetoprole, ethiprole, fipronil, pyrafluprole, pyriprole, vaniliprole;

I6) chloride channel activators, for example abamectin, emamectin, emamectin benzoate, ivermectin, lepimectin, milbemycin;

I7) juvenile hormone mimetics, for example diofenolan, epofenonane, fenoxycarb, hydroprene, kinoprene, methoprene, pyriproxifen, triprene;

I8) ecdysone agonists/disruptors, for example chromafenozide, halofenozide, methoxyfenozide, tebufenozide;

I9) chitin biosynthesis inhibitors, for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine;

I10) inhibitors of oxidative phosphorylation, a) ATP disruptors, for example diafenthiuron, b) organotin compounds, for example azocyclotin, cyhexatin, fenbutatin oxide;

I11) decouplers of oxidative phosphorylation by interruption of the H-proton gradient, a) from the group of the pyrroles, for example chlorfenapyr, b) from the class of the dinitrophenols, for example binapacyrl, dinobuton, dinocap, DNOC, meptyldinocap;

I12) site I electron transport inhibitors, for example METIs, especially, as examples, fenazaquin, fenpyroximate, pyrimidifen, pyridaben, tebufenpyrad, tolfenpyrad or else hydramethylnon, dicofol;

I13) site II electron transport inhibitors, for example rotenone;

I14) site III electron transport inhibitors, for example acequinocyl, fluacrypyrim;

I15) microbial disruptors of the insect gut membrane, for example *Bacillus thuringiensis* strains;

I16) lipid synthesis inhibitors, a) from the group of the tetronic acids, for example spirodiclofen, spiromesifen, b) from the class of the tetramic acids, for example spirotetramat, cis-3-(2,5-dimethylphenyl)-4-hydroxy-8-methoxy-1-azaspiro[4.5]dec-3-en-2-one;

I17) octopaminergic agonists, for example amitraz;

I18) inhibitors of magnesium-stimulated ATPase, for example propargite;

I19) nereistoxin analogs, for example thiocyclam hydrogen oxalate, thiosultap-sodium;

I20) ryanodine receptor agonists, a) from the group of the benzenedicarboxamides, for example flubendiamide, b) from the group of the anthranilamides, for example rynaxypyr (3-bromo-N-{4-chloro-2-methyl-6-[(methylamino)carbonyl]phenyl}-1-(3-chloropyridin-2-O-1H-pyrazole-5-carboxamide), cyazypyr (ISO-proposed) (3-bromo-N-{4-cyano-2-methyl-6-[(methylamino)carbonyl]phenyl}-1-(3-chloropyridin-2-yl)-1H-pyrazole-5-carboxamide) (known from WO 2004067528);

I21) biologics, hormones or pheromones, for example azadirachtin, *Bacillus* spec., *Beauveria* spec., codlemone, *Metarrhizium* spec., *Paecilomyces* spec., thuringiensin, *Verticillium* spec.;

I22) active ingredients with unknown or nonspecific mechanisms of action, a) fumigants, for example aluminum phosphide, methyl bromide, sulfuryl fluoride, b) antifeedants, for example cryolite, flonicamide, pymetrozine, c) mite growth inhibitors, for example clofentezine, etoxazole, hexythiazox, d) amidoflumet, benclothiaz, benzoximate, bifenazate, bromopropylate, buprofezin, chinomethionat, chlorodimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnon, japonilure, metoxadiazone, petroleum, piperonyl butoxide, potassium oleate, pyridalyl, sulfluramid, tetradifon, tetrasul, triarathene, verbutin or lepimectin.

Safeners are preferably selected from the group consisting of:

S1) compounds of the formula (S1)

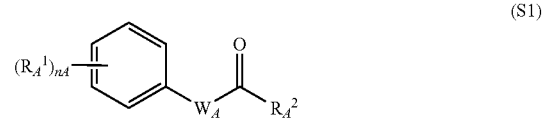

(S1)

where the symbols and indices have the following meanings:
$n_A$ is a natural number from 0 to 5, preferably 0 to 3;
$R_A^1$ is halogen, $(C_1$-$C_4)$-alkyl, $(C_1$-$C_4)$-alkoxy, nitro or $(C_1$-$C_4)$-haloalkyl;

$(W_A^1)$

$(W_A^2)$

$(W_A^3)$

$(W_A^4)$ $W_A$ is an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$;
$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is joined to the carbonyl group in (S1) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;

$R_A^3$ is hydrogen or an unsubstituted or substituted aliphatic hydrocarbon radical, preferably having a total of 1 to 18 carbon atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ in which $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6, R_A^7, R_A^8$ are identical or different and are each hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid $(S1^a)$ type, preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid $(S1^b)$, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid $(S1^c)$, preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type $(S1^d)$, preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid type or of the 5,5-diphenyl-2-isoxazoline-3-carboxylic acid type $(S1^e)$, preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

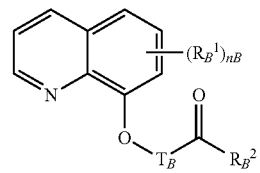

(S2)

where the symbols and indices have the following meanings:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably 0 to 3;

$R_B^2$ is $OR_B^3$, $SR_B^3$ or $NR_B^3 R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;

$R_B^3$ is hydrogen or an unsubstituted or substituted aliphatic hydrocarbon radical, preferably having a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$ or $C_2)$-alkanediyl chain which is unsubstituted or substituted by one or two $(C_1-C_4)$-alkyl radicals or by $[(C_1-C_3)$-alkoxy]carbonyl;

preferably:

a) compounds of the 8-quinolinoxyacetic acid type $(S2^a)$, preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type $(S2^b)$, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

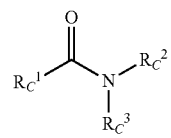

(S3)

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and are each hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring; preferably: active compounds of the type of the dichloroacetamides which are frequently used as pre-emergence safeners (soil-active safeners), such as, for example, "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N—[(allylaminocarbonyl)methyl] dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138"(S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulfonamides of the formula (S4) and salts thereof

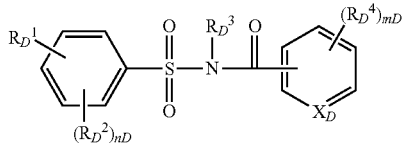

(S4)

where the symbols and indices have the following meanings:
$X_D$ is CH or N;
$R_D^1$ is CO—$NR_D^5R_D^6$ or NHCO—$R_D^7$;
$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;
$R_D^3$ is hydrogen, $(C_1-C_4)$-alkyl, $(C_2-C_4)$-alkenyl or $(C_2-C_4)$-alkynyl;
$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;
$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group consisting of nitrogen, oxygen and sulfur, where the seven latter radicals are substituted by $v_D$ substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;
$R_D^6$ is hydrogen, $(C_1-C_6)$-alkyl, $(C_2-C_6)$-alkenyl or $(C_2-C_6)$-alkynyl, where the three latter radicals are substituted by $v_D$ radicals from the group consisting of halogen, hydroxy, $(C_1-C_4)$-alkyl, $(C_1-C_4)$-alkoxy and $(C_1-C_4)$-alkylthio, or
$R_D^5$ and $R_D^6$ together with the nitrogen atom which bears them form a pyrrolidinyl or piperidinyl radical;
$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 latter radicals are substituted by $V_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;
$n_D$ is 0, 1 or 2;
$m_D$ is 1 or 2;
$v_D$ is 0, 1, 2 or 3;
among these, preference is given to compounds of the N-acylsulfonamide type, for example of the formula (S4$^a$) below, which are known, for example, from WO-A-97/45016

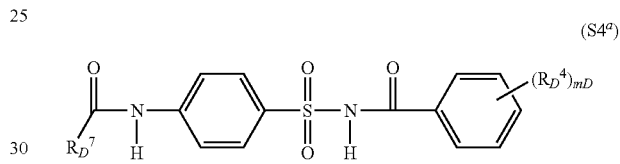

(S4$^a$)

in which
$R_D^4$ is $(C_1-C_6)$-alkyl, $(C_3-C_6)$-cycloalkyl, where the 2 latter radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;
$R_D^4$ is halogen, $(C_1-C_8)$-alkyl, $(C_1-C_4)$-alkoxy, $CF_3$;
$m_D$ is 1 or 2;
$v_D$ is 0, 1, 2 or 3;
and also to acylsulfamoylbenzamides, for example of the formula (S4$^b$) below, which are known, for example, from WO-A-99/16744,

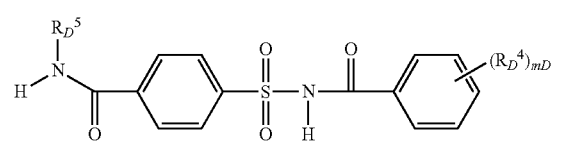

(S4$^b$)

for example those in which
$R_D^5$=cyclopropyl and $(R_D^4)$=2-OMe ("cyprosulfamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)
and to compounds of the N-acylsulfamoylphenylurea type, of the formula (S4$^c$), which are known, for example, from EP-A-365484,

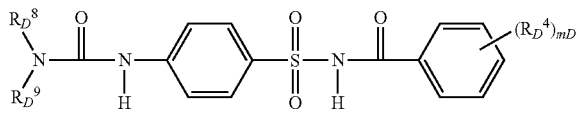 (S4c)

in which
$R_D^8$ and $R_D^9$ are each independently of one another hydrogen, $(C_1-C_8)$-alkyl, $(C_3-C_8)$-cycloalkyl, $(C_3-C_6)$-alkenyl, $(C_3-C_6)$-alkynyl,
$R_D^4$ is halogen, $(C_1-C_4)$-alkyl, $(C_1-C_4)$-alkoxy, $CF_3$;
$m_D$ is 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example
1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

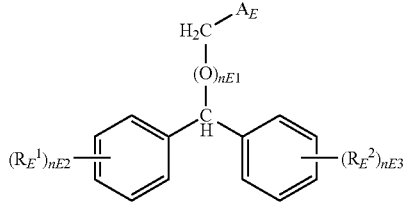 (S7)

where the symbols and indices have the following meanings:
$R_E^1$, $R_E^2$ are each independently halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
$A_E$ is $COOR_E^3$ or $COSR_E^4$
$R_E^3$, $R_E^4$ are each independently hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium,
$n_E^1$ is 0 or 1
$n_E^2$, $n_E^3$ are each independently of one another 0, 1 or 2,
preferably diphenylmethoxyacetic acid, ethyl diphenylmethoxyacetate, methyl diphenylmethoxyacetate (CAS reg. no. 41858-19-9) (S7-1).

S8) Compounds of the formula (S8), as described in WO-A-98/27049,

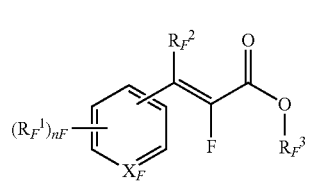 (S8)

in which
$X_E$ is CH or N,
$n_F$ in the case that $X_F$=N is an integer from 0 to 4 and in the case that $X_F$=CH is an integer from 0 to 5,
$R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy,
$R_F^2$ is hydrogen or $(C_1-C_4)$-alkyl
$R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy; or salts thereof, preferably compounds in which
$X_F$ is CH,
$n_F$ is an integer from 0 to 2,
$R_F^1$ is halogen, $(C_1-C_4)$-alkyl, $(C_1-C_4)$-haloalkyl, $(C_1-C_4)$-alkoxy, $(C_1-C_4)$-haloalkoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy,
or salts thereof.

S9) Active compounds from the class of the 3-(5-tetrazolylcarbonyl)-2-quinolones (S9), for example
1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formulae (S10$^a$) or (S10$^b$) as described in WO-A-2007/023719 and WO-A-2007/023764,

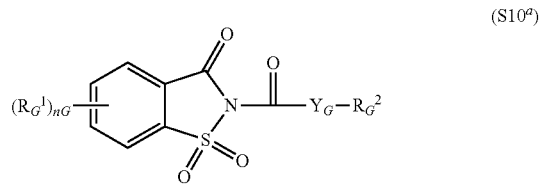 (S10$^a$)

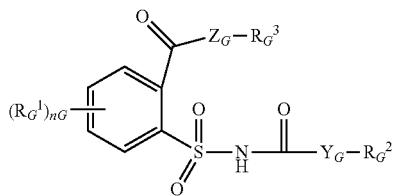

in which
$R_G^1$ is halogen, $(C_1-C_4)$-alkyl, methhoxy, nitro, cyano, $CF_3$, $OCF_3$,
$Y_G$, $Z_G$ are each independently of one another O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl; benzyl, halobenzyl,
$R_G^3$ is hydrogen or $(C_1-C_6)$-alkyl.

S11) Active compounds of the oxyimino compounds type (S11), which are known as seed-dressing compositions, for example "oxabetrinil" ((Z)-1,3-dioxolan-2-yl-methoxyimino(phenyl)acetonitrile) (S11-1), which is known as a seed-dressing safener for millet/sorghum against damage by metolachlor, "fluxofenim" (1-(4-chlorophenyl)-2,2,2-trifluoro-1-ethanone 0-(1,3-dioxolan-2-ylmethyl)oxime) (S11-2), which is known as a seed-dressing safener for millet/sorghum against damage by metolachlor, and "cyometrinil" or "CGA-43089" ((Z)-cyanomethoxyimino(phenyl)acetonitrile) (S11-3), which is known as a seed-dressing safener for millet/sorghum against damage by metolachlor.

S12) Active compounds from the class of the isothiochromanones (S12), for example methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13): "naphthalic anhydride" (1,8-naphthalenedicarboxylic anhydride) (S13-1), which is known as a seed-dressing safener for corn against damage by thiocarbamate herbicides, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against damage by alachlor and metolachlor, "CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS reg. no. 96420-72-3) (2-dichloromethyl-2-methyl-1,3-dioxolane) (S13-5) from Nitrokemia, which is known as a safener for corn, "MG-838" (CAS reg. no. 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenylphosphorothioate) (S13-8), "mephenate" (4-chlorophenyl methylcarbamate) (S13-9).

S14) Active compounds which, in addition to herbicidal action against harmful plants, also have safener action on crop plants such as rice, for example "dimepiperate" or "MY-93" (S-1-methyl-1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against damage by the herbicide imazosulfuron, "cumyluron"="JC-940" (3-(2-chlorophenylmethyl)-1-(1-methyl-1-phenylethyl)urea, see JP-A-60087254), which is known as a safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS reg. no. 54091-06-4), which is known as a safener against damage by some herbicides in rice.

S15) Compounds of the formula (S15) or tautomers thereof as described in WO-A-2008/131861 and WO-A-2008/131860

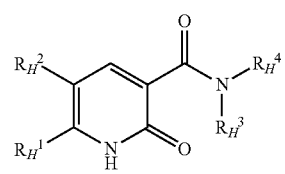

in which
$R_H^1$ is a $(C_1-C_6)$-haloalkyl radical and
$R_H^2$ is hydrogen or halogen and
$R_H^3$, $R_H^4$ are each independently of one another hydrogen, $(C_1-C_{16})$-alkyl, $(C_2-C_{16})$-alkenyl or $(C_2-C_{16})$-alkynyl, where each of the latter 3 radicals is unsubstituted or substituted by one or more radicals from the group of halogen, hydroxy, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl which is fused on one side of the ring to a 4- to 6-membered saturated or unsaturated carbocyclic ring, or $(C_4-C_6)$-cycloalkenyl which is fused on one side of the ring to a 4- to 6-membered saturated or unsaturated carbocyclic ring, where each of the latter 4 radicals is unsubstituted or substituted by one or more radicals from the group of halogen, hydroxy, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or
$R_H^3$ is $(C_1-C_4)$-alkoxy, $(C_2-C_4)$-alkenyloxy, $(C_2-C_6)$-alkynyloxy or $(C_2-C_4)$-haloalkoxy and
$R_H^4$ is hydrogen or $(C_1-C_4)$-alkyl or
$R_H^3$ and $R_H^4$ together with the directly attached nitrogen atom are a four- to eight-membered
heterocyclic ring which, in addition to the nitrogen atom, may also contain further ring heteroatoms, preferably up to two further ring heteroatoms from the group consisting of N, O and S, and which is unsubstituted or substituted by one or more radicals from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy) butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

Substances which Influence Plant Maturity:

Combination partners usable for the compounds of the general formula (I) in mixture formulations or in a tankmixe are, for example, known active compounds based on inhibition of, for example, 1-aminocyclopropane-1-carboxylate synthase, 1-aminocyclopropane-1-carboxylate oxidase and the ethylene receptors, for example ETR1, ETR2, ERS1, ERS2 or EIN4, as described, for example, in Biotechn. Adv. 2006, 24, 357-367; Bot. Bull. Acad. Sin. 199, 40, 1-7 or Plant Growth Reg. 1993, 13, 41-46 and literature cited therein.

Examples of known substances which influence plant maturity and can be combined with the compounds of the general formula (I) include the active compounds which follow (the compounds are designated either by the "common name" according to the International Organization for Standardization (ISO) or by the chemical name or by the code number) and always encompass all use forms, such as acids, salts, esters and isomers, such as stereoisomers and optical isomers. In this case, one or else, in some cases, more than one use form is mentioned by way of example:

rhizobitoxine, 2-aminoethoxyvinylglycine (AVG), methoxyvinylglycine (MVG), vinylglycine, aminooxyacetic acid, sinefungin, S-adenosylhomocysteine, 2-keto-4-methyl thiobutyrate, 2-(methoxy)-2-oxoethyl (isopropylidene)aminooxyacetate, 2-(hexyloxy)-2-oxoethyl (isopropylidene) aminooxyacetate, 2-(isopropyloxy)-2-oxoethyl (cyclohexylidene)aminooxyacetate, putrescine, spermidine, spermine, 1,8-diamino-4-aminoethyloctane, L-canaline, daminozide, methyl 1-aminocyclopropyl-1-carboxylate, N-methyl-1-aminocyclopropyl-1-carboxylic acid, 1-aminocyclopropyl-1-carboxamide, substituted 1-aminocyclopropyl-1-carboxylic acid derivatives as described in DE3335514, EP30287, DE2906507 or US5123951, 1-aminocyclopropyl-1-hydroxamic acid, 1-methylcyclopropene, 3-methylcyclopropene, 1-ethylcyclopropene, 1-n-propylcyclopropene, 1-cyclopropenylmethanol, carvone, eugenol Herbicides or Plant Growth Regulators:

Combination partners usable for the compounds of the general formula (I) in mixture formulations or in a tankmix are, for example, known active compounds based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 14th edition, The British Crop Protection Council and the Royal Soc. of Chemistry, 2006 and literature cited therein.

Examples of known herbicides or plant growth regulators which can be combined with compounds of the general formula (I) include the active compounds which follow (the compounds are designated either by the "common name" according to the International Organization for Standardization (ISO) or by the chemical name or by the code number) and always encompass all use forms, such as acids, salts, esters and isomers, such as stereoisomers and optical isomers. One administration form or else, in some cases, more than one administration form is mentioned by way of example:

acetochlor, acibenzolar, acibenzolar-5-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

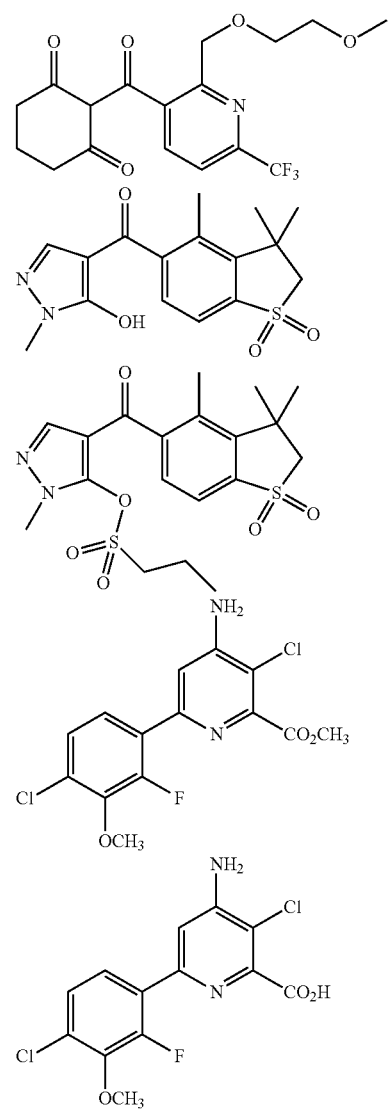

-continued

[Chemical structure: pyrimidinedione with CF3, N-methyl, fluorophenyl with Cl, pyridyloxy, and EtO2CCH2O substituents]

The invention is to be illustrated by the biological examples which follow, but without restricting it thereto.

Biological Examples

Seeds of monocotyledonous and dicotyledonous crop plants were laid out in sandy loam in wood-fiber pots, covered with soil and cultivated in a greenhouse under good growth conditions. The test plants were treated at the early leaf stage (BBCH10-BBCH13). To ensure uniform water supply before commencement of stress, the potted plants were supplied with the maximum amount of water immediately beforehand by dam irrigation and, after application, transferred into plastic inserts in order to prevent subsequent, excessively rapid drying. The compounds according to the invention, formulated in the form of wettable powders (WP), wettable granules (WG), suspension concentrates (SC) or emulsion concentrates (EC), were sprayed onto the green parts of the plants as an aqueous suspension at an equivalent water application rate of 600 l/ha with addition of 0.2% wetting agent (agrotin). Substance application is followed immediately by stress treatment of the plants (cold or drought stress). For cold stress treatment, the plants were kept under the following controlled conditions:

"day": 12 hours with illumination at 8° C.
"night": 12 hours without illumination at 1° C.

Drought stress was induced by gradual drying out under the following conditions:

"day": 14 hours with illumination at 26° C.
"night": 10 hours without illumination at 18° C.

The duration of the respective stress phases was guided mainly by the state of the untreated, stressed control plants and thus varied from crop to crop. It was ended (by re-irrigating or transferring it to a greenhouse with good growth conditions) as soon as irreversible damage was observed on the untreated, stressed control plants. In the case of dicotyledonous crops, for example oilseed rape and soybeans, the duration of the drought stress phase varied between 3 and 5 days; in the case of monocotyledonous crops, for example wheat, barley or corn, it varied between 6 and 10 days. The duration of the cold stress phase varied between 12 and 14 days. The end of the stress phase was followed by an approx. 5-7-day recovery phase, during which the plants were once again kept under good growth conditions in a greenhouse. In order to rule out any influence of the effects observed by any fungicidal action of the test compounds, it was additionally ensured that the tests proceeded without fungal infection and without infection pressure.

After the recovery phase had ended, the intensities of damage were rated visually in comparison to untreated, unstressed controls of the same age (in the case of drought stress) or the same growth stage (in the case of cold stress). The intensity of damage was first recorded as a percentage (100%=plants have died, 0%=like control plants). These values were then used to calculate the efficacy of the test compounds (=percentage reduction in the intensity of damage as a result of substance application) by the following formula:

$$EF = \frac{(DV_{us} - DV_{ts}) \times 100}{DV_{us}}$$

EF: efficacy (%)
$DV_{us}$: damage value of the untreated, stressed control
$DV_{ts}$: damage value of the plants treated with test compound Effects of selected compounds of the formula (I) under drought stress exemplified by HORVS, BRSNS, ZEAMX and TRZAS, where Tables A-1 to A-4 below each list the means of three results of the same test

TABLE A-1

| No. | Substance | Dosage | Unit | EF (HORVS) |
|---|---|---|---|---|
| 1 | 1-843 | 100 | g/ha | >5 |

TABLE A-2

| No. | Substance | Dosage | Unit | EF (TRZAS) |
|---|---|---|---|---|
| 1 | 1-810 | 100 | g/ha | >5 |

TABLE A-3

| No. | Substance | Dosage | Unit | EF (ZEAMX) |
|---|---|---|---|---|
| 1 | 1-845 | 250 | g/ha | >5 |

TABLE A-4

| No. | Substance | Dosage | Unit | EF (BRSNS) |
|---|---|---|---|---|
| 1 | 1-17 | 25 | g/ha | >5 |
| 2 | 1-40 | 250 | g/ha | >5 |
| 3 | 1-843 | 100 | g/ha | >5 |
| 4 | 1-878 | 250 | g/ha | >5 |
| 5 | 4-61 | 2.5 | g/ha | >5 |

In the above tables:
BRSNS=*Brassica napus*
HORVS=*Hordeum vulgare*
TRZAS=*Triticum aestivum*
ZEAMX=*Zea mays*

Similar results were also achieved with further compounds of the formula (I), also in the case of application to different plant species.

The invention claimed is:

1. A compound comprising a 4-substituted 1-phenylpyrazole-3-carboxylic acid derivative of formula (I) and/or a salt thereof

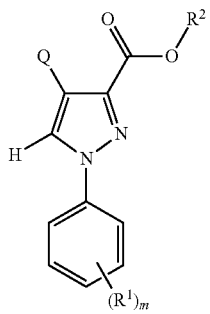
(I)

capable of being used for increasing tolerance to abiotic stress in a plant, where
Q represents

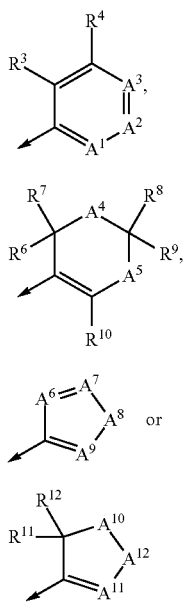

Q-I

Q-II

Q-III or

Q-IV where the $R^3$ to $R^{12}$ and $A^1$ to $A^{12}$ moieties each have the meaning according to the definitions below, and where the arrow represents a bond to the pyrazole, $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1-C_{10})$-alkyl, $(C_1-C_{10})$-alkoxy or $(C_1-C_{10})$-alkylthio, where each of the three last-mentioned radicals independently of the others is unsubstituted or substituted by one or more radicals from the group consisting of halogen, CN, $(C_1-C_{10})$-alkoxy and $(C_1-C_{10})$-alkylthio, $R^2$ represents hydrogen or a radical which can be hydrolyzed to afford the carboxylic acid, optionally an optionally substituted hydrocarbon radical or an optionally substituted heterocyclyl radical, where each of the two last-mentioned carbon-containing radicals including substituents has 1 to 30 carbon atoms, optionally 1 to 24 carbon atoms optionally 1 to 20 carbon atoms, or
a radical of the formula $-N=CR^aR^b$, $-NR^cR^d$ or $SiR^eR^fR^g$,
where in the 3 last-mentioned formulae each of the radicals $R^a$, $R^b$, $R^c$, $R^d$, $R^e$, $R^f$ and $R^g$ independently of the others represents hydrogen or an optionally substituted hydrocarbon radical,
or $R^a$ and $R^b$ together with the carbon atom to which they are attached represent a 3- to 9-membered carbocyclic radical or a heterocyclic radical which may contain 1 to 3 ring heteroatoms from the group consisting of N, O and S, where the carbocyclic or heterocyclic radical is unsubstituted or substituted,
or $R^c$ and $R^d$ together with the nitrogen atom represent a 3- to 8-membered heterocycle which, in addition to the nitrogen atom, may contain one or two further ring heteroatoms from the group consisting of N, O and S and which is unsubstituted or substituted by one or more radicals from the group consisting of $(C_1-C_4)$-alkyl and $(C_1-C_4)$-haloalkyl,
where each of the radicals $R^a$, $R^b$, $R^c$, $R^d$, $R^e$, $R^f$ and $R^g$ including substituents has 1 to 30 carbon atoms, optionally 1 to 24 carbon atoms, optionally 1 to 20 carbon atoms,
wherein
m represents 1, 2, 3, 4 or 5, optionally 1, 2, 3 or 4, optionally 1 or 2,
$A^1$, $A^2$, $A^3$ are the same or different and independently of one another represent N (nitrogen) or the $C-R^5$ moiety, but there are never more than two adjacent nitrogen atoms, and where each $R^5$ in the $C-R^5$ moiety has identical or different meanings according to the definition below, and
$A^1$ and $A^2$, when each is a $C-R^5$ group, with the atoms to which they are attached form a fully saturated, partly saturated or fully unsaturated 5- to 6-membered ring optionally interrupted by heteroatoms and optionally with further substitution,
$A^2$ and $A^3$, when each is a $C-R^5$ group, with the atoms to which they are attached form a fully saturated, partly saturated or fully unsaturated 5- to 6-membered ring optionally interrupted by heteroatoms and optionally with further substitution,
$R^3$, $R^4$ and $R^5$ independently of one another represent hydrogen, nitro, amino, cyano, thiocyanato, isothiocyanato, halogen, $(C_1-C_{10})$-alkyl, $(C_1-C_{10})$-cycloalkyl, $(C_1-C_{10})$-alkenyl, $(C_1-C_{10})$-alkynyl, aryl, aryl-$(C_1-C_{10})$-alkyl, $(C_1-C_{10})$-alkenylalkyl, $(C_1-C_{10})$-alkynylalkyl, aryl-$(C_1-C_{10})$-alkoxy, heteroaryl, $(C_1-C_{10})$-alkoxyalkyl, $(C_1-C_{10})$-hydroxyalkyl, $(C_1-C_{10})$-haloalkyl, $(C_1-C_{10})$-halocycloalkyl, $(C_1-C_{10})$-alkoxy, $(C_1-C_{10})$-haloalkoxy, aryloxy, heteroaryloxy, $(C_1-C_{10})$-cycloalkyloxy, hydroxy, $(C_1-C_{10})$-cycloalkylalkoxy, $(C_1-C_{10})$-alkoxycarbonyl, hydroxycarbonyl, aminocarbonyl, $(C_1-C_{10})$-alkylaminocarbonyl, $(C_1-C_{10})$-cycloalkylaminocarbonyl, $(C_1-C_{10})$-cyanoalkylaminocarbonyl, $(C_1-C_{10})$-alkenylaminocarbonyl, $(C_1-C_{10})$-alkynylaminocarbonyl, $(C_1-C_{10})$-alkylamino, $(C_1-C_{10})$-alkylthio, $(C_1-C_{10})$-haloalkylthio, hydrothio, $(C_1-C_{10})$-bisalkylamino, $(C_1-C_{10})$-cycloalkylamino, $(C_1-C_{10})$-alkylcarbonylamino, $(C_1-C_{10})$-cycloalkylcarbonylamino, formylamino, $(C_1-C_{10})$-haloalkylcarbonylamino, $(C_1-C_{10})$-alkoxycarbonylamino, $(C_1-C_{10})$-alkylaminocarbonylamino, $((C_1-C_{10})$-alkyl)aminocarbonylamino, $(C_1-C_{10})$-alkylsulfonylamino, $(C_1-C_{10})$-cycloalkylsulfonylamino, arylsulfonylamino, hetarylsulfonylamino, $(C_1-C_{10})$-sulfonylhaloalkylamino, aminosulfonyl, $(C_1-C_{10})$-aminoalkylsulfonyl, $(C_1-C_{10})$-aminohaloalkylsulfonyl, $(C_1-C_{10})$-alkylaminosulfonyl, $(C_1-C_{10})$-bisalkylaminosulfonyl, $(C_1-C_{10})$-cycloalkylaminosulfonyl, $(C_1-C_{10})$-haloalkylaminosulfonyl, arylaminosulfonyl, $(C_1-C_{10})$-arylalkylaminosulfonyl, $(C_1-C_{10})$-alkylsulfonyl, $(C_1-C_{10})$-cycloalkylsulfonyl, arylsulfonyl, $(C_1-C_{10})$-alkylsulfinyl, $(C_1-C_{10})$-cycloalkylsulfinyl, arylsulfinyl, $(C_1-C_{10})$—N,S-dialkylsulfonimidoyl, $(C_1-C_{10})$—S-alkylsulfonimidoyl, $(C_1-C_{10})$-alkylsulfonylaminocarbonyl, $(C_1-C_{10})$-cycloalkylsulfonylaminocarbonyl, $(C_1-C_{10})$-cycloalkylaminosulfonyl, $(C_1-C_{10})$-arylalkylcarbonylamino, $(C_1-C_{10})$-cycloalkylalkylcarbonylamino, heteroarylcarbonylamino, $(C_1-C_{10})$-alkoxyalkylcarbonylamino, $(C_1-C_{10})$-hydroxyalkylcarbonylamino, $(C_1-C_{10})$-trialkylsilyl, $R^6$ and $R^7$ independently of one another each represent hydrogen, nitro, amino, hydroxy, hydrothio, thiocyanato, isothiocyanato, halogen, $(C_1-C_{10})$-alkyl, $(C_1-C_{10})$-cycloalkyl, $(C_1-C_{10})$-alkenyl, $(C_1-C_{10})$-alkynyl, aryl, $(C_1-C_{10})$-arylalkyl, $(C_1-C_{10})$-arylalkoxy, heteroaryl, $(C_1-C_{10})$-haloalkyl, $(C_1-C_{10})$-halocycloalkyl, $(C_1-C_{10})$-alkoxy, $(C_1-C_{10})$-haloalkoxy, aryloxy, heteroaryloxy, $(C_1-C_{10})$-cycloalkyloxy, $(C_1-C_{10})$-cycloalkylalkoxy, $(C_1-C_{10})$-hydroxyalkyl, $(C_1-C_{10})$-alkoxyalkyl, $(C_1-C_{10})$-aryloxyalkyl, $(C_1-C_{10})$-heteroaryloxyalkyl, $(C_1-C_{10})$-alkenylaminocarbonyl, $(C_1-C_{10})$-alkylamino, $(C_1-C_{10})$-alkylthio, $(C_1-C_{10})$-haloalkylthio, $(C_1-C_{10})$-bisalkylamino, $(C_1-C_{10})$-cycloalkylamino, $(C_1-C_{10})$-alkylcarbonylamino, $(C_1-C_{10})$-cycloalkylcarbonylamino, formylamino, $(C_1-C_{10})$-haloalkylcarbonylamino, $(C_1-C_{10})$-alkoxycarbonylamino, $(C_1-C_{10})$-alkylaminocarbonylamino, $(C_1-C_{10})$-(alkyl)aminocarbonylamino, $(C_1-C_{10})$-alkylsulfonylamino, $(C_1-C_{10})$-cycloalkylsulfonylamino, arylsulfonylamino, hetarylsulfonylamino, $(C_1-C_{10})$-sulfonylhaloalkylamino, $(C_1-C_{10})$-aminoalkylsulfonyl, $(C_1-C_{10})$-aminohaloalkylsulfonyl, $(C_1-C_{10})$-alkylaminosulfonyl, $(C_1-C_{10})$-bisalkylaminosulfonyl, $(C_1-C_{10})$-cycloalkylaminosulfonyl, haloalkylaminosulfonyl, arylaminosulfonyl, $(C_1-C_{10})$-arylalkylaminosulfonyl, $(C_1-C_{10})$-alkylsulfonyl, $(C_1-C_{10})$-cycloalkylsulfonyl, arylsulfonyl, $(C_1-C_{10})$-alkylsulfinyl, $(C_1-C_{10})$-cycloalkylsulfinyl, arylsulfinyl, $(C_1-C_{10})$—N,S-dialkylsulfonimidoyl, $(C_1-C_{10})$—S-alkylsulfonimidoyl, $(C_1-C_{10})$-alkylsulfonylaminocarbonyl, $(C_1-C_{10})$-cycloalkylsulfonylaminocarbonyl, $(C_1-C_{10})$-cycloalkylaminosulfonyl, $(C_1-C_{10})$-arylalkylcarbonylamino, $(C_1-C_{10})$-cycloalkylalkylcarbonylamino, heteroarylcarbonylamino, $(C_1-C_{10})$-alkoxyalkylcarbonylamino, $(C_1-C_{10})$-hydroxyalkylcarbonylamino, cyano, $(C_1-C_{10})$-cyanoalkyl, hydroxycarbonyl, $(C_1-C_{10})$-alkoxycarbonyl, $(C_1-C_{10})$-cycloalkoxycarbonyl, $(C_1-C_{10})$-cycloalkylalkoxycarbonyl, aryloxycarbonyl, $(C_1-C_{10})$-arylalkoxycarbonyl, aminocarbonyl, $(C_1-C_{10})$-alkylaminocarbonyl, $(C_1-C_{10})$-bisalkylaminocarbonyl, $(C_1-C_{10})$-alkyl-$((C_1-C_{10})$-alkoxy)aminocarbonyl, $(C_1-C_{10})$-cycloalkylaminocarbonyl, $(C_1-C_{10})$-arylalkylaminocarbonyl, $(C_1-C_{10})$-heteroarylalkylaminocarbonyl, $(C_1-C_{10})$-cyanoalkylaminocarbonyl, $(C_1-C_{10})$-haloalkylaminocarbonyl, $(C_1-C_{10})$-alkynylalkylaminocarbonyl, $(C_1-C_{10})$-alkoxycarbonylaminocarbonyl, $(C_1-C_{10})$-arylalkoxycarbonylaminocarbonyl, hydroxycarbonylalkyl, $(C_1-C_{10})$-alkoxycarbonylalkyl, $(C_1-C_{10})$-cycloalkoxycarbonylalkyl, $(C_1-C_{10})$-cycloalkylalkoxycarbonylalkyl, $(C_1-C_{10})$-alkylaminocarbonylalkyl, $(C_1-C_{10})$-aminocarbonylalkyl, $(C_1-C_{10})$-bisalkylaminocarbonylalkyl, $(C_1-C_{10})$-cycloalkylaminocarbonylalkyl, $(C_1-C_{10})$-arylalkylaminocarbonylalkyl, $(C_1-C_{10})$-heteroarylalkylaminocarbonylalkyl, $(C_1-C_{10})$-cyanoalkylaminocarbonylalkyl, $(C_1-C_{10})$-haloalkylaminocarbonylalkyl, $(C_1-C_{10})$-alkynylalkylaminocarbonylalkyl, $(C_1-C_{10})$-cycloalkylalkylaminocarbonylalkyl, $(C_1-C_{10})$-alkoxycarbonylaminocarbonylalkyl, $(C_1-C_{10})$-arylalkoxycarbonylaminocarbonylalkyl, $(C_1-C_{10})$-alkoxycarbonylalkylaminocarbonyl, $(C_1-C_{10})$-hydroxycarbonylalkylaminocarbonyl, $(C_1-C_{10})$-aminocarbonylalkylaminocarbonyl, $(C_1-C_{10})$-alkylaminocarbonylalkylaminocarbonyl, $(C_1-C_{10})$-cycloalkylaminocarbonylalkylaminocarbonyl, $(C_1-C_{10})$-cycloalkylalkylaminocarbonyl, $(C_1-C_{10})$-cycloalkylalkylaminocarbonylalkyl, $(C_1-C_{10})$-alkenyloxycarbonyl, $(C_1-C_{10})$-alkenyloxycarbonylalkyl, $(C_1-C_{10})$-alkenylaminocarbonyl, $(C_1-C_{10})$-alkenylalkylaminocarbonyl, $(C_1-C_{10})$-alkenylaminocarbonylalkyl, $(C_1-C_{10})$-alkenylalkylaminocarbonylalkyl, $(C_1-C_{10})$-alkylcarbonyl, $(C_1-C_{10})$-cycloalkylcarbonyl, formyl, hydroxyiminomethyl, aminoiminomethyl, alkoxyiminomethyl, alkylaminoiminomethyl, $(C_1-C_{10})$-dialkylaminoiminomethyl, $(C_1-C_{10})$-cycloalkoxyiminomethyl, $(C_1-C_{10})$-cycloalkylalkoximinomethyl, $(C_1-C_{10})$-aryloximinomethyl, $(C_1-C_{10})$-arylalkoxyiminomethyl, $(C_1-C_{10})$-arylalkylaminoiminomethyl, $(C_1-C_{10})$-alkenyloxyiminomethyl, arylaminoiminomethyl, arylsulfonylaminoiminomethyl, $(C_1-C_{10})$-heteroarylalkyl, $(C_1-C_{10})$-heterocyclylalkyl, $R^8$, $R^9$ and $R^{10}$ independently of one another represent hydrogen, $(C_1-C_{10})$-alkyl, $(C_1-C_{10})$-alkenylalkyl, $(C_1-C_{10})$-alkoxyalkyl, $(C_1-C_{10})$-alkylcarbonyl, arylcarbonyl, heteroarylcarbonyl, $(C_1-C_{10})$-cycloalkylcarbonyl, $(C_1-C_{10})$-alkoxycarbonyl, $(C_1-C_{10})$-allyloxycarbonyl, $(C_1-C_{10})$-aryloxyalkyl, $(C_1-C_{10})$-arylalkyl, $(C_1-C_{10})$-haloalkyl, $R^{11}$ and $R^{12}$ independently of one another represent hydrogen, halogen, $(C_1-C_{10})$-alkyl, $(C_1-C_{10})$-alkoxy, $(C_1-C_{10})$-haloalkyl, $(C_1-C_{10})$-haloalkoxy, aryl, heteroaryl, $(C_1-C_{10})$-arylalkyl or together with the atom to which they are attached form a carbonyl group, $A^4$, $A^5$ are identical or different and independently of one another represent N—$R^{13}$, oxygen, sulfur or the C—$R^{13}$ moiety, but there is never more than one oxygen atom present in the heterocycle, and where each $R^9$ in the N—$R^{13}$ and C—$R^{13}$ moieties has identical or different meanings according to the definition below, $R^{13}$ represents hydrogen, halogen, $(C_1-C_{10})$-alkyl, $(C_1-C_{10})$-alkoxy, $(C_1-C_{10})$-haloalkyl, $(C_1-C_{10})$-haloalkoxy, aryl, heteroaryl, $(C_1-C_{10})$-arylalkyl or together with the atom to which it is attached forms a carbonyl group, $A^6$, $A^7$, $A^8$, $A^9$ are identical or different and independently of one another represent O, S, N, NH, N-alkyl, alkoxycarbonyl-N, N-aryl, N-heteroaryl or the C—$R^{14}$ moiety, where at most two oxygen or sulfur atoms are present in the heterocycle, and where no oxygen or sulfur atoms are adjacent to one another, and where each $R^{14}$ in the C—$R^{14}$ moiety has identical or different meanings according to the definition below, and $R^{14}$ represents hydrogen, nitro, amino, hydroxy, hydrothio, thiocyanato, isothiocyanato, halogen, $(C_1-C_{10})$-alkyl, $(C_1-C_{10})$-cycloalkyl, $(C_1-C_{10})$-alkenyl, $(C_1-C_{10})$-alkynyl, aryl, $(C_1-C_{10})$-arylalkyl, $(C_1-C_{10})$-arylalkoxy, heteroaryl, $(C_1-C_{10})$-haloalkyl, $(C_1-C_{10})$-halocycloalkyl, $(C_1-C_{10})$-alkoxy, $(C_1-C_{10})$-haloalkoxy, aryloxy, heteroaryloxy, $(C_1-C_{10})$-cycloalkyloxy, $(C_1-C_{10})$-cycloalkylalkoxy, $(C_1-C_{10})$-hydroxyalkyl, $(C_1-C_{10})$-alkoxyalkyl, $(C_1-C_{10})$-aryloxyalkyl, $(C_1-C_{10})$-heteroaryloxyalkyl, $(C_1-C_{10})$-alkenylaminocarbonyl, $(C_1-C_{10})$-alkylamino, $(C_1-C_{10})$-alkylthio, $(C_1-C_{10})$-haloalkylthio, $(C_1-C_{10})$-bisalkylamino, $(C_1-C_{10})$-cycloalkylamino, $(C_1-C_{10})$-alkylcarbonylamino, $(C_1-C_{10})$-cycloalkylcarbonylamino, formylamino, $(C_1-C_{10})$-haloalkylcarbonylamino, $(C_1-C_{10})$-alkoxycarbonylamino, $(C_1-C_{10})$-alkylaminocarbonylamino, $(C_1-C_{10})$-(alkyl)aminocarbonylamino, $(C_1-C_{10})$-alkylsulfonylamino, $(C_1-C_{10})$-cycloalkylsulfonylamino, arylsulfonylamino, hetarylsulfonylamino, $(C_1-C_{10})$-sulfonylhaloalkylamino, $(C_1-C_{10})$-aminoalkylsulfonyl, $(C_1-C_{10})$-aminohaloalkylsulfonyl, $(C_1-C_{10})$-alkylaminosulfonyl, $(C_1-C_{10})$-bisalkylaminosulfonyl, $(C_1-C_{10})$-cycloalkylaminosulfonyl, $(C_1-C_{10})$-haloalkylaminosulfonyl, arylaminosulfonyl, $(C_1-C_{10})$-arylalkylaminosulfonyl, $(C_1-C_{10})$-alkylsulfonyl, $(C_1-C_{10})$-cycloalkylsulfonyl, arylsulfonyl, $(C_1-C_{10})$-alkylsulfinyl, $(C_1-C_{10})$-cycloalkylsulfinyl, arylsulfinyl, $(C_1-C_{10})$—N,S-dialkylsulfonimidoyl, $(C_1-C_{10})$—S-alkylsulfonimidoyl, $(C_1-C_{10})$-alkylsulfonylaminocarbonyl, $(C_1-C_{10})$-cycloalkylsulfonylaminocarbonyl, $(C_1-C_{10})$-cycloalkylaminosulfonyl, $(C_1-C_{10})$-arylalkylcarbonylamino, $(C_1-C_{10})$-cycloalkylalkylcarbonylamino, heteroarylcarbonylamino, $(C_1-C_{10})$-alkoxyalkylcarbonylamino, $(C_1-C_{10})$-hydroxyalkylcarbonylamino, cyano, $(C_1-C_{10})$-cyanoalkyl, hydroxycarbonyl, $(C_1-C_{10})$-alkoxycarbonyl, $(C_1-C_{10})$-cycloalkoxycarbonyl, $(C_1-C_{10})$-cycloalkylalkoxycarbonyl, aryloxycarbonyl, $(C_1-C_{10})$-arylalkoxycarbonyl, aminocarbonyl, $(C_1-C_{10})$-alkylaminocarbonyl, $(C_1-C_{10})$-bisalkylaminocarbonyl, $(C_1-C_{10})$-alkyl-$((C_1-C_{10})$-alkoxy)aminocarbonyl, $(C_1-C_{10})$-cycloalkylaminocarbonyl, $(C_1-C_{10})$-arylalkylaminocarbonyl, $(C_1-C_{10})$-heteroarylalkylaminocarbonyl, $(C_1-C_{10})$-cyanoalkylaminocarbonyl, $(C_1-C_{10})$-haloalkylaminocarbonyl, $(C_1-C_{10})$-alkynylalkylaminocarbonyl, $(C_1-C_{10})$-alkoxycarbonylaminocarbonyl, $(C_1-C_{10})$-arylalkoxycarbonylaminocarbonyl, $(C_1-C_{10})$-hydroxycarbonylalkyl, $(C_1-C_{10})$-alkoxycarbonylalkyl, $(C_1-C_{10})$-cycloalkoxycarbonylalkyl, $(C_1-C_{10})$-cycloalkylalkoxycarbonylalkyl, $(C_1-C_{10})$-alkylaminocarbonylalkyl, $(C_1-C_{10})$-aminocarbonylalkyl, $(C_1-C_{10})$-bisalkylaminocarbonylalkyl, $(C_1-C_{10})$-cycloalkylaminocarbonylalkyl, $(C_1-C_{10})$-arylalkylaminocarbonylalkyl, $(C_1-C_{10})$-heteroarylalkylaminocarbonylalkyl, $(C_1-C_{10})$-cyanoalkylaminocarbonylalkyl, $(C_1-C_{10})$-haloalkylaminocarbonylalkyl, $(C_1-C_{10})$-alkynylalkylaminocarbonylalkyl, $(C_1-C_{10})$-cycloalkylalkylaminocarbonylalkyl, $(C_1-C_{10})$-alkoxycarbonylaminocarbonylalkyl, $(C_1-C_{10})$-arylalkoxycarbonylaminocarbonylalkyl, $(C_1-C_{10})$-alkoxycarbonylalkylaminocarbonyl, $(C_1-C_{10})$-hydroxycarbonylalkylaminocarbonyl, $(C_1-C_{10})$-aminocarbonylalkylaminocarbonyl, $(C_1-C_{10})$-alkylaminocarbonylalkylaminocarbonyl, $(C_1-C_{10})$-cycloalkylaminocarbonylalkylaminocarbonyl, $(C_1-C_{10})$-cycloalkylalkylaminocarbonyl, $(C_1-C_{10})$-cycloalkylalkylaminocarbonylalkyl, $(C_1-C_{10})$-alkenyloxycarbonyl, $(C_1-C_{10})$-alkenyloxycarbonylalkyl, $(C_1-C_{10})$-alkenylaminocarbonyl, $(C_1-C_{10})$-alkenylalkylaminocarbonyl, $(C_1-C_{10})$-alkenylaminocarbonylalkyl, $(C_1-C_{10})$-alkenylalkylaminocarbonylalkyl, $(C_1-C_{10})$-alkylcarbonyl, $(C_1-C_{10})$-cycloalkylcarbonyl, formyl, hydroxyiminomethyl, aminoiminomethyl, alkoxyiminomethyl, alkylaminoiminomethyl, $(C_1-C_{10})$-dialkylaminoiminomethyl, $(C_1-C_{10})$-cycloalkoxyiminomethyl, $(C_1-C_{10})$-cycloalkylalkoximinomethyl, $(C_1-C_{10})$-aryloximinomethyl, $(C_1-C_{10})$-arylalkoxyiminomethyl, $(C_1-C_{10})$-arylalkylaminoiminomethyl, $(C_1-C_{10})$-alkenyloxyiminomethyl, arylaminoiminomethyl, arylsulfonylaminoiminomethyl, $(C_1-C_{10})$-heteroarylalkyl, $(C_1-C_{10})$-heterocyclylalkyl, $A^{10}$ represents N—$R^{15}$, oxygen or the C—$R^{15}$ moiety, and where each $R^{15}$ in the N—$R^{15}$ and C—$R^{15}$ moieties has identical or different meanings according to the definition below, $A^{11}$ represents N or the C—$R^{18}$ moiety, and where $R^{18}$ in the C—$R^{18}$ moiety has the meaning according to the definition below, $A^{12}$ represents N—$R^{15}$ or the C($R^{16}$)$R^{17}$ moiety, and where $R^{16}$ and $R^{17}$ in the C($R^{16}$)$R^{17}$ moiety have the meaning according to the definition below, $R^{15}$ represents hydrogen, $(C_1-C_{10})$-alkyl, $(C_1-C_{10})$-alkenylalkyl, $(C_1-C_{10})$-alkoxyalkyl, $(C_1-C_{10})$-alkylcarbonyl, arylcarbonyl, heteroarylcarbonyl, $(C_1-C_{10})$-cycloalkylcarbonyl, $(C_1-C_{10})$-alkoxycarbonyl, $(C_1-C_{10})$-allyloxycarbonyl, $(C_1-C_{10})$-aryloxyalkyl, $(C_1-C_{10})$-arylalkyl, $(C_1-C_{10})$-haloalkyl, aryl, $R^{16}$ and $R^{17}$ independently of one another represent hydrogen, halogen, alkyl, alkoxy, haloalkyl, haloalkoxy, aryl, heteroaryl, arylalkyl or together with the atom to which they are attached form a carbonyl group, and $R^{18}$ represents hydrogen, nitro, amino, hydroxy, hydrothio, thiocyanato, isothiocyanato, halogen, $(C_1-C_{10})$-alkyl, $(C_1-C_{10})$-cycloalkyl, $(C_1-C_{10})$-alkenyl, $(C_1-C_{10})$-alkynyl, aryl, $(C_1-C_{10})$-arylalkyl, $(C_1-C_{10})$-arylalkoxy, heteroaryl, $(C_1-C_{10})$-haloalkyl, $(C_1-C_{10})$-halocycloalkyl, $(C_1-C_{10})$-alkoxy, $(C_1-C_{10})$-haloalkoxy, aryloxy, heteroaryloxy, $(C_1-C_{10})$-cycloalkyloxy, $(C_1-C_{10})$-cycloalkylalkoxy, $(C_1-C_{10})$-hydroxyalkyl, $(C_1-C_{10})$-alkoxyalkyl, $(C_1-C_{10})$-aryloxyalkyl, $(C_1-C_{10})$-heteroaryloxyalkyl, $(C_1-C_{10})$-alkenylaminocarbonyl, $(C_1-C_{10})$-alkylamino, $(C_1-C_{10})$-alkylthio, $(C_1-C_{10})$-haloalkylthio, $(C_1-C_{10})$-bisalkylamino, $(C_1-C_{10})$-cycloalkylamino, $(C_1-C_{10})$-alkylcarbonylamino, $(C_1-C_{10})$-cycloalkylcarbonylamino, formylamino, $(C_1-C_{10})$-haloalkylcarbonylamino, $(C_1-C_{10})$-alkoxycarbonylamino, $(C_1-C_{10})$-alkylaminocarbonylamino, $(C_1-C_{10})$-(alkyl)aminocarbonylamino, $(C_1-C_{10})$-alkylsulfonylamino, $(C_1-C_{10})$-cycloalkylsulfonylamino, arylsulfonylamino, hetarylsulfonylamino, $(C_1-C_{10})$-sulfonylhaloalkylamino, $(C_1-C_{10})$-aminoalkylsulfonyl, $(C_1-C_{10})$-aminohaloalkylsulfonyl, $(C_1-C_{10})$-alkylaminosulfonyl, $(C_1-C_{10})$-bisalkylaminosulfonyl, $(C_1-C_{10})$-cycloalkylaminosulfonyl, $(C_1-C_{10})$-haloalkylaminosulfonyl, arylaminosulfonyl, $(C_1-C_{10})$-arylalkylaminosulfonyl, $(C_1-C_{10})$-alkylsulfonyl, $(C_1-C_{10})$-cycloalkylsulfonyl, arylsulfonyl, $(C_1-C_{10})$-alkylsulfinyl, $(C_1-C_{10})$-cycloalkylsulfinyl, arylsulfinyl, $(C_1-C_{10})$—N,S-dialkylsulfonimidoyl, $(C_1-C_{10})$—S-alkylsulfonimidoyl, $(C_1-C_{10})$-alkylsulfonylaminocarbonyl, (C$_1$-C$_{10}$)-cycloalkylsulfonylaminocarbonyl, (C$_1$-C$_{10}$)-cycloalkylaminosulfonyl, (C$_1$-C$_{10}$)-arylalkylcarbonylamino, (C$_1$-C$_{10}$)-cycloalkylalkylcarbonylamino, heteroarylcarbonylamino, (C$_1$-C$_{10}$)-alkoxyalkylcarbonylamino, (C$_1$-C$_{10}$)-hydroxyalkylcarbonylamino, cyano, (C$_1$-C$_{10}$)-cyanoalkyl, hydroxycarbonyl, (C$_1$-C$_{10}$)-alkoxycarbonyl, (C$_1$-C$_{10}$)-cycloalkoxycarbonyl, (C$_1$-C$_{10}$)-cycloalkylalkoxycarbonyl, aryloxycarbonyl, (C$_1$-C$_{10}$)-arylalkoxycarbonyl, aminocarbonyl, (C$_1$-C$_{10}$)-alkylaminocarbonyl, (C$_1$-C$_{10}$)-bisalkylaminocarbonyl, (C$_1$-C$_{10}$)-alkyl-((C$_1$-C$_{10}$)-alkoxy)aminocarbonyl, (C$_1$-C$_{10}$)-cycloalkylaminocarbonyl, (C$_1$-C$_{10}$)-arylalkylaminocarbonyl, (C$_1$-C$_{10}$)-heteroarylalkylaminocarbonyl, (C$_1$-C$_{10}$)-cyanoalkylaminocarbonyl, (C$_1$-C$_{10}$)-haloalkylaminocarbonyl, (C$_1$-C$_{10}$)-alkynylalkylaminocarbonyl, (C$_1$-C$_{10}$)-alkoxycarbonylaminocarbonyl, (C$_1$-C$_{10}$)-arylalkoxycarbonylaminocarbonyl, (C$_1$-C$_{10}$)-hydroxycarbonylalkyl, (C$_1$-C$_{10}$)-alkoxycarbonylalkyl, (C$_1$-C$_{10}$)-cycloalkoxycarbonylalkyl, (C$_1$-C$_{10}$)-cycloalkylalkoxycarbonylalkyl, (C$_1$-C$_{10}$)-alkylaminocarbonylalkyl, (C$_1$-C$_{10}$)-aminocarbonylalkyl, (C$_1$-C$_{10}$)-bisalkylaminocarbonylalkyl, (C$_1$-C$_{10}$)-cycloalkylaminocarbonylalkyl, (C$_1$-C$_{10}$)-arylalkylaminocarbonylalkyl, (C$_1$-C$_{10}$)-heteroarylalkylaminocarbonylalkyl, (C$_1$-C$_{10}$)-cyanoalkylaminocarbonylalkyl, (C$_1$-C$_{10}$)-haloalkylaminocarbonylalkyl, (C$_1$-C$_{10}$)-alkynylalkylaminocarbonylalkyl, (C$_1$-C$_{10}$)-cycloalkylalkylaminocarbonylalkyl, (C$_1$-C$_{10}$)-alkoxycarbonylaminocarbonylalkyl, (C$_1$-C$_{10}$)-arylalkoxycarbonylaminocarbonylalkyl, (C$_1$-C$_{10}$)-alkoxycarbonylalkylaminocarbonyl, (C$_1$-C$_{10}$)-hydroxycarbonylalkylaminocarbonyl, (C$_1$-C$_{10}$)-aminocarbonylalkylaminocarbonyl, (C$_1$-C$_{10}$)-alkylaminocarbonylalkylaminocarbonyl, (C$_1$-C$_{10}$)-cycloalkylaminocarbonylalkylaminocarbonyl, (C$_1$-C$_{10}$)-cycloalkylalkylaminocarbonyl, (C$_1$-C$_{10}$)-cycloalkylalkylaminocarbonylalkyl, (C$_1$-C$_{10}$)-alkenyloxycarbonyl, (C$_1$-C$_{10}$)-alkenyloxycarbonylalkyl, (C$_1$-C$_{10}$)-alkenylaminocarbonyl, (C$_1$-C$_{10}$)-alkenylalkylaminocarbonyl, (C$_1$-C$_{10}$)-alkenylaminocarbonylalkyl, (C$_1$-C$_{10}$)-alkenylalkylaminocarbonylalkyl, (C$_1$-C$_{10}$)-alkylcarbonyl, (C$_1$-C$_{10}$)-cycloalkylcarbonyl, formyl, hydroxyiminomethyl, aminoiminomethyl, alkoxyiminomethyl, alkylaminoiminomethyl, (C$_1$-C$_{10}$)-dialkylaminoiminomethyl, (C$_1$-C$_{10}$)-cycloalkoxyiminomethyl, (C$_1$-C$_{10}$)-cycloalkylalkoximinomethyl, (C$_1$-C$_{10}$)-aryloximinomethyl, (C$_1$-C$_{10}$)-arylalkoxyiminomethyl, (C$_1$-C$_{10}$)-arylalkylaminoiminomethyl, (C$_1$-C$_{10}$)-alkenyloxyiminomethyl, arylaminoiminomethyl, arylsulfonylaminoiminomethyl, (C$_1$-C$_{10}$)-heteroarylalkyl, (C$_1$-C$_{10}$)-heterocyclylalkyl.

2. The compound as claimed in claim 1, where, in formula (I),

Q represents

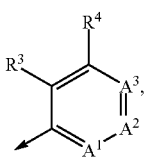

Q-I

-continued

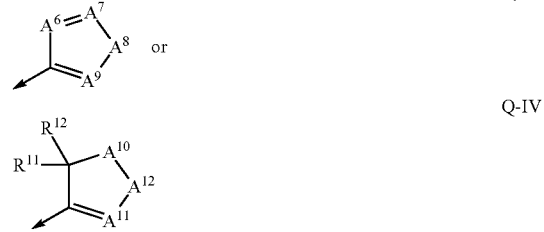

where the R$^3$ to R$^{12}$ and A$^1$ to A$^{12}$ moieties each have the meaning according to the definitions below, and where the arrow represents a bond to the pyrazole, (R$^1$)$_m$ represents m substituents R$^1$, where in the case that m is the number 1 the radical R$^1$ or, in the case that m is greater than 1, each of the radicals R$^1$ in each case independently of the others represents halogen, CN, (C$_1$-C$_8$)-alkyl, (C$_1$-C$_8$)-alkoxy or (C$_1$-C$_8$)-alkylthio, where each of the three last-mentioned radicals independently of the others is unsubstituted or substituted by one or more radicals from the group consisting of halogen, CN, (C$_1$-C$_8$)-alkoxy and (C$_1$-C$_8$)-alkylthio, R$^2$ represents hydrogen or a radical which can be hydrolyzed to afford the carboxylic acid, optionally an optionally substituted hydrocarbon radical or an optionally substituted heterocyclyl radical, where each of the two last-mentioned carbon-containing radicals including substituents has 1 to 30 carbon atoms, optionally 1 to 24 carbon atoms, optionally 1 to 20 carbon atoms, or a radical of the formula —N=CR$^a$R$^b$, —NR$^c$R$^d$ or SiR$^e$R$^f$R$^g$, where in the 3 last-mentioned formulae each of the radicals R$^a$, R$^b$, R$^c$, R$^d$, R$^e$, R$^f$ and R$^g$ independently of the others represents hydrogen or an optionally substituted hydrocarbon radical, or R$^a$ and R$^b$ together with the carbon atom to which they are attached represent a 3- to 9-membered carbocyclic radical or a heterocyclic radical which may contain 1 to 3 ring heteroatoms from the group consisting of N, O and S, where the carbocyclic or heterocyclic radical is unsubstituted or substituted, or R$^c$ and R$^d$ together with the nitrogen atom represent a 3- to 8-membered heterocycle which, in addition to the nitrogen atom, may contain one or two further ring heteroatoms from the group consisting of N, O and S and which is unsubstituted or substituted by one or more radicals from the group consisting of (C$_1$-C$_{10}$)-alkyl and (C$_1$-C$_{10}$)-haloalkyl, where each of the radicals R$^a$, R$^b$, R$^c$, R$^d$, R$^e$, R$^f$ and R$^e$ including substituents has 1 to 30 carbon atoms, optionally 1 to 24 carbon atoms, optionally 1 to 20 carbon atoms, wherein m represents 1, 2, 3, 4 or 5, optionally 1, 2, 3 or 4, optionally 1 or 2, A$^1$, A$^2$, A$^3$ are identical or different and each independently of one another represent N (nitrogen) or the C—R$^5$ moiety, but there are never more than two adjacent nitrogen atoms, and where each R$^5$ in the C—R$^5$ moiety has identical or different meanings according to the definition below, and A$^1$ and A$^2$, when each is a C—R$^5$ group, with the atoms to which they are attached form a fully saturated, partly saturated or fully unsaturated 5- to 6-membered ring optionally interrupted by heteroatoms and optionally with further substitution, $A^2$ and $A^3$, when each is a C—$R^5$ group, with the atoms to which they are attached form a fully saturated, partly saturated or fully unsaturated 5- to 6-membered ring optionally interrupted by heteroatoms and optionally with further substitution, $R^3$, $R^4$ and $R^5$ independently of one another represent hydrogen, nitro, amino, cyano, thiocyanato, isothiocyanato, halogen, ($C_1$-$C_8$)-alkyl, ($C_1$-$C_8$)-cycloalkyl, ($C_1$-$C_8$)-alkenyl, ($C_1$-$C_8$)-alkynyl, aryl, aryl-($C_1$-$C_8$)-alkyl, ($C_1$-$C_8$)-alkenylalkyl, ($C_1$-$C_8$)-alkynylalkyl, aryl-($C_1$-$C_8$)-alkoxy, heteroaryl, ($C_1$-$C_8$)-alkoxyalkyl, ($C_1$-$C_8$)-hydroxyalkyl, ($C_1$-$C_8$)-haloalkyl, ($C_1$-$C_8$)-halocycloalkyl, ($C_1$-$C_8$)-alkoxy, ($C_1$-$C_8$)-haloalkoxy, aryloxy, heteroaryloxy, ($C_1$-$C_8$)-cycloalkyloxy, hydroxy, ($C_1$-$C_8$)-cycloalkylalkoxy, ($C_1$-$C_8$)-alkoxycarbonyl, hydroxycarbonyl, aminocarbonyl, ($C_1$-$C_8$)-alkylaminocarbonyl, ($C_1$-$C_8$)-cycloalkylaminocarbonyl, ($C_1$-$C_8$)-cyanoalkylaminocarbonyl, ($C_1$-$C_8$)-alkenylaminocarbonyl, ($C_1$-$C_8$)-alkynylaminocarbonyl, ($C_1$-$C_8$)-alkylamino, ($C_1$-$C_8$)-alkylthio, ($C_1$-$C_8$)-haloalkylthio, hydrothio, ($C_1$-$C_8$)-bisalkylamino, ($C_1$-$C_8$)-cycloalkylamino, ($C_1$-$C_8$)-alkylcarbonylamino, ($C_1$-$C_8$)-cycloalkylcarbonylamino, formylamino, ($C_1$-$C_8$)-haloalkylcarbonylamino, ($C_1$-$C_8$)-alkoxycarbonylamino, ($C_1$-$C_8$)-alkylaminocarbonylamino, (($C_1$-$C_8$)-alkyl)aminocarbonylamino, ($C_1$-$C_8$)-alkylsulfonylamino, ($C_1$-$C_8$)-cycloalkylsulfonylamino, arylsulfonylamino, hetarylsulfonylamino, ($C_1$-$C_8$)-sulfonylhaloalkylamino, aminosulfonyl, ($C_1$-$C_8$)-aminoalkylsulfonyl, ($C_1$-$C_8$)-aminohaloalkylsulfonyl, ($C_1$-$C_8$)-alkylaminosulfonyl, ($C_1$-$C_8$)-bisalkylaminosulfonyl, ($C_1$-$C_8$)-cycloalkylaminosulfonyl, ($C_1$-$C_8$)-haloalkylaminosulfonyl, arylaminosulfonyl, ($C_1$-$C_8$)-arylalkylaminosulfonyl, ($C_1$-$C_8$)-alkylsulfonyl, ($C_1$-$C_8$)-cycloalkylsulfonyl, arylsulfonyl, ($C_1$-$C_8$)-alkylsulfinyl, ($C_1$-$C_8$)-cycloalkylsulfinyl, arylsulfinyl, ($C_1$-$C_8$)—N,S-dialkylsulfonimidoyl, ($C_1$-$C_8$)—S-alkylsulfonimidoyl, ($C_1$-$C_8$)-alkylsulfonylaminocarbonyl, ($C_1$-$C_8$)-cycloalkylsulfonylaminocarbonyl, ($C_1$-$C_8$)-cycloalkylaminosulfonyl, ($C_1$-$C_8$)-arylalkylcarbonylamino, ($C_1$-$C_8$)-cycloalkylalkylcarbonylamino, heteroarylcarbonylamino, ($C_1$-$C_8$)-alkoxyalkylcarbonylamino, ($C_1$-$C_8$)-hydroxyalkylcarbonylamino, ($C_1$-$C_8$)-trialkylsilyl, $A^6$, $A^7$, $A^8$, $A^9$ are identical or different and independently of one another represent O, S, N, NH, N-alkyl, alkoxycarbonyl-N, N-aryl, N-heteroaryl or the C—$R^{14}$ moiety, where at most two oxygen or sulfur atoms are present in the heterocycle, and where no oxygen or sulfur atoms are adjacent to one another, and where each $R^{14}$ in the C—$R^{14}$ moiety has identical or different meanings according to the definition below, and $R^{14}$ represents hydrogen, nitro, amino, cyano, thiocyanato, isothiocyanato, halogen, ($C_1$-$C_8$)-alkyl, ($C_1$-$C_8$)-cycloalkyl, ($C_1$-$C_8$)-alkenyl, ($C_1$-$C_8$)-alkynyl, aryl, aryl-($C_1$-$C_8$)-alkyl, ($C_1$-$C_8$)-alkenylalkyl, ($C_1$-$C_8$)-alkynylalkyl, aryl-($C_1$-$C_8$)-alkoxy, heteroaryl, ($C_1$-$C_8$)-alkoxyalkyl, ($C_1$-$C_8$)-hydroxyalkyl, ($C_1$-$C_8$)-haloalkyl, ($C_1$-$C_8$)-halocycloalkyl, ($C_1$-$C_8$)-alkoxy, ($C_1$-$C_8$)-haloalkoxy, aryloxy, heteroaryloxy, ($C_1$-$C_8$)-cycloalkyloxy, hydroxy, ($C_1$-$C_8$)-cycloalkylalkoxy, ($C_1$-$C_8$)-alkoxycarbonyl, hydroxycarbonyl, aminocarbonyl, ($C_1$-$C_8$)-alkylaminocarbonyl, ($C_1$-$C_8$)-cycloalkylaminocarbonyl, ($C_1$-$C_8$)-cyanoalkylaminocarbonyl, ($C_1$-$C_8$)-alkenylaminocarbonyl, ($C_1$-$C_8$)-alkynylaminocarbonyl, ($C_1$-$C_8$)-alkylamino, ($C_1$-$C_8$)-alkylthio, ($C_1$-$C_8$)-haloalkylthio, hydrothio, ($C_1$-$C_8$)-bisalkylamino, ($C_1$-$C_8$)-cycloalkylamino, ($C_1$-$C_8$)-alkylcarbonylamino, ($C_1$-$C_8$)-cycloalkylcarbonylamino, formylamino, ($C_1$-$C_8$)-haloalkylcarbonylamino, ($C_1$-$C_8$)-alkoxycarbonylamino, ($C_1$-$C_8$)-alkylaminocarbonylamino, (($C_1$-$C_8$)-alkyl)aminocarbonylamino, ($C_1$-$C_8$)-alkylsulfonylamino, ($C_1$-$C_8$)-cycloalkylsulfonylamino, arylsulfonylamino, hetarylsulfonylamino, ($C_1$-$C_8$)-sulfonylhaloalkylamino, aminosulfonyl, ($C_1$-$C_8$)-aminoalkylsulfonyl, ($C_1$-$C_8$)-aminohaloalkylsulfonyl, ($C_1$-$C_8$)-alkylaminosulfonyl, ($C_1$-$C_8$)-bisalkylaminosulfonyl, ($C_1$-$C_8$)-cycloalkylaminosulfonyl, ($C_1$-$C_8$)-haloalkylaminosulfonyl, arylaminosulfonyl, ($C_1$-$C_8$)-arylalkylaminosulfonyl, ($C_1$-$C_8$)-alkylsulfonyl, ($C_1$-$C_8$)-cycloalkylsulfonyl, arylsulfonyl, ($C_1$-$C_8$)-alkylsulfinyl, ($C_1$-$C_8$)-cycloalkylsulfinyl, arylsulfinyl, ($C_1$-$C_8$)—N,S-dialkylsulfonimidoyl, ($C_1$-$C_8$)—S-alkylsulfonimidoyl, ($C_1$-$C_8$)-alkylsulfonylaminocarbonyl, ($C_1$-$C_8$)-cycloalkylsulfonylaminocarbonyl, ($C_1$-$C_8$)-cycloalkylaminosulfonyl, ($C_1$-$C_8$)-arylalkylcarbonylamino, ($C_1$-$C_8$)-cycloalkylalkylcarbonylamino, heteroarylcarbonylamino, ($C_1$-$C_8$)-alkoxyalkylcarbonylamino, ($C_1$-$C_8$)-hydroxyalkylcarbonylamino, ($C_1$-$C_8$)-trialkylsilyl, $A^{10}$ represents N—$R^{15}$, oxygen or the C—$R^{15}$ moiety, and where each $R^{15}$ in the N—$R^{15}$ and C—$R^{15}$ moieties has identical or different meanings according to the definition below, $A^{11}$ represents N or the C—$R^{18}$ moiety, and where $R^{18}$ in the C—$R^{18}$ moiety has the meaning according to the definition below, $A^{12}$ represents N—$R^{15}$ or the C($R^{16}$)$R^{17}$ moiety, and where $R^{16}$ and $R^{17}$ in the C($R^{16}$)$R^{17}$ moiety have the meaning according to the definition below, $R^{15}$ represents hydrogen, ($C_1$-$C_{10}$)-alkyl, ($C_1$-$C_{10}$)-alkenylalkyl, ($C_1$-$C_{10}$)-alkoxyalkyl, ($C_1$-$C_{10}$)-alkylcarbonyl, arylcarbonyl, heteroarylcarbonyl, ($C_1$-$C_{10}$)-cycloalkyloarbonyl, ($C_1$-$C_{10}$)-alkoxycarbonyl, ($C_1$-$C_{10}$)-allyloxycarbonyl, ($C_1$-$C_{10}$)-aryloxyalkyl, ($C_1$-$C_{10}$)-arylalkyl, ($C_1$-$C_{10}$)-haloalkyl, aryl, $R^{16}$ and $R^{17}$ independently of one another represent hydrogen, halogen, ($C_1$-$C_8$)-alkyl, ($C_1$-$C_8$)-alkoxy, ($C_1$-$C_8$)-haloalkyl, ($C_1$-$C_8$)-haloalkoxy, aryl, heteroaryl, ($C_1$-$C_8$)-arylalkyl or together with the atom to which they are attached form a carbonyl group, and $R^{18}$ represents hydrogen, nitro, amino, cyano, thiocyanato, isothiocyanato, halogen, ($C_1$-$C_8$)-alkyl, ($C_1$-$C_8$)-cycloalkyl, ($C_1$-$C_8$)-alkenyl, ($C_1$-$C_8$)-alkynyl, aryl, aryl-($C_1$-$C_8$)-alkyl, ($C_1$-$C_8$)-alkenylalkyl, ($C_1$-$C_8$)-alkynylalkyl, aryl-($C_1$-$C_8$)-alkoxy, heteroaryl, ($C_1$-$C_8$)-alkoxyalkyl, ($C_1$-$C_8$)-hydroxyalkyl, ($C_1$-$C_8$)-haloalkyl, ($C_1$-$C_8$)-halocycloalkyl, ($C_1$-$C_8$)-alkoxy, ($C_1$-$C_8$)-haloalkoxy, aryloxy, heteroaryloxy, ($C_1$-$C_8$)-cycloalkyloxy, hydroxy, ($C_1$-$C_8$)-cycloalkylalkoxy, ($C_1$-$C_8$)-alkoxycarbonyl, hydroxycarbonyl, aminocarbonyl, ($C_1$-$C_8$)-alkylaminocarbonyl, ($C_1$-$C_8$)-cycloalkylaminocarbonyl, ($C_1$-$C_8$)-cyanoalkylaminocarbonyl, ($C_1$-$C_8$)-alkenylaminocarbonyl, ($C_1$-$C_8$)-alkynylaminocarbonyl, ($C_1$-$C_8$)-alkylamino, ($C_1$-$C_8$)-alkylthio, ($C_1$-$C_8$)-haloalkylthio, hydrothio, ($C_1$-$C_8$)-bisalkylamino, ($C_1$-$C_8$)- cycloalkylamino, $(C_1-C_8)$-alkylcarbonylamino, $(C_1-C_8)$-cycloalkylcarbonylamino, formylamino, $(C_1-C_8)$-haloalkylcarbonylamino, $(C_1-C_8)$-alkoxycarbonylamino, $(C_1-C_8)$-alkylaminocarbonylamino, $((C_1-C_8)$-alkyl) aminocarbonylamino, $(C_1-C_8)$-alkylsulfonylamino, $(C_1-C_8)$-cycloalkylsulfonylamino, arylsulfonylamino, hetarylsulfonylamino, $(C_1-C_8)$-sulfonylhaloalkylamino, aminosulfonyl, $(C_1-C_8)$-aminoalkylsulfonyl, $(C_1-C_8)$-aminohaloalkylsulfonyl, $(C_1-C_8)$-alkylaminosulfonyl, $(C_1-C_8)$-bisalkylaminosulfonyl, $(C_1-C_8)$-cycloalkylaminosulfonyl, $(C_1-C_8)$-haloalkylaminosulfonyl, arylaminosulfonyl, $(C_1-C_8)$-arylalkylaminosulfonyl, $(C_1-C_8)$-alkylsulfonyl, $(C_1-C_8)$-cycloalkylsulfonyl, arylsulfonyl, $(C_1-C_8)$-alkylsulfinyl, $(C_1-C_8)$-cycloalkylsulfinyl, arylsulfinyl, $(C_1-C_8)$—N,S-dialkylsulfonimidoyl, $(C_1-C_8)$—S-alkylsulfonimidoyl, $(C_1-C_8)$-alkylsulfonylaminocarbonyl, $(C_1-C_8)$-cycloalkylsulfonylaminocarbonyl, $(C_1-C_8)$-cycloalkylaminosulfonyl, $(C_1-C_8)$-arylalkylcarbonylamino, $(C_1-C_8)$-cycloalkylalkylcarbonylamino, heteroarylcarbonylamino, $(C_1-C_8)$-alkoxyalkylcarbonylamino, $(C_1-C_8)$-hydroxyalkylcarbonylamino, $(C_1-C_8)$-trialkylsilyl.

3. The compound as claimed in claim 1, where, in formula (I),
Q represents

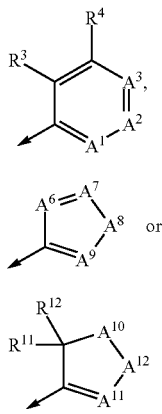

Q-I

Q-III

Q-IV where the $R^3$ to $R^{12}$ and $A^1$ to $A^{12}$ moieties each have the meaning according to the definitions below, and where the arrow represents a bond to the pyrazole, $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1-C_6)$-alkyl, $(C_1-C_6)$-alkoxy or $(C_1-C_6)$-alkylthio, where each of the three last-mentioned radicals independently of the others is unsubstituted or substituted by one or more radicals from the group consisting of halogen, CN, $(C_1-C_6)$-alkoxy and $(C_1-C_6)$-alkylthio, $R^2$ represents hydrogen or a radical which can be hydrolyzed to afford the carboxylic acid, optionally an optionally substituted hydrocarbon radical or an optionally substituted heterocyclyl radical, where each of the two last-mentioned carbon-containing radicals including substituents has 1 to 30 carbon atoms, optionally 1 to 24 carbon atoms, optionally 1 to 20 carbon atoms, or a radical of the formula —N=$CR^aR^b$, —$NR^cR^d$ or $SiR^eR^fR^g$, where in the 3 last-mentioned formulae each of the radicals $R^a$, $R^b$, $R^c$, $R^d$, $R^e$, $R^f$ and $R^g$ independently of the others represents hydrogen or an optionally substituted hydrocarbon radical, or $R^a$ and $R^b$ together with the carbon atom to which they are attached represent a 3- to 9-membered carbocyclic radical or a heterocyclic radical which may contain 1 to 3 ring heteroatoms from the group consisting of N, O and S, where the carbocyclic or heterocyclic radical is unsubstituted or substituted, or $R^c$ and $R^d$ together with the nitrogen atom represent a 3- to 8-membered heterocycle which, in addition to the nitrogen atom, may contain one or two further ring heteroatoms from the group consisting of N, O and S and which is unsubstituted or substituted by one or more radicals from the group consisting of $(C_1-C_6)$-alkyl and $(C_1-C_6)$-haloalkyl, where each of the radicals $R^a$, $R^b$, $R^c$, $R^d$, $R^e$, $R^f$ and $R^e$ including substituents has 1 to 30 carbon atoms, preferably 1 to 24 carbon atoms, optionally 1 to 20 carbon atoms, wherein m represents 1, 2, 3, 4 or 5, optionally 1, 2, 3 or 4, optionally 1 or 2, $A^1$, $A^2$, $A^3$ are the same or different and independently of one another represent N (nitrogen) or
the C—$R^5$ moiety, but there are never more than two adjacent nitrogen atoms, and where each $R^5$ in the C—$R^5$ moiety has identical or different meanings according to the definition below, and $A^1$ and $A^2$, when each is a C—$R^5$ group, with the atoms to which they are attached form a fully saturated, partly saturated or fully unsaturated 5- to 6-membered ring optionally interrupted by heteroatoms and optionally with further substitution, $A^2$ and $A^3$, when each is a C—$R^5$ group, with the atoms to which they are attached form a fully saturated, partly saturated or fully unsaturated 5- to 6-membered ring optionally interrupted by heteroatoms and optionally with further substitution, $R^3$, $R^4$ and $R^5$ independently of one another represent hydrogen, nitro, amino, cyano, thiocyanato, isothiocyanato, halogen, $(C_1-C_6)$-alkyl, $(C_1-C_6)$-cycloalkyl, $(C_1-C_6)$-alkenyl, $(C_1-C_6)$-alkynyl, aryl, aryl-$(C_1-C_6)$-alkyl, $(C_1-C_6)$-alkenylalkyl, $(C_1-C_6)$-alkynylalkyl, aryl-$(C_1-C_6)$-alkoxy, heteroaryl, $(C_1-C_6)$-alkoxyalkyl, $(C_1-C_6)$-hydroxyalkyl, $(C_1-C_6)$-haloalkyl, $(C_1-C_6)$-halocycloalkyl, $(C_1-C_6)$-alkoxy, $(C_1-C_6)$-haloalkoxy, aryloxy, heteroaryloxy, $(C_1-C_6)$-cycloalkyloxy, hydroxy, $(C_1-C_6)$-cycloalkylalkoxy, $(C_1-C_6)$-alkoxycarbonyl, hydroxycarbonyl, aminocarbonyl, $(C_1-C_6)$-alkylaminocarbonyl, $(C_1-C_6)$-cycloalkylaminocarbonyl, $(C_1-C_6)$-cyanoalkylaminocarbonyl, $(C_1-C_6)$-alkenylaminocarbonyl, $(C_1-C_6)$-alkynylaminocarbonyl, $(C_1-C_6)$-alkylamino, $(C_1-C_6)$-alkylthio, $(C_1-C_6)$-haloalkylthio, hydrothio, $(C_1-C_6)$-bisalkylamino, $(C_1-C_6)$-cycloalkylamino, $(C_1-C_6)$-alkylcarbonylamino, $(C_1-C_6)$-cycloalkylcarbonylamino, formylamino, $(C_1-C_6)$-haloalkylcarbonylamino, $(C_1-C_6)$-alkoxycarbonylamino, $(C_1-C_6)$-alkylaminocarbonylamino, $((C_1-C_6)$-alkyl) aminocarbonylamino, $(C_1-C_6)$-alkylsulfonylamino, $(C_1-C_6)$-cycloalkylsulfonylamino, arylsulfonylamino, hetarylsulfonylamino, $(C_1-C_6)$-sulfonylhaloalkylamino, aminosulfonyl, $(C_1-C_6)$-aminoalkylsulfonyl, $(C_1-C_6)$-aminohaloalkylsulfonyl, $(C_1-C_6)$-alkylaminosulfonyl, $(C_1-C_6)$-bisalkylaminosulfonyl, $(C_1-C_6)$-cycloalkylaminosulfonyl, $(C_1-C_6)$-haloalkylaminosulfonyl, arylaminosulfonyl, $(C_1-C_6)$-arylalkylaminosulfonyl, $(C_1-C_6)$-alkylsulfonyl, $(C_1-C_6)$-cycloalkylsulfonyl, arylsulfonyl, $(C_1-C_6)$-alkylsulfinyl, $(C_1-C_6)$-cycloalkylsulfinyl, arylsulfinyl, $(C_1-C_6)$—N,S-dialkylsulfonimidoyl, $(C_1-C_6)$—S-alkylsulfonimidoyl, $(C_1-C_6)$-alkylsulfonylaminocarbonyl, $(C_1-C_6)$-cycloalkylsulfonylaminocarbonyl, $(C_1-C_6)$-cycloalkylaminosulfonyl, $(C_1-C_6)$-arylalkylcarbonylamino, $(C_1-C_6)$-cycloalkylalkylcarbonylamino, heteroarylcarbonylamino, $(C_1-C_{10})$-alkoxyalkylcarbonylamino, $(C_1-C_6)$-hydroxyalkylcarbonylamino, $(C_1-C_6)$-trialkylsilyl, $A^6, A^7, A^8, A^9$ are identical or different and independently of one another represent O, S, N, NH, N-alkyl, alkoxycarbonyl-N, N-aryl, N-heteroaryl or the $C—R^{14}$ moiety, where at most two oxygen or sulfur atoms are present in the heterocycle, and where no oxygen or sulfur atoms are adjacent to one another, and where each $R^{14}$ in the $C—R^{14}$ moiety has identical or different meanings according to the definition below, and $R^{14}$ represents hydrogen, nitro, amino, cyano, thiocyanato, isothiocyanato, halogen, $(C_1-C_6)$-alkyl, $(C_1-C_6)$-cycloalkyl, $(C_1-C_6)$-alkenyl, $(C_1-C_6)$-alkynyl, aryl, aryl-$(C_1-C_6)$-alkyl, $(C_1-C_6)$-alkenylalkyl, $(C_1-C_6)$-alkynylalkyl, aryl-$(C_1-C_6)$-alkoxy, heteroaryl, $(C_1-C_6)$-alkoxyalkyl, $(C_1-C_6)$-hydroxyalkyl, $(C_1-C_6)$-haloalkyl, $(C_1-C_6)$-halocycloalkyl, $(C_1-C_6)$-alkoxy, $(C_1-C_6)$-haloalkoxy, aryloxy, heteroaryloxy, $(C_1-C_6)$-cycloalkyloxy, hydroxy, $(C_1-C_6)$-cycloalkylalkoxy, $(C_1-C_6)$-alkoxycarbonyl, hydroxycarbonyl, aminocarbonyl, $(C_1-C_6)$-alkylaminocarbonyl, $(C_1-C_6)$-cycloalkylaminocarbonyl, $(C_1-C_6)$-cyanoalkylaminocarbonyl, $(C_1-C_6)$-alkenylaminocarbonyl, $(C_1-C_6)$-alkynylaminocarbonyl, $(C_1-C_6)$-alkylamino, $(C_1-C_6)$-alkylthio, $(C_1-C_6)$-haloalkylthio, hydrothio, $(C_1-C_6)$-bisalkylamino, $(C_1-C_6)$-cycloalkylamino, $(C_1-C_6)$-alkylcarbonylamino, $(C_1-C_6)$-cycloalkylcarbonylamino, formylamino, $(C_1-C_6)$-haloalkylcarbonylamino, $(C_1-C_6)$-alkoxycarbonylamino, $(C_1-C_6)$-alkylaminocarbonylamino, $((C_1-C_6)$-alkyl)aminocarbonylamino, $(C_1-C_6)$-alkylsulfonylamino, $(C_1-C_6)$-cycloalkylsulfonylamino, arylsulfonylamino, hetarylsulfonylamino, $(C_1-C_6)$-sulfonylhaloalkylamino, aminosulfonyl, $(C_1-C_6)$-aminoalkylsulfonyl, $(C_1-C_6)$-aminohaloalkylsulfonyl, $(C_1-C_6)$-alkylaminosulfonyl, $(C_1-C_6)$-bisalkylaminosulfonyl, $(C_1-C_6)$-cycloalkylaminosulfonyl, $(C_1-C_6)$-haloalkylaminosulfonyl, arylaminosulfonyl, $(C_1-C_6)$-arylalkylaminosulfonyl, $(C_1-C_6)$-alkylsulfonyl, $(C_1-C_6)$-cycloalkylsulfonyl, arylsulfonyl, $(C_1-C_6)$-alkylsulfinyl, $(C_1-C_6)$-cycloalkylsulfinyl, arylsulfinyl, $(C_1-C_6)$—N,S-dialkylsulfonimidoyl, $(C_1-C_6)$—S-alkylsulfonimidoyl, $(C_1-C_6)$-alkylsulfonylaminocarbonyl, $(C_1-C_6)$-cycloalkylsulfonylaminocarbonyl, $(C_1-C_6)$-cycloalkylaminosulfonyl, $(C_1-C_6)$-arylalkylcarbonylamino, $(C_1-C_6)$-cycloalkylalkylcarbonylamino, heteroarylcarbonylamino, $(C_1-C_{10})$-alkoxyalkylcarbonylamino, $(C_1-C_6)$-hydroxyalkylcarbonylamino, $(C_1-C_6)$-trialkylsilyl, $A^{10}$ represents $N—R^{15}$, oxygen or the $C—R^{15}$ moiety, and where each $R^{15}$ in the $N—R^{15}$ and $C—R^{15}$ moieties has identical or different meanings according to the definition below, $A^{11}$ represents N or the $C—R^{18}$ moiety, and where $R^{18}$ in the $C—R^{18}$ moiety has the meaning according to the definition below, $A^{12}$ represents $N—R^{15}$ or the $C(R^{16})R^{17}$ moiety, and where $R^{16}$ and $R^{17}$ in the $C(R^{16})R^{17}$ moiety have the meaning according to the definition below, $R^{15}$ represents hydrogen, $(C_1-C_6)$-alkyl, $(C_1-C_6)$-alkenylalkyl, $(C_1-C_6)$-alkoxyalkyl, $(C_1-C_6)$-alkylcarbonyl, arylcarbonyl, heteroarylcarbonyl, $(C_1-C_6)$-cycloalkylcarbonyl, $(C_1-C_6)$-alkoxycarbonyl, $(C_1-C_6)$-allyloxycarbonyl, $(C_1-C_6)$-aryloxyalkyl, $(C_1-C_6)$-arylalkyl, $(C_1-C_6)$-haloalkyl, aryl, $R^{16}$ and $R^{17}$ independently of one another represent hydrogen, halogen, $(C_1-C_6)$-alkyl, $(C_1-C_6)$-alkoxy, $(C_1-C_6)$-haloalkyl, $(C_1-C_6)$-haloalkoxy, aryl, heteroaryl, $(C_1-C_6)$-arylalkyl or together with the atom to which they are attached form a carbonyl group, and $R^{18}$ in each case represents hydrogen, nitro, amino, cyano, thiocyanato, isothiocyanato, halogen, $(C_1-C_6)$-alkyl, $(C_1-C_6)$-cycloalkyl, $(C_1-C_6)$-alkenyl, $(C_1-C_6)$-alkynyl, aryl, aryl-$(C_1-C_6)$-alkyl, $(C_1-C_6)$-alkenylalkyl, $(C_1-C_6)$-alkynylalkyl, aryl-$(C_1-C_6)$-alkoxy, heteroaryl, $(C_1-C_6)$-alkoxyalkyl, $(C_1-C_6)$-hydroxyalkyl, $(C_1-C_6)$-haloalkyl, $(C_1-C_6)$-halocycloalkyl, $(C_1-C_6)$-alkoxy, $(C_1-C_6)$-haloalkoxy, aryloxy, heteroaryloxy, $(C_1-C_6)$-cycloalkyloxy, hydroxy, $(C_1-C_6)$-cycloalkylalkoxy, $(C_1-C_6)$-alkoxycarbonyl, hydroxycarbonyl, aminocarbonyl, $(C_1-C_6)$-alkylaminocarbonyl, $(C_1-C_6)$-cycloalkylaminocarbonyl, $(C_1-C_6)$-cyanoalkylaminocarbonyl, $(C_1-C_6)$-alkenylaminocarbonyl, $(C_1-C_6)$-alkynylaminocarbonyl, $(C_1-C_6)$-alkylamino, $(C_1-C_6)$-alkylthio, $(C_1-C_6)$-haloalkylthio, hydrothio, $(C_1-C_6)$-bisalkylamino, $(C_1-C_6)$-cycloalkylamino, $(C_1-C_6)$-alkylcarbonylamino, $(C_1-C_6)$-cycloalkylcarbonylamino, formylamino, $(C_1-C_6)$-haloalkylcarbonylamino, $(C_1-C_6)$-alkoxycarbonylamino, $(C_1-C_6)$-alkylaminocarbonylamino, $((C_1-C_6)$-alkyl)aminocarbonylamino, $(C_1-C_6)$-alkylsulfonylamino, $(C_1-C_6)$-cycloalkylsulfonylamino, arylsulfonylamino, hetarylsulfonylamino, $(C_1-C_6)$-sulfonylhaloalkylamino, aminosulfonyl, $(C_1-C_6)$-aminoalkylsulfonyl, $(C_1-C_6)$-aminohaloalkylsulfonyl, $(C_1-C_6)$-alkylaminosulfonyl, $(C_1-C_6)$-bisalkylaminosulfonyl, $(C_1-C_6)$-cycloalkylaminosulfonyl, $(C_1-C_6)$-haloalkylaminosulfonyl, arylaminosulfonyl, $(C_1-C_6)$-arylalkylaminosulfonyl, $(C_1-C_6)$-alkylsulfonyl, $(C_1-C_6)$-cycloalkylsulfonyl, arylsulfonyl, $(C_1-C_6)$-alkylsulfinyl, $(C_1-C_6)$-cycloalkylsulfinyl, arylsulfinyl, $(C_1-C_6)$—N,S-dialkylsulfonimidoyl, $(C_1-C_6)$—S-alkylsulfonimidoyl, $(C_1-C_6)$-alkylsulfonylaminocarbonyl, $(C_1-C_6)$-cycloalkylsulfonylaminocarbonyl, $(C_1-C_6)$-cycloalkylaminosulfonyl, $(C_1-C_6)$-arylalkylcarbonylamino, $(C_1-C_6)$-cycloalkylalkylcarbonylamino, heteroarylcarbonylamino, $(C_1-C_{10})$-alkoxyalkylcarbonylamino, $(C_1-C_6)$-hydroxyalkylcarbonylamino, $(C_1-C_6)$-trialkylsilyl.

4. A treatment for plants, comprising applying a nontoxic amount, effective for increasing resistance of plants to one or more abiotic stress factors, one or more compounds as claimed in claim 1.

5. The treatment as claimed in claim 4, wherein the abiotic stress condition comprises at least one condition selected from the group of drought, cold and hot conditions, aridity stress, osmotic stress, waterlogging, elevated soil salinity, elevated exposure to minerals, ozone conditions, strong light conditions, limited availability of nitrogen nutrients, and limited availability of phosphorus nutrients.

6. The compound as claimed in claim 1 capable of being used in a spray application to a plant and/or plant part in combination with one or more active compounds selected from the group consisting of insecticides, attractants, acaricides, fungicides, nematicides, herbicides, growth regulators, safeners, substances which influence plant maturity and bactericides.

7. The compound as claimed in claim 1 capable of being used in a spray application to a plant and/or plant part in combination with one or more fertilizers.

8. The compound as claimed in claim 1 capable of being used for application to a genetically modified cultivar, seed thereof, and/or to a cultivated area on which a cultivar grows.

9. The compound of claim 1 capable of being used in a spray solution which comprises one or more of the compounds of the formula (I) and/or salt for enhancing resistance of a plant to one or more abiotic stress factors.

10. A method for increasing stress tolerance in a plant selected from the group consisting of useful plants, ornamental plants, turfgrasses and trees, comprising applying a sufficient, nontoxic amount of one or more of the compounds as claimed in claim 1 to an area where a corresponding effect is desired, and/or applying to a plant, seed thereof and/or to an area on which a plant grows.

11. The method as claimed in claim 10, wherein resistance of a plant thus treated to abiotic stress is increased by at least 3% compared to an untreated plant under otherwise identical physiological conditions.

12. A compound comprising a 4-substituted 1-phenylpyrazole-3-carboxylic acid derivative of formula (I) and/or a salt thereof

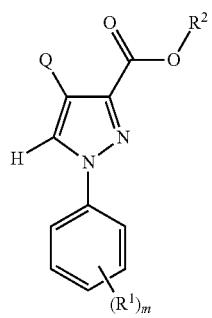

(I)

where

Q represents

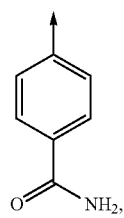

Q-1

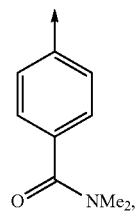

Q-2

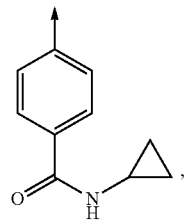

Q-3

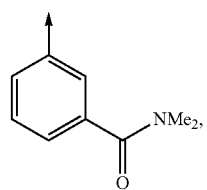

Q-4

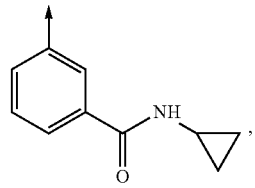

Q-5

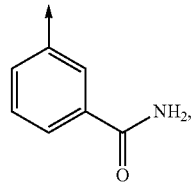

Q-6

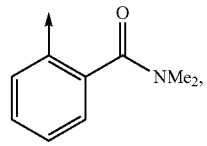

Q-7

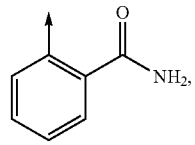

Q-8

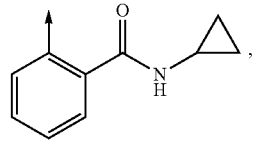

Q-9

165
-continued
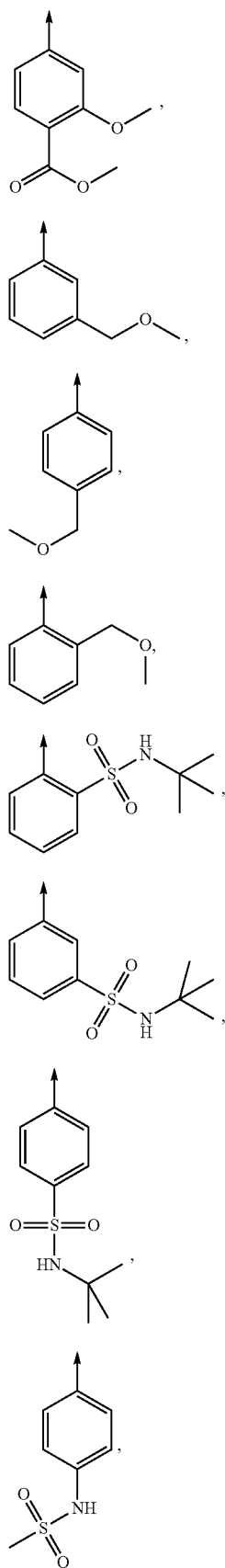
166
-continued
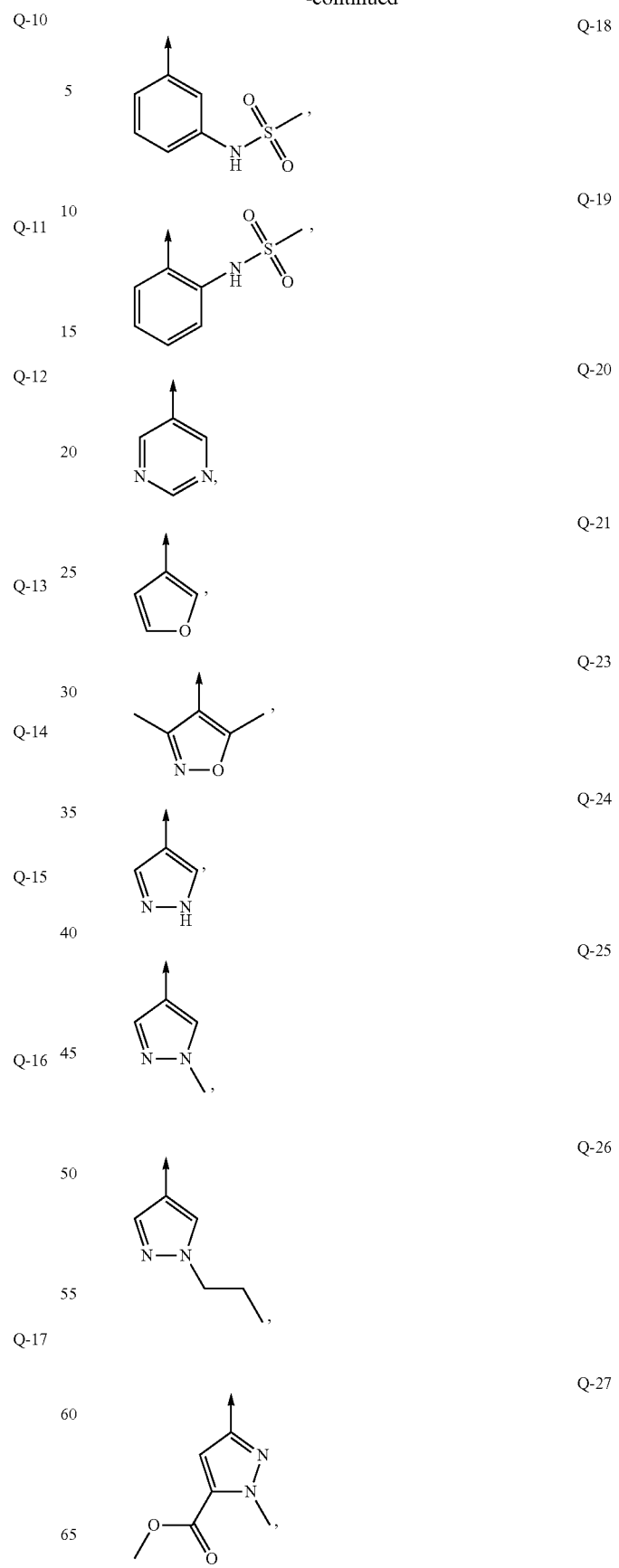

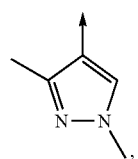
Q-28
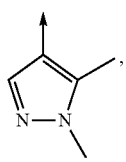
Q-29
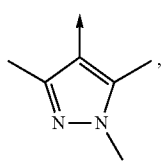
Q-30
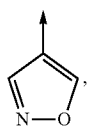
Q-31
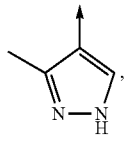
Q-32
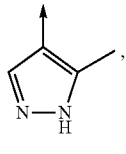
Q-33
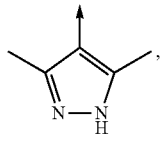
Q-34
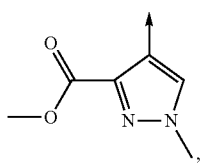
Q-35
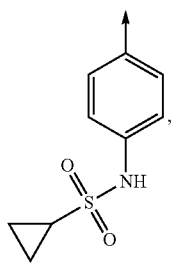
Q-36
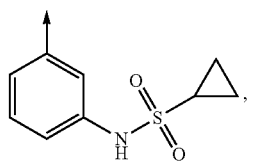
Q-37
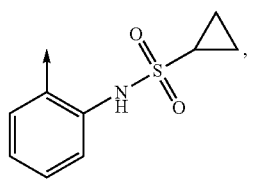
Q-38
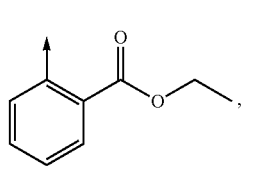
Q-39
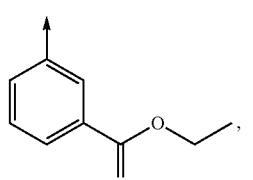
Q-40
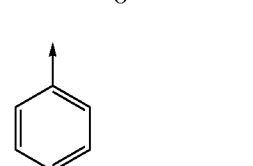
Q-41
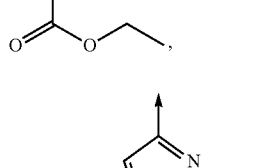
Q-42
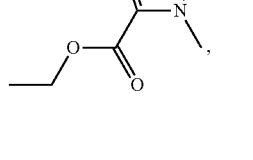
Q-43
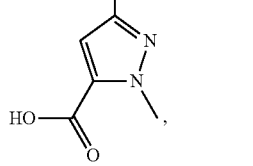
Q-44
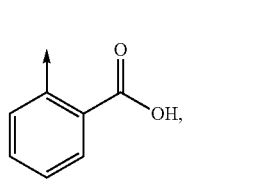

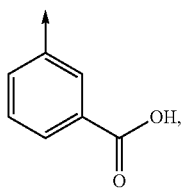
Q-45

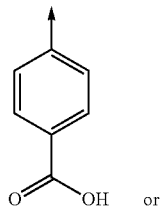
Q-46

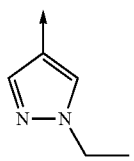 or
Q-47

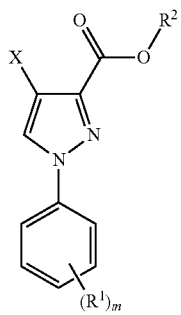

and $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1$-$C_4)$-alkyl, $(C_1$-$C_4)$-alkoxy or $(C_1$-$C_4)$-alkylthio, where each of the three last-mentioned radicals independently of the others is unsubstituted or substituted by one or more radicals from the group consisting of halogen, CN, $(C_1$-$C_4)$-alkoxy and $(C_1$-$C_4)$-alkylthio, m represents 1, 2, 3 or 4, and $R^2$ represents H, $(C_1$-$C_6)$-alkyl, $(C_2$-$C_6)$-alkenyl, $(C_2$-$C_6)$-alkynyl or $(C_3$-$C_6)$-cycloalkyl, where each of the 4 last-mentioned radicals is unsubstituted or substituted by one or more radicals from the group consisting of halogen, $(C_1$-$C_6)$-alkyl, the latter only being a substituent in the case of cyclic parent radicals, $(C_1$-$C_4)$-alkoxy, $(C_1$-$C_4)$-alkylthio, $(C_3$-$C_6)$-cycloalkyl, which is unsubstituted or substituted by one or more radicals from the group consisting of halogen and $(C_1$-$C_4)$-alkyl, and phenyl which is unsubstituted or substituted by one or more radicals from the group consisting of halogen, $(C_1$-$C_4)$-alkyl, $(C_1$-$C_4)$-alkoxy and $(C_1$-$C_4)$-haloalkyl, and heterocyclyl which is unsubstituted or substituted by one or more radicals from the group consisting of halogen, $(C_1$-$C_4)$-alkyl, $(C_1$-$C_4)$-alkoxy, $(C_1$-$C_4)$-haloalkyl and $(C_1$-$C_4)$-haloalkoxy.

13. The compound as claimed in claim 12 in which $(R^1)_m$ represents m substituents $R^1$, where in the case that m is the number 1 the radical $R^1$ or, in the case that m is greater than 1, each of the radicals $R^1$ in each case independently of the others represents halogen, CN, $(C_1$-$C_4)$-alkyl or $(C_1$-$C_4)$-alkoxy, where each of the two last-mentioned radicals independently of the others is unsubstituted or substituted by one or more radicals from the group consisting of halogen, $(C_1$-$C_3)$-alkoxy and $(C_1$-$C_3)$-alkylthio, and where m represents 1, 2, 3 or 4, and $R^2$ represents H, $(C_1$-$C_4)$-alkyl, $(C_2$-$C_4)$-alkenyl or $(C_2$-$C_4)$-alkynyl, and where each of the 3 last-mentioned radicals is unsubstituted or substituted by one or more radicals from the group consisting of halogen, $(C_1$-$C_4)$-alkoxy, $(C_1$-$C_4)$-alkylthio, cyclopropyl, cyclobutyl, where each of the two last-mentioned radicals is unsubstituted or substituted by one or more radicals from the group consisting of halogen and $(C_1$-$C_4)$-alkyl, and phenyl which is unsubstituted or substituted by one or more radicals from the group consisting of halogen, $(C_1$-$C_4)$-alkyl, $(C_1$-$C_4)$-alkoxy and $(C_1$-$C_4)$-haloalkyl, and heterocyclyl which is unsubstituted or substituted by one or more radicals from the group consisting of halogen, $(C_1$-$C_4)$-alkyl, $(C_1$-$C_4)$-alkoxy and $(C_1$-$C_4)$-haloalkyl.

14. A spray solution for treatment of a plant, comprising an amount, effective for enhancing resistance of a plant to one or more abiotic stress factors, of one or more compounds as claimed in claim 12.

15. A process for preparing a compound as claimed in claim 1 comprising
reacting
a) a compound of formula (XI)

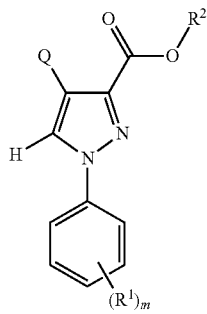
(XI)

where X corresponds to a halogen
with a compound of formula (XII)

Q-M    (XII)

to give a compound of formula (I) and/or a salt thereof (I)

or b) in the case that $R^2$ in formula (I) is different from hydrogen, esterified, or transesterified, to give the compound of formula (I), c) in the case that $R^2$ in formula (I) represents hydrogen and/or a salt thereof, hydrolyzed to give a compound of formula (I), and/or reacted to give a salt thereof, and where M in formula (XII) represents Mg-Hal, Zn-Hal, $Sn((C_1$-$C_4)alkyl)_3$, lithium, copper or $B(OR^a)(OR^b)$, where the radicals $R^a$ and $R^b$ independently of 16. A process for preparing a compound as claimed in claim 1 or salts thereof, comprising reacting in a multi-step process in (e1)

a compound of formula (IV),

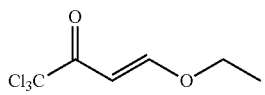

with a substituted phenylhydrazine of formula (VI)

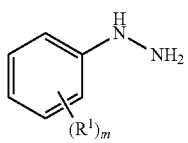

to give a compound of formula (VII)

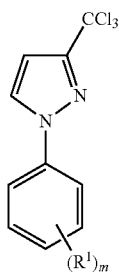

and in (e2)

reacting a compound of formula (VII) obtained in (e1) with an alcohol to give a compound of formula (IX)

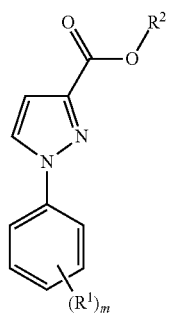

and in (e3)

reacting a compound of formula (IX) obtained in (e2) with a halogenating agent to give a compound of formula (XI)

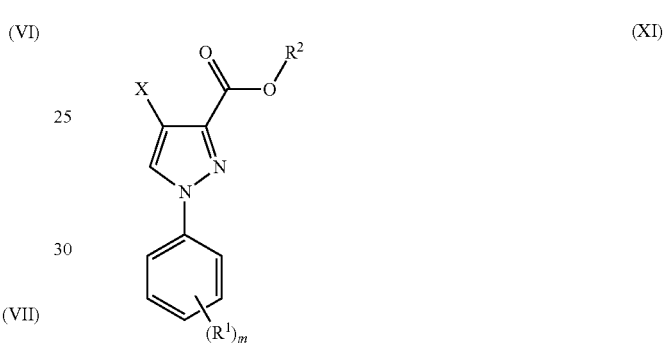

where X corresponds to a halogen and in (e4)

reacting compound (XI) obtained in (e3) with a compound of formula (XII)

Q-M  (XII)

to give a compound of the formula (I) and/or a salt thereof, where M in formula (XII) represents Mg-Hal, Zn-Hal, Sn(($C_1$-$C_4$)alkyl)$_3$, lithium, copper or B(OR$^a$)(OR$^b$), where the radicals R$^a$ and R$^b$ independently of one another represent hydrogen, ($C_1$-$C_4$)-alkyl, or, if the radicals R$^a$ and R$^b$ are attached to one another, together represent ethylene or propylene.

* * * * *